United States Patent
Cheng et al.

(10) Patent No.: US 8,507,491 B2
(45) Date of Patent: Aug. 13, 2013

(54) COMPOUNDS AND COMPOSITIONS AS HEDGEHOG PATHWAY INHIBITORS

(75) Inventors: Dai Cheng, San Diego, CA (US); Dong Han, San Diego, CA (US); Guobao Zhang, San Diego, CA (US); Yongqin Wan, Irvine, CA (US); Yun Feng Xie, San Diego, CA (US); Jiqing Jiang, San Diego, CA (US); Wenqi Gao, San Diego, CA (US); Shifeng Pan, San Diego, CA (US)

(73) Assignee: IRM LLC, Hamilton (BM)

( * ) Notice: Subject to any disclaimer, the term of this patent is extended or adjusted under 35 U.S.C. 154(b) by 116 days.

(21) Appl. No.: 13/060,426

(22) PCT Filed: Aug. 24, 2009

(86) PCT No.: PCT/US2009/054802
§ 371 (c)(1),
(2), (4) Date: Feb. 23, 2011

(87) PCT Pub. No.: WO2010/027746
PCT Pub. Date: Mar. 11, 2010

(65) Prior Publication Data
US 2011/0152282 A1   Jun. 23, 2011

Related U.S. Application Data

(60) Provisional application No. 61/091,496, filed on Aug. 25, 2008.

(51) Int. Cl.
| | |
|---|---|
| A61K 31/501 | (2006.01) |
| A61K 31/4725 | (2006.01) |
| A61K 31/4439 | (2006.01) |
| A61K 31/497 | (2006.01) |
| A61K 31/472 | (2006.01) |
| A61K 31/4427 | (2006.01) |
| A61P 35/00 | (2006.01) |

(52) U.S. Cl.
USPC ......... 514/252.04; 514/310; 514/263.22; 514/260.1; 514/303; 514/255.05; 514/309; 514/308; 544/238; 544/264; 544/255; 544/331; 544/408; 546/143; 546/118; 546/141; 546/140

(58) Field of Classification Search
USPC ......... 546/140, 141, 143, 118; 514/426, 514/309, 308, 310, 264.11, 263.22, 260.1, 514/269, 255.05, 252.04, 303; 544/279, 544/238, 264, 255, 298, 405, 331, 58.2, 408
See application file for complete search history.

(56) References Cited

U.S. PATENT DOCUMENTS

| | | | |
|---|---|---|---|
| 2005/0277643 A1 | 12/2005 | Kelly | |
| 2009/0209561 A1* | 8/2009 | Hatley et al. | 514/263.22 |
| 2010/0179152 A1* | 7/2010 | Dunkern et al. | 514/243 |
| 2010/0298285 A1* | 11/2010 | Kelly et al. | 514/210.18 |
| 2011/0034481 A1* | 2/2011 | Uto et al. | 514/255.05 |
| 2011/0105503 A1* | 5/2011 | Li et al. | 514/235.5 |
| 2011/0160183 A1* | 6/2011 | Kelly et al. | 514/210.21 |
| 2011/0190292 A1* | 8/2011 | Dhar et al. | 514/234.2 |
| 2011/0251226 A1* | 10/2011 | Plettenburg et al. | 514/278 |
| 2011/0269760 A1* | 11/2011 | Burns et al. | 514/235.8 |
| 2011/0275671 A1* | 11/2011 | Yuan et al. | 514/323 |

FOREIGN PATENT DOCUMENTS

| | | |
|---|---|---|
| WO | WO2005042537 | 5/2005 |
| WO | WO2005066171 | 7/2005 |
| WO | WO2006028958 | 3/2006 |
| WO | WO2008125839 | 10/2008 |

OTHER PUBLICATIONS

Rubin, et al., Nature Reviews: Drug Discovery, vol. 5, Dec. 2006, 1026-1033.*
Booth, Cancer & Metastasis Reviews 18: 261-284, 1999.*
Singh, et al., Leukemia (2010) 24, 1025-1036.*
Von Hoff, et al., N. Engl. J. Med., Sep. 17, 2009; 361:1164-1172.*

* cited by examiner

*Primary Examiner* — Susanna Moore
*Assistant Examiner* — Cecilia M Jaisle
(74) *Attorney, Agent, or Firm* — Daniel E. Raymond; Genomics Institute of the Novartis Research Foundation

(57) ABSTRACT

The invention provides a method, compounds and compositions for modulating the activity of the hedgehog signaling pathway. In particular, the invention provides a method for inhibiting aberrant growth states resulting from phenotypes such as Ptc loss-of-function, hedgehog gain-of-function, smoothened gain-of-function or Gli gain-of-function, comprising contacting a cell with a sufficient amount of a compound of Formula (I).

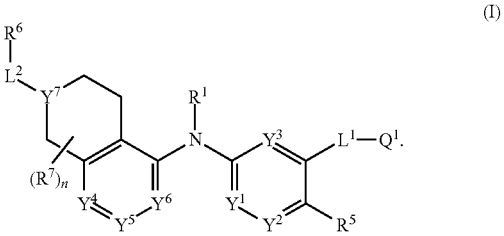

18 Claims, No Drawings

COMPOUNDS AND COMPOSITIONS AS HEDGEHOG PATHWAY INHIBITORS

CROSS-REFERENCE TO RELATED APPLICATIONS

This application is a 371 U.S. national phase application of international application number PCT/US2009/054802 filed 24 Aug. 2009, which application claims the benefit of priority under 35 U.S.C. §119(e) to U.S. Provisional Patent Application No. 61/091,496, filed Aug. 25, 2008 now abandoned, the disclosure of which is incorporated herein by reference in its entirety and for all purposes.

FIELD OF THE INVENTION

The invention relates to compounds, compositions and methods for modulating the activity of the hedgehog signaling pathway.

BACKGROUND OF THE INVENTION

During embryonic development, the hedgehog signaling pathway is essential for numerous processes such as the control of cell proliferation, differentiation and tissue patterning. The aberrant activity of the hedgehog signaling pathway, for example, as a result of enhanced activation, however may have pathological consequences. In this regard, activation of the hedgehog pathway in adult tissues can result in diseases such as psoriasis and specific types of cancer that include, but are not limited to, malignant lymphoma (LM), multiple myeloma (MM), cancers of the brain, muscle and skin, prostrate, medulloblastoma, pancreatic adenocarcinomas and small-cell lung carcinomas. Enhanced activation of the hedgehog signaling pathway contributes to the pathology and/or symptomology of a number of diseases. Accordingly, molecules that modulate the activity of the hedgehog signaling pathway are useful as therapeutic agents in the treatment of such diseases.

SUMMARY OF THE INVENTION

Provided herein are compounds, compositions and methods for modulating the activity of the hedgehog signaling pathway. Such methods include contacting a cell with a sufficient amount of a compound of Formula (I), or a composition containing a sufficient amount of a compound of Formula (I). In certain embodiments, such compounds, compositions and methods inhibit aberrant growth states resulting from phenotypes of Ptc loss-of-function, hedgehog gain-of-function, smoothened gain-of-function, Gli gain-of-function, or over expression of hedgehog ligands.

In one aspect, the compounds, and the pharmaceutically acceptable salts, pharmaceutically acceptable solvates, hydrates, the N-oxides, prodrugs, protected derivatives, individual isomers and mixture of isomers thereof, provided herein, have a structure according to Formula (I):

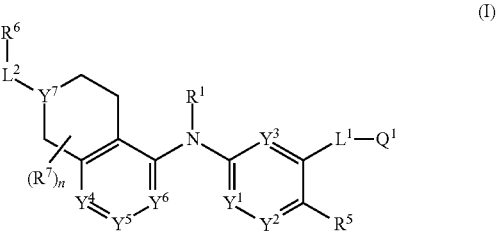

wherein:
Q$^1$ is selected from an aryl, heteroaryl, cycloalkyl, and heterocycloalkyl, wherein the aryl, heteroaryl, cycloalkyl and heterocycloalkyl of Q$^1$ are optionally substituted with 1 to 3 substituents independently selected from R$^9$, R$^{10}$, R$^{11}$, R$^{12}$ and R$^{13}$;

Y$^1$ is N or CR$^3$;
Y$^2$ is N or CR$^4$;
Y$^3$ is N or CR$^2$;
Y$^4$, Y$^5$, Y$^6$ are independently selected from N and CR$^8$;
Y$^7$ is N or N$^+$O$^-$;
L$^1$, L$^2$ and L$^3$ are independently selected from a bond, —(CR$^{14}$R$^{14}$)$_m$—, —(CR$^{14}$R$^{14}$)$_m$—, —C(O)—, —O—, —C(O)O—, —OC(O)—, —C(O)(CR$^{14}$R$^{14}$)$_m$—, C(O)O(CR$^{14}$R$^{14}$)$_m$—, —NR$^{16}$C(O)—, —O(CR$^{14}$R$^{14}$)$_m$—, —(CR$^{14}$R$^{14}$)$_m$O—, —O(CR$^{14}$R$^{15}$)$_m$—, —(CR$^{14}$R$^{15}$)$_m$O—, —C(O)(CR$^{14}$R$^{15}$)$_m$, and —C(O)NR$^{16}$—;

R$^1$ is H or C$_1$-C$_6$alkyl;
R$^2$, R$^3$ and R$^4$ are each independently selected from H, halo, CN, C$_1$-C$_6$alkyl and halosubstituted-C$_1$-C$_6$alkyl, C$_1$-C$_6$alkoxy, halosubstituted-C$_1$-C$_6$alkoxy, L$^3$OR$^{13}$, —C(O)OR$^{13}$ and L$^3$NR$^{16}$R$^{17}$;

each R$^5$ is independently selected from H, CN, halo, C$_1$-C$_6$alkyl, halosubstituted-C$_1$-C$_6$alkyl, C$_1$-C$_6$alkoxy, halosubstituted-C$_1$-C$_6$alkoxy, L$^3$OR$^{13}$, C(O)OR$^{13}$ and L$^3$NR$^{16}$R$^{17}$;

each R$^6$ is independently selected from H, S(O)R$^{13}$, SO$_2$R$^{13}$, SO$_2$NR$^{16}$R$^{17}$, L$^3$NR$^{16}$R$^{17}$, C(O)OR$^{13}$, OR$^{13}$, R$^{13}$, NR$^{16}$R$^{17}$, C(O)NR$^{16}$R$^{17}$, C$_1$-C$_6$alkyl, C$_1$-C$_6$haloalkyl, C$_3$-C$_8$cycloalkyl, C$_1$-C$_6$alkyl substituted with 1-4 OH groups, heteroaryl, heterocycloalkyl, C$_2$-C$_6$cyclic sulfinyl, C$_2$-C$_6$cyclic sulfonyl and aryl, wherein the heteroaryl, heterocycloalkyl, C$_3$-C$_8$cycloalkyl, C$_2$-C$_6$cyclic sulfinyl, C$_2$-C$_6$cyclic sulfonyl and aryl of R$^6$ are optionally substituted with 1-4 substituents selected from H, halo, CN, C$_1$-C$_6$alkyl, halosubstituted-C$_1$-C$_6$alkyl, C$_1$-C$_6$alkoxy, halosubstituted-C$_1$-C$_6$alkoxy, C$_1$-C$_6$alkyl substituted with 1-4 —OH groups, C$_3$-C$_8$cycloalkyl, C$_3$-C$_8$heterocycloalkyl, heteroaryl, and aryl;

each R$^7$ and R$^8$ are independently selected from H, C$_1$-C$_6$alkyl; halosubstituted-C$_1$-C$_6$alkyl, C$_1$-C$_6$alkoxy, halosubstituted-C$_1$-C$_6$alkoxy, C$_6$-C$_{10}$aryl-C$_0$-C$_4$alkyl, C$_5$-C$_{10}$heteroaryl-C$_0$-C$_{64}$alkyl, C$_3$-C$_{12}$cycloalkyl and C$_3$-C$_8$heterocycloalkyl;

or two R$^7$ along with the carbon to which they are attached from a C=O group;

each R$^9$, R$^{10}$, R$^{11}$ and R$^{12}$ are independently selected from H, CN, halo, C$_1$-C$_6$alkyl, halosubstituted-C$_1$-C$_6$alkyl, C$_1$-C$_6$alkoxy, halosubstituted-C$_1$-C$_6$alkoxy, L$^3$OR$^{13}$, L$^3$NR$^{16}$R$^{17}$, L$^3$R$^{13}$, L$^3$R$^{14}$, aryl optionally substituted with 1 to 3 substituents selected from C$_1$-C$_6$alkyl, halo, CN, L$^3$NR$^{16}$R$^{17}$ and OR$^{13}$, and heteroaryl optionally substituted with 1 to 3 substituents selected from C$_1$-C$_6$alkyl, halo, CN, L$^3$NR$^{16}$R$^{17}$ and L$^3$OR$^{13}$;

alternatively $R^{10}$ and $R^{11}$ together with the carbons atoms to which they are attached form a 5-6 membered aryl optionally substituted with 1 to 3 substituents selected from $C_1$-$C_6$alkyl, halo, CN, $L^3NR^{16}R^{17}$ and $L^3OR^{13}$ or a 5-6 membered heteroaryl optionally substituted with 1 to 3 substituents selected from $C_1$-$C_6$alkyl, halo, CN, $L^3NR^{16}R^{17}$ and $L^3OR^{13}$;

alternatively $R^{11}$ and $R^{12}$ together with the carbons atoms to which they are attached form a 5-6 membered aryl optionally substituted with 1 to 3 substituents selected from $C_1$-$C_6$alkyl, halo, CN, $L^3NR^{16}R^{17}$ and $L^3OR^{13}$ or a 5-6 membered heteroaryl optionally substituted with 1 to 3 substituents selected from $C_1$-$C_6$alkyl, halo, CN, $L^3NR^{16}R^{17}$ and $L^3OR^{13}$;

each $R^{13}$ is independently selected from H, $C_1$-$C_6$alkyl, $C_1$-$C_6$haloalkyl, $C_3$-$C_8$cycloalkyl, $C_3$-$C_8$heterocycloalkyl, $C_1$-$C_6$alkyl substituted with 1-4 —OH groups, heteroaryl and aryl, where the heteroaryl and aryl of $R^{13}$ are optionally substituted with 1 to 3 substituents selected from $C_1$-$C_6$alkyl, $C_1$-$C_6$haloalkyl, $C_3$-$C_8$cycloalkyl, $C_3$-$C_8$heterocycloalkyl, and $C_1$-$C_6$alkyl substituted with 1-4 —OH groups;

each $R^{14}$ and $R^{15}$ are independently selected from H, halo, OH, CN, $C_1$-$C_6$alkyl, $C_1$-$C_6$alkyl substituted with 1-4 —OH groups, halosubstituted-$C_1$-$C_6$alkyl, $C_1$-$C_6$alkoxy and halosubstituted-$C_1$-$C_6$alkoxy;

or $R^{14}$ and $R^{15}$ together with the carbon they are attached form a $C_3$-$C_8$cycloalkyl;

each $R^{16}$ and $R^{17}$ are independently selected from H, $C_1$-$C_6$alkyl, $C_1$-$C_6$alkyl substituted with 1-4 —OH groups;

or $R^{16}$ and $R^{17}$ together with the N atom they are attached form a $C_3$-$C_8$heterocycloalkyl;

each m is independently 1, 2, 3, 4, 5 or 6;

each n is independently 1, 2, 3, 4, 5 or 6, and the pharmaceutically acceptable salts, hydrates, N-oxides, solvates and isomers thereof.

In certain embodiments of such compounds $R^1$ is H.

In certain embodiments of the aforementioned compounds $Q^1$ is

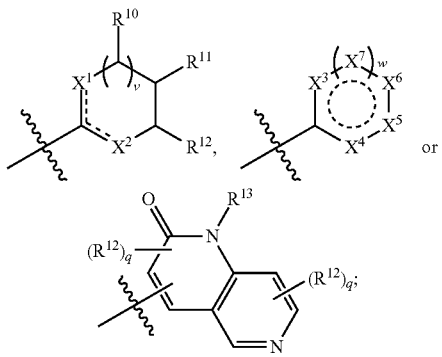

wherein,
v is 0, 1 or 3;
w is 0 or 1;
each q is independently 1, 2 or 3;
$X^1$ and $X^2$ are independently selected from N, S and $NR^{16}$;
$X^7$ is N or $CR^{10}$;
when w is 1 then: $X^3$ is N or $CR^9$;
  $X^4$ is N or $CR^9$;
  $X^5$ is N or $CR^{12}$, and
  $X^6$ is N or $CR^{11}$;

when w is 0 then: $X^3$ is N, O or $CR^9$;
  $X^4$ is N, O or $CR^9$;
  $X^5$ is N, $CR^{12}$ or $NR^{16}$, and
  $X^6$ is N, $CR^{11}$ or $NR^{16}$;

provided that when $X^3$ is O, then $X^4$ is N or $CR^9$, or when $X^4$ is O, then $X^3$ is N or $CR^9$; and provided that when $X^5$ is $NR^{16}$, then $X^6$ is N or $CR^{11}$, or when $X^6$ is $NR^{16}$, then $X^5$ is N or $CR^{12}$.

In certain embodiments of the aforementioned compounds $Q^1$ is

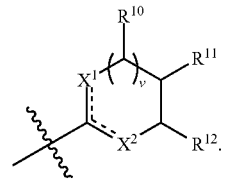

In certain embodiments of the aforementioned compounds $Q^1$ is

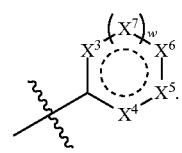

In certain embodiments of the aforementioned compounds each $R^6$ is

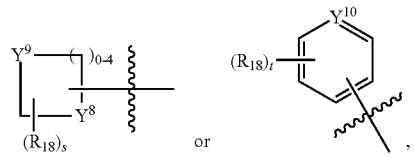

wherein;
$Y^8$ is N, $NR^{16}$, —($CR^{13}R^{13}$)—, or $CR^{13}$;
$Y^9$ is $SO_2$, S=O, O, $NR^{16}$, —($CR^{13}R^{13}$)—, C(O) or $COR^{13}$;
$Y^{10}$ is N or $N^+O^-$;
each $R^{18}$ is independently selected from halo, CN, $C_1$-$C_6$alkyl, halosubstituted-$C_1$-$C_6$alkyl, $C_1$-$C_6$alkoxy, halosubstituted-$C_1$-$C_6$alkoxy, $C_1$-$C_6$alkyl substituted with 1 to 4 —OH groups, $C_3$-$C_8$cycloalkyl, $C_3$-$C_8$heterocycloalkyl, heteroaryl, and aryl;
s is 1, 2, 3, 4 or 5, and
t is 1, 2, 3 or 4.

In certain embodiments of compounds of Formula (I), $L^2$ is a bond, and each $R^6$ is independently selected from H, S(O)$R^{13}$, $SO_2R^{13}$, $SO_2NR^{16}R^{17}$, $C(O)NR^{16}R^{17}$, $C_1$-$C_6$alkyl, $C_1$-$C_6$haloalkyl, $C_3$-$C_8$cycloalkyl, $C_1$-$C_6$alkyl substituted with 1-4 OH groups, heteroaryl, heterocycloalkyl, $C_2$-$C_6$cyclic sulfinyl, $C_2$-$C_6$cyclic sulfonyl and aryl, wherein the heteroaryl, heterocycloalkyl, $C_3$-$C_8$cycloalkyl, $C_2$-$C_6$cyclic sulfinyl, $C_2$-$C_6$cyclic sulfonyl and aryl of $R^6$ are optionally substituted with 1-4 substituents selected from H, halo, CN, $C_1$-$C_6$alkyl, halosubstituted-$C_1$-$C_6$alkyl, $C_1$-$C_6$alkoxy, halosubstituted-$C_1$-$C_6$alkoxy, $C_1$-$C_6$alkyl substituted with 1-4 —OH groups, $C_3$-$C_8$cycloalkyl, $C_3$-$C_8$heterocycloalkyl, heteroaryl, and aryl.

In certain embodiments of compounds of Formula (I), $L^2$ is a —$(CR^{14}R^{14})_m$—, —$(CR^{14}R^{15})_m$—, $C(O)(CR^{14}R^{14})_m$—, or —$C(O)(CR^{14}R^{15})_m$, and each $R^6$ is independently selected from H, $S(O)R^{13}$, $SO_2R^{13}$, $NR^{16}R^{17}$, $L^3NR^{16}R^{17}$, $C(O)OR^{13}$, $C(O)NR^{16}R^{17}$, $C_1$-$C_6$haloalkyl, $C_1$-$C_6$alkyl substituted with 1-4 OH groups, heteroaryl, heterocycloalkyl, $C_3$-$C_8$cycloalkyl, $C_2$-$C_6$cyclic sulfinyl, $C_2$-$C_6$cyclic sulfonyl and aryl, wherein the heteroaryl, heterocycloalkyl, $C_3$-$C_8$cycloalkyl, $C_2$-$C_6$cyclic sulfinyl, $C_2$-$C_6$cyclic sulfonyl and aryl of $R^6$ are optionally substituted with 1-4 substituents selected from H, halo, CN, $C_1$-$C_6$alkyl, halosubstituted-$C_1$-$C_6$alkyl, $C_1$-$C_6$alkoxy, halosubstituted-$C_1$-$C_6$alkoxy, $C_1$-$C_6$alkyl substituted with 1-4 —OH groups, $C_3$-$C_8$cycloalkyl, $C_3$-$C_8$heterocycloalkyl, heteroaryl, and aryl.

In certain embodiments of compounds of Formula (I), $L^2$ is a —C(O)—, or —C(O)O—, and each $R^6$ is independently selected from H, $NR^{16}R^{17}$, $L^3NR^{16}R^{17}$, $C(O)OR^{13}$, $C_1$-$C_6$alkyl, $C_1$-$C_6$haloalkyl, $C_3$-$C_8$cycloalkyl, $C_1$-$C_6$alkyl substituted with 1-4 OH groups, heteroaryl, heterocycloalkyl, $C_2$-$C_6$cyclic sulfinyl, $C_2$-$C_6$cyclic sulfonyl and aryl, wherein the heteroaryl, heterocycloalkyl, $C_3$-$C_8$cycloalkyl, $C_2$-$C_6$cyclic sulfinyl, $C_2$-$C_6$cyclic sulfonyl and aryl of $R^6$ are optionally substituted with 1-4 substituents selected from H, halo, CN, $C_1$-$C_6$alkyl, halosubstituted-$C_1$-$C_6$alkyl, $C_1$-$C_6$alkoxy, halosubstituted-$C_1$-$C_6$alkoxy, $C_1$-$C_6$alkyl substituted with 1-4 —OH groups, $C_3$-$C_8$cycloalkyl, $C_3$-$C_8$heterocycloalkyl, heteroaryl, and aryl.

In certain embodiments of the aforementioned compounds each $R^{18}$ is independently selected from halo, $C_1$-$C_6$alkyl and $C_1$-$C_6$alkyl substituted with 1 to 4 —OH groups.

In certain embodiments of the aforementioned compounds $R^2$, $R^3$ and $R^4$ are each independently selected from H, halo, CN, $C_1$-$C_6$alkyl and halosubstituted-$C_1$-$C_6$alkyl.

In certain embodiments of the aforementioned compounds each $R^5$ is independently selected from H, CN, halo, $C_1$-$C_6$alkyl, $L^3OR^{13}$, —$C(O)OR^{13}$ and $L^3NR^{16}R^{17}$.

In certain embodiments of the aforementioned compounds each $R^7$ is independently selected from H and $C_1$-$C_6$alkyl, or two $R^7$ along with the carbon to which they are attached from a C=O group.

In certain embodiments of the aforementioned compounds each $R^8$ is independently selected from H and $C_1$-$C_6$alkyl.

In certain embodiments of the aforementioned compounds each $R^9$ is independently selected from H, halo and $C_1$-$C_6$alkyl.

In certain embodiments of the aforementioned compounds each $R^{10}$ is independently selected from H, halo, $C_1$-$C_6$alkyl, $L^3OR^{13}$ and $L^3NR^{16}R^{17}$.

In certain embodiments of the aforementioned compounds each $R^{11}$ is independently selected from H, $C_1$-$C_6$alkyl, $C_1$-$C_6$haloalkyl, halo, CN, $L^3R^{13}$, $L^3R^{14}$, $L^3OR^{13}$, $L^3NR^{16}R^{17}$, an aryl optionally substituted with 1 to 3 substituents selected from $C_1$-$C_6$alkyl, halo, CN, $L^3NR^{16}R^{17}$ and $OR^{13}$, and a heteroaryl optionally substituted with 1 to 3 substituents selected from $C_1$-$C_6$alkyl, halo, CN, $L^3NR^{16}R^{17}$ and $L^3OR^{13}$.

In certain embodiments of the aforementioned compounds each $R^{12}$ is independently selected from H, $C_1$-$C_6$alkyl, CN, $L^3OR^{13}$ and $L^3NR^{16}R^{17}$.

In certain embodiments of the aforementioned compounds each $R^5$ is independently selected from —Cl or methyl.

In certain embodiments of such compounds are selected from 4-(5-{[4-chloro-3-(5-phenyl-1H-imidazol-2-yl)phenyl]amino}-1,2,3,4-tetrahydroisoquinolin-2-yl)-1-1{4}-thian-1-one; 1-(5-{[4-chloro-3-(5-phenyl-1H-imidazol-2-yl)phenyl]amino}-1,2,3,4-tetrahydroisoquinolin-2-yl)-3-hydroxy-2-(hydroxymethyl)-2-methylpropan-1-one; 4-(5-{[4-chloro-3-(5-phenyl-1H-imidazol-2-yl)phenyl]amino}-1,2,3,4-tetrahydroisoquinolin-2-yl)-thiane-1,1-dione; N-[4-chloro-3-(5-phenyl-1H-imidazol-2-yl)phenyl]-2-methanesulfonyl-1,2,3,4-tetrahydroisoquinolin-5-amine; N-[3-(1H-1,3-benzodiazol-2-yl)-4-methylphenyl]-2-methanesulfonyl-1,2,3,4-tetrahydroisoquinolin-5-amine; N-[4-chloro-3-(5-phenyl-1H-imidazol-2-yl)phenyl]-2-(1-ethylpiperidin-4-yl)-1,2,3,4-tetrahydroisoquinolin-5-amine; 1-(5-{[4-chloro-3-(5-phenyl-1H-imidazol-2-yl)phenyl]amino}-1,2,3,4-tetrahydroisoquinolin-2-yl)-2-methanesulfonylethan-1-one; (2R)-1-(5-{[4-chloro-3-(5-phenyl-1H-imidazol-2-yl)phenyl]amino}-1,2,3,4-tetrahydroisoquinolin-2-yl)-2-hydroxypropan-1-one; 1-(5-{[4-chloro-3-(5-phenyl-1H-imidazol-2-yl)phenyl]amino}-1,2,3,4-tetrahydroisoquinolin-2-yl)-2,3-dihydroxypropan-1-one; 1-(5-{[4-chloro-3-(5-phenyl-1H-imidazol-2-yl)phenyl]amino}-1,2,3,4-tetrahydroisoquinolin-2-yl)-2-hydroxypropan-1-one; 1-[4-(5-{[4-chloro-3-(5-phenyl-1H-imidazol-2-yl)phenyl]amino}-1,2,3,4-tetrahydroisoquinolin-2-yl)piperidin-1-yl]ethan-1-one; 4-(5-{[4-chloro-3-(5-phenyl-1H-imidazol-2-yl)phenyl]amino}-1,2,3,4-tetrahydroisoquinolin-2-yl)-thian-1-one; 5-{[4-chloro-3-(5-phenyl-1H-imidazol-2-yl)phenyl]amino}-1,2,3,4-tetrahydroisoquinoline-2-sulfonamide; 1-(5-{[4-chloro-3-(5-phenyl-1H-imidazol-2-yl)phenyl]amino}-1,2,3,4-tetrahydroisoquinolin-2-yl)-3-hydroxy-2,2-dimethylpropan-1-one; 2-methanesulfonyl-N-[3-(5-methoxy-1H-1,3-benzodiazol-2-yl)-4-methylphenyl]-1,2,3,4-tetrahydroisoquinolin-5-amine; N-{4-chloro-3-[6-(dimethylamino)-1H-1,3-benzodiazol-2-yl]phenyl}-2-methanesulfonyl-1,2,3,4-tetrahydroisoquinolin-5-amine; 2-[(5-{[4-chloro-3-(5-phenyl-1H-imidazol-2-yl)phenyl]amino}-1,2,3,4-tetrahydroisoquinoline-2-sulfonyl)amino]ethan-1-ol; (2R)-3-(5-{[4-chloro-3-(5-phenyl-1H-imidazol-2-yl)phenyl]amino}-1,2,3,4-tetrahydroisoquinolin-2-yl)propane-1,2-diol; 1-(5-{[4-chloro-3-(5-phenyl-1H-imidazol-2-yl)phenyl]amino}-1,2,3,4-tetrahydroisoquinolin-2-yl)-2-methanesulfinylethan-1-one; (2S)-1-(5-{[4-chloro-3-(5-phenyl-1H-imidazol-2-yl)phenyl]amino}-1,2,3,4-tetrahydroisoquinolin-2-yl)-2-hydroxypropan-1-one; N-[4-chloro-3-(5-phenyl-1H-imidazol-2-yl)phenyl]-2-(2,2,6,6-tetramethylpiperidin-4-yl)-1,2,3,4-tetrahydroisoquinolin-5-amine; N-[4-chloro-3-(5-phenyl-1H-imidazol-2-yl)phenyl]-2-cyclohexyl-1,2,3,4-tetrahydroisoquinolin-5-amine; N-[4-chloro-3-(5-phenyl-1H-imidazol-2-yl)phenyl]-2-(cyclohexylmethyl)-1,2,3,4-tetrahydroisoquinolin-5-amine; 1-(5-{[4-chloro-3-(5-phenyl-1H-imidazol-2-yl)phenyl]amino}-1,2,3,4-tetrahydroisoquinolin-2-yl)-2-hydroxyethan-1-one; 5-{[4-chloro-3-(5-phenyl-1H-imidazol-2-yl)phenyl]amino}-N-methyl-1,2,3,4-tetrahydroisoquinoline-2-sulfonamide; 5-{[4-chloro-3-(5-phenyl-1H-imidazol-2-yl)phenyl]amino}-2-oxido-2-(1-oxo-thian-4-yl)-1,2,3,4-tetrahydroisoquinolin-2-ium; (2S)-1-(5-{[4-chloro-3-(4-phenyl-1H-imidazol-2-yl)phenyl]amino}-1,2,3,4-tetrahydroisoquinolin-2-yl)-2,3-dihydroxypropan-1-one; N-[4-chloro-3-(5-phenyl-1H-imidazol-2-yl)phenyl]-2-{[(4S)-2,2-dimethyl-1,3-dioxolan-4-yl]methyl}-1,2,3,4-tetrahydroisoquinolin-5-amine; N-[4-chloro-3-(5-phenyl-1H-imidazol-2-yl)phenyl]-2-(oxan-4-yl)-1,2,3,4-tetrahydroisoquinolin-5-amine; N-[4- chloro-3-(5-phenyl-1H-imidazol-2-yl)phenyl]-2-cycloheptyl-1,2,3,4-tetrahydroisoquinolin-5-amine; N-[4-chloro-3-(5-phenyl-1H-imidazol-2-yl)phenyl]-2-(pentan-3-yl)-1,2,3,4-tetrahydroisoquinolin-5-amine; 5-{[4-chloro-3-(5-phenyl-1H-imidazol-2-yl)phenyl]amino}-2-(1-ethylpiperidin-4-yl)-1,2,3,4-tetrahydroisoquinolin-1-one; 4-(5-{[4-chloro-3-(5-phenyl-1H-imidazol-2-yl)phenyl]amino}-1,2,3,4-tetrahydroisoquinolin-2-yl)cyclohexan-1-one; 2-(5-{[4-chloro-3-(5-phenyl-1H-imidazol-2-yl)phenyl]amino}-1,2,3,4-tetrahydroisoquinolin-2-yl)propane-1,3-diol; 5-{[4-chloro-3-(5-phenyl-1H-imidazol-2-yl)phenyl]amino}-2-[(2S)-2,3-dihydroxypropyl]-1,2,3,4-tetrahydroisoquinolin-1-one; N-[4-chloro-3-(5-phenyl-1H-imidazol-2-yl)phenyl]-2-[1-(propan-2-yl)piperidin-4-yl]-1,2,3,4-tetrahydroisoquinolin-5-amine; 4-(5-{[4-chloro-3-(5-phenyl-1H-imidazol-2-yl)phenyl]amino}-1,2,3,4-tetrahydroisoquinolin-2-yl)cyclohexan-1-ol; (2R)-1-(5-{[4-chloro-3-(4-phenyl-1H-imidazol-2-yl)phenyl]amino}-1,2,3,4-tetrahydroisoquinolin-2-yl)-2,3-dihydroxypropan-1-one; N-[4-chloro-3-(5-phenyl-1H-imidazol-2-yl)phenyl]-2-(oxan-4-ylmethyl)-1,2,3,4-tetrahydroisoquinolin-5-amine; 3-(5-{[4-chloro-3-(5-phenyl-1H-imidazol-2-yl)phenyl]amino}-1,2,3,4-tetrahydroisoquinolin-2-yl)propane-1,2-diol; N-[4-chloro-3-(5-phenyl-1H-imidazol-2-yl)phenyl]-2-(1-methylpiperidin-4-yl)-1,2,3,4-tetrahydroisoquinolin-5-amine; 5-{[4-chloro-3-(5-phenyl-1H-imidazol-2-yl)phenyl]amino}-N-(2-hydroxyethyl)-1,2,3,4-tetrahydroisoquinoline-2-carboxamide; 5-{[4-chloro-3-(5-phenyl-1H-imidazol-2-yl)phenyl]amino}-1,2,3,4-tetrahydroisoquinoline-2-carboxamide; 3-(5-{[4-chloro-3-(4-phenyl-1H-imidazol-2-yl)phenyl]amino}-1,2,3,4-tetrahydroisoquinolin-2-yl)-3-oxopropanoic acid; tert-butyl 5-{[4-chloro-3-(5-phenyl-1H-imidazol-2-yl)phenyl]amino}-1,2,3,4-tetrahydroisoquinoline-2-carboxylate; N-[4-chloro-3-(5-phenyl-1H-imidazol-2-yl)phenyl]-2-(propan-2-yl)-1,2,3,4-tetrahydroisoquinolin-5-amine; N-[4-chloro-3-(5-phenyl-1H-imidazol-2-yl)phenyl]-2-(3-methanesulfinylpropyl)-1,2,3,4-tetrahydroisoquinolin-5-amine; (2S,3S)-4-(5-{[4-chloro-3-(5-phenyl-1H-imidazol-2-yl)phenyl]amino}-1,2,3,4-tetrahydroisoquinolin-2-yl)butane-1,2,3-triol; 4-(5-{[4-chloro-3-(5-phenyl-1H-imidazol-2-yl)phenyl]amino}-1,2,3,4-tetrahydroisoquinolin-2-yl)-1-oxidopyridin-1-ium; 3-(5-{[4-chloro-3-(4-phenyl-1H-imidazol-2-yl)phenyl]amino}-1-oxo-1,2,3,4-tetrahydroisoquinolin-2-yl)propanoic acid; N-[4-chloro-3-(5-phenyl-1H-imidazol-2-yl)phenyl]-2-(pyridin-3-ylmethyl)-1,2,3,4-tetrahydroisoquinolin-5-amine; 4-[5-({4-methyl-3-[5-(pyridin-3-yl)-1H-imidazol-2-yl]phenyl}amino)-1,2,3,4-tetrahydroisoquinolin-2-yl]-thiane-1,1-dione; 2-(5-{[4-chloro-3-(4-phenyl-1H-imidazol-2-yl)phenyl]amino}-1,2,3,4-tetrahydroisoquinolin-2-yl)acetic acid; N-[4-chloro-3-(5-phenyl-1H-imidazol-2-yl)phenyl]-2-{2-[(dimethylamino)methyl]-2-methylpropyl}-1,2,3,4-tetrahydroisoquinolin-5-amine; 1-(5-{[4-chloro-3-(5-phenyl-1H-imidazol-2-yl)phenyl]amino}-1,2,3,4-tetrahydroisoquinolin-2-yl)-2-methylpropan-1-one; 1-(5-{[4-chloro-3-(5-phenyl-1H-imidazol-2-yl)phenyl]amino}-1,2,3,4-tetrahydroisoquinolin-2-yl)ethan-1-one; N-[4-chloro-3-(5-phenyl-1H-imidazol-2-yl)phenyl]-1,2,3,4-tetrahydroisoquinolin-5-amine; 2-(5-{[4-chloro-3-(5-phenyl-1H-imidazol-2-yl)phenyl]amino}-1,2,3,4-tetrahydroisoquinolin-2-yl)propanoic acid; 2-methanesulfonyl-N-{4-methyl-3-[5-(pyrimidin-5-yl)-1H-imidazol-2-yl]phenyl}-1,2,3,4-tetrahydroisoquinolin-5-amine; 2-methanesulfonyl-N-{4-methyl-3-[5-(pyridin-3-yl)-1H-imidazol-2-yl]phenyl}-1,2,3,4-tetrahydroisoquinolin-5-amine; N-[3-(5-fluoro-1H-1,3-benzodiazol-2-yl)-4-methylphenyl]-2-methanesulfonyl-1,2,3,4-tetrahydroisoquinolin-5-amine; N-[4-chloro-3-(5-phenyl-1H-imidazol-2-yl)phenyl]-2-(2,2,2-trifluoroethyl)-1,2,3,4-tetrahydroisoquinolin-5-amine; 2-methanesulfonyl-N-[4-methyl-3-(7H-purin-8-yl)phenyl]-1,2,3,4-tetrahydroisoquinolin-5-amine; 3-(5-{[4-chloro-3-(4-phenyl-1H-imidazol-2-yl)phenyl]amino}-1,2,3,4-tetrahydroisoquinolin-2-yl)-2,2-difluoropropanoic acid; 2-(5-{[4-chloro-3-(4-phenyl-1H-imidazol-2-yl)phenyl]amino}-1,2,3,4-tetrahydroisoquinolin-2-yl)-2-methylpropanoic acid; 2-[(5-{[4-chloro-3-(5-phenyl-1H-imidazol-2-yl)phenyl]amino}-1,2,3,4-tetrahydroisoquinolin-2-yl)carbonyl]-2-ethylbutanoic acid; 3-(5-{[4-chloro-3-(5-phenyl-1H-imidazol-2-yl)phenyl]amino}-1,2,3,4-tetrahydroisoquinolin-2-yl)-2,2-dimethyl-3-oxopropanoic acid; 1-[(5-{[4-chloro-3-(5-phenyl-1H-imidazol-2-yl)phenyl]amino}-1,2,3,4-tetrahydroisoquinolin-2-yl)carbonyl]cyclopropane-1-carboxylic acid; 1-[(5-{[4-chloro-3-(5-phenyl-1H-imidazol-2-yl)phenyl]amino}-1,2,3,4-tetrahydroisoquinolin-2-yl)carbonyl]cyclobutane-1-carboxylic acid; 1-(5-{[3-(1H-1,3-benzodiazol-2-yl)-4-methylphenyl]amino}-1,2,3,4-tetrahydroisoquinolin-2-yl)-3-hydroxy-2-(hydroxymethyl)-2-methylpropan-1-one; 3-(5-{[4-chloro-3-(4-phenyl-1H-imidazol-2-yl)phenyl]amino}-1,2,3,4-tetrahydroisoquinolin-2-yl)-2,2-difluoropropan-1-ol; 1-(5-{[4-chloro-3-(5-phenyl-1H-imidazol-2-yl)phenyl]amino}-1,2,3,4-tetrahydroisoquinolin-2-yl)-2-hydroxyethan-1-one; N-[4-chloro-3-(5-phenyl-1H-imidazol-2-yl)phenyl]-2-[(1-methylcyclopropyl)carbonyl]-1,2,3,4-tetrahydroisoquinolin-5-amine; 1-[(5-{[4-chloro-3-(5-phenyl-1H-imidazol-2-yl)phenyl]amino}-1,2,3,4-tetrahydroisoquinolin-2-yl)carbonyl]cyclopropan-1-ol; 4-[5-({4-methyl-3-[5-(pyridin-3-yl)-1H-imidazol-2-yl]phenyl}amino)-1,2,3,4-tetrahydroisoquinolin-2-yl]-thiane-1,1-dione; 3-hydroxy-2-(hydroxymethyl)-2-methyl-1-[5-({4-methyl-3-[5-(pyridin-3-yl)-1H-imidazol-2-yl]phenyl}amino)-1,2,3,4-tetrahydroisoquinolin-2-yl]propan-1-one; 2-(5-{[4-chloro-3-(4-phenyl-1H-imidazol-2-yl)phenyl]amino}-1-oxo-1,2,3,4-tetrahydroisoquinolin-2-yl)propanoic acid; (2R)-2-(5-{[4-chloro-3-(4-phenyl-1H-imidazol-2-yl)phenyl]amino}-1,2,3,4-tetrahydroisoquinolin-2-yl)propanoic acid; (2S)-2-(5-{[4-chloro-3-(4-phenyl-1H-imidazol-2-yl)phenyl]amino}-1,2,3,4-tetrahydroisoquinolin-2-yl)propanoic acid; N-[4-chloro-3-(5-phenyl-1H-imidazol-2-yl)phenyl]-2-(1-methylcyclopropyl)-1,2,3,4-tetrahydroisoquinolin-5-amine; 5-{[3-(1H-1,3-benzodiazol-2-yl)-4-methylphenyl]amino}-2-[(2S)-2,3-dihydroxypropyl]-1,2,3,4-tetrahydroisoquinolin-1-one; N-[4-chloro-3-(5-phenyl-1H-imidazol-2-yl)phenyl]-2-cyclopropyl-1,2,3,4-tetrahydroisoquinolin-5-amine; 2-(5-{[4-chloro-3-(5-phenyl-1H-imidazol-2-yl)phenyl]amino}-1,2,3,4-tetrahydroisoquinolin-2-yl)-2-oxoacetic acid; [1-(5-{[4-chloro-3-(5-phenyl-1H-imidazol-2-yl)phenyl]amino}-1,2,3,4-tetrahydroisoquinolin-2-yl)cyclopropyl]methanol; 3-(5-{[3-(1H-1,3-benzodiazol-2-yl)-4-methylphenyl]amino}-1,2,3,4-tetrahydroisoquinolin-2-yl)-2,2-difluoropropan-1-ol; N-[4-chloro-3-(5-phenyl-1H-imidazol-2-yl)phenyl]-2-(2H-1,2,3,4-tetrazol-5-ylmethyl)-1,2,3,4-tetrahydroisoquinolin-5-amine; N-[4-chloro-3-(5-phenyl-1H-imidazol-2-yl)phenyl]-2-(2H-1,2,3,4-tetrazol-5-yl)-1,2,3,4-tetrahydroisoquinolin-5-amine; 5-{[4-chloro-3-(5-phenyl-1H-imidazol-2-yl)phenyl]amino}-2-[1-(hydroxymethyl)cyclopropyl]-1,2,3,4-tetrahydroisoquinolin-1-one; [1-(5-{[3-(1H-1,3-benzodiazol-2-yl)-4-methylphenyl]amino}-1,2,3,4-tetrahydroisoquinolin-2-yl)cyclopropyl]methanol; 4-{3-[(2-methanesulfonyl-1,2,3,4-tetrahydroisoquinolin-5-yl)amino]-2-methylphenyl}benzonitrile; 2-methanesulfonyl- N-{4-methyl-3-[5-(6-methylpyridin-3-yl)-1H-imidazol-2-yl]phenyl}-1,2,3,4-tetrahydroisoquinolin-5-amine; [1-(5-{[4-chloro-3-(5-phenyl-1H-imidazol-2-yl)phenyl]amino}-1,2,3,4-tetrahydroisoquinolin-2-yl)cyclopropyl]methanol; (2S)-3-(5-{[4-chloro-3-(5-phenyl-1H-imidazol-2-yl)phenyl]amino}-1,2,3,4-tetrahydroisoquinolin-2-yl)propane-1,2-diol; 2-methanesulfonyl-N-{4-methyl-3-[5-(methylamino)pyrimido[5,4-d][1,3]thiazol-2-yl]phenyl}-1,2,3,4-tetrahydroisoquinolin-5-amine; N-[4-chloro-3-(5-phenyl-1H-imidazol-2-yl)phenyl]-2-[(1-methylcyclopropyl)methyl]-1,2,3,4-tetrahydroisoquinolin-5-amine; N-[4-chloro-3-(4-phenyl-1,3-oxazol-2-yl)phenyl]-2-methanesulfonyl-1,2,3,4-tetrahydroisoquinolin-5-amine; N-[3-(1H-1,3-benzodiazol-2-yl)-4-methylphenyl]-2-[(1-methylcyclopropyl)methyl]-1,2,3,4-tetrahydroisoquinolin-5-amine; 2-methanesulfonyl-N-[3-(6-methoxypyridin-3-yl)-4-methylphenyl]-1,2,3,4-tetrahydroisoquinolin-5-amine; 2-methanesulfonyl-N-[3-(4-methoxyphenyl)-4-methylphenyl]-1,2,3,4-tetrahydroisoquinolin-5-amine; 2-methanesulfonyl-N-{3-[5-(6-methoxypyridin-3-yl)-1H-imidazol-2-yl]-4-methylphenyl}-1,2,3,4-tetrahydroisoquinolin-5-amine; 4-(2-{5-[(2-methanesulfonyl-1,2,3,4-tetrahydroisoquinolin-5-yl)amino]-2-methylphenyl}-1H-imidazol-5-yl)benzonitrile; 4-{5-[(2-methanesulfonyl-1,2,3,4-tetrahydroisoquinolin-5-yl)amino]-2-methylphenyl}benzonitrile; N-{3-[6-(dimethylamino)-1H-imidazo[4,5-c]pyridin-2-yl]-4-methylphenyl}-2-methanesulfonyl-1,2,3,4-tetrahydroisoquinolin-5-amine; 2-methanesulfonyl-N-{3-[5-(6-methoxypyridin-2-yl)-1H-imidazol-2-yl]-4-methylphenyl}-1,2,3,4-tetrahydroisoquinolin-5-amine; N-[3-(1,3-benzoxazol-2-yl)-4-methylphenyl]-2-methanesulfonyl-1,2,3,4-tetrahydroisoquinolin-5-amine; N-[3-(5-{4-[(dimethylamino)methyl]phenyl}-1H-imidazol-2-yl)-4-methylphenyl]-2-methanesulfonyl-1,2,3,4-tetrahydroisoquinolin-5-amine; N-(3-{5-[2-(dimethylamino)pyrimidin-5-yl]-1H-imidazol-2-yl}-4-methylphenyl)-2-methanesulfonyl-1,2,3,4-tetrahydroisoquinolin-5-amine; N-(3-{4-[(dimethylamino)methyl]phenyl}-4-methylphenyl)-2-methanesulfonyl-1,2,3,4-tetrahydroisoquinolin-5-amine; 2-methanesulfonyl-N-[4-methyl-3-(4-phenylphenyl)phenyl]-1,2,3,4-tetrahydroisoquinolin-5-amine; 2-methanesulfonyl-N-(3-{6-methoxy-1H-imidazo[4,5-c]pyridin-2-yl}-4-methylphenyl)-1,2,3,4-tetrahydroisoquinolin-5-amine; N-[5-(1H-1,3-benzodiazol-2-yl)-6-methylpyridin-3-yl]-2-methanesulfonyl-1,2,3,4-tetrahydroisoquinolin-5-amine; 4-(5-{[2-(2,2-difluoro-3-hydroxypropyl)-1,2,3,4-tetrahydroisoquinolin-5-yl]amino}-2-methylphenyl)benzonitrile; N-[3-(4-tert-butylphenyl)-4-methylphenyl]-2-methanesulfonyl-1,2,3,4-tetrahydroisoquinolin-5-amine; 1-(4-{5-[(2-methanesulfonyl-1,2,3,4-tetrahydroisoquinolin-5-yl)amino]-2-methylphenyl}phenyl)ethan-1-one; 2-methanesulfonyl-N-(4-methyl-3-phenylphenyl)-1,2,3,4-tetrahydroisoquinolin-5-amine; 3-{5-[(2-methanesulfonyl-1,2,3,4-tetrahydroisoquinolin-5-yl)amino]-2-methylphenyl}-1,7-dimethyl-1,2-dihydro-1,6-naphthyridin-2-one; 2-methanesulfonyl-N-{4-methyl-3-[4-(propan-2-yl)phenyl]phenyl}-1,2,3,4-tetrahydroisoquinolin-5-amine; 2-methanesulfonyl-N-{4-methyl-3-[4-(1H-pyrazol-1-ylmethyl)phenyl]phenyl}-1,2,3,4-tetrahydroisoquinolin-5-amine; 3-{5-[(2-methanesulfonyl-1,2,3,4-tetrahydroisoquinolin-5-yl)amino]-2-methylphenyl}benzonitrile; 2-methanesulfonyl-N-{4-methyl-3-[4-(2-methyl-1,3-thiazol-4-yl)phenyl]phenyl}-1,2,3,4-tetrahydroisoquinolin-5-amine; N-{3-[4-(furan-2-yl)phenyl]-4-methylphenyl}-2-methanesulfonyl-1,2,3,4-tetrahydroisoquinolin-5-amine; N-[3-(4-fluorophenyl)-4-methylphenyl]-2-methanesulfonyl-1,2,3,4-tetrahydroisoquinolin-5-amine; 2-methanesulfonyl-N-(4-methyl-3-phenoxyphenyl)-1,2,3,4-tetrahydroisoquinolin-5-amine; N-{3-[2-(dimethylamino)pyrimidin-5-yl]-4-methylphenyl}-2-methanesulfonyl-1,2,3,4-tetrahydroisoquinolin-5-amine; 4-{5-[(6-methanesulfonyl-5,6,7,8-tetrahydro-2,6-naphthyridin-1-yl)amino]-2-methylphenyl}benzonitrile; N-[4-(1H-1,3-benzodiazol-2-yl)-5-chloropyridin-2-yl]-2-methanesulfonyl-1,2,3,4-tetrahydroisoquinolin-5-amine; 5-{[3-(1H-1,3-benzodiazol-2-yl)-4-methylphenyl]amino}-2-[(1-methylcyclopropyl)methyl]-1,2,3,4-tetrahydroisoquinolin-1-one; 2-methanesulfonyl-N-[4-methyl-3-(1-methyl-1H-pyrazol-4-yl)phenyl]-1,2,3,4-tetrahydroisoquinolin-5-amine; 5-{5-[(2-methanesulfonyl-1,2,3,4-tetrahydroisoquinolin-5-yl)amino]-2-methylphenyl}pyridine-2-carbonitrile; N-[3-(benzyloxy)-4-methylphenyl]-2-methanesulfonyl-1,2,3,4-tetrahydroisoquinolin-5-amine; 4-{2-fluoro-5-[(2-methanesulfonyl-1,2,3,4-tetrahydroisoquinolin-5-yl)amino]phenyl}benzonitrile; 4-{3-[(2-methanesulfonyl-1,2,3,4-tetrahydroisoquinolin-5-yl)amino]phenyl}benzonitrile; N-[4-chloro-3-(5-phenyl-1H-imidazol-2-yl)phenyl]-6-methanesulfonyl-5,6,7,8-tetrahydro-2,6-naphthyridin-1-amine; 4-{2-chloro-5-[(2-methanesulfonyl-1,2,3,4-tetrahydroisoquinolin-5-yl)amino]phenyl}benzonitrile; 3-{5-[(2-methanesulfonyl-1,2,3,4-tetrahydroisoquinolin-5-yl)amino]-2-methylphenyl}-N-methylbenzamide; 2-methanesulfonyl-N-{4-methyl-3-[4-(trifluoromethyl)phenyl]phenyl}-1,2,3,4-tetrahydroisoquinolin-5-amine; 2-methanesulfonyl-N-{4-methyl-3-[4-(trifluoromethoxy)phenyl]phenyl}-1,2,3,4-tetrahydroisoquinolin-5-amine; 4-{5-[(2-methanesulfonyl-1,2,3,4-tetrahydroisoquinolin-5-yl)amino]-2-methylphenyl}-N,N-dimethylbenzamide; 2-(4-{5-[(2-methanesulfonyl-1,2,3,4-tetrahydroisoquinolin-5-yl)amino]-2-methylphenyl}phenyl)acetonitrile; 2-methanesulfonyl-N-{4-methyl-3-[3-(pyrrolidin-1-ylcarbonyl)phenyl]phenyl}-1,2,3,4-tetrahydroisoquinolin-5-amine; methyl 4-{5-[(2-methanesulfonyl-1,2,3,4-tetrahydroisoquinolin-5-yl)amino]-2-methylphenyl}benzoate; 4-{5-[(2-methanesulfonyl-1,2,3,4-tetrahydroisoquinolin-5-yl)amino]-2-methylphenyl}benzamide; 2-methanesulfonyl-N-{4-methyl-3-[4-(1H-1,2,3,4-tetrazol-5-yl)phenyl]phenyl}-1,2,3,4-tetrahydroisoquinolin-5-amine; 4-{5-[(2-methanesulfonyl-1,2,3,4-tetrahydroisoquinolin-5-yl)amino]-2-methylphenyl}benzoic acid; N-(2-hydroxyethyl)-4-{5-[(2-methanesulfonyl-1,2,3,4-tetrahydroisoquinolin-5-yl)amino]-2-methylphenyl}benzamide; N-(2,3-dihydroxypropyl)-4-{5-[(2-methanesulfonyl-1,2,3,4-tetrahydroisoquinolin-5-yl)amino]-2-methylphenyl}benzamide; N,N-bis(2-hydroxyethyl)-4-{5-[(2-methanesulfonyl-1,2,3,4-tetrahydroisoquinolin-5-yl)amino]-2-methylphenyl}benzamide; N-(2-hydroxypropyl)-4-{5-[(2-methanesulfonyl-1,2,3,4-tetrahydroisoquinolin-5-yl)amino]-2-methylphenyl}benzamide; 4-{5-[(2-methanesulfonyl-1,2,3,4-tetrahydroisoquinolin-5-yl)amino]-2-methoxyphenyl}benzonitrile; 4-{5-[(2-methanesulfonyl-1,2,3,4-tetrahydroisoquinolin-5-yl)amino]-2-(trifluoromethoxy)phenyl}benzonitrile; N-[3-(1H-indol-2-yl)-4-methylphenyl]-2-methanesulfonyl-1,2,3,4-tetrahydroisoquinolin-5-amine; 2-methanesulfonyl-N-[4-methyl-3-(1-methyl-1H-indol-2-yl)phenyl]-1,2,3,4-tetrahydroisoquinolin-5-amine; 2-methanesulfonyl-N-{4-methyl-3-[5-(trifluoromethyl)pyridin-2-yl]phenyl}-1,2,3,4-tetrahydroisoquinolin-5-amine; 6-{5-[(2-methanesulfonyl-1,2,3,4-tetrahydroisoquinolin-5-yl)amino]-2-methylphenyl}pyridine-3-carbonitrile; 2-(4-cyanophenyl)-4-[(2-methanesulfonyl-1,2,3,4-tetrahydroisoquinolin-5-yl)amino]benzonitrile; (4-{5-[(2-methanesulfonyl-1,2,3,4- tetrahydroisoquinolin-5-yl)amino]-2-methylphenyl}phenyl)methanol; 3-{[(4-{5-[(2-methanesulfonyl-1,2,3,4-tetrahydroisoquinolin-5-yl)amino]-2-methylphenyl}phenyl)methyl]amino}propane-1,2-diol; 2-{[(4-{5-[(2-methanesulfonyl-1,2,3,4-tetrahydroisoquinolin-5-yl)amino]-2-methylphenyl}phenyl)methyl]amino}ethan-1-ol; 5-[(2-methanesulfonyl-1,2,3,4-tetrahydroisoquinolin-5-yl)amino]-2-methyl-N-phenylbenzamide; N-(4-cyanophenyl)-5-[(2-methanesulfonyl-1,2,3,4-tetrahydroisoquinolin-5-yl)amino]-2-methylbenzamide; 5-[(2-methanesulfonyl-1,2,3,4-tetrahydroisoquinolin-5-yl)amino]-N-(4-methoxyphenyl)-2-methylbenzamide; 5-[(2-methanesulfonyl-1,2,3,4-tetrahydroisoquinolin-5-yl)amino]-2-methyl-N-(pyridin-2-yl)benzamide; 4-{5-[(2-methanesulfonyl-1,2,3,4-tetrahydroisoquinolin-5-yl)amino]-2-methylphenyl}-3-methylbenzonitrile; N-[3-(5-fluoropyridin-2-yl)-4-methylphenyl]-2-methanesulfonyl-1,2,3,4-tetrahydroisoquinolin-5-amine; 2-methanesulfonyl-N-[3-(6-methoxypyridin-2-yl)-4-methylphenyl]-1,2,3,4-tetrahydroisoquinolin-5-amine; 4-{5-[(2-methanesulfonyl-1,2,3,4-tetrahydroisoquinolin-5-yl)amino]-2-methylphenoxymethyl}benzonitrile; 2-methane sulfonyl-N-{4-methyl-3-[5-(trifluoromethyl)pyridin-2-yl]phenyl}-1,2,3,4-tetrahydroisoquinolin-5-amine; N-[4-chloro-3-(5-phenyl-1H-imidazol-2-yl)phenyl]-4-(1,1-dioxothiomorpholin-4-yl)piperidine-1-carboxamide; 4-{3-[(2-methanesulfonyl-1,2,3,4-tetrahydroisoquinolin-5-yl)amino]phenyl}-3-methylbenzonitrile; 2-methanesulfonyl-N-[4-methyl-3-(5-methylpyridin-2-yl)phenyl]-1,2,3,4-tetrahydroisoquinolin-5-amine; 2-methanesulfonyl-N-[4-methyl-3-(6-methylpyridazin-3-yl)phenyl]-1,2,3,4-tetrahydroisoquinolin-5-amine; 4-{5-chloro-2-[(2-methanesulfonyl-1,2,3,4-tetrahydroisoquinolin-5-yl)amino]pyridin-4-yl}benzonitrile; 2-(4-cyanophenyl)-4-[(2-methanesulfonyl-1,2,3,4-tetrahydroisoquinolin-5-yl)amino]benzoic acid; N-[3-(5-chloropyridin-2-yl)-4-methylphenyl]-2-methanesulfonyl-1,2,3,4-tetrahydroisoquinolin-5-amine; 2-methanesulfonyl-N-[3-(5-methoxypyridin-2-yl)-4-methylphenyl]-1,2,3,4-tetrahydroisoquinolin-5-amine; 4-{2-chloro-5-[(2-methanesulfonyl-1,2,3,4-tetrahydroisoquinolin-5-yl)amino]pyridin-3-yl}benzonitrile; 2-methanesulfonyl-N-[3-(5-methoxypyrimidin-2-yl)-4-methylphenyl]-1,2,3,4-tetrahydroisoquinolin-5-amine; 6-{5-[(2-methanesulfonyl-1,2,3,4-tetrahydroisoquinolin-5-yl)amino]-2-methylphenyl}pyridine-3-carbonitrile; 4-[2-(hydroxymethyl)-5-[(2-methanesulfonyl-1,2,3,4-tetrahydroisoquinolin-5-yl)amino]phenyl]benzonitrile; 4-{2-[(dimethylamino)methyl]-5-[(2-methanesulfonyl-1,2,3,4-tetrahydroisoquinolin-5-yl)amino]phenyl}benzonitrile; 2-(4-cyanophenyl)-4-[(2-methanesulfonyl-1,2,3,4-tetrahydroisoquinolin-5-yl)amino]-N-methylbenzamide; 1-(5-{[3-(5-fluoropyridin-2-yl)-4-methylphenyl]amino}-1,2,3,4-tetrahydroisoquinolin-2-yl)-2-methylpropan-2-ol; 2-(2-fluoro-2-methylpropyl)-N-[3-(5-fluoropyridin-2-yl)-4-methylphenyl]-1,2,3,4-tetrahydroisoquinolin-5-amine; 2-methanesulfonyl-N-[3-(6-methoxypyridazin-3-yl)-4-methylphenyl]-1,2,3,4-tetrahydroisoquinolin-5-amine; 5-[(2-methanesulfonyl-1,2,3,4-tetrahydroisoquinolin-5-yl)amino]-2-methyl-N-[4-(trifluoromethyl)phenyl]benzamide; N-(4-fluorophenyl)-5-[(2-methanesulfonyl-1,2,3,4-tetrahydroisoquinolin-5-yl)amino]-2-methylbenzamide; 5-[(2-methanesulfonyl-1,2,3,4-tetrahydroisoquinolin-5-yl)amino]-2-methyl-N-(4-methylphenyl)benzamide; 5-[(2-methanesulfonyl-1,2,3,4-tetrahydroisoquinolin-5-yl)amino]-2-methyl-N-[4-(trifluoromethoxy)phenyl]benzamide; 5-[(2-methanesulfonyl-1,2,3,4-tetrahydroisoquinolin-5-yl)amino]-2-methyl-N-phenylbenzamide; 2-methanesulfonyl-N-[4-methyl-3-(pyridin-2-yl)phenyl]-1,2,3,4-tetrahydroisoquinolin-5-amine; 2-methanesulfonyl-N-[3-(5-methoxypyrazin-2-yl)-4-methylphenyl]-1,2,3,4-tetrahydroisoquinolin-5-amine; 2-methanesulfonyl-N-[4-methyl-3-(6-methylpyridin-2-yl)phenyl]-1,2,3,4-tetrahydroisoquinolin-5-amine; 2-methanesulfonyl-N-[4-methyl-3-(4-methylpyridin-2-yl)phenyl]-1,2,3,4-tetrahydroisoquinolin-5-amine; 5-[(2-methanesulfonyl-1,2,3,4-tetrahydroisoquinolin-5-yl)amino]-N,2-dimethyl-N-phenylbenzamide; N-(2-hydroxyethyl)-5-[(2-methanesulfonyl-1,2,3,4-tetrahydroisoquinolin-5-yl)amino]-2-methyl-N-phenylbenzamide; (2S)-3-(5-{[3-(5-fluoropyridin-2-yl)-4-methylphenyl]amino}-1,2,3,4-tetrahydroisoquinolin-2-yl)propane-1,2-diol; 6-(2-methyl-5-{[2-(3,3,3-trifluoropropyl)-1,2,3,4-tetrahydroisoquinolin-5-yl]amino}-phenyl)pyridine-3-carbonitrile; N-{3-[(dimethylamino)methyl]-5-(5-fluoropyridin-2-yl)-4-methylphenyl}-2-methanesulfonyl-1,2,3,4-tetrahydroisoquinolin-5-amine; 6-(5-{[2-(2-fluoro-2-methylpropyl)-1,2,3,4-tetrahydroisoquinolin-5-yl]amino}-2-methylphenyl)pyridine-3-carbonitrile; 6-(5-{[2-(2-hydroxy-2-methylpropyl)-1,2,3,4-tetrahydroisoquinolin-5-yl]amino}-2-methylphenyl)pyridine-3-carbonitrile; 2-(2-fluoro-2-methylpropyl)-N-[4-methyl-3-(5-methylpyridin-2-yl)phenyl]-1,2,3,4-tetrahydroisoquinolin-5-amine; 2-methyl-1-(5-{[4-methyl-3-(5-methylpyridin-2-yl)phenyl]amino}-1,2,3,4-tetrahydroisoquinolin-2-yl)propan-2-ol; N-[5-(5-fluoropyridin-2-yl)-6-methylpyridin-3-yl]-2-methanesulfonyl-1,2,3,4-tetrahydroisoquinolin-5-amine; 5-chloro-2-[(2-methanesulfonyl-1,2,3,4-tetrahydroisoquinolin-5-yl)amino]-N-phenylpyridine-4-carboxamide; 2-methanesulfonyl-N-[3-(5-methoxypyridin-2-yl)-4-methylphenyl]-1,2,3,4-tetrahydroisoquinolin-5-amine; 4-{2-chloro-5-[(2-methanesulfonyl-1,2,3,4-tetrahydroisoquinolin-5-yl)amino]pyridin-3-yl}benzonitrile; N-[3-(5-chloropyridin-2-yl)-4-methylphenyl]-2-methanesulfonyl-1,2,3,4-tetrahydroisoquinolin-5-amine; 6-{5-[(2-methanesulfonyl-1,2,3,4-tetrahydroisoquinolin-5-yl)amino]-2-methylphenyl}pyridazine-3-carbonitrile; 5-{5-[(2-methanesulfonyl-1,2,3,4-tetrahydroisoquinolin-5-yl)amino]-2-methylphenyl}pyrazine-2-carbonitrile; (2S)-3-(5-{[4-methyl-3-(6-methylpyridazin-3-yl)phenyl]amino}-1,2,3,4-tetrahydroisoquinolin-2-yl)propane-1,2-diol; (2S)-3-(5-{[4-methyl-3-(5-methylpyridin-2-yl)phenyl]amino}-1,2,3,4-tetrahydroisoquinolin-2-yl)propane-1,2-diol; 6-(5-{[2-(2,2-difluoro-3-hydroxypropyl)-1,2,3,4-tetrahydroisoquinolin-5-yl]amino}-2-methylphenyl)pyridine-3-carbonitrile; 2,2-difluoro-3-(5-{[4-methyl-3-(5-methylpyridin-2-yl)phenyl]amino}-1,2,3,4-tetrahydroisoquinolin-2-yl)propan-1-ol; 2-(2,2-dimethylpropyl)-N-[4-methyl-3-(5-methylpyridin-2-yl)phenyl]-1,2,3,4-tetrahydroisoquinolin-5-amine; 2-methanesulfonyl-N-[4-methyl-3-(pyridin-2-yloxy)phenyl]-1,2,3,4-tetrahydroisoquinolin-5-amine; 2-methanesulfonyl-N-[4-methyl-3-(pyridin-2-ylmethoxy)phenyl]-1,2,3,4-tetrahydroisoquinolin-5-amine; 2-methanesulfonyl-N-[4-methyl-3-(5-methylpyrimidin-2-yl)phenyl]-1,2,3,4-tetrahydroisoquinolin-5-amine; N-[3-(4-fluoropyridin-2-yl)-4-methylphenyl]-2-methanesulfonyl-1,2,3,4-tetrahydroisoquinolin-5-amine; N-[3-(6-fluoropyridin-2-yl)-4-methylphenyl]-2-methanesulfonyl-1,2,3,4-tetrahydroisoquinolin-5-amine; 2-methanesulfonyl-N-[4-methyl-3-(4-methylpyrimidin-2-yl)phenyl]-1,2,3,4-tetrahydroisoquinolin-5-amine; N-[3-(5-fluoropyrimidin-2-yl)-4-methylphenyl]-2-methanesulfonyl-1,2,3,4-tetrahydroisoquinolin-5-amine; 5-{[2-(2-fluoro-2-methylpropyl)-1,2,3,4-tetrahydroisoquinolin-5-yl]amino}-2-methyl-N-phenylbenzamide; 5-{[2-(2-hydroxy-2- methylpropyl)-1,2,3,4-tetrahydroisoquinolin-5-yl]amino}-2-methyl-N-phenylbenzamide; 2-(2-methanesulfonylethyl)-N-[4-methyl-3-(5-methylpyridin-2-yl)phenyl]-1,2,3,4-tetrahydroisoquinolin-5-amine; 2-(2,2-difluoropropyl)-N-[4-methyl-3-(5-methylpyridin-2-yl)phenyl]-1,2,3,4-tetrahydroisoquinolin-5-amine; 5-[(2-methanesulfonyl-1,2,3,4-tetrahydroisoquinolin-5-yl)amino]-2-methyl-N-phenylpyridine-3-carboxamide; 3-chloro-6-[(2-methanesulfonyl-1,2,3,4-tetrahydroisoquinolin-5-yl)amino]-N-phenylpyridine-2-carboxamide; N-[3-(3-fluoropyridin-2-yl)-4-methylphenyl]-2-methanesulfonyl-1,2,3,4-tetrahydroisoquinolin-5-amine; N-[3-(3-fluoro-5-methylpyridin-2-yl)-4-methylphenyl]-2-methanesulfonyl-1,2,3,4-tetrahydroisoquinolin-5-amine; N-[3-(isoquinolin-3-yl)-4-methylphenyl]-2-methanesulfonyl-1,2,3,4-tetrahydroisoquinolin-5-amine; 2-methanesulfonyl-N-[3-(4-methoxypyridin-2-yl)-4-methylphenyl]-1,2,3,4-tetrahydroisoquinolin-5-amine; 2-methanesulfonyl-N-[4-methyl-3-(quinolin-2-yl)phenyl]-1,2,3,4-tetrahydroisoquinolin-5-amine; N-[3-(5-fluoropyridin-2-yl)-4-methylphenyl]-2-(2-methanesulfonylethyl)-1,2,3,4-tetrahydroisoquinolin-5-amine; N,N-dimethyl-2-(5-{[4-methyl-3-(5-methylpyridin-2-yl)phenyl]amino}-1,2,3,4-tetrahydroisoquinolin-2-yl)acetamide; 4-(5-{[3-(5-fluoropyridin-2-yl)-4-methylphenyl]amino}-1,2,3,4-tetrahydroisoquinolin-2-yl)-thiane-1,1-dione; 4-(5-{[4-methyl-3-(5-methylpyridin-2-yl)phenyl]amino}-1,2,3,4-tetrahydroisoquinolin-2-yl)-thiane-1,1-dione; 6-methanesulfonyl-N-[4-methyl-3-(5-methylpyridin-2-yl)phenyl]-5,6,7,8-tetrahydro-2,6-naphthyridin-1-amine; 2-methanesulfonyl-N-{4-methyl-3-[(pyridin-2-yloxy)methyl]phenyl}-1,2,3,4-tetrahydroisoquinolin-5-amine; 5-[(2-methanesulfonyl-1,2,3,4-tetrahydroisoquinolin-5-yl)amino]-2-methyl-N-[4-(trifluoromethyl)phenyl]benzamide; 2-methanesulfonyl-N-[3-(4-methoxypyrimidin-2-yl)-4-methylphenyl]-1,2,3,4-tetrahydroisoquinolin-5-amine; 2-methanesulfonyl-N-[3-(5-methoxypyrazin-2-yl)-4-methylphenyl]-1,2,3,4-tetrahydroisoquinolin-5-amine; N-[3-(4,5-dimethylpyridin-2-yl)-4-methylphenyl]-2-methanesulfonyl-1,2,3,4-tetrahydroisoquinolin-5-amine; 2-methanesulfonyl-N-[3-(6-methoxypyridazin-3-yl)-4-methylphenyl]-1,2,3,4-tetrahydroisoquinolin-5-amine; 3-chloro-6-[(2-methanesulfonyl-1,2,3,4-tetrahydroisoquinolin-5-yl)amino]-N-phenylpyridine-2-carboxamide; N-[3-(5-fluoropyridin-2-yl)-4-methylphenyl]-6-methanesulfonyl-5,6,7,8-tetrahydro-2,6-naphthyridin-1-amine; 6-(5-{[2-(2-methanesulfonylethyl)-1,2,3,4-tetrahydroisoquinolin-5-yl]amino}-2-methylphenyl)pyridine-3-carbonitrile; 5-{[2-(2-methanesulfonylethyl)-1,2,3,4-tetrahydroisoquinolin-5-yl]amino}-2-methyl-N-phenylbenzamide; 5-[(6-methanesulfonyl-5,6,7,8-tetrahydro-2,6-naphthyridin-1-yl)amino]-2-methyl-N-phenylbenzamide; 7-methanesulfonyl-N-[4-methyl-3-(5-methylpyridin-2-yl)phenyl]-5H,6H,7H,8H-pyrido[3,4-d]pyrimidin-4-amine; 3-(5-{[4-methyl-3-(5-methylpyridin-2-yl)phenyl]amino}-1,2,3,4-tetrahydroisoquinolin-2-yl)-thiolane-1,1-dione; 3-(5-{[3-(5-fluoropyridin-2-yl)-4-methylphenyl]amino}-1,2,3,4-tetrahydroisoquinolin-2-yl)-thiolane-1,1-dione; N-[4-methyl-3-(5-methylpyridin-2-yl)phenyl]-2-(3,3,3-trifluoropropyl)-1,2,3,4-tetrahydroisoquinolin-5-amine; N-[3-(5-fluoropyridin-2-yl)-4-methylphenyl]-2-(3,3,3-trifluoropropyl)-1,2,3,4-tetrahydroisoquinolin-5-amine; N-{3-[5-(dimethylamino)pyrazin-2-yl]-4-methylphenyl}-2-methanesulfonyl-1,2,3,4-tetrahydroisoquinolin-5-amine; N-[3-(5-fluoropyrimidin-2-yl)-4-methylphenyl]-2-methanesulfonyl-1,2,3,4-tetrahydroisoquinolin-5-amine; N-{3-[6-(dimethylamino)pyridazin-3-yl]-4-methylphenyl}-2-methanesulfonyl-1,2,3,4-tetrahydroisoquinolin-5-amine; 2-methanesulfonyl-N-[3-(6-methoxypyrazin-2-yl)-4-methylphenyl]-1,2,3,4-tetrahydroisoquinolin-5-amine; 3-(5-{[3-(6-methoxypyridazin-3-yl)-4-methylphenyl]amino}-1,2,3,4-tetrahydroisoquinolin-2-yl)-thiolane-1,1-dione; N-[3-(5-chloropyridin-2-yl)-4-methylphenyl]-2-(2-methanesulfonylethyl)-1,2,3,4-tetrahydroisoquinolin-5-amine; 2-(2-methanesulfonylethyl)-N-[3-(6-methoxypyridazin-3-yl)-4-methylphenyl]-1,2,3,4-tetrahydroisoquinolin-5-amine; 2-(2-methanesulfonylethyl)-N-{4-methyl-3-[5-(trifluoromethyl)pyridin-2-yl]phenyl}-1,2,3,4-tetrahydroisoquinolin-5-amine; N-[3-(3-fluoropyridin-2-yl)-4-methylphenyl]-2-(2-methanesulfonylethyl)-1,2,3,4-tetrahydroisoquinolin-5-amine; 2-[2-(ethanesulfonyl)ethyl]-N-[4-methyl-3-(5-methylpyridin-2-yl)phenyl]-1,2,3,4-tetrahydroisoquinolin-5-amine; 2-(2-methanesulfonylethyl)-N-[4-methyl-3-(pyridin-2-yl)phenyl]-1,2,3,4-tetrahydroisoquinolin-5-amine; 2-(2-methanesulfonylethyl)-N-[4-methyl-3-(5-methylpyrimidin-2-yl)phenyl]-1,2,3,4-tetrahydroisoquinolin-5-amine; 2-(2-methanesulfonylethyl)-N-[3-(5-methoxypyrazin-2-yl)-4-methylphenyl]-1,2,3,4-tetrahydroisoquinolin-5-amine; 3-(5-{[4-methyl-3-(pyridin-2-yl)phenyl]amino}-1,2,3,4-tetrahydroisoquinolin-2-yl)-thiolane-1,1-dione; 3-(5-{[3-(5-methoxypyrazin-2-yl)-4-methylphenyl]amino}-1,2,3,4-tetrahydroisoquinolin-2-yl)-thiolane-1,1-dione; 3-(5-{[4-methyl-3-(5-methylpyrimidin-2-yl)phenyl]amino}-1,2,3,4-tetrahydroisoquinolin-2-yl)-thiolane-1,1-dione; 3-(5-{[3-(3-fluoropyridin-2-yl)-4-methylphenyl]amino}-1,2,3,4-tetrahydroisoquinolin-2-yl)-thiolane-1,1-dione; 4-(5-{[3-(3-fluoropyridin-2-yl)-4-methylphenyl]amino}-1,2,3,4-tetrahydroisoquinolin-2-yl)-thiane-1,1-dione; 2-methanesulfonyl-N-[3-(5-methoxypyridazin-3-yl)-4-methylphenyl]-1,2,3,4-tetrahydroisoquinolin-5-amine; N-[3-(6-ethoxypyridazin-3-yl)-4-methylphenyl]-2-methanesulfonyl-1,2,3,4-tetrahydroisoquinolin-5-amine; N-[3-(3,5-difluoropyridin-2-yl)-4-methylphenyl]-2-methanesulfonyl-1,2,3,4-tetrahydroisoquinolin-5-amine; N-[5-chloro-6-(5-methylpyridin-2-yl)pyridin-2-yl]-2-methanesulfonyl-1,2,3,4-tetrahydroisoquinolin-5-amine; 2-methanesulfonyl-N-[5-methyl-6-(5-methylpyridin-2-yl)pyridin-2-yl]-1,2,3,4-tetrahydroisoquinolin-5-amine; 3-(5-{[3-(3-fluoropyridin-2-yl)-4-methylphenyl]amino}-1,2,3,4-tetrahydroisoquinolin-2-yl)-thietane-1,1-dione; 3-(5-{[3-(6-methoxypyridazin-3-yl)-4-methylphenyl]amino}-1,2,3,4-tetrahydroisoquinolin-2-yl)-thietane-1,1-dione; 4-(4-{[4-methyl-3-(5-methylpyridin-2-yl)phenyl]amino}-5H,6H,7H,8H-pyrido[3,4-d]pyrimidin-7-yl)-thiane-1,1-dione; N-[5-chloro-6-(5-methylpyridin-2-yl)pyridin-2-yl]-2-(2-methanesulfonylethyl)-1,2,3,4-tetrahydroisoquinolin-5-amine; (3R)-3-(5-{[4-methyl-3-(5-methylpyridin-2-yl)phenyl]amino}-1,2,3,4-tetrahydroisoquinolin-2-yl)-thiolane-1,1-dione; (3S)-3-(5-{[4-methyl-3-(5-methylpyridin-2-yl)phenyl]amino}-1,2,3,4-tetrahydroisoquinolin-2-yl)-thiolane-1,1-dione; 2-[2-(ethanesulfonyl)ethyl]-N-[3-(5-fluoropyridin-2-yl)-4-methylphenyl]-1,2,3,4-tetrahydroisoquinolin-5-amine; 2-[2-(ethanesulfonyl)ethyl]-N-[3-(6-methoxypyridazin-3-yl)-4-methylphenyl]-1,2,3,4-tetrahydroisoquinolin-5-amine; 2-[2-(ethanesulfonyl)ethyl]-N-[3-(3-fluoropyridin-2-yl)-4-methylphenyl]-1,2,3,4-tetrahydroisoquinolin-5-amine; 2-(2-methanesulfonylethyl)-N-{4-methyl-3-[5-(trifluoromethyl)pyridin-2-yl]phenyl}-1,2,3,4-tetrahydroisoquinolin-5-amine; 3-(5-{[5-methyl-6-(5-methylpyridin-2-yl)pyridin-2-yl]amino}-1,2,3,4-tetrahydroisoquinolin-2-yl)-thietane-1,1-dione; (3S)-3-(5-{[3-(3-fluoropyridin-2-yl)-4- methylphenyl]amino}-1,2,3,4-tetrahydroisoquinolin-2-yl)-thiolane-1,1-dione; (3R)-3-(5-{[3-(3-fluoropyridin-2-yl)-4-methylphenyl]amino}-1,2,3,4-tetrahydroisoquinolin-2-yl)-thiolane-1,1-dione; 3-(4-{[4-methyl-3-(5-methylpyridin-2-yl)phenyl]amino}-5H,6H,7H, 8H-pyrido[3,4-d]pyrimidin-7-yl)-thietane-1,1-dione; 2-{[2-(dimethylamino)ethane]sulfonyl}-N-[3-(3-fluoropyridin-2-yl)-4-methylphenyl]-1,2,3,4-tetrahydroisoquinolin-5-amine; N-[3-(5-chloro-3-fluoropyridin-2-yl)-4-methylphenyl]-2-methanesulfonyl-1,2,3,4-tetrahydroisoquinolin-5-amine; N-{3-[5-(dimethylamino)pyridin-2-yl]-4-methylphenyl}-2-methanesulfonyl-1,2,3,4-tetrahydroisoquinolin-5-amine; N-[4-methyl-3-(5-methylpyridin-2-yl)phenyl]-7-(propane-2-sulfonyl)-5H,6H,7H,8H-pyrido[3,4-d]pyrimidin-4-amine; 7-(ethanesulfonyl)-N-[4-methyl-3-(5-methylpyridin-2-yl)phenyl]-5H,6H,7H, 8H-pyrido[3,4-d]pyrimidin-4-amine; N-[3-(6-ethoxypyridazin-3-yl)-4-methylphenyl]-2-(2-methanesulfonylethyl)-1,2,3,4-tetrahydroisoquinolin-5-amine; 3-(5-{[3-(6-ethoxypyridazin-3-yl)-4-methylphenyl]amino}-1,2,3,4-tetrahydroisoquinolin-2-yl)-thietane-1,1-dione; 3-(5-{[3-(6-ethoxypyridazin-3-yl)-4-methylphenyl]amino}-1,2,3,4-tetrahydroisoquinolin-2-yl)-thiolane-1,1-dione; 2-[2-(ethanesulfonyl)ethyl]-N-[3-(6-ethoxypyridazin-3-yl)-4-methylphenyl]-1,2,3,4-tetrahydroisoquinolin-5-amine; N-[3-(5-fluoropyridin-2-yl)-4-methylphenyl]-7-methanesulfonyl-5H,6H,7H, 8H-pyrido[3,4-d]pyrimidin-4-amine; 7-(ethanesulfonyl)-N-[3-(5-fluoropyridin-2-yl)-4-methylphenyl]-5H,6H,7H,8H-pyrido[3,4-d]pyrimidin-4-amine; N-[3-(5-fluoropyridin-2-yl)-4-methylphenyl]-7-(propane-2-sulfonyl)-5H,6H,7H,8H-pyrido[3,4-d]pyrimidin-4-amine; 5-({7-methanesulfonyl-5H,6H,7H,8H-pyrido[3,4-d]pyrimidin-4-yl}amino)-2-methyl-N-phenylbenzamide; N-[5-chloro-6-(5-fluoropyridin-2-yl)pyridin-2-yl]-2-(2-methanesulfonylethyl)-1,2,3,4-tetrahydroisoquinolin-5-amine; N-[5-chloro-6-(5-fluoropyridin-2-yl)pyridin-2-yl]-2-methanesulfonyl-1,2,3,4-tetrahydroisoquinolin-5-amine; 3-(4-{[3-(isoquinolin-3-yl)-4-methylphenyl]amino}-5H,6H,7H, 8H-pyrido[3,4-d]pyrimidin-7-yl)-thietane-1,1-dione; N-[3-(isoquinolin-3-yl)-4-methylphenyl]-7-(2-methanesulfonylethyl)-5H,6H,7H,8H-pyrido[3,4-d]pyrimidin-4-amine; N-[3-(isoquinolin-3-yl)-4-methylphenyl]-2-methanesulfonyl-1,2,3,4-tetrahydroisoquinolin-5-amine; 4-(5-{[3-(6-methoxypyridazin-3-yl)-4-methylphenyl]amino}-1,2,3,4-tetrahydroisoquinolin-2-yl)-thiane-1,1-dione; N-[3-(isoquinolin-3-yl)-4-methylphenyl]-7-methanesulfonyl-5H,6H,7H,8H-pyrido[3,4-d]pyrimidin-4-amine; 3-(5-{[3-(5-ethoxypyrazin-2-yl)-4-methylphenyl]amino}-1,2,3,4-tetrahydroisoquinolin-2-yl)-thiolane-1,1-dione; 2-(2-methanesulfonylethyl)-N-[5-methyl-6-(5-methylpyridin-2-yl)pyridin-2-yl]-1,2,3,4-tetrahydroisoquinolin-5-amine; N-[3-(5-ethoxypyrazin-2-yl)-4-methylphenyl]-2-(2-methanesulfonylethyl)-1,2,3,4-tetrahydroisoquinolin-5-amine; 2-(2-methanesulfonylethyl)-N-[5-methyl-6-(pyridin-2-yl)pyridin-2-yl]-1,2,3,4-tetrahydroisoquinolin-5-amine; 2-methanesulfonyl-N-[5-methyl-6-(pyridin-2-yl)pyridin-2-yl]-1,2,3,4-tetrahydroisoquinolin-5-amine; 3-(5-{[3-(5-ethoxypyrazin-2-yl)-4-methylphenyl]amino}-1,2,3,4-tetrahydroisoquinolin-2-yl)-thietane-1,1-dione; N-[3-(5-ethoxypyrazin-2-yl)-4-methylphenyl]-2-methanesulfonyl-1,2,3,4-tetrahydroisoquinolin-5-amine; N-[3-(isoquinolin-3-yl)-4-methylphenyl]-2-(2-methanesulfonylethyl)-1,2,3,4-tetrahydroisoquinolin-5-amine; 3-(5-{[3-(isoquinolin-3-yl)-4-methylphenyl]amino}-1,2,3,4-tetrahydroisoquinolin-2-yl)-thietane-1,1-dione; 3-(5-{[5-chloro-6-(5-methylpyridin-2-yl)pyridin-2-yl]amino}-1,2,3,4-tetrahydroisoquinolin-2-yl)-thietane-1,1-dione; 2-(ethanesulfonyl)-N-[6-(6-methoxypyridazin-3-yl)-5-methylpyridin-2-yl]-1,2,3,4-tetrahydroisoquinolin-5-amine; N-[6-(6-methoxypyridazin-3-yl)-5-methylpyridin-2-yl]-2-(propane-2-sulfonyl)-1,2,3,4-tetrahydroisoquinolin-5-amine; 3-(5-{[3-(6-methoxypyridazin-3-yl)-4-methylphenyl]amino}-1,2,3,4-tetrahydroisoquinolin-2-yl)-thietane-1,1-dione; (3R)-3-(5-{[3-(6-methoxypyridazin-3-yl)-4-methylphenyl]amino}-1,2,3,4-tetrahydroisoquinolin-2-yl)-thiolane-1,1-dione; (3S)-3-(5-{[3-(6-methoxypyridazin-3-yl)-4-methylphenyl]amino}-1,2,3,4-tetrahydroisoquinolin-2-yl)-thiolane-1,1-dione; 3-(5-{[3-(6-ethoxypyridazin-3-yl)-4-methylphenyl]amino}-1,2,3,4-tetrahydroisoquinolin-2-yl)-thiolane-1,1-dione; 3-(5-{[3-(isoquinolin-3-yl)-4-methylphenyl]amino}-1,2,3,4-tetrahydroisoquinolin-2-yl)-thiolane-1,1-dione; 3-(5-{[3-(3,5-difluoropyridin-2-yl)-4-methylphenyl]amino}-1,2,3,4-tetrahydroisoquinolin-2-yl)-thietane-1,1-dione; 3-(5-{[3-(3,5-difluoropyridin-2-yl)-4-methylphenyl]amino}-1,2,3,4-tetrahydroisoquinolin-2-yl)-thiolane-1,1-dione; 4-(5-{[3-(6-ethoxypyridazin-3-yl)-4-methylphenyl]amino}-1,2,3,4-tetrahydroisoquinolin-2-yl)-thiane-1,1-dione; N-[6-(6-ethoxypyridazin-3-yl)-5-methylpyridin-2-yl]-2-(propane-2-sulfonyl)-1,2,3,4-tetrahydroisoquinolin-5-amine; 3-(5-{[6-(6-ethoxypyridazin-3-yl)-5-methylpyridin-2-yl]amino}-1,2,3,4-tetrahydroisoquinolin-2-yl)-thietane-1,1-dione; 2-(ethanesulfonyl)-N-[6-(5-ethoxypyrazin-2-yl)-5-methylpyridin-2-yl]-1,2,3,4-tetrahydroisoquinolin-5-amine; N-[3-(isoquinolin-3-yl)-4-methylphenyl]-6-methanesulfonyl-5,6,7,8-tetrahydro-2,6-naphthyridin-1-amine; 3-(5-{[3-(isoquinolin-3-yl)-4-methylphenyl]amino}-1,2,3,4-tetrahydro-2,6-naphthyridin-2-yl)-thietane-1,1-dione; N-[6-(5-ethoxypyrazin-2-yl)-5-methylpyridin-2-yl]-2-methanesulfonyl-1,2,3,4-tetrahydroisoquinolin-5-amine; 3-(5-{[6-(6-ethoxypyridazin-3-yl)-5-methylpyridin-2-yl]amino}-1,2,3,4-tetrahydroisoquinolin-2-yl)-thiolane-1,1-dione; 4-(5-{[3-(5-ethoxypyrazin-2-yl)-4-methylphenyl]amino}-1,2,3,4-tetrahydroisoquinolin-2-yl)-thiane-1,1-dione; N-[6-(5-ethoxypyrazin-2-yl)-5-methylpyridin-2-yl]-2-(propane-2-sulfonyl)-1,2,3,4-tetrahydroisoquinolin-5-amine; 3-(5-{[3-(isoquinolin-3-yl)-4-methylphenyl]amino}-1,2,3,4-tetrahydro-2,6-naphthyridin-2-yl)-thietane-1,1-dione; 3-(5-{[3-(3,5-difluoropyridin-2-yl)-4-methylphenyl]amino}-1,2,3,4-tetrahydroisoquinolin-2-yl)-thiolane-1,1-dione; (3R)-3-(5-{[3-(6-ethoxypyridazin-3-yl)-4-methylphenyl]amino}-1,2,3,4-tetrahydroisoquinolin-2-yl)-thiolane-1,1-dione; (3S)-3-(5-{[3-(6-ethoxypyridazin-3-yl)-4-methylphenyl]amino}-1,2,3,4-tetrahydroisoquinolin-2-yl)-thiolane-1,1-dione; (3R)-3-(5-{[3-(3-fluoropyridin-2-yl)-4-methylphenyl]amino}-1,2,3,4-tetrahydroisoquinolin-2-yl)-thiolane-1,1-dione; 4-(4-{[3-(isoquinolin-3-yl)-4-methylphenyl]amino}-5H,6H,7H, 8H-pyrido[3,4-d]pyrimidin-7-yl)-thiane-1,1-dione; 4-(5-{[3-(isoquinolin-3-yl)-4-methylphenyl]amino}-1,2,3,4-tetrahydro-2,6-naphthyridin-2-yl)-thiane-1,1-dione; (3S)-3-(5-{[3-(3-fluoropyridin-2-yl)-4-methylphenyl]amino}-1,2,3,4-tetrahydroisoquinolin-2-yl)-thiolane-1,1-dione; N-(4-chloro-3-(4-phenyl-1H-imidazol-2-yl)phenyl)-2-(1-ethylpiperidin-4-yl)-1,2,3,4-tetrahydroisoquinolin-7-amine; N-(3-(5-fluoropyrimidin-2-yl)-4-methylphenyl)-2-(methylsulfonyl)-1,2,3,4-tetrahydroisoquinolin-5-amine, and N-(3-(isoquinolin-3-yl)-4-methylphenyl)-2-(methylsulfonyl)-1,2,3,4-tetrahydroisoquinolin-5-amine.

Another aspect provided herein are processes for preparing compounds of Formula (I) and the N-oxide derivatives, solvates, hydrates, prodrug derivatives, protected derivatives, individual isomers and mixture of isomers thereof, and the pharmaceutically acceptable salts thereof.

Another aspect provided herein are pharmaceutical compositions which contain one or more compounds of Formula (I) or a N-oxide derivative, individual isomers and mixture of isomers thereof; or a pharmaceutically acceptable salt thereof, in admixture with one or more pharmaceutically acceptable excipients.

Another aspect provided herein are pharmaceutical compositions for treating a disease associated with the hedgehog pathway comprising a therapeutically effective amount of a compound of Formula (I) of claim 1 and one or more pharmaceutically acceptable excipients. In certain embodiments of such pharmaceutical compositions, the disease or disorder is a cell-proliferative disease, a dermatological disease or an autoimmune disease. In certain embodiments of such methods, the disease or disorder is cancer, dermatitis, actinic keratosis, basal cell carcinoma, psoriasis, lymphoma, myeloma, breast cancer, medulloblastoma, squamous cell carcinoma, carcinosarcoma, adenocystic carcinoma, epidermoid carcinoma, nasopharyngeal carcinoma, renal cell carcinoma, papilloma, or an epidermoidoma.

Another aspect provided herein are medicaments for treating a disease associated with the hedgehog pathway comprising a therapeutically effective amount of a compound of Formula (I) of claim 1 and one or more pharmaceutically acceptable excipients. In certain embodiments of such pharmaceutical compositions, the disease or disorder is a cell-proliferative disease, a dermatological disease or an autoimmune disease. In certain embodiments of such methods, the disease or disorder is cancer, dermatitis, actinic keratosis, basal cell carcinoma, psoriasis, lymphoma, myeloma, breast cancer, medulloblastoma, squamous cell carcinoma, carcinosarcoma, adenocystic carcinoma, epidermoid carcinoma, nasopharyngeal carcinoma, renal cell carcinoma, papilloma, or an epidermoidoma.

Another aspect provided herein is the use of a compound of Formula (I) in the manufacture of a medicament for treating a disease or disorder in a patient, wherein hedgehog pathway activity is implicated in such disease or disorder. In certain embodiments of such uses, the disease or disorder is a cell-proliferative disease, a dermatological disease or an autoimmune disease. In certain embodiments of such methods, the disease or disorder is cancer, dermatitis, actinic keratosis, basal cell carcinoma, psoriasis, lymphoma, myeloma, breast cancer, medulloblastoma, squamous cell carcinoma, carcinosarcoma, adenocystic carcinoma, epidermoid carcinoma, nasopharyngeal carcinoma, renal cell carcinoma, papilloma, or an epidermoidoma.

Certain embodiments provided herein include the use of a compound of Formula (I) in the manufacture of a medicament for treating psoriasis, lymphoma or myeloma in an animal in which hedgehog pathway activity, contributes to the pathology and/or symptomology of the disease.

Another aspect provided herein are methods for modulating hedgehog pathway activity, wherein such methods include administering to a system or a subject in need thereof, a therapeutically effective amount of a compound of Formula (I) or a pharmaceutical compositions containing one or more compounds of Formula (I). In certain embodiments such modulation is inhibition of hedgehog pathway activity and the compounds of Formula (I) are antagonists of hedgehog pathway activity.

Another aspect provided herein are methods of inhibiting the hedgehog pathway in a cell, comprising contacting the cell with a compound of Formula (I), or pharmaceutically acceptable salts, hydrates, N-oxides, solvates and isomers thereof. In certain embodiments of such methods, the cell has a phenotype of Ptc loss-of-function, hedgehog gain-of-function, smoothened gain-of-function, Gli gain-of-function, or over expression of hedgehog ligands. In certain embodiments of such methods, the cell is contacted with the hedgehog antagonist in-vivo or in-vitro. In certain embodiments of such methods, the compound is administered to an animal as part of a therapeutic application. In certain embodiments of such methods, the therapeutic application is selected from non-melanoma skin cancer, myeloma, lymphoma and psoriasis. In certain embodiments of such methods, the therapeutic application is selected from basal cell nevus syndrome, basal cell carcinoma and bone overgrowth disorders. In certain embodiments of such methods, the bone overgrowth disorders are selected from acromegaly, macrocephaly, Sotos syndrome, progressive diaphyseal dysplasia, craniodiaphyseal dysplasia, endosteal hyperostosis disorders including Van Buchem disease (types I and II) and sclerosteosis. In certain embodiments of such methods, the endosteal hyperostosis disorders are selected from Van Buchem disease types I and II. In certain embodiments of such methods, the therapeutic application is the treatment of unwanted hair growth selected from hairy moles and cosmetic prevention of hair regrowth after epilation.

Another aspect provided herein are methods of inhibiting unwanted proliferation of a cell, comprising contacting the cell with a compound of Formula (I) of claim 1. In certain embodiments of such methods, the compound is administered to an animal as part of a therapeutic application. In certain embodiments of such methods, the therapeutic application is selected from non-melanoma skin cancer, myeloma, lymphoma and psoriasis.

In another aspect provided herein are methods for inducing apoptosis of lymphoma or myeloma cells. Such methods involve contacting the cells with an effective amount of a compound of Formula (I), or pharmaceutical compositions containing one or more compounds of Formula (I), that inhibits hedgehog signaling pathway. In certain embodiments, the methods are directed to inducing apoptosis of tumor cells that are present in a subject. In other embodiments the methods are directed to inducing apoptosis of lymphoma or myeloma cells that do not express Gli3.

Another aspect provided herein are methods of treating or ameliorating a disease or disorder in a patient, wherein hedgehog pathway activity is implicated in such disease or disorder and modulation of the hedgehog pathway activity can prevent, inhibit or ameliorate the pathology and/or symptomology of such diseases or disorders. Such methods includes administering to the subject a therapeutically effective amount of a compound of Formula (I), N-oxide, solvate, hydrate, individual isomers and mixture of isomers thereof, or a pharmaceutically acceptable salt thereof. In certain embodiments of such methods, the disease or disorder is a cell-proliferative disease, a dermatological disease or an autoimmune disease. In certain embodiments of such methods, the disease or disorder is cancer, dermatitis, actinic keratosis, basal cell carcinoma, psoriasis, lymphoma, myeloma, breast cancer, medulloblastoma, squamous cell carcinoma, carcinosarcoma, adenocystic carcinoma, epidermoid carcinoma, nasopharyngeal carcinoma, renal cell carcinoma, papilloma, or an epidermoidoma. In certain embodiments are methods of treating or ameliorating psoriasis, lymphoma or myeloma in a subject in which modulation of the hedgehog pathway activity, can prevent, inhibit or ameliorate the pathology and/or symptomology of psoriasis, lymphoma or myeloma, Such methods includes administering to the subject a therapeutically effective amount of a compound of Formula (I), N-oxide, solvate, hydrate, individual isomers and mixture of isomers thereof, or a pharmaceutically acceptable salt thereof.

Another aspect provided herein are compounds for use in a method of medical treatment, wherein the method of medical treatment is for treating a disease or disorder where the hedgehog pathway is implicated, wherein the disease or disorder is selected from basal cell nevus syndrome, basal cell carcinoma, bone overgrowth disorders, non-melanoma skin cancer, myeloma, lymphoma and psoriasis, and wherein the compound is a compound of Formula (I) provided herein.

DETAILED DESCRIPTION OF THE INVENTION

Definitions

Unless defined otherwise, all technical and scientific terms used herein have the same meaning as commonly understood by those of ordinary skill in the art to which this invention pertains. The following references provide one of skill with a general definition of many of the terms used in this invention: *Oxford Dictionary of Biochemistry and Molecular Biology*, Smith et al. (eds.), Oxford University Press (revised ed., 2000); *Dictionary of Microbiology and Molecular Biology*, Singleton et al. (Eds.), John Wiley & Sons (3$^{rd}$ ed., 2002); and *A Dictionary of Biology* (*Oxford Paperback Reference*), Martin and Hine (Eds.), Oxford University Press (4$^{th}$ ed., 2000). In addition, the following definitions are provided to assist the reader in the practice of the invention.

The term "alkyl," as used herein, refers to a saturated branched or straight chain hydrocarbon. In certain embodiments an alkyl group is optionally substituted. As used herein, the terms "$C_1$-$C_3$alkyl", "$C_1$-$C_4$alkyl", "$C_1$-$C_5$alkyl", "$C_1$-$C_6$alkyl", "$C_1$-$C_7$alkyl" and "$C_1$-$C_8$alkyl" refer to an alkyl group containing at least 1, and at most 3, 4, 5, 6, 7 or 8 carbon atoms, respectively. Non-limiting examples of alkyl groups as used herein include methyl, ethyl, n-propyl, isopropyl, n-butyl, isobutyl, sec-butyl, t-butyl, n-pentyl, isopentyl, hexyl, heptyl, octyl, nonyl, decyl and the like.

The term "alkylene," as used herein, refers to a saturated branched or straight chain divalent hydrocarbon radical derived from an alkyl group. In certain embodiments an alkylene group is optionally substituted. As used herein, the terms "$C_1$-$C_3$alkylene", "$C_1$-$C_4$alkylene", "$C_1$-$C_5$alkylene", "$C_1$-$C_6$alkylene", "$C_1$-$C_7$alkylene" and "$C_1$-$C_8$alkylene" refer to an alkylene group containing at least 1, and at most 3, 4, 5, 6, 7 or 8 carbon atoms respectively. Non-limiting examples of alkylene groups as used herein include, methylene, ethylene, n-propylene, isopropylene, n-butylene, isobutylene, sec-butylene, t-butylene, n-pentylene, isopentylene, hexylene and the like.

The term "alkoxy," as used herein, refers to the group —$OR_a$, where $R_a$ is an alkyl group as defined herein. An alkoxy group can be optionally substituted. As used herein, the terms "$C_1$-$C_3$alkoxy", "$C_1$-$C_4$alkoxy", "$C_1$-$C_5$alkoxy", "$C_1$-$C_6$alkoxy", "$C_1$-$C_7$alkoxy" and "$C_1$-$C_8$alkoxy" refer to an alkoxy group wherein the alkyl moiety contains at least 1, and at most 3, 4, 5, 6, 7 or 8, carbon atoms. Non-limiting examples of alkoxy groups, as used herein, include methoxy, ethoxy, n-propoxy, isopropoxy, n-butyloxy, t-butyloxy, pentyloxy, hexyloxy, heptyloxy, octyloxy, nonyloxy, decyloxy and the like.

The term "aryl," as used herein, refers to monocyclic, fused bicyclic, and fused tricyclic ring systems having a total of five to fourteen ring members, wherein at least one ring in the system is aromatic and wherein each ring in the system contains 3 to 7 ring members. In certain embodiments an aryl group is optionally substituted. Non-limiting examples of aryl groups, as used herein, include phenyl, naphthyl, fluorenyl, indenyl, azulenyl, anthracenyl and the like.

The term "arylene," as used means a divalent radical derived from an aryl group. In certain embodiments an arylene group is optionally substituted.

The term "cyano," as used herein, refers to a —CN group.

The term "cyclic sulfinyl," as used herein, refers to a group having the structure

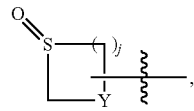

where j is an integer from 0 to 4; Y is N, NR, CR' or —(CR'R')—; R and each R' are independently selected from H, halo, $C_1$-$C_8$alkyl, $C_1$-$C_8$alkoxy, aryl, heteroaryl, cycloalkyl, heterocycloalkyl, halo-substituted $C_1$-$C_8$alkyl, and halo-substituted $C_1$-$C_8$alkoxy. In certain embodiments such cyclic sulfinyl moieties are optionally substituted. As used herein, the terms "$C_2$-$C_3$cyclic sulfinyl", "$C_2$-$C_4$cyclic sulfinyl", "$C_2$-$C_5$cyclic sulfinyl" and "$C_2$-$C_6$cyclic sulfinyl" refer to a cyclic sulfinyl group containing at least 2, and at most 3, 4, 5 or 6 carbon atoms.

The term "cyclic sulfonyl," as used herein, refers to a group having the structure

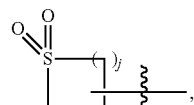

where j is an integer from 0 to 4, Y is N, NR, CR' or —(CR'R')—; R and each R' are independently selected from H, halo, $C_1$-$C_8$alkyl, $C_1$-$C_8$alkoxy, aryl, heteroaryl, cycloalkyl, heterocycloalkyl, halo-substituted $C_1$-$C_8$alkyl, and halo-substituted $C_1$-$C_8$alkoxy. In certain embodiments such cyclic sulfonyl moieties are optionally substituted. As used herein, the terms "$C_2$-$C_3$cyclic sulfonyl", "$C_2$-$C_4$cyclic sulfonyl", "$C_2$-$C_5$cyclic sulfonyl" and "$C_2$-$C_6$cyclic sulfonyl" refer to a cyclic sulfonyl group containing at least 2, and at most 3, 4, 5 or 6 carbon atoms.

The term "cycloalkyl," as used herein, refers to a saturated or partially unsaturated, monocyclic, fused bicyclic, fused tricyclic or bridged polycyclic ring assembly. As used herein, the terms "$C_3$-$C_5$cycloalkyl", "$C_3$-$C_6$cycloalkyl", "$C_3$-$C_7$cycloalkyl", "$C_3$-$C_8$cycloalkyl", "$C_3$-$C_9$cycloalkyl and "$C_3$-$C_{10}$cycloalkyl refer to a cycloalkyl group wherein the saturated or partially unsaturated, monocyclic, fused bicyclic or bridged polycyclic ring assembly contain at least 3, and at most 5, 6, 7, 8, 9 or 10, carbon atoms. In certain embodiments a cycloalkyl group is optionally substituted. Non-limiting examples of cycloalkyl groups, as used herein, include cyclopropyl, cyclobutyl, cyclopentyl, cyclohexyl, cycloheptyl, cyclooctyl, cyclononyl, cyclodecyl, cyclopentenyl, cyclohexenyl, decahydronaphthalenyl, 2,3,4,5,6,7-hexahydro-1H-indenyl and the like.

The term "halogen," as used herein, refers to fluorine (F), chlorine (Cl), bromine (Br), or iodine (I).

The term "halo," as used herein, refers to the halogen radicals: fluoro (—F), chloro (—Cl), bromo (—Br), and iodo (—I).

The terms "haloalkyl" or "halo-substituted alkyl," as used herein, refers to an alkyl group as defined herein, substituted with one or more halogen groups, wherein the halogen groups are the same or different. In certain embodiments a haloalkyl group is optionally substituted. Non-limiting examples of such branched or straight chained haloalkyl groups, as used herein, include methyl, ethyl, propyl, isopropyl, isobutyl and n-butyl substituted with one or more halogen groups, wherein the halogen groups are the same or different, including, but not limited to, trifluoromethyl, pentafluoroethyl, and the like.

The term "haloalkoxy" or "halo-substituted-alkoxy," as used herein, refers to an alkoxy group as defined herein, substituted with one or more halogen groups, wherein the halogen groups are the same or different. In certain embodiments a haloalkoxy group is optionally substituted. Non-limiting examples of such branched or straight chained haloalkynyl groups, as used herein, include methoxy, ethoxy, n-propoxy, isopropoxy, n-butyloxy, t-butyloxy, pentyloxy, hexyloxy, heptyloxy, octyloxy, nonyloxy, decyloxy and the like, substituted with one or more halogen groups, wherein the halogen groups are the same or different.

The term "heteroalkyl," as used herein, refers to an alkyl group as defined herein wherein one or more carbon atoms are independently replaced by one or more of oxygen, sulfur, nitrogen, or combinations thereof.

The term "heteroaryl," as used herein, refers to monocyclic, fused bicyclic, and fused tricyclic ring systems having a total of five to fourteen ring members, wherein at least one ring in the system is aromatic, at least one ring in the system contains one or more heteroatoms selected from nitrogen, oxygen and sulfur, and wherein each ring in the system contains 3 to 7 ring members. A heteroaryl group may contain one or more substituents. In certain embodiments a heteroaryl group is optionally substituted. Non-limiting examples of heteroaryl groups, as used herein, include benzofuranyl, benzofurazanyl, benzoxazolyl, benzopyranyl, benzthiazolyl, benzothienyl, benzazepinyl, benzimidazolyl, benzothiopyranyl, benzo[1,3]dioxole, benzo[b]furyl, benzo[b]thienyl, cinnolinyl, furazanyl, furyl, furopyridinyl, imidazolyl, indolyl, indolizinyl, indolin-2-one, indazolyl, isoindolyl, isoquinolinyl, isoxazolyl, isothiazolyl, 1,8-naphthyridinyl, oxazolyl, oxaindolyl, oxadiazolyl, pyrazolyl, pyrrolyl, phthalazinyl, pteridinyl, purinyl, pyridyl, pyridazinyl, pyrazinyl, pyrimidinyl, quinoxalinyl, quinolinyl, quinazolinyl, 4H-quinolizinyl, thiazolyl, thiadiazolyl, thienyl, triazinyl, triazolyl and tetrazolyl.

The term "heterocycloalkyl," as used herein, refers to a cycloalkyl, as defined herein, wherein one or more of the ring carbons are replaced by a moiety selected from —O—, —N=, —NR—, —C(O)—, —S—, —S(O)— or —S(O)$_2$—, wherein R is hydrogen, $C_1$-$C_4$alkyl or a nitrogen protecting group, with the proviso that the ring of said group does not contain two adjacent O or S atoms. In certain embodiments a heterocycloalkyl group is optionally substituted. Non-limiting examples of heterocycloalkyl groups, as used herein, include morpholino, pyrrolidinyl, pyrrolidinyl-2-one, piperazinyl, piperidinyl, piperidinyl-2-one, piperidinyl-3-one, piperidinyl-4-one, 1,4-dioxa-8-aza-spiro[4.5]dec-8-yl, 2H-pyrrolyl, 2-pyrrolinyl, 3-pyrrolinyl, 1,3-dioxolanyl, 2-imidazolinyl, imidazolidinyl, 2-pyrazolinyl, pyrazolidinyl, 1,4-dioxanyl, 1,4-dithianyl, thiomorpholinyl, azepanyl, hexahydro-1,4-diazepinyl, tetrahydrofuranyl, dihydrofuranyl, tetrahydrothienyl, tetrahydropyranyl, dihydropyranyl, tetrahydrothiopyranyl, thioxanyl, azetidinyl, oxetanyl, thietanyl, oxepanyl, thiepanyl, 1,2,3,6-tetrahydropyridinyl, 2H-pyranyl, 4H-pyranyl, dioxanyl, 1,3-dioxolanyl, dithianyl, dithiolanyl, dihydropyranyl, dihydrothienyl, dihydrofuranyl, imidazolinyl, imidazolidinyl, 3-azabicyclo[3.1.0]hexanyl, and 3-azabicyclo[4.1.0]heptanyl.

The term "heteroatom," as used herein, refers to one or more of oxygen, sulfur, nitrogen, phosphorus, or silicon.

The term "hydroxyl," as used herein, refers to the group —OH.

The term "hydroxyalkyl" or hydroxyl-substituted-alkyl," as used herein, refers to an alkyl group as defined herein substituted with one or more hydroxyl group. Non-limiting examples of branched or straight chained "$C_1$-$C_6$ hydroxyalkyl groups as used herein include methyl, ethyl, propyl, isopropyl, isobutyl and n-butyl groups substituted with one or more hydroxyl groups.

The term "optionally substituted," as used herein, means that the referenced group may or may not be substituted with one or more additional group(s) individually and independently selected from alkyl, alkenyl, alkynyl, cycloalkyl, aryl, heteroaryl, heterocycloalkyl, hydroxyl, alkoxy, mercaptyl, cyano, halo, carbonyl, thiocarbonyl, isocyanato, thiocyanato, isothiocyanato, nitro, perhaloalkyl, perfluoroalkyl, and amino, including mono- and di-substituted amino groups, and the protected derivatives thereof. Non-limiting examples of optional substituents include, halo, —CN, =O, —OR, —C(O)R, —C(O)OR, —OC(O)R, —OC(O)OR, —C(O)NHR, —C(O)NR$_2$, —OC(O)NHR, —OC(O)NR$_2$, —SR—, —S(O)R, —S(O)$_2$R, —NHR, —N(R)$_2$, —NHC(O)R, —NRC(O)R, —NHC(O)OR, —NRC(O)OR, S(O)$_2$NHR, —S(O)$_2$N(R)$_2$, —NHS(O)$_2$, —NRS(O)$_2$, —NHS(O)$_2$R, —NRS(O)$_2$R, $C_1$-$C_8$alkyl, $C_1$-$C_8$alkoxy, aryl, heteroaryl, cycloalkyl, heterocycloalkyl, halo-substituted $C_1$-$C_8$alkyl, halo-substituted $C_1$-$C_8$alkoxy, where each R is independently selected from H, halo, $C_1$-$C_8$alkyl, $C_1$-$C_8$alkoxy, aryl, heteroaryl, cycloalkyl, heterocycloalkyl, halo-substituted $C_1$-$C_8$alkyl, and halo-substituted $C_1$-$C_8$alkoxy. The placement and number of such substituent groups is done in accordance with the well-understood valence limitations of each group, for example =O is a suitable substituent for an alkyl group but not for an aryl group.

The term "solvate," as used herein, refers to a complex of variable stoichiometry formed by a solute (by way of example, a compound of Formula (I), or a salt thereof, as described herein) and a solvent. Non-limiting examples of a solvent are water, acetone, methanol, ethanol and acetic acid.

The term "acceptable" with respect to a formulation, composition or ingredient, as used herein, means having no persistent detrimental effect on the general health of the subject being treated.

The term "administration" or "administering" of the subject compound means providing a compound of Formula (I), a pharmaceutically acceptable salt, a pharmaceutically acceptable solvate, or prodrug thereof to a subject in need of treatment.

The term "agent" or "test agent," as used herein, includes any substance, molecule, element, compound, entity, or a combination thereof. It includes, but is not limited to a protein, a polypeptide, a small organic molecule, a polysaccharide, a polynucleotide, and the like. It can be a natural product, a synthetic compound, or a chemical compound, or a combination of two or more substances. Unless otherwise specified, the terms "agent", "substance", and "compound" can be used interchangeably.

The term "cancer," as used herein refers to an abnormal growth of cells which tend to proliferate in an uncontrolled way and, in some cases, to metastasize (spread). The type of cancer includes, but is not limited to, solid mammalian tumors as well as hematological malignancies. "Solid mammalian tumors" include cancers of the head and neck, lung, heart, mesothelioma, mediastinum, esophagus, endometrium, stomach, pancreas or other endocrine organ, thyroid, hepatobiliary system, small intestine, colon, colorectal, rectum, anus, kidney, urethra, bladder, bowel, prostate, urethra, penis, testis, gynecological organs, ovaries, breast, endocrine system, skin (melanoma), central nervous system including brain; sarcomas of the soft tissue and bone; and melanoma of cutaneous and intraocular origin. "Hematological malignancies" includes childhood leukemia and lymphomas, Hodgkin's disease, lymphomas of lymphocytic and cutaneous origin, acute and chronic leukemia, plasma cell neoplasm and cancers associated with AIDS. In addition, a cancer at any stage of progression can be treated, such as primary, metastatic, and recurrent cancers. Information regarding numerous types of cancer can be found, e.g., from the American Cancer Society, or from, e.g., Wilson et al. (1991) Harrison's Principles of Internal Medicine, 12th Edition, McGraw-Hill, Inc. Both human and veterinary uses are contemplated. Cancers which are particularly amenable to treatment by the compounds and methods of the invention include but are not limited to gliomas, medulloblastomas, primitive neuroectodermal tumors (PNETS), basal cell carcinoma (BCC), small cell lung cancers, large cell lung cancers, tumors of the gastrointestinal tract, rhabdomyosarcomas, soft tissue sarcomas, pancreatic tumors, bladder tumors and prostate tumors. As used herein, the term "malignant hyperproliferative disorder(s)" includes but is not limited to cancers, neuronal proliferative disorders, bone marrow proliferative diseases and leukemias. As used herein, the term "non-malignant hyperproliferative disorder(s)" includes but is not limited to non-malignant and non-neoplastic proliferative disorders, such as smooth muscle hyperplasia in blood vessels, cutaneous scarring, and pulmonary fibrosis.

The term "carrier," as used herein, refers to chemical compounds or agents that facilitate the incorporation of a compound described herein into cells or tissues.

The terms "co-administration" or "combined administration" or the like as used herein are meant to encompass administration of the selected therapeutic agents to a single patient, and are intended to include treatment regimens in which the agents are not necessarily administered by the same route of administration or at the same time.

The term "contacting," as used herein, has its normal meaning and refers to combining two or more molecules (by way of example only, a small molecule organic compound and a polypeptide) or combining molecules and cells (by way of example only, a compound and a cell). Contacting can occur in-vitro, by way of example only, combining two or more agents or combining a compound and a cell or a cell lysate in a test tube or other container. Contacting can also occur in a cell or in-situ, by way of example only, contacting two polypeptides in a cell by coexpression in the cell of recombinant polynucleotides encoding the two polypeptides, or in a cell lysate. Contacting can occur in-vivo.

The term "dermatological disorder," as used herein refers to a skin disorder. Such dermatological disorders include, but are not limited to, proliferative or inflammatory disorders of the skin such as, atopic dermatitis, bullous disorders, collagenoses, contact dermatitis eczema, Kawasaki Disease, rosacea, Sjogren-Larsso Syndrome, actinic keratosis, basal cell carcinoma and urticaria.

The term "diluent," as used herein, refers to chemical compounds that are used to dilute a compound described herein prior to delivery. Diluents can also be used to stabilize compounds described herein.

The terms "effective amount" or "therapeutically effective amount," as used herein, refer to a sufficient amount of a compound described herein being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "fibrosis" or "fibrosing disorder," as used herein, refers to conditions that follow acute or chronic inflammation and are associated with the abnormal accumulation of cells and/or collagen and include but are not limited to fibrosis of individual organs or tissues such as the heart, liver, kidney, joints, lung, or skin, and includes such disorders as idiopathic pulmonary fibrosis and cryptogenic fibrosing alveolitis.

The term "iatrogenic," as used herein, means a condition, disorder, or disease created or worsened by medical or surgical therapy.

The term "hedgehog," as used herein, refers to any member of the hedgehog family, including sonic, indian, desert and tiggy winkle. The term may be used to indicate protein or gene. The term is also used to describe homolog/ortholog sequences in different animal species.

The terms "hedgehog (Hh) signaling pathway" and "hedgehog (Hh) signaling," as used herein, are used interchangeably and refer to the chain of events normally mediated by various members of the signaling cascade such as hedgehog, patched (Ptch), smoothened (Smo), and Gli. The hedgehog pathway can be activated even in the absence of a hedgehog protein by activating a downstream component. By way of example only, overexpression of Smo will activate the pathway in the absence of hedgehog. Hh signaling components or members of Hh signaling pathway refer to gene products that participate in the Hh signaling pathway. An Hh signaling component frequently materially or substantially affects the transmission of the Hh signal in cells/tissues, typically resulting in changes in degree of downstream gene expression level and/or phenotypic changes. Hh signaling components, depending on their biological function and effects on the final outcome of the downstream gene activation/expression, may be divided into positive and negative regulators. A positive regulator is an Hh signaling component that positively affects the transmission of the Hh signal, i.e., stimulates downstream biological events when Hh is present. Examples include hedgehog, Smo, and Gli. A negative regulator is an Hh signaling component that negatively affects the transmission of the Hh signal, i.e., inhibits downstream biological events when Hh is present. Examples include (but are not limited to) Ptch and SuFu.

The terms "hedgehog signaling antagonist(s)", "antagonists of Hh signaling" and "inhibitors of Hh signaling pathway," as used herein, are used interchangeably and refer to agents that inhibit the bioactivity of a positive Hh signaling component (such as hedgehog, Ptch, or Gli) or down-regulate the expression of the Hh signaling component. They also include agents which up-regulate a negative regulator of Hh signaling component. A hedgehog signaling antagonists may be directed to a protein encoded by any of the genes in the hedgehog pathway, including (but not limited to) sonic, indian or desert hedgehog, smoothened, ptch-1, ptch-2, gli-1, gli-2, gli-3, etc.

The term "hedgehog gain-of-function," as used herein, refers to an aberrant modification or mutation of a Ptc gene, hedgehog gene, or smoothened gene, or a decrease (or loss) in the level of expression of such a gene, which results in a phenotype which resembles contacting a cell with a hedgehog protein, e.g., aberrant activation of a hedgehog pathway. The gain-of-function may include a loss of the ability of the Ptc gene product to regulate the level of expression of Gli genes, e.g., Gli1, Gli2, and Gli3. The term 'hedgehog gain-of-function' is also used herein to refer to any similar cellular phenotype (e.g., exhibiting excess proliferation) which occurs due to an alteration anywhere in the hedgehog signal transduction pathway, including, but not limited to, a modification or mutation of hedgehog itself. For example, a tumor cell with an abnormally high proliferation rate due to activation of the hedgehog signaling pathway would have a 'hedgehog gain-of-function' phenotype, even if hedgehog is not mutated in that cell.

The terms "Hedgehog-related disorder(s), or "Hedgehog-related disease(s)," as used herein, includes diseases and disorders associated with disruption or aberrance of the Hedgehog pathway, as well as disorders associated with normal but undesired growth states relating to activation of the Hedgehog pathway. "Hedgehog-related disorder(s)" include but are not limited to tumor formation, cancer, neoplasia, malignant hyperproliferative disorders, and non-malignant hyperproliferative disorders. "Hedgehog-related disorder(s)" also include benign prostate hyperplasia, psoriasis, wet macular degeneration, osteopetrosis and unwanted hair growth.

The term "patched loss-of-function," as used herein, refers to an aberrant modification or mutation of a Ptc gene, or a decreased level of expression of the gene, which results in a phenotype which resembles contacting a cell with a hedgehog protein, e.g., aberrant activation of a hedgehog pathway. The loss-of-function may include a loss of the ability of the Ptc gene product to regulate the level of expression of Gli genes, e.g., Gli1, Gli2 and Gli3.

The term "Gli gain-of-function," as used herein, refers to an aberrant modification or mutation of a Gli gene, or an increased level of expression of the gene, which results in a phenotype which resembles contacting a cell with a hedgehog protein, e.g., aberrant activation of a hedgehog pathway.

The terms "inhibiting" or "inhibition," as used herein in the context of tumor growth or tumor cell growth, refers to delayed appearance of primary or secondary tumors, slowed development of primary or secondary tumors, decreased occurrence of primary or secondary tumors, slowed or decreased severity of secondary effects of disease, or arrested tumor growth and regression of tumors. In the context of modulation of enzymatic activities, inhibition relates to reversible suppression or reduction of an enzymatic activity including competitive, uncompetitive, and noncompetitive inhibition. This can be experimentally distinguished by the effects of the inhibitor on the reaction kinetics of the enzyme, which may be analyzed in terms of the basic Michaelis-Menten rate equation. Competitive inhibition occurs when the inhibitor can combine with the free enzyme in such a way that it competes with the normal substrate for binding at the active site. A competitive inhibitor reacts reversibly with the enzyme to form an enzyme-inhibitor complex [EI], analogous to the enzyme-substrate complex.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist or an antagonist.

The term "pharmaceutically acceptable," as used herein, refers a material, such as a carrier or diluent, which does not abrogate the biological activity or properties of the compounds described herein. Such materials are administered to an individual without causing undesirable biological effects or interacting in a deleterious manner with any of the components of the composition in which it is contained.

The term "pharmaceutically acceptable salt," as used herein, refers to a formulation of a compound that does not cause significant irritation to an organism to which it is administered and does not abrogate the biological activity and properties of the compounds described herein.

The term "prevent" or "prevention," as used herein, refers to a complete inhibition of development of primary or secondary tumors or any secondary effects of disease.

The terms "combination" or "pharmaceutical combination," as used herein mean a product that results from the mixing or combining of more than one active ingredient and includes both fixed and non-fixed combinations of the active ingredients. The term "fixed combination" means that the active ingredients, by way of example, a compound of Formula (I) and an additional therapeutic agent, are both administered to a patient simultaneously in the form of a single entity or dosage. The term "non-fixed combination" means that the active ingredients, by way of example, a compound of Formula (I) and an additional therapeutic agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

The terms "composition" or "pharmaceutical composition," as used herein, refers to a mixture of at least one compound of Formula (I) described herein with other chemical components, such as carriers, stabilizers, diluents, dispersing agents, suspending agents, thickening agents, and/or excipients.

The term "prodrug," as used herein, refers to an agent that is converted into the parent drug in vivo. A non-limiting example of a prodrug of the compounds described herein is a compound described herein administered as an ester which is then metabolically hydrolyzed to a carboxylic acid, the active entity, once inside the cell. A further example of a prodrug is a short peptide bonded to an acid group where the peptide is metabolized to reveal the active moiety.

The term "smoothened gain-of-function," as used herein, refers to an aberrant modification or mutation of a Smo gene, or an increased level of expression of the gene, which results in a phenotype which resembles contacting a cell with a hedgehog protein, e.g., aberrant activation of a hedgehog pathway.

The term "subject" includes mammals, especially humans. It also encompasses other non-human animals such as cows, horses, sheep, pigs, cats, dogs, mice, rats, rabbits, guinea pigs, monkeys.

The term "therapeutically effective amount," as used herein, refers to any amount of a compound which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The terms "treat," "treating" or "treatment," as used herein, refers to methods of alleviating, abating or ameliorating a disease or condition symptoms, preventing additional symptoms, ameliorating or preventing or delaying the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically (prevent or delay the onset of the disease, or to prevent the manifestation of clinical or subclinical symptoms thereof) and/or therapeutically. In context of tumor growth, the terms "treat," "treating" or "treatment," refers to arresting tumor growth, and to partial or complete regression of tumors.

The compound names provided herein were obtained using ChemDraw Ultra 10.0 (CambridgeSoft®) or JChem version 5.0.3 (ChemAxon).

Other objects, features and advantages of the methods, compositions and combinations described herein will become apparent from the following detailed description. It should be understood, however, that the detailed description and the specific examples, while indicating specific embodiments, are given by way of illustration only.

DESCRIPTION OF PREFERRED EMBODIMENTS

Provided herein are compounds of Formula (I), pharmaceutically acceptable salts, solvates, N-oxides, prodrugs and isomers thereof that are modulators of the hedgehog signaling pathway. Also provided herein are compounds of Formula (I) that modulate signal transduction pathways regulated by hedgehog, patched (Ptc), gli and/or smoothened.

In certain embodiments, certain compounds described herein, and pharmaceutical compositions thereof, are antagonists of the hedgehog signaling pathway. In other embodiments, certain compounds described herein, and pharmaceutical compositions thereof, are agonists of the hedgehog signaling pathway.

Further provided herein are compounds, pharmaceutically acceptable salts, solvates, N-oxides, prodrugs and isomers thereof, and pharmaceutical compositions containing such pharmaceutically acceptable salts, solvates, N-oxides, prodrugs and isomers thereof, for the treatment and/or prevention of Hedgehog-related diseases or disorders. Such diseases and/or disorders include, but are not limited to, tumor formation, cancer, neoplasia, malignant hyperproliferative disorders, and non-malignant hyperproliferative disorders, benign prostate hyperplasia, psoriasis, wet macular degeneration, osteopetrosis and unwanted hair growth.

Compounds and Compositions

The aforementioned compounds and pharmaceutically acceptable salts, solvates, N-oxides, prodrugs and isomers thereof, are compounds having structures according to Formula (I), wherein Formula (I) is

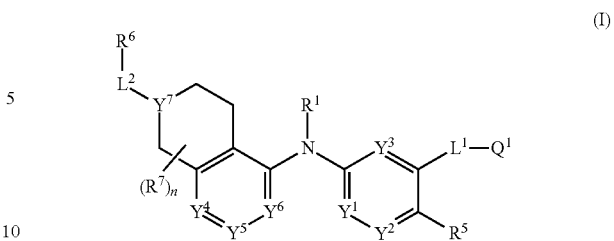

wherein:
$Q^1$ is selected from an aryl, heteroaryl, cycloalkyl, and heterocycloalkyl, wherein the aryl, heteroaryl, cycloalkyl and heterocycloalkyl of $Q^1$ are optionally substituted with 1 to 3 substituents independently selected from $R^9$, $R^{10}$, $R^{11}$, $R^{12}$ and $R^{13}$;

$Y^1$ is N or $CR^3$;
$Y^2$ is N or $CR^4$;
$Y^3$ is N or $CR^2$;
$Y^4$, $Y^5$, $Y^6$ are independently selected from N and $CR^8$;
$Y^7$ is N or $N^+O^-$;
$L^1$, $L^2$ and $L^3$ are independently selected from a bond, —$(CR^{14}R^{14})_m$—, —$(CR^{14}R^{15})_m$—, —C(O)—, —O—, —C(O)O—, —OC(O)—, —C(O)(CR^{14}R^{14})_m$—, —C(O)O(CR^{14}R^{14})_m$—, —NR^{16}C(O)—, —O(CR^{14}R^{14})_m$—, —(CR^{14}R^{14})_mO$—, —O(CR^{14}R^{15})_m$—, —(CR^{14}R^{15})_mO$—, —C(O)(CR^{14}R^{15})_m$, and —C(O)NR^{16}—;

$R^1$ is H or $C_1$-$C_6$alkyl;
$R^2$, $R^3$ and $R^4$ are each independently selected from H, halo, CN, $C_1$-$C_6$alkyl and halosubstituted-$C_1$-$C_6$alkyl, $C_1$-$C_6$alkoxy, halosubstituted-$C_1$-$C_6$alkoxy, $L^3OR^{13}$, —C(O)OR^{13}$ and $L^3NR^{16}R^{17}$;
each $R^5$ is independently selected from H, CN, halo, $C_1$-$C_6$alkyl, halosubstituted-$C_1$-$C_6$alkyl, $C_1$-$C_6$alkoxy, halosubstituted-$C_1$-$C_6$alkoxy, $L^3OR^{13}$, $C(O)OR^{13}$ and $L^3NR^{16}R^{17}$;
each $R^6$ is independently selected from H, $S(O)R^{13}$, $SO_2R^{13}$, $SO_2NR^{16}R^{17}$, $L^3NR^{16}R^{17}$, $C(O)OR^{13}$, $OR^{13}$, $R^{13}$, $NR^{16}R^{17}$, $C(O)NR^{16}R^{17}$, $C_1$-$C_6$alkyl, $C_1$-$C_6$haloalkyl, $C_3$-$C_8$cycloalkyl, $C_1$-$C_6$alkyl substituted with 1-4 OH groups, heteroaryl, heterocycloalkyl, $C_2$-$C_6$cyclic sulfinyl, $C_2$-$C_6$cyclic sulfonyl and aryl, wherein the heteroaryl, heterocycloalkyl, $C_3$-$C_8$cycloalkyl, $C_2$-$C_6$cyclic sulfinyl, $C_2$-$C_6$cyclic sulfonyl and aryl of $R^6$ are optionally substituted with 1-4 substituents selected from H, halo, CN, $C_1$-$C_6$alkyl, halosubstituted-$C_1$-$C_6$alkyl, $C_1$-$C_6$alkoxy, halosubstituted-$C_1$-$C_6$alkoxy, $C_1$-$C_6$alkyl substituted with 1-4 —OH groups, $C_3$-$C_8$cycloalkyl, $C_3$-$C_8$heterocycloalkyl, heteroaryl, and aryl;
each $R^7$ and $R^8$ are independently selected from H, $C_1$-$C_6$alkyl; halosubstituted-$C_1$-$C_6$alkyl, $C_1$-$C_6$alkoxy, halosubstituted-$C_1$-$C_6$alkoxy, $C_6$-$C_{10}$aryl-$C_0$-$C_4$alkyl, $C_5$-$C_{10}$heteroaryl-$C_0$-$C_{64}$alkyl, $C_3$-$C_{12}$cycloalkyl and $C_3$-$C_8$heterocycloalkyl;
or two $R^7$ along with the carbon to which they are attached from a C=O group;
each $R^9$, $R^{10}$, $R^{11}$ and $R^{12}$ are independently selected from H, CN, halo, $C_1$-$C_6$alkyl, halosubstituted-$C_1$-$C_6$alkyl, $C_1$-$C_6$alkoxy, halosubstituted-$C_1$-$C_6$alkoxy, $L^3OR^{13}$, $L^3NR^{16}R^{17}$, $L^3R^{13}$, $L^3R^{14}$, aryl optionally substituted with 1 to 3 substituents selected from $C_1$-$C_6$alkyl, halo, CN, $L^3NR^{16}R^{17}$ and $OR^{13}$, and heteroaryl optionally substituted with 1 to 3 substituents selected from C$_1$-C$_6$alkyl, halo, CN, L$^3$NR$^{16}$R$^{17}$ and L$^3$OR$^{13}$;

alternatively R$^{10}$ and R$^{11}$ together with the carbons atoms to which they are attached form a 5-6 membered aryl optionally substituted with 1 to 3 substituents selected from C$_1$-C$_6$alkyl, halo, CN, L$^3$NR$^{16}$R$^{17}$ and L$^3$OR$^{13}$ or a 5-6 membered heteroaryl optionally substituted with 1 to 3 substituents selected from C$_1$-C$_6$alkyl, halo, CN, L$^3$NR$^{16}$R$^{17}$ and L$^3$OR$^{13}$;

alternatively R$^{11}$ and R$^{12}$ together with the carbons atoms to which they are attached form a 5-6 membered aryl optionally substituted with 1 to 3 substituents selected from C$_1$-C$_6$alkyl, halo, CN, L$^3$NR$^{16}$R$^{17}$ and L$^3$OR$^{13}$ or a 5-6 membered heteroaryl optionally substituted with 1 to 3 substituents selected from C$_1$-C$_6$alkyl, halo, CN, L$^3$NR$^{16}$R$^{17}$ and L$^3$OR$^{13}$;

each R$^{13}$ is independently selected from H, C$_1$-C$_6$alkyl, C$_1$-C$_6$haloalkyl, C$_3$-C$_8$cycloalkyl, C$_3$-C$_8$heterocycloalkyl, C$_1$-C$_6$alkyl substituted with 1-4 —OH groups, heteroaryl and aryl, where the heteroaryl and aryl of R$^{13}$ are optionally substituted with 1 to 3 substituents selected from C$_1$-C$_6$alkyl, C$_1$-C$_6$haloalkyl, C$_3$-C$_8$cycloalkyl, C$_3$-C$_8$heterocycloalkyl, and C$_1$-C$_6$alkyl substituted with 1-4 —OH groups;

each R$^{14}$ and R$^{15}$ are independently selected from H, halo, OH, CN, C$_1$-C$_6$alkyl, C$_1$-C$_6$alkyl substituted with 1-4 —OH groups, halosubstituted-C$_1$-C$_6$alkyl, C$_1$-C$_6$alkoxy and halosubstituted-C$_1$-C$_6$alkoxy;

or R$^{14}$ and R$^{15}$ together with the carbon they are attached form a C$_3$-C$_8$cycloalkyl;

each R$^{16}$ and R$^{17}$ are independently selected from H, C$_1$-C$_6$alkyl, C$_1$-C$_6$alkyl substituted with 1-4 —OH groups;

or R$^{16}$ and R$^{17}$ together with the N atom they are attached form a C$_3$-C$_8$heterocycloalkyl;

each m is independently 1, 2, 3, 4, 5 or 6;
each n is independently 1, 2, 3, 4, 5 or 6,
and the pharmaceutically acceptable salts, hydrates, N-oxides, solvates and isomers thereof.

In certain embodiments of such compounds R$^1$ is H.

In certain embodiments of the aforementioned compounds Q$^1$ is

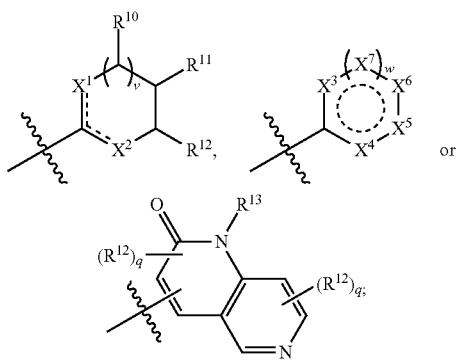

wherein,
v is 0, 1 or 3;
w is 0 or 1;
each q is independently 1, 2 or 3;
X$^1$ and X$^2$ are independently selected from N, S and NR$^{16}$;
X$^7$ is N or CR$^{10}$;

when w is 1 then: X$^3$ is N or CR$^9$;
X$^4$ is N or CR$^9$;
X$^5$ is N or CR$^{12}$, and
X$^6$ is N or CR$^{11}$;
when w is O then: X$^3$ is N, O or CR$^9$;
X$^4$ is N, O or CR$^9$;
X$^5$ is N, CR$^{12}$ or NR$^{16}$, and
X$^6$ is N, CR$^{11}$ or NR$^{16}$;
provided that when X$^3$ is O, then X$^4$ is N or CR$^9$, or when X$^4$ is O, then X$^3$ is N or CR$^9$; and
provided that when X$^5$ is NR$^{16}$, then X$^6$ is N or CR$^{11}$, or when X$^6$ is NR$^{16}$, then X$^5$ is N or CR$^{12}$.

In certain embodiments of the aforementioned compounds Q$^1$ is

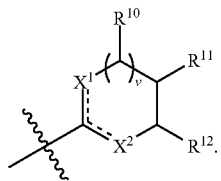

In certain embodiments of the aforementioned compounds Q$^1$ is

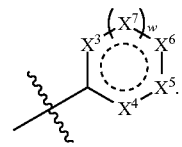

In certain embodiments of the aforementioned compounds each R$^6$ is

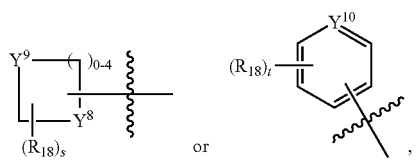

wherein;
Y$^8$ is N, NR$^{16}$, —(CR$^{13}$R$^{13}$)—, or CR$^{13}$;
Y$^9$ is SO$_2$, S=O, O, NR$^{16}$, —(CR$^{13}$R$^{13}$)—, C(O) or COR$^{13}$;
Y$^{10}$ is N or N$^+$O$^-$;
each R$^{18}$ is independently selected from halo, CN, C$_1$-C$_6$alkyl, halosubstituted-C$_1$-C$_6$alkyl, C$_1$-C$_6$alkoxy, halosubstituted-C$_1$-C$_6$alkoxy, C$_1$-C$_6$alkyl substituted with 1 to 4 —OH groups, C$_3$-C$_8$cycloalkyl, C$_3$-C$_8$heterocycloalkyl, heteroaryl, and aryl;
s is 1, 2, 3, 4 or 5, and
t is 1, 2, 3 or 4.

In certain embodiments of compounds of Formula (I), L$^2$ is a bond, and each R$^6$ is independently selected from H, S(O)R$^{13}$, SO$_2$R$^{13}$, SO$_2$NR$^{16}$R$^{17}$, C(O)NR$^{16}$R$^{17}$, C$_1$-C$_6$alkyl, C$_1$-C$_6$haloalkyl, C$_3$-C$_8$cycloalkyl, C$_1$-C$_6$alkyl substituted with 1-4 OH groups, heteroaryl, heterocycloalkyl, C$_2$-C$_6$cyclic sulfinyl, C$_2$-C$_6$cyclic sulfonyl and aryl, wherein the heteroaryl, heterocycloalkyl, C$_3$-C$_8$cycloalkyl, C$_2$-C$_6$cyclic sulfinyl, C$_2$-C$_6$cyclic sulfonyl and aryl of R$^6$ are optionally substituted with 1-4 substituents selected from H, halo, CN, C$_1$-C$_6$alkyl, halosubstituted-C$_1$-C$_6$alkyl, $C_1$-$C_6$alkoxy, halosubstituted-$C_1$-$C_6$alkoxy, $C_1$-$C_6$alkyl substituted with 1-4 —OH groups, $C_3$-$C_8$cycloalkyl, $C_3$-$C_8$heterocycloalkyl, heteroaryl, and aryl.

In certain embodiments of compounds of Formula (I), $L^2$ is a —$(CR^{14}R^{14})_m$—, —$(CR^{14}R^{15})_m$—, —C(O)($CR^{14}R^{14})_m$—, or —C(O)($CR^{14}R^{15})_m$—, and each $R^{16}$ is independently selected from H, S(O)$R^{13}$, SO$_2R^{13}$, $NR^{16}R^{17}$, $L^3NR^{16}R^{17}$, C(O)O$R^{13}$, C(O)$NR^{16}R^{17}$, $C_1$-$C_6$haloalkyl, $C_1$-$C_6$alkyl substituted with 1-4 OH groups, heteroaryl, heterocycloalkyl, $C_3$-$C_8$cycloalkyl, $C_2$-$C_6$cyclic sulfinyl, $C_2$-$C_6$cyclic sulfonyl and aryl, wherein the heteroaryl, heterocycloalkyl, $C_3$-$C_8$cycloalkyl, $C_2$-$C_6$cyclic sulfinyl, $C_2$-$C_6$cyclic sulfonyl and aryl of $R^6$ are optionally substituted with 1-4 substituents selected from H, halo, CN, $C_1$-$C_6$alkyl, halosubstituted-$C_1$-$C_6$alkyl, $C_1$-$C_6$alkoxy, halosubstituted-$C_1$-$C_6$alkoxy, $C_1$-$C_6$alkyl substituted with 1-4 —OH groups, $C_3$-$C_8$cycloalkyl, $C_3$-$C_8$heterocycloalkyl, heteroaryl, and aryl.

In certain embodiments of compounds of Formula (I), $L^2$ is a —C(O)—, or —C(O)O—, and each $R^6$ is independently selected from H, $NR^{16}R^{17}$, $L^3NR^{16}R^{17}$, C(O)O$R^{13}$, $C_1$-$C_6$alkyl, $C_1$-$C_6$haloalkyl, $C_3$-$C_8$cycloalkyl, $C_1$-$C_6$alkyl substituted with 1-4 OH groups, heteroaryl, heterocycloalkyl, $C_2$-$C_6$cyclic sulfinyl, $C_2$-$C_6$cyclic sulfonyl and aryl, wherein the heteroaryl, heterocycloalkyl, $C_3$-$C_8$cycloalkyl, $C_2$-$C_6$cyclic sulfinyl, $C_2$-$C_6$cyclic sulfonyl and aryl of $R^6$ are optionally substituted with 1-4 substituents selected from H, halo, CN, $C_1$-$C_6$alkyl, halosubstituted-$C_1$-$C_6$alkyl, $C_1$-$C_6$alkoxy, halosubstituted-$C_1$-$C_6$alkoxy, $C_1$-$C_6$alkyl substituted with 1-4 —OH groups, $C_3$-$C_8$cycloalkyl, $C_3$-$C_8$heterocycloalkyl, heteroaryl, and aryl.

In certain embodiments of the aforementioned compounds each $R^{18}$ is independently selected from halo, $C_1$-$C_6$alkyl and $C_1$-$C_6$alkyl substituted with 1 to 4 —OH groups.

In certain embodiments of the aforementioned compounds $R^2$, $R^3$ and $R^4$ are each independently selected from H, halo, CN, $C_1$-$C_6$alkyl and halosubstituted-$C_1$-$C_6$alkyl.

In certain embodiments of the aforementioned compounds each $R^5$ is independently selected from H, CN, halo, $C_1$-$C_6$alkyl, $L^3OR^{13}$, —C(O)O$R^{13}$ and $L^3NR^{16}R^{17}$.

In certain embodiments of the aforementioned compounds each $R^7$ is independently selected from H and $C_1$-$C_6$alkyl, or two $R^7$ along with the carbon to which they are attached from a C=O group.

In certain embodiments of the aforementioned compounds each $R^8$ is independently selected from H and $C_1$-$C_6$alkyl.

In certain embodiments of the aforementioned compounds each $R^9$ is independently selected from H, halo and $C_1$-$C_6$alkyl.

In certain embodiments of the aforementioned compounds each $R^{10}$ is independently selected from H, halo, $C_1$-$C_6$alkyl, $L^3OR^{13}$ and $L^3NR^{16}R^{17}$.

In certain embodiments of the aforementioned compounds each $R^{11}$ is independently selected from H, $C_1$-$C_6$alkyl, $C_1$-$C_6$haloalkyl, halo, CN, $L^3R^{13}$, $L^3R^{14}$, $L^3OR^{13}$, $L^3NR^{16}R^{17}$, an aryl optionally substituted with 1 to 3 substituents selected from $C_1$-$C_6$alkyl, halo, CN, $L^3NR^{16}R^{17}$ and O$R^{13}$, and a heteroaryl optionally substituted with 1 to 3 substituents selected from $C_1$-$C_6$alkyl, halo, CN, $L^3NR^{16}R^{17}$ and $L^3OR^{13}$.

In certain embodiments of the aforementioned compounds each $R^{12}$ is independently selected from H, $C_1$-$C_6$alkyl, CN, $L^3OR^{13}$ and $L^3NR^{16}R^{17}$.

In certain embodiments of the aforementioned compounds each $R^5$ is independently selected from —Cl or methyl.

The compounds of Formulas (I), pharmaceutically acceptable salts, solvates, N-oxides, prodrugs and isomers thereof, and pharmaceutical compositions provided herein also includes all suitable isotopic variations of such compounds, and pharmaceutically acceptable salts, solvates, N-oxides, prodrugs and isomers thereof, and pharmaceutical compositions. An isotopic variation of a compound of the invention or a pharmaceutically acceptable salt thereof is defined as one in which at least one atom is replaced by an atom having the same atomic number but an atomic mass different from the atomic mass usually found in nature. Examples of isotopes that may be incorporated into the compounds of the invention and pharmaceutically acceptable salts thereof include but are not limited to isotopes of hydrogen, carbon, nitrogen and oxygen such as $^2$H, $^3$H, $^{11}$C, $^{13}$C, $^{14}$C, $^{15}$N, $^{17}$O, $^{18}$O, $^{35}$S, $^{18}$F, $^{36}$Cl and $^{123}$I. Certain isotopic variations of the compounds of the invention and pharmaceutically acceptable salts thereof, for example, those in which a radioactive isotope such as $^3$H or $^{14}$C is incorporated, are useful in drug and/or substrate tissue distribution studies. In particular examples, $^3$H and $^{14}$C isotopes may be used for their ease of preparation and detectability. In other examples, substitution with isotopes such as $^2$H may afford certain therapeutic advantages resulting from greater metabolic stability, such as increased in vivo half-life or reduced dosage requirements. Isotopic variations of the compounds, and pharmaceutically acceptable salts, solvates, N-oxides, prodrugs and isomers thereof, and pharmaceutical compositions provided herein are prepared by conventional procedures using appropriate isotopic variations of suitable reagents.

Processes for Making Compounds of Formula (I)

General procedures for preparing compounds of Formula (I) are described in the Examples, infra. In the reactions described, reactive functional groups, for example hydroxyl, amino, imino, thio or carboxy groups, where these are desired in the final product, may be protected to avoid their unwanted participation in the reactions. Conventional protecting groups may be used in accordance with standard practice (see e.g., T. W. Greene and P. G. M. Wuts in "Protective Groups in Organic Chemistry," John Wiley and Sons, 1991).

In certain embodiments, the compounds of Formula (I) described herein are prepared as a pharmaceutically acceptable acid addition salt by reacting the free base form of the compound of Formula (I) with a pharmaceutically acceptable organic acid or inorganic acid. In other embodiments, a pharmaceutically acceptable base addition salt of compounds of Formula (I) described herein is prepared by reacting the free acid form of the compound of Formula (I) with a pharmaceutically acceptable organic base or inorganic base. Alternatively, the salt forms of the compounds of Formula (I) described herein are prepared using salts of the starting materials or intermediates. In certain embodiments, the compounds of Formula (I) described herein are in the form of other salts including, but not limited to, oxalates and trifluoroacetates. In certain embodiments, hemisalts of acids and bases are formed, for example, hemisulphate and hemicalcium salts.

Such pharmaceutically acceptable acid addition salts of compounds of Formula (I) include, but are not limited to, a hydrobromide, hydrochloride, hydroiodide, sulfate, bisulphate, nitrate, phosphate, succinate, maleate, formate, acetate, adipate, besylatye, bicarbonate/carbonate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate), hexanoate salt, bisulphate/sulphate, borate, camsylate, cyclamate, edisylate, esylate, gluceptate, gluconate, glucuronate, pyruvate, hexafluorophosphate, hibenzate, hydrochloride/chloride, hydrobromide/ bromide, hydroiodide/iodide, isethionate, lactate, malate, malonate, mesylate, methylsulphate, naphthylate, 2-napsylate, nicotinate, orotate, oxalate, oxaloacetate, palmitate, pamoate, phosphate/hydrogen phosphate/dihydrogen phosphate, pyroglutamate, saccharate, stearate, tannate, tosylate, trifluoroacetate and xinofoate salts.

The organic acid or inorganic acids used to form certain pharmaceutically acceptable acid addition salts of compounds of Formula (I) include, but are not limited to, hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, or hexanoic acid.

Such pharmaceutically acceptable base addition salt of a compound of Formula (I) include, but are not limited to, aluminium, arginine, benzathine, calcium, choline, diethylamine, diolamine, glycine, lysine, magnesium, meglumine, olamine, potassium, sodium, tromethamine and zinc salts.

In certain embodiments, the free acid or free base forms of the compounds of Formula (I) described herein are prepared from the corresponding base addition salt or acid addition salt from, respectively. For example a compound Formula (I) in an acid addition salt form is converted to the corresponding free base by treating with a suitable base (by way of example only, an ammonium hydroxide solution, a sodium hydroxide, and the like). For example, a compound of Formula (I) in a base addition salt form is converted to the corresponding free acid by treating with a suitable acid (by way of example only, hydrochloric acid).

In certain embodiments, the compounds of Formula (I) described herein in unoxidized form are prepared from N-oxides of compounds Formula (I) by treating with a reducing agent (by way of example only, sulfur, sulfur dioxide, triphenyl phosphine, lithium borohydride, sodium borohydride, phosphorus trichloride, tribromide, or the like) in a suitable inert organic solvent (by way of example only, acetonitrile, ethanol, aqueous dioxane, or the like) at 0 to 80° C.

In certain embodiments, prodrug derivatives of compounds Formula (I) described herein are prepared using methods known to those of ordinary skill in the art (e.g., for further details see Saulnier et al., (1994), Bioorganic and Medicinal Chemistry Letters, Vol. 4, p. 1985). For example, appropriate prodrugs are prepared by reacting a non-derivatized compound of Formula (I) with a suitable carbamylating agent (by way of example only, 1,1-acyloxyalkylcarbanochloridate, para-nitrophenyl carbonate, or the like).

In certain embodiments, the compounds of Formula (I) described herein are prepared as protected derivatives using methods known to those of ordinary skill in the art. A detailed description of the techniques applicable to the creation of protecting groups and their removal can be found in T. W. Greene, "Protecting Groups in Organic Chemistry," 3$^{rd}$ edition, John Wiley and Sons, Inc., 1999.

In certain embodiments, the compounds of Formula (I) described herein are prepared or formed, as solvates (e.g., hydrates). In certain embodiments, hydrates of compounds of Formula (I) are prepared by recrystallization from an aqueous/organic solvent mixture, using organic solvents such as dioxin, tetrahydrofuran or methanol.

In certain embodiments, the compounds of Formula (I) described herein are prepared as their individual stereoisomers. In other embodiments, the compounds of Formula (I) described herein are prepared as their individual stereoisomers by reacting a racemic mixture of the compound with an optically active resolving agent to form a pair of diastereoisomeric compounds, separating the diastereomers and recovering the optically pure enantiomers. In certain embodiments, resolution of enantiomers is carried out using covalent diastereomeric derivatives of the compounds of Formula (I), or by using dissociable complexes (e.g., crystalline diastereomeric salts). Diastereomers have distinct physical properties (e.g., melting points, boiling points, solubility, reactivity, etc.) and are readily separated by taking advantage of these dissimilarities. In certain embodiments, the diastereomers are separated by chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions," John Wiley And Sons, Inc., 1981.

Compounds of Formula (I) are made by processes described herein and as illustrated in the Examples. In certain embodiments, compounds of Formula (I) are made by (a) optionally converting a compound of the invention into a pharmaceutically acceptable salt;

(b) optionally converting a salt form of a compound of the invention to a non-salt form;

(c) optionally converting an unoxidized form of a compound of the invention into a pharmaceutically acceptable N-oxide;

(d) optionally converting an N-oxide form of a compound of the invention to its unoxidized form;

(e) optionally resolving an individual isomer of a compound of the invention from a mixture of isomers;

(f) optionally converting a non-derivatized compound of the invention into a pharmaceutically acceptable prodrug derivative; and (g) optionally converting a prodrug derivative of a compound of the invention to its non-derivatized form.

Non-limiting examples of synthetic schemes used to make compounds of Formula (I) described herein are illustrated in reaction schemes (I)-(IX), wherein n, $L^1$, $L^2$, $R^1$, $R^2$, $R^3$, $R^4$, $R^5$, $R^6$, $R^7$, $R^8$, $R^9$, $R^{10}$, $R^{11}$ and $R^{12}$ are as defined herein.

Reaction scheme (I) illustrates the synthesis of certain embodiments of compounds of Formula (I) by the amination of a halo-substituted dihydroisoquinolin-1(2H)-one with a substituted imidazol-2-yl-phenylamino moiety in the presence of a phosphine ligand, a catalyst, a base and a suitable solvent. Such phosphine ligand, a catalyst, a base and a suitable solvent include, but are not limited to, Xantphos, $Pd_2(dba)_3$, $K_3PO_4$, and dioxane, respectively.

Reaction Scheme (I)

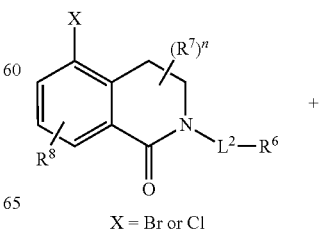

X = Br or Cl

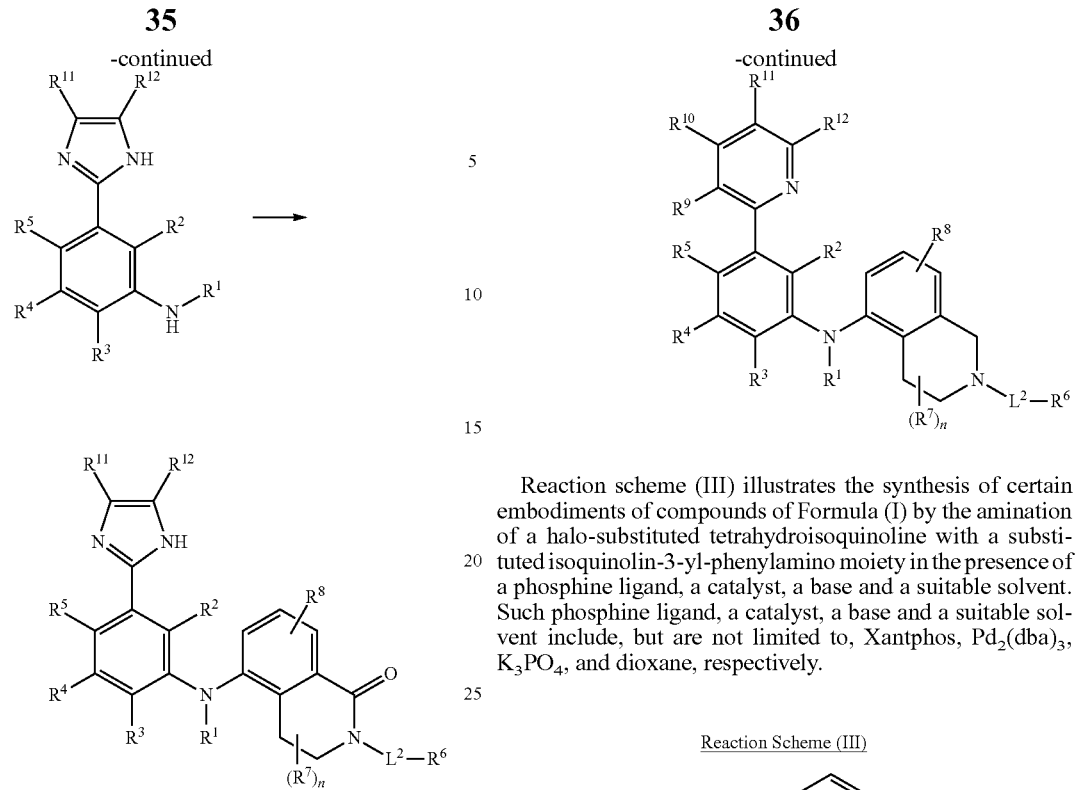

Reaction scheme (II) illustrates the synthesis of certain embodiments of compounds of Formula (I) by the amination of a halo-substituted tetrahydroisoquinoline with a substituted pyridin-2-yl-phenylamino moiety in the presence of a phosphine ligand, a catalyst, a base and a suitable solvent. Such phosphine ligand, a catalyst, a base and a suitable solvent include, but are not limited to, Xantphos, $Pd_2(dba)_3$, $K_3PO_4$, and dioxane, respectively.

Reaction scheme (III) illustrates the synthesis of certain embodiments of compounds of Formula (I) by the amination of a halo-substituted tetrahydroisoquinoline with a substituted isoquinolin-3-yl-phenylamino moiety in the presence of a phosphine ligand, a catalyst, a base and a suitable solvent. Such phosphine ligand, a catalyst, a base and a suitable solvent include, but are not limited to, Xantphos, $Pd_2(dba)_3$, $K_3PO_4$, and dioxane, respectively.

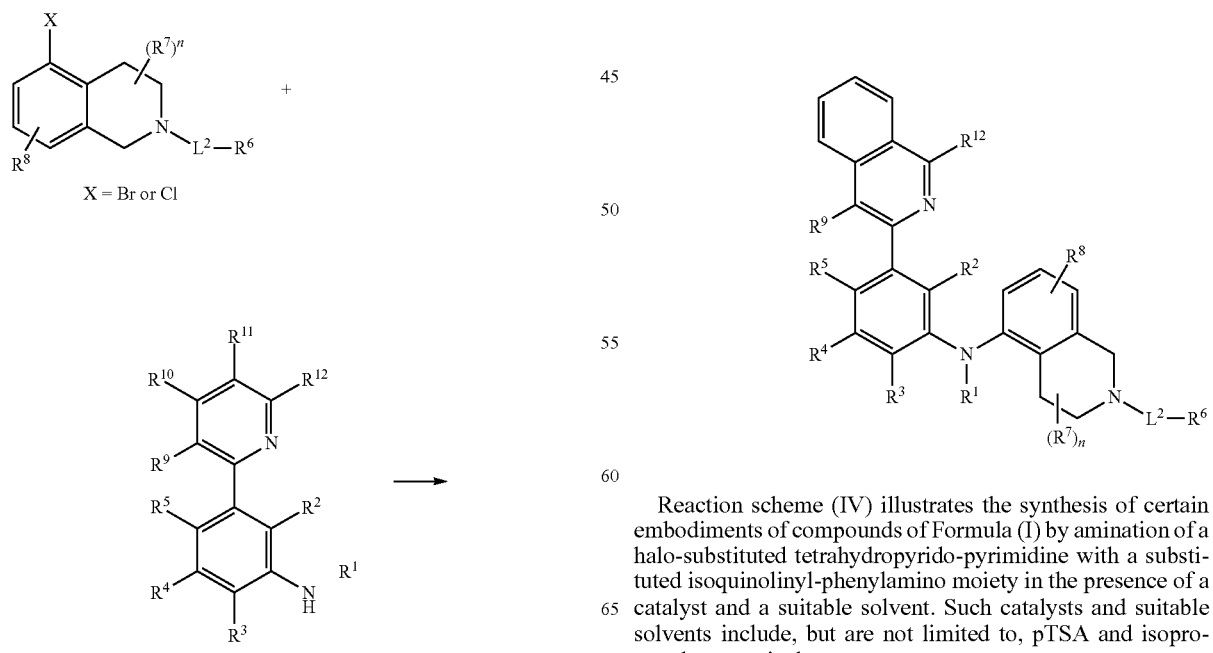

Reaction scheme (IV) illustrates the synthesis of certain embodiments of compounds of Formula (I) by amination of a halo-substituted tetrahydropyrido-pyrimidine with a substituted isoquinolinyl-phenylamino moiety in the presence of a catalyst and a suitable solvent. Such catalysts and suitable solvents include, but are not limited to, pTSA and isopropanol, respectively.

Reaction Scheme (IV)

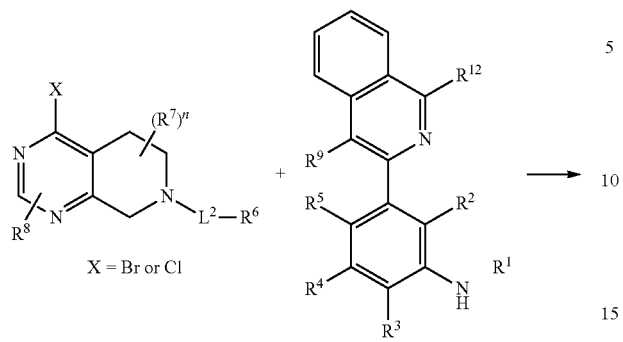

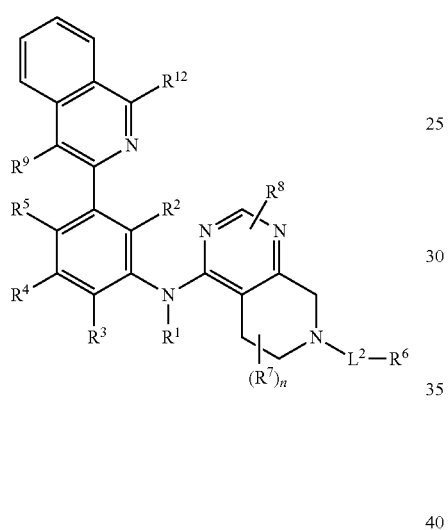

Reaction scheme (V) illustrates the synthesis of certain embodiments of compounds of Formula (I) by amination of a halo-substituted tetrahydroisoquinoline with a substituted bipyrimidine-amine moiety in the presence of a phosphine ligand, a catalyst, a base and a suitable solvent. Such phosphine ligand, a catalyst, a base and a suitable solvent include, but are not limited to, Xantphos, $Pd_2(dba)_3$, $K_3PO_4$, and dioxane, respectively.

Reaction Scheme (V)

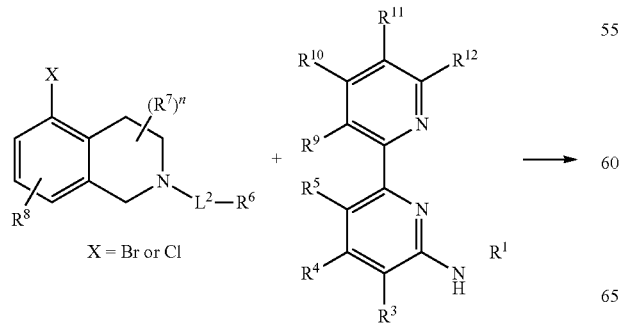

-continued

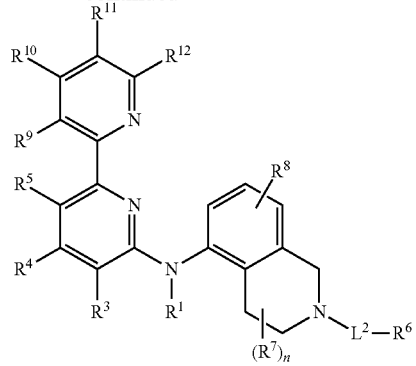

Reaction scheme (VI) illustrates the synthesis of certain embodiments of compounds of Formula (I) by amination of a halo-substituted tetrahydroisoquinoline with a substituted pyrimidine-amine moiety in the presence of a phosphine ligand, a catalyst, a base and a suitable solvent. Such phosphine ligand, a catalyst, a base and a suitable solvent include, but are not limited to, BINAP, $Pd_2(dba)_3$, $K_3PO_4$, and dioxane, respectively.

Reaction Scheme (VI)

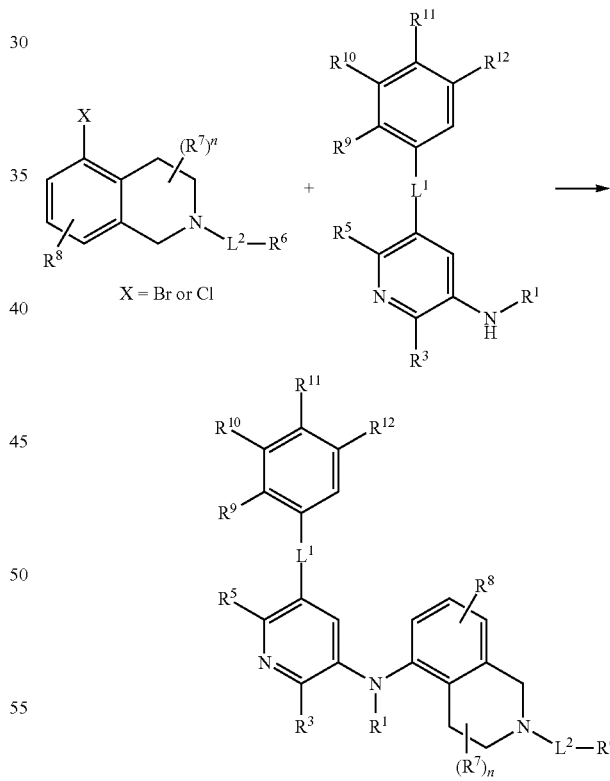

Reaction scheme (VII) illustrates the synthesis of certain embodiments of compounds of Formula (I) by amination of a halo-substituted tetrahydroisoquinoline with a pyridazinyl-substituted aniline moiety in the presence of a phosphine ligand, a catalyst, a base and a suitable solvent. Such phosphine ligand, a catalyst, a base and a suitable solvent include, but are not limited to, Xantphos, $Pd_2(dba)_3$, $K_3PO_4$, and dioxane, respectively.

Reaction Scheme (VII)

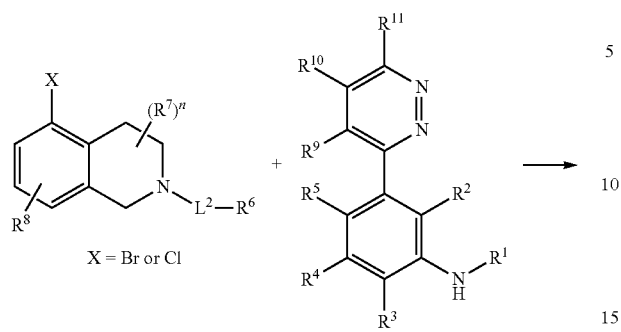

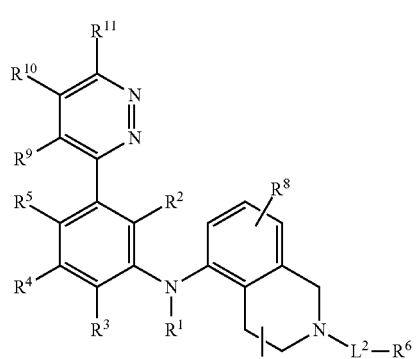

Reaction scheme (VIII) illustrates the synthesis of certain embodiments of compounds of Formula (I) by amination of a halo-substituted tetrahydroisoquinoline with a pyridinyl-substituted aniline moiety in the presence of a phosphine ligand, a catalyst, a base and a suitable solvent. Such phosphine ligand, a catalyst, a base and a suitable solvent include, but are not limited to, Xantphos, $Pd_2(dba)_3$, $K_3PO_4$, and dioxane, respectively

Reaction Scheme (VIII)

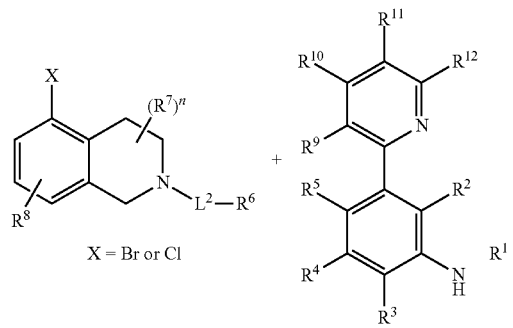

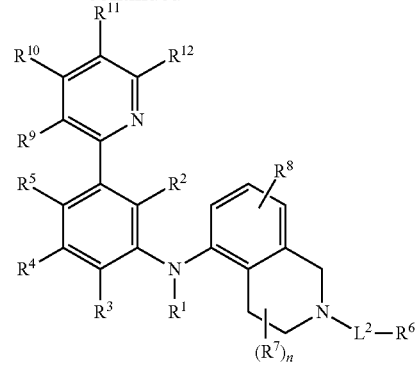

Reaction scheme (IX) illustrates the synthesis of certain embodiments of compounds of Formula (I) by amination of a halo-substituted tetrahydroisoquinoline with an isoquinolinyl-substituted aniline in the presence of a phosphine ligand, a catalyst, a base and a suitable solvent. Such phosphine ligand, a catalyst, a base and a suitable solvent include, but are not limited to, Xantphos, $Pd_2(dba)_3$, $K_3PO_4$, and dioxane, respectively.

Reaction Scheme (IX)

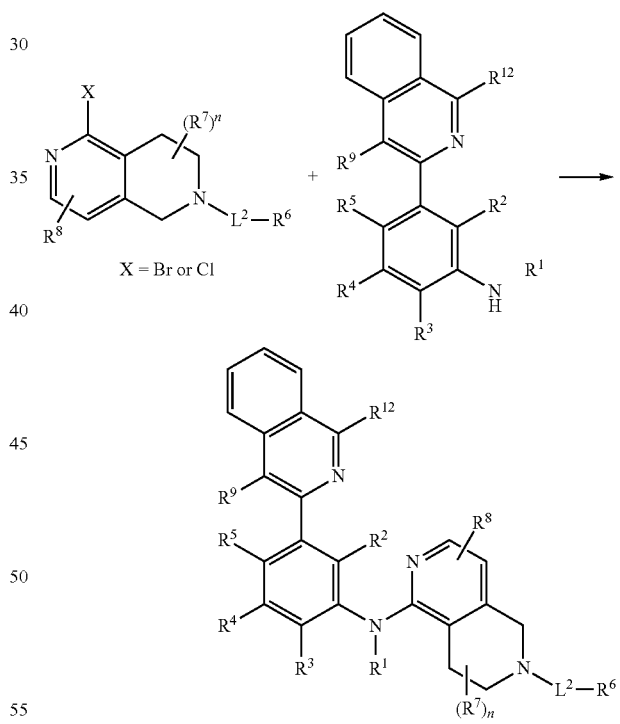

Insofar as the production of the starting materials is not particularly described, the compounds are known or can be prepared analogously to methods known in the art or as disclosed in the Examples hereinafter.

Detailed examples of the synthesis of compounds of Formula (I) can be found in the Examples, infra.

Pharmacology and Utility

Members of the Hedgehog family of signaling molecules mediate many important short- and long-range patterning processes during vertebrate development. Pattern formation is the activity by which embryonic cells form ordered spatial arrangements of differentiated tissues. The physical complexity of higher organisms arises during embryogenesis through the interplay of cell-intrinsic lineage and cell-extrinsic signaling. Inductive interactions are essential to embryonic patterning in vertebrate development from the earliest establishment of the body plan, to the patterning of the organ systems, to the generation of diverse cell types during tissue differentiation. The effects of developmental cell interactions are varied: responding cells are diverted from one route of cell differentiation to another by inducing cells that differ from both the uninduced and induced states of the responding cells (inductions). Sometimes cells induce their neighbors to differentiate like themselves (homeogenetic induction); in other cases a cell inhibits its neighbors from differentiating like itself. Cell interactions in early development may be sequential, such that an initial induction between two cell types leads to a progressive amplification of diversity. Moreover, inductive interactions occur not only in embryos, but in adult cells as well, and can act to establish and maintain morphogenetic patterns as well as induce differentiation.

The vertebrate family of hedgehog genes includes three members that exist in mammals, known as Desert (Dhh), Sonic (Shh) and Indian (Ihh) hedgehogs, all of which encode secreted proteins. These various Hedgehog proteins consist of a signal peptide, a highly conserved N-terminal region, and a more divergent C-terminal domain. Biochemical studies have shown that autoproteolytic cleavage of the Hh precursor protein proceeds through an internal thioester intermediate which subsequently is cleaved in a nucleophilic substitution. It is likely that the nucleophile is a small lipophilic molecule which becomes covalently bound to the C-terminal end of the N-peptide, tethering it to the cell surface. The biological implications are profound. As a result of the tethering, a high local concentration of N-terminal Hedgehog peptide is generated on the surface of the Hedgehog producing cells. It is this N-terminal peptide which is both necessary and sufficient for short- and long-range Hedgehog signaling activities.

An inactive Hedgehog signaling pathway is where the transmembrane protein receptor Patched (Ptc) inhibits the activity of Smoothened (Smo), a seven transmembrane protein. The transcription factor Gli, a downstream component of Hh signaling, is prevented from entering the nucleus through interactions with cytoplasmic proteins, including Fused and Suppressor of fused (Sufu). As a consequence, transcriptional activation of Hedgehog target genes is repressed. Activation of the pathway is initiated through binding of any of the three mammalian ligands (Dhh, Shh or Ihh) to Ptc. Ligand binding results in a reversal of the repression of Smo, thereby activating a cascade that leads to the translocation of the active form of the transcription factor Gli to the nucleus. Nuclear Gli activates target gene expression, including Ptc and Gli itself.

Increased levels of Hedgehog signaling are sufficient to initiate cancer formation and are required for tumor survival. These cancers include, but are not limited to, prostate cancer ("Hedgehog signaling in prostate regeneration, neoplasia and metastasis", Karhadkar S S, Bova G S, Abdallah N, Dhara S, Gardner D, Maitra A, Isaacs J T, Berman D M, Beachy P A., Nature. 2004 Oct. 7; 431(7009):707-12; "Inhibition of prostate cancer proliferation by interference with SONIC HEDGEHOG-GLI1 signaling", Sanchez P, Hernandez A M, Stecca B, Kahler A J, DeGueme A M, Barrett A, Beyna M, Datta M W, Datta S, Ruiz i Altaba A., Proc Natl Acad Sci USA. 2004 Aug. 24; 101(34):12561-6), ("Cytotoxic effects induced by a combination of cyclopamine and gefitinib, the selective hedgehog and epidermal growth factor receptor signaling inhibitors, in prostate cancer cells," Mimeault M, Moore E, Moniaux N, et al (2006), International Journal of Cancer; 118 (4):1022-31) breast cancer ("Hedgehog signaling pathway is a new therapeutic target for patients with breast cancer", Kubo M, Nakamura M, Tasaki A, Yamanaka N, Nakashima H, Nomura M, Kuroki S, Katano M., Cancer Res. 2004 Sep. 1; 64(17):6071-4), ("Hedgehog signaling and Bmi-1 regulate self-renewal of normal and malignant human mammary stem cells," Liu S, Dontu G, Mantle I D, et al (2006) Cancer Res; 66 (12):6063-71), ("Constitutive activation of smoothened (SMO) in mammary glands of transgenic mice leads to increased proliferation, altered differentiation and ductal dysplasia," Moraes R C, Zhang X M, Harrington N, et al (2007), Development; 134 (6):1231-42), medulloblastoma ("Medulloblastoma growth inhibition by hedgehog pathway blockade", Berman D M, Karhadkar S S, Hallahan A R, Pritchard J I, Eberhart C G, Watkins D N, Chen J K, Cooper M K, Taipale J, Olson J M, Beachy P A., Science. 2002 Aug. 30; 297(5586):1559-61), non-melanoma skin cancer, i.e. squamous cell carcinoma (SCC) and basal cell carcinoma (BCC) ("Identification of a small molecule inhibitor of the hedgehog signaling pathway: effects on basal cell carcinoma-like lesions", Williams J A, Guicherit O M, Zaharian B I, Xu Y, Chai L, Wichterle H, Kon C, Gatchalian C, Porter J A, Rubin L L, Wang F Y., Proc Natl Acad Sci USA. 2003 Apr. 15; 100(8):4616-21; "Activating Smoothened mutations in sporadic basal-cell carcinoma", Xie J, Murone M, Luoh S M, Ryan A, Gu Q, Zhang C, Bonifas J M, Lam C W, Hynes M, Goddard A, Rosenthal A, Epstein E H Jr, de Sauvage F J., Nature. 1998 Jan. 1; 391(6662):90-2), pancreatic, esophagus, stomach, and billary cancers ("Hedgehog is an early and late mediator of pancreatic cancer tumorigenesis", Thayer S P, di Magliano M P, Heiser P W, Nielsen C M, Roberts D J, Lauwers G Y, Qi Y P, Gysin S, Fernandez-del Castillo C, Yajnik V, Antoniu B, McMahon M, Warshaw A L, Hebrok M., Nature. 2003 Oct. 23; 425(6960):851-6; "Widespread requirement for Hedgehog ligand stimulation in growth of digestive tract tumours", Berman D M, Karhadkar S S, Maitra A, Montes De Oca R, Gerstenblith M R, Briggs K, Parker A R, Shimada Y, Eshleman J R, Watkins D N, Beachy P A., Nature. 2003 Oct. 23; 425(6960):846-51), ("Nuclear factor-kappa B contributes to hedgehog signaling pathway activation through sonic hedgehog induction in pancreatic cancer," Nakashima H, Nakamura M, Yamaguchi H, et al (2006), Cancer Research; 66 (14):7041-9), ("Blockade of hedgehog signaling inhibits pancreatic cancer invasion and metastases: A new paradigm for combination therapy in solid cancers," Feldmann G, Dhara S, Fendrich V, et al (2007) Cancer Research; 67 (5): 2187-96), ("Oncogenic KRAS suppresses Gli1 degradation and activates Hedgehog signaling pathway in pancreatic cancer cells," Ji Z, Mei F C, Xie J, et al (2007), J Biol Chem; 282 (19):14048-55), and small-cell lung cancer ("Hedgehog signalling within airway epithelial progenitors and in small-cell lung cancer", Watkins D N, Berman D M, Burkholder S G, Wang B, Beachy P A, Baylin S B., Nature. 2003 Mar. 20; 422(6929):313-7), ("Hedgehog signaling in small-cell lung cancer: Frequent in vivo but a rare event in vitro," Vestergaard J, Pedersen M W, Pedersen N, et al (2006), Lung Cancer; 52 (3):281-90).

Additional cancers in which increased levels of Hedgehog signaling are sufficient to initiate cancer formation and are required for tumor survival include, but are not limited to colon cancer ("Sonic Hedgehog-dependent proliferation in a series of patients with colorectal cancer," Douard R, Moutereau S, Pernet P, et al (2006) Surgery; 139 (5):665-70), ("Hedgehog signaling in colorectal tumour cells: Induction of apoptosis with cyclopamine treatment," Qualtrough D, Buda A, Gaffield W, et al (2004), International Journal of Cancer;

110 (6):831-7), glioma, ("Cyclopamine-mediated Hedgehog pathway inhibition depletes stem-like cancer cells in glioblastoma," Bar E E, Chaudhry A, Lin A, et al, Neuro-Oncology; 2007, 9 (4):594), ("HEDGEHOG-GLI signaling regulates human glioma growth, cancer stem cell self-renewal, and tumorigenicity," Clement V, Sanchez P, de Tribolet N, et al, (2007) Current Biology 17 (2):165-72), ("Ligand-dependent activation of the hedgehog pathway in glioma progenitor cells," Ehteshan M, Sarangi A, Valadez J G, et al (2007) Oncogene; Mar. 12, 2007, Epub ahead of print), melanoma ("Melanomas require HEDGEHOG-GLI signaling regulated by interactions between GLI1 and the RAS-MEK/AKT pathways," Stecca B, Mas C, Clement V, et al (2007), Proceedings of the National Academy of Sciences of the United States of America; 104 (14):5895-900), non small cell lung cancer (NSCLC) ("Frequent requirement of hedgehog signaling in non-small cell lung carcinoma," Yuan Z, Goetz J A, Singh S, et al (2007), Oncogene; 26 (7):1046-55), ovarian, ("Hedgehog signal pathway is activated in ovarian carcinomas, correlating with cell proliferation: It's inhibition leads to growth suppression and apoptosis," Chen X J, Horiuchi A, Kikuchi N, et al, Cancer Science; (2007) 98 (1):68-76), liver ("Activation of the hedgehog pathway in human hepatocellular carcinomas," Huang S H, He J, Zhang X L, et al (2006), Carcinogenesis; 27 (7):1334-40), ("Dysregulation of the Hedgehog pathway in human hepatocarcinogenesis," Sicklick J K, Li Y X, Jayaraman A, et al (2006), Carcinogenesis; 27 (4):748-57), renal ("Clear cell sarcoma of the kidney: Up-regulation of neural markers with activation of the sonic hedgehog and Akt pathways," Cutcliffe C, Kersey D, Huang C C, et al (2005), Clinical Cancer Research; 11 (22):7986-94), Rhabdomyosarcoma, ("Rhabdomyosarcomas and radiation hypersensitivity in a mouse model of Gorlin syndrome," Hahn H, Wojnowski L, Zimmer A M, et al (1998), Nature Medicine; 4 (5):619-22), ("Deregulation of the hedgehog signalling pathway: a possible role for the PTCH and SUFU genes in human rhabdomyoma and rhabdomyosarcoma development," Tostar U, Malm C J, Meis-Kindblom J M, et al (2006), Journal of Pathology; 208 (1):17-25), and Chondrosarcoma ("Constitutive hedgehog signaling in chondrosarcoma up-regulates tumor cell proliferation," Tiet T D, Hopyan S, Nadesan P, et al (2006), American Journal of Pathology; 168 (1):321-30).

Hedgehog pathway inhibitors (e.g. cyclopamine) have been shown to be useful in the treatment of psoriasis ("Cyclopamine: inhibiting hedgehog in the treatment of psoriasis" Cutis, 2006, 78(3):185-8; Br. J. Dermatology, 2006 April; 154(4):619-23, "Psoriatic skin expresses the transcription factor Gli1: possible contribution of decreased neurofibromin expression", Endo H, Momota Y, Oikawa A, Shinkai H.).

Malignant lymphoma (ML) involves the cells of the lymphatic system, and is the fifth most common cancer in the U.S. ML includes Hodgkin's disease, and non-Hodgkin's diseases which are a heterogeneous group of lymphoid proliferative diseases. Hodgkin's disease accounts for approximately 14% of all malignant lymphomas. The non-Hodgkin's lymphomas are a diverse group of malignancies that are predominately of B-cell origin. These lymphomas have been divided into low-, intermediate-, and high-grade categories by virtue of their natural histories (see "The Non-Hodgkin's Lymphoma Pathologic Classification Project," Cancer 49:2112-2135, 1982). The low-grade lymphomas are indolent, with a median survival of 5 to 10 years (Horning and Rosenberg, N. Engl. J. Med. 311:1471-1475, 1984). Although chemotherapy can induce remissions in the majority of indolent lymphomas, cures are rare and most patients eventually relapse, requiring further therapy. The intermediate- and high-grade lymphomas are more aggressive tumors, but they have a greater chance for cure with chemotherapy. However, a significant proportion of these patients will relapse and require further treatment.

Multiple myeloma (MM) is malignant tumor composed of plasma cells of the type normally found in the bone marrow. These malignant plasma cells accumulate in bone marrow and typically produce monoclonal IgG or IgA molecules. The malignant plasma cells home to and expand in the bone marrow causing anemia and immunosuppression due to loss of normal hematopoiesis. Individuals suffering from multiple myeloma often experience anemia, osteolytic lesions, renal failure, hypercalcemia, and recurrent bacterial infections. MM represents the second most common hematopoietic malignancy.

The present invention is predicated in part on the discoveries by the present inventors that lymphoma and multiple myeloma diseases are dependent on the hedgehog (Hh) signaling pathway using lymphoma and plasmacytoma cells isolated from transgenic Eµ-Myc mice and Cdkn2a knockout mice, and discovering that hedgehog ligands mediate the interaction between stroma and lymphoma cells. The same was found for lymphoma and multiple myeloma samples isolated from patient samples from the bone (multiple myeloma) or from lymph nodes, bone marrow or spleens from non-Hodgkin's lymphoma (NHL) patients and also for chronic lymphocytic leukemia (CLL) samples. In addition, it was found that inhibition of the Hh signaling pathway induces apoptosis of stroma dependent lymphoma cells, and that overexpression of hedgehog pathway members inhibit cyclopamine induced apoptosis of lymphoma cells in vitro. Further, the inventors found that treating mice with hedgehog pathway inhibitors abrogates lymphoma expansion in vivo. Finally, the inventors discovered that there is no expression of Gli3 in spleen B-cells and in the majority of cyclopamine responsive lymphomas, but a predominant expression in all cyclopamine resistant lymphomas.

These data indicate that Hh signaling provides an important anti-apoptotic signal for the initial steps of transformation by c-Myc and plays an important role for lymphoma maintenance. Thus, disruption of the Hh signaling pathway provides novel means for treating lymphomas (e.g., NHL), multiple myelomas, CLL and other hematopoietic malignancies. In addition, expression of Gli3 in lymphomas provides a negative predictive factor for responsiveness to Hh inhibition and an important means for patient stratification.

In accordance with these discoveries, provided herein are methods, compounds and compositions for inhibiting growth of tumor cells. In addition, the methods, compounds and compositions are also used to prevent tumorigenesis in a subject. Such methods involve administering to the subject in need of treatment a pharmaceutical composition that contains one or more compounds of Formula (I), wherein such compounds are an antagonizing agent of Hh signaling. In certain embodiments, such compounds down-regulate cellular level or inhibit a biological activity of an Hh signaling pathway member. In certain embodiments, such methods, compounds and compositions are used to treat lymphoma and/or myeloma in a subject by inhibiting growth of tumor cells. In other embodiments, such methods, compounds and compositions are directed to treating lymphomas which do not have significant expression of Gli3 relative to spleen B cells.

This methods provided herein are either prophylactic or therapeutic treatment of Hedgehog-related disorders and/or Hedgehog-related diseases. Such methods involve administering to a subject in need of treatment a pharmaceutical composition that contains a therapeutically effective amount of one or more compounds of Formula (I), wherein such compounds are an antagonizing agent of Hh signaling. In certain embodiments, such prophylactic or therapeutic treatment methods are used to treat cancers of the blood and lymphatic systems, including but not limited to, lymphomas, leukemia, and myelomas. Lymphoma is malignant tumor of lymphoblasts derived from B lymphocytes. Myeloma is a malignant tumor composed of plasma cells of the type normally found in the bone marrow. Leukemia is an acute or chronic disease that involves the blood forming organs. NHLs are characterized by an abnormal increase in the number of leucocytes in the tissues of the body with or without a corresponding increase of those in the circulating blood and are classified according to the type of leucocyte most prominently involved. In certain embodiments, compounds of Formula (I) are antagonist of hedgehog signaling pathway and thereby inhibit growth and proliferation of lymphoma cells, leukemia cells, or myeloma cells.

In certain embodiments, subjects suffering from or at risk of development of lymphoma (such as, by way of example only, B-cell lymphoma, plasmoblastoma, plasmacytoma or CLL) are treated with methods, compounds and compositions provided herein. The methods entail administering to the subject a pharmaceutical composition containing an effective amount of one or more compounds of Formula (I) to inhibit the hedgehog signaling pathway. Such subjects include humans and non-human animals including, but not limited to, cows, horses, sheep, pigs, cats, dogs, mice, rats, rabbits, guinea pigs and monkeys. In certain embodiments, such subjects are human beings. In such embodiments, the subject diagnosed with lymphoma is at any stage of the disease (e.g., stage I to IV, Ann Arbor Staging System) and is either with or without metastasis. Lymphomas suitable for treatment with methods, compounds and compositions provided herein include, but are not limited to, Hodgkin's disease and non-Hodgkin's disease.

Hodgkin's disease is a human malignant disorder of lymph tissue (lymphoma) that appears to originate in a particular lymph node and later spreads to the spleen, liver and bone marrow. It occurs mostly in individuals between the ages of 15 and 35. It is characterized by progressive, painless enlargement of the lymph nodes, spleen and general lymph tissue. Classic Hodgkin's disease is divided into four subtypes: (1) nodular sclerosis Hodgkin's disease (NSHD); (2) mixed cellularity Hodgkin's disease (MCHD); (3) lymphocyte depletion Hodgkin's disease (LDHD); and (4) lymphocyte-rich classic Hodgkin's disease (cLRHD).

Non-Hodgkin's disease, also referred to herein as lymphosarcoma or Non-Hodgkin's Lymphoma (NHL), is a group of lymphomas which are classified according to the microscopic appearance of the cancer cells, and differ in important ways from Hodgkin's disease. Non-Hodgkin's lymphoma includes, but is not limited to, (1) slow-growing lymphomas and lymphoid leukemia (such as, by way of example only, chronic lymphocytic leukemia, small lymphocytic leukemia, lymphoplasmacytoid lymphoma, follicle center lymphoma, follicular small cleaved cell, follicular mixed cell, marginal zone B-cell lymphoma, hairy cell leukemia, plasmacytoma, myeloma, large granular lymphocyte leukemia, mycosis fungoides, szary syndrome); (2) moderately aggressive lymphomas and lymphoid leukemia (such as, by way of example only, prolymphocytic leukemia, mantle cell lymphoma, follicle center lymphoma, follicular small cleaved cell, follicle center lymphoma, chronic lymphocytic leukemia/prolymphocytic leukemia, angiocentric lymphoma, angioimmunoblastic lymphoma); (3) aggressive lymphomas (such as, by way of example only, large B-cell lymphoma, peripheral T-cell lymphomas, intestinal T-cell lymphoma, anaplastic large cell lymphoma); and (4) highly aggressive lymphomas and lymphoid leukemia (such as, by way of example only, B-cell precursor B-lymphoblastic leukemia/lymphoma, Burkitt's lymphoma, high-grade B-cell lymphoma, Burkitt's-like T-cell precursor T-lymphoblastic leukemia/lymphoma).

In certain embodiments, the methods, compounds and compositions provided herein are used to treat Hodgkin's disease, including, but not limited to, nodular sclerosis Hodgkin's disease (NSHD), mixed cellularity Hodgkin's disease (MCHD), lymphocyte depletion Hodgkin's disease (LDHD) and lymphocyte-rich classic Hodgkin's disease (cLRHD).

In certain embodiments, the methods, compounds and compositions provided herein are used to treat non-Hodgkin's Lymphoma (NHL) including, but is not limited to, chronic lymphocytic leukemia (CLL), small lymphocytic leukemia, lymphoplasmacytoid lymphoma, follicle center lymphoma, follicular small cleaved cell, follicular mixed cell, marginal zone B-cell lymphoma, hairy cell leukemia, plasmacytoma, myeloma, large granular lymphocyte leukemia, mycosis fungoides, szary syndrome, prolymphocytic leukemia, mantle cell lymphoma, follicle center lymphoma, follicular small cleaved cell, follicle center lymphoma, chronic lymphocytic leukemia/prolymphocytic leukemia, angiocentric lymphoma, angioimmunoblastic lymphoma, large B-cell lymphoma, peripheral T-cell lymphomas, intestinal T-cell lymphoma, anaplastic large cell lymphoma, B-cell precursor B-lymphoblastic leukemia/lymphoma, Burkitt's lymphoma, high-grade B-cell lymphoma and Burkitt's-like T-cell precursor T-lymphoblastic leukemia/lymphoma. The methods, compounds and compositions provided herein are useful in the treatment of adult or childhood forms of lymphoma, as well as lymphomas at any stage, e.g., stage I, II, III, or IV. In certain embodiments, the methods, compounds and compositions provided herein are used to treat other forms of leukemia including, but not limited to, acute lymphocytic leukemia (ALL).

In other embodiments, the methods, compounds and compositions provided herein are used to treat lymphomas or myelomas which do not express Gli3. As disclosed in the Examples below, it was observed that, while Gli1 and Gli2 were expressed in all lymphomas, detectable Gli3 expression was present mainly in lymphomas which were resistant to Hh pathway inhibition by cyclopamine. There is no expression of Gli3 in normal spleen B-cells and in the majority of cyclopamine responsive lymphomas. Therefore, prior to administration with a compound of Formula (I) or a pharmaceutical composition containing a compound of Formula (I), the treatment methods provided herein further includes analysis of a lymphoma cell sample obtained from a subject with lymphoma for expression of Gli3. Gli3 expression levels in the sample are compared to Gli3 expression levels in normal spleen B cells obtained from the subject. Gli3 expression levels in the lymphoma or myeloma samples and the control cells are determined using methods well known in the art, including, but not limited to those described in the Examples below. Responsiveness to treatment with a Hh antagonists (compounds of Formula (I)) provided herein is indicated by the lack of detectable Gli3 expression in the lymphoma or myeloma samples, or an expression level that is not significantly higher (e.g., not more than 25%, 50%, or 100% higher) than Gli3 expression level in the normal B cell. In certain embodiments, such pre-screening for lack of Gli3 expression is used as a method for patient stratification independent of administration of a compound of Formula (I) or a pharmaceutical composition containing a compound of Formula (I).

In other embodiments, such pre-screening for lack of Gli3 expression is used as a method for patient stratification followed by administration of a compound of Formula (I) or a pharmaceutical composition containing a compound of Formula (I).

In addition to lymphomas, the methods, compounds and compositions provided herein are also used for the treatment of myelomas. Multiple myeloma is a fatal neoplasm characterized by an accumulation of a clone of plasma cells, frequently accompanied by the secretion of Ig chains. Bone marrow invasion by the tumor is associated with anemia, hypogammaglobinemia, and granulocytopenia with concomitant bacterial infections. An abnormal cytokine environment, principally raised IL-6 and IL-1β levels, often results in increased osteoclasis leading to bone pain, fractures, and hypercalcemia. Despite aggressive chemotherapy and transplantation, multiple myeloma is a universally fatal plasma proliferative disorder.

In other embodiments, the methods, compounds and compositions provided herein are useful in the treatment of hedgehog related disorders such as basal cell nevus syndrome (also called Gorlin's syndrome and/or nevoid basal cell carcinoma), a rare autosomal dominant cancer genetic syndrome.

In other embodiments, the methods, compounds and compositions provided herein are useful in the treatment of basal cell carcinoma (BCC or rodent ulcer), tumors of the adrenal glands arising from the cortex or the medulla part of the adrenal gland medulla, and ovarian tumors.

In other embodiments, the methods, compounds and compositions provided herein are useful in the treatment of bone overgrowth disorders including, but are not limited to, acromegaly, macrocephaly, Sotos syndrome, progressive diaphyseal dysplasia (PDD or Camurati-Engelmann disease), craniodiaphyseal dysplasia, and endosteal hyperostosis disorders including Van Buchem disease (types I and II) and sclerosteosis.

In other embodiments, the methods, compounds and compositions provided herein are useful in the treatment of unwanted hair growth, for example, hairy moles and cosmetic prevention of hair regrowth after epilation.

In other embodiments, the methods, compounds and compositions provided herein are useful in the treatment of liver fibrosis.

In certain embodiments compounds of Formula (I) interfere with aspects of hedgehog, Ptc, or smoothened signal transduction activity and thereby inhibit proliferation (or other biological consequences) in normal cells and/or cells having a patched loss-of-function phenotype, a hedgehog gain-of-function phenotype, a smoothened gain-of-function phenotype, a Gli gain-of-function phenotype, or an over expression of hedgehog ligands phenotype. Thus, in certain embodiments, such compounds are useful for inhibiting hedgehog activity in normal cells, such as those that do not have a genetic mutation that activates the hedgehog pathway. In other embodiments, compounds of Formula (I) inhibit at least one or more of the biological activities of hedgehog proteins, including those specifically in target cells.

In other embodiments, the methods, compounds and compositions provided herein agonize Ptc inhibition of Hedgehog signaling, such as by inhibiting activation of smoothened or downstream components of the signal pathway in the regulation of repair and/or functional performance of a wide range of cells, tissues and organs, including normal cells, tissues, and organs, as well as those having the phenotype of Ptc loss-of-function, Hedgehog gain-of-function, smoothened gain-of-function or Gli gain-of-function. In addition, the methods, compounds and compositions provided herein, have therapeutic and cosmetic applications ranging from regulation of neural tissues, bone and cartilage formation and repair, regulation of spermatogenesis, regulation of smooth muscle, regulation of lung, liver and other organs arising from the primitive gut, regulation of hematopoietic function, regulation of skin and hair growth, regulation of benign prostate hyperplasia, regulation of blood vessel formation in wet macular degeneration, and regulation of psoriasis. Moreover, the subject methods can be performed on cells which are provided in culture (in-vitro), or on cells in a whole animal (in-vivo).

In another embodiment, the methods, compounds and compositions provided herein are used to treat epithelial cells having a phenotype of Ptc loss-of-function, Hedgehog gain-of-function, smoothened gain-of-function or Gli gain-of-function. In certain embodiments, the methods, compounds and compositions provided herein are used to treat or prevent basal cell carcinoma or other Hedgehog pathway-related disorders or diseases.

In another embodiment, the methods, compounds and compositions provided herein are used as part of a treatment regimen for malignant medulloblastomas and other primary CNS malignant neuroectodermal tumors.

The methods, compounds and compositions provided herein are used to treat or prevent tumor formation, cancer, neoplasia, malignant hyperproliferative disorders, non-malignant hyperproliferative disorders, benign prostate hyperplasia, psoriasis, wet macular degeneration, osteopetrosis, unwanted hair growth, prostate cancer, breast cancer, medulloblastoma, non-melanoma skin cancer, squamous cell carcinoma, basal cell carcinoma, pancreatic cancer, esophageal cancer, stomach cancer, biliary cancer, digestive tract tumors, small-cell lung cancer, colon cancer, colorectal cancer, glioma, glioblastoma, melanoma, non-small cell lung cancer, ovarian cancer, renal cancer, rhabdomyosarcoma, rhabdomyoma, chondosarcoma, psoriasis, multiple-myloma, malignant lymphoma, Hodgkin's disease and non-Hodgkin's disease.

The therapeutic methods provided herein employ an antagonist of the hedgehog signaling pathway to inhibit growth and proliferation of psoriasis, lymphoma cells, leukemia cells, or myeloma cells. These methods involve contacting such a tumor cell (in vitro or in vivo) with a compound of Formula (I), thereby inhibiting the Hh signaling pathway.

The methods, compounds and compositions provided herein makes available methods, compounds and compositions for inhibiting activation of the hedgehog signaling pathway, e.g., to inhibit aberrant growth states resulting from phenotypes such as Ptc loss-of-function, hedgehog gain-of-function, smoothened gain-of-function or Gli gain-of-function. Such methods comprise contacting a cell with a compound of Formula (I) in a sufficient amount to agonize a normal Ptc activity, antagonize a normal hedgehog activity, antagonize smoothened activity, or antagonize Gli activity e.g., to reverse or control the aberrant growth state.

In certain embodiments, compounds of Formula (I) are antagonist that inhibit activation of a Hedgehog pathway by binding to smoothened or its downstream proteins. In other embodiments, compounds of Formula (I) are antagonist that inhibit activation of a Hedgehog pathway by binding to patched or its downstream proteins.

The methods of treatment provide herein are effective for both human and animal subjects. Animal subjects include both domestic animals and livestock, raised either as pets or for commercial purposes. Examples include, but are not limited to, dogs, cats, cattle, horses, sheep, hogs, and goats.

In accordance with the foregoing, the present invention further provides a method for preventing or treating any of the diseases or disorders described above in a subject in need of such treatment, which method comprises administering to a subject a therapeutically effective amount (See, "Administration and Pharmaceutical Compositions", infra) of a compound of Formula (I) or a pharmaceutically acceptable salt, solvate, N-oxide, prodrug or isomers thereof. Also provided herein are methods for preventing or treating any of the diseases or disorders described above in a subject in need of such treatment, which method comprises administering to a subject a pharmaceutical compositions containing therapeutically effective amount of a compound of Formula (I) or a pharmaceutically acceptable salt, solvate, N-oxide, prodrug or isomers thereof. For any of the above uses, the required dosage will vary depending on the mode of administration, the particular condition to be treated and the effect desired.

Administration and Pharmaceutical Compositions

For the therapeutic uses of compounds of Formula (I), or pharmaceutically acceptable salts, solvates, N-oxides, prodrugs and isomers thereof, described herein, such compounds are administered in therapeutically effective amounts either alone or as part of a pharmaceutical composition. Accordingly, provided herein are pharmaceutical compositions, which comprise at least one compound of Formulas (I) described herein, pharmaceutically acceptable salts and/or solvates thereof, and one or more pharmaceutically acceptable carriers, diluents, or excipients. In addition, such compounds and compositions are administered singly or in combination with one or more additional therapeutic agents. The method of administration of such compounds and compositions include, but are not limited to, oral administration, rectal administration, parenteral, intravenous administration, intravitreal administration, intramuscular administration, inhalation, intranasal administration, topical administration, ophthalmic administration or otic administration.

In certain embodiments such compounds of Formula (I) are Hedgehog signaling modulators, including Ptc agonists, a smoothened antagonists, and downstream hedgehog pathway protein antagonists, formulated in an amount sufficient to inhibit, in-vivo, proliferation or other biological consequences of Ptc loss-of-function, hedgehog gain-of-function, smoothened gain-of-function or Gli gain-of-function.

The therapeutically effective amount will vary depending on, among others, the disease indicated, the severity of the disease, the age and relative health of the subject, the potency of the compound administered, the mode of administration and the treatment desired. In certain embodiments, the daily dosage of a compound of Formula (I), satisfactory results are indicated to be obtained systemically at daily dosages of from about 0.03 to 2.5 mg/kg per body weight. In certain embodiments, the daily dosage of a compound of Formula (I), administered by inhalation, is in the range from 0.05 micrograms per kilogram body weight (μg/kg) to 100 micrograms per kilogram body weight (μg/kg). In other embodiments, the daily dosage of a compound of Formula (I), administered orally, is in the range from 0.01 micrograms per kilogram body weight (μg/kg) to 100 milligrams per kilogram body weight (mg/kg). An indicated daily dosage in the larger mammal, e.g. humans, is in the range from about 0.5 mg to about 100 mg of a compound of Formula (I), conveniently administered, e.g. in divided doses up to four times a day or in controlled release form. In certain embodiment, unit dosage forms for oral administration comprise from about 1 to 50 mg of a compound of Formula (I).

Other aspects provided herein are processes for the preparation of pharmaceutical composition which comprise at least one compound of Formulas (I) described herein, or pharmaceutically acceptable salts and/or solvates thereof. In certain embodiments, such processes include admixing a compound of the Formula (I) described herein, and pharmaceutically acceptable salts and solvates thereof, with one or more pharmaceutically acceptable carriers, diluents or excipients. In certain embodiments, the pharmaceutical compositions comprising a compound of Formula (I) in free form or in a pharmaceutically acceptable salt or solvate form, in association with at least one pharmaceutically acceptable carrier, diluent or excipient are manufactured by mixing, granulating and/or coating methods. In other embodiments, such compositions are optionally contain excipients, such as preserving, stabilizing, wetting or emulsifying agents, solution promoters, salts for regulating the osmotic pressure and/or buffers. In other embodiments, such compositions are sterilized.

Oral Dosage Forms

In certain embodiments, the pharmaceutical compositions containing at least one compound of Formula (I) are administered orally as discrete dosage forms, wherein such dosage forms include, but are not limited to, capsules, gelatin capsules, caplets, tablets, chewable tablets, powders, granules, syrups, flavored syrups, solutions or suspensions in aqueous or non-aqueous liquids, edible foams or whips, and oil-in-water liquid emulsions or water-in-oil liquid emulsions.

The capsules, gelatin capsules, caplets, tablets, chewable tablets, powders or granules, used for the oral administration of at least one compound of Formula (I) are prepared by admixing at least one compound of Formula (I) (active ingredient) together with at least one excipient using conventional pharmaceutical compounding techniques. Non-limiting examples of excipients used in oral dosage forms described herein include, but are not limited to, binders, fillers, disintegrants, lubricants, absorbents, colorants, flavors, preservatives and sweeteners.

Non-limiting examples of such binders include, but are not limited to, corn starch, potato starch, starch paste, pre-gelatinized starch, or other starches, sugars, gelatin, natural and synthetic gums such as acacia, sodium alginate, alginic acid, other alginates, tragacanth, guar gum, cellulose and its derivatives (by way of example only, ethyl cellulose, cellulose acetate, carboxymethyl cellulose calcium, sodium carboxymethylcellulose, methyl cellulose, hydroxypropyl methylcellulose and microcrystalline cellulose), magnesium aluminum silicate, polyvinyl pyrrolidone and combinations thereof.

Non-limiting examples of such fillers include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. In certain embodiments, the binder or filler in pharmaceutical compositions provided herein are present in from about 50 to about 99 weight percent of the pharmaceutical composition or dosage form.

Non-limiting examples of such disintegrants include, but are not limited to, agar-agar, alginic acid, sodium alginate, calcium carbonate, sodium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and combinations thereof. In certain embodiments, the amount of disintegrant used in the pharmaceutical compositions provided herein is from about 0.5 to about 15 weight percent of disintegrant, while in other embodiments the amount is from about 1 to about 5 weight percent of disintegrant.

Non-limiting examples of such lubricants include, but are not limited to, sodium stearate, calcium stearate, magnesium stearate, stearic acid, mineral oil, light mineral oil, glycerin, sorbitol, mannitol, polyethylene glycol, other glycols, sodium lauryl sulfate, talc, hydrogenated vegetable oil (by way of example only, peanut oil, cottonseed oil, sunflower oil, sesame oil, olive oil, corn oil, and soybean oil), zinc stearate, sodium oleate, ethyl oleate, ethyl laureate, agar, silica, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.) and combinations thereof. In certain embodiments, the amount of lubricants used in the pharmaceutical compositions provided herein is in an amount of less than about 1 weight percent of the pharmaceutical compositions or dosage forms.

Non-limiting examples of such diluents include, but are not limited to, lactose, dextrose, sucrose, mannitol, sorbitol, cellulose, glycine or combinations thereof.

In certain embodiments, tablets and capsules are prepared by uniformly admixing at least one compound of Formula (I) (active ingredients) with liquid carriers, finely divided solid carriers, or both, and then shaping the product into the desired presentation if necessary. In certain embodiments, tablets are prepared by compression. In other embodiments, tablets are prepared by molding.

In certain embodiments, at least one compound of Formula (I) is orally administered as a controlled release dosage form. Such dosage forms are used to provide slow or controlled-release of one or more compounds of Formula (I). Controlled release is obtained using, for example, hydroxypropylmethyl cellulose, other polymer matrices, gels, permeable membranes, osmotic systems, multilayer coatings, microparticles, liposomes, microspheres, or a combination thereof. In certain embodiments, controlled-release dosage forms are used to extend activity of the compound of Formula (I), reduce dosage frequency, and increase patient compliance.

Administration of compounds of Formula (I) as oral fluids such as solution, syrups and elixirs are prepared in unit dosage forms such that a given quantity of solution, syrups or elixirs contains a predetermined amount of a compound of Formula (I). Syrups are prepared by dissolving the compound in a suitably flavored aqueous solution, while elixirs are prepared through the use of a non-toxic alcoholic vehicle. Suspensions are formulated by dispersing the compound in a non-toxic vehicle. Non-limiting examples of excipients used in as oral fluids for oral administration include, but are not limited to, solubilizers, emulsifiers, flavoring agents, preservatives, and coloring agents. Non-limiting examples of solubilizers and emulsifiers include, but are not limited to, water, glycols, oils, alcohols, ethoxylated isostearyl alcohols and polyoxy ethylene sorbitol ethers. Non-limiting examples of preservatives include, but are not limited to, sodium benzoate. Non-limiting examples of flavoring agents include, but are not limited to, peppermint oil or natural sweeteners or saccharin or other artificial sweeteners.

Parenteral Dosage Forms

In certain embodiments pharmaceutical compositions containing at least one compound of Formula (I) are administered parenterally by various routes including, but not limited to, subcutaneous, intravenous (including bolus injection), intramuscular, and intraarterial.

Such parenteral dosage forms are administered in the form of sterile or sterilizable injectable solutions, suspensions, dry and/or lyophylized products ready to be dissolved or suspended in a pharmaceutically acceptable vehicle for injection (reconstitutable powders) and emulsions. Vehicles used in such dosage forms include, but are not limited to, Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Transdermal Dosage Forms

In certain embodiments pharmaceutical compositions containing at least one compound of Formula (I) are administered transdermally. Such transdermal dosage forms include "reservoir type" or "matrix type" patches, which are applied to the skin and worn for a specific period of time to permit the penetration of a desired amount of a compound of Formula (I). By way of example only, such transdermal devices are in the form of a bandage comprising a backing member, a reservoir containing the compound optionally with carriers, optionally a rate controlling bather to deliver the compound to the skin of the host at a controlled and predetermined rate over a prolonged period of time, and means to secure the device to the skin. In other embodiments, matrix transdermal formulations are used.

Formulations for transdermal delivery of a compound of Formula (I) include an effective amount of a compound of Formula (I), a carrier and an optional diluent. A carrier includes, but is not limited to, absorbable pharmacologically acceptable solvents to assist passage through the skin of the host, such as water, acetone, ethanol, ethylene glycol, propylene glycol, butane-1,3-diol, isopropyl myristate, isopropyl palmitate, mineral oil, and combinations thereof.

In certain embodiments, such transdermal delivery systems include penetration enhancers to assist in delivering one or more compounds of Formula (I) to the tissue. Such penetration enhancers include, but are not limited to, acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

In other embodiments, the pH of such a transdermal pharmaceutical composition or dosage form, or of the tissue to which the pharmaceutical composition or dosage form is applied, is adjusted to improve delivery of one or more compounds of Formula (I). In other embodiments, the polarity of a solvent carrier, its ionic strength, or tonicity are adjusted to improve delivery. In other embodiments, compounds such as stearates are added to advantageously alter the hydrophilicity or lipophilicity of one or more compounds of Formula (I) so as to improve delivery. In certain embodiments, such stearates serve as a lipid vehicle for the formulation, as an emulsifying agent or surfactant, and as a delivery-enhancing or penetration-enhancing agent. In other embodiments, different salts, hydrates or solvates of the compounds of Formula (I) are used to further adjust the properties of the resulting composition.

Topical Dosage Forms

In certain embodiments at least one compound of Formula (I) is administered by topical application of pharmaceutical composition containing at least one compound of Formula (I) in the form of lotions, gels, ointments solutions, emulsions, suspensions or creams. Suitable formulations for topical application to the skin are aqueous solutions, ointments, creams or gels, while formulations for ophthalmic administration are aqueous solutions. Such formulations optionally contain solubilizers, stabilizers, tonicity enhancing agents, buffers and preservatives.

Such topical formulations include at least one carrier, and optionally at least one diluent. Such carriers and diluents include, but are not limited to, water, acetone, ethanol, ethylene glycol, propylene glycol, butane-1,3-diol, isopropyl myristate, isopropyl palmitate, mineral oil, and combinations thereof.

In certain embodiments, such topical formulations include penetration enhancers to assist in delivering one or more compounds of Formula (I) to the tissue. Such penetration enhancers include, but are not limited to, acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

In certain embodiments pharmaceutical compositions containing at least one compound of Formula (I) are administered by inhalation. Dosage forms for inhaled administration are formulated as aerosols or dry powders. Aerosol formulations for inhalation administration comprise a solution or fine suspension of at least one compound of Formula (I) in a pharmaceutically acceptable aqueous or non-aqueous solvent. In addition, such pharmaceutical compositions optionally comprise a powder base such as lactose, glucose, trehalose, mannitol or starch, and optionally a performance modifier such as L-leucine or another amino acid, and/or metals salts of stearic acid such as magnesium or calcium stearate.

In certain embodiments, compounds of Formula (I) are be administered directly to the lung by inhalation using a Metered Dose Inhaler ("MDI"), which utilizes canisters that contain a suitable low boiling propellant, e.g., dichlorodifluoromethane, trichlorofluoromethane, dichlorotetrafluoroethane, carbon dioxide or other suitable gas, or a Dry Powder Inhaler (DPI) device which uses a burst of gas to create a cloud of dry powder inside a container, which is then be inhaled by the patient. In certain embodiments, capsules and cartridges of gelatin for use in an inhaler or insufflator are formulated containing a powder mixture of a compound of Formula (I) and a powder base such as lactose or starch. In certain embodiments, compounds of Formula (I) are delivered to the lung using a liquid spray device, wherein such devices use extremely small nozzle holes to aerosolize liquid drug formulations that can then be directly inhaled into the lung. In other embodiments, compounds of Formula (I) are delivered to the lung using a nebulizer device, wherein a nebulizers creates an aerosols of liquid drug formulations by using ultrasonic energy to form fine particles that can be readily inhaled. In other embodiments, compounds of Formula (I) are delivered to the lung using an electrohydrodynamic ("EHD") aerosol device wherein such EHD aerosol devices use electrical energy to aerosolize liquid drug solutions or suspensions.

In certain embodiments, the pharmaceutical composition containing at least one compound of Formula (I), or pharmaceutically acceptable salts and solvates thereof, described herein, also contain one or more absorption enhancers. In certain embodiments, such absorption enhancers include, but are not limited to, sodium glycocholate, sodium caprate, N-lauryl-β-D-maltopyranoside, EDTA, and mixed micelles.

In certain embodiments pharmaceutical compositions containing at least one compound of Formula (I) are administered nasally. The dosage forms for nasal administration are formulated as aerosols, solutions, drops, gels or dry powders.

In certain embodiments pharmaceutical compositions containing at least one compound of Formula (I) are administered rectally in the form of suppositories, enemas, ointment, creams rectal foams or rectal gels. In certain embodiments such suppositories are prepared from fatty emulsions or suspensions, cocoa butter or other glycerides.

In certain embodiments pharmaceutical compositions containing at least one compound of Formula (I) are administered opthamically as eye drops. Such formulations are aqueous solutions that optionally contain solubilizers, stabilizers, tonicity enhancing agents, buffers and preservatives.

In certain embodiments pharmaceutical compositions containing at least one compound of Formula (I) are administered otically as ear drops. Such formulations are aqueous solutions that optionally contain solubilizers, stabilizers, tonicity enhancing agents, buffers and preservatives.

In certain embodiments pharmaceutical compositions containing at least one compound of Formula (I) are formulated as a depot preparation. Such long acting formulations are administered by implantation (for example subcutaneously or intramuscularly) or by intramuscular injection. In certain embodiments, such formulations include polymeric or hydrophobic materials (for example, as an emulsion in an acceptable oil) or ion exchange resins, or as sparingly soluble derivatives, for example, as a sparingly soluble salt.

Combination Treatment

In certain embodiments, a compound of Formulas (I) provided herein, or a pharmaceutically acceptable salt, N-oxide, isomer or solvate thereof, or a pharmaceutical composition containing at least one compound of Formula (I) provided herein, is administered alone (without an additional therapeutic agent) for the treatment of one or more of the Hedgehog-related diseases and/or disorders described herein.

In other embodiments, a compound of Formulas (I) provided herein, or a pharmaceutically acceptable salt, N-oxide, isomer or solvate thereof, or a pharmaceutical composition containing at least one compound of Formula (I) provided herein, is administered in combination with one or more additional therapeutic agents, for the treatment of one or more of the Hedgehog-related diseases and/or disorders described herein.

In other embodiments, a compound of Formulas (I) provided herein, or a pharmaceutically acceptable salt, N-oxide, isomer or solvate thereof, or a pharmaceutical composition containing at least one compound of Formula (I) provided herein, is formulated in combination with one or more additional therapeutic agents and administered for the treatment of one or more of the Hedgehog-related diseases and/or disorders described herein.

In other embodiments, a compound of Formulas (I) provided herein, or a pharmaceutically acceptable salt, N-oxide, isomer or solvate thereof, or a pharmaceutical composition containing at least one compound of Formula (I) provided herein, is administered sequentially with one or more additional therapeutic agents, for the treatment of one or more of the Hedgehog-related diseases and/or disorders described herein.

In other embodiments, the combination treatments provided herein include administration of a compound of Formulas (I) provided herein, or a pharmaceutically acceptable salt, N-oxide, isomer or solvate thereof, or a pharmaceutical composition containing at least one compound of Formula (I) provided herein, prior to administration of one or more additional therapeutic agents, for the treatment of one or more of the Hedgehog-related diseases and/or disorders described herein.

In other embodiments, the combination treatments provided herein include administration of a compound of Formulas (I) provided herein, or a pharmaceutically acceptable salt, N-oxide, isomer or solvate thereof, or a pharmaceutical composition containing at least one compound of Formula (I) provided herein, subsequent to administration of one or more additional therapeutic agents, for the treatment of one or more of the Hedgehog-related diseases and/or disorders described herein.

In certain embodiments, the combination treatments provided herein include administration of a compound of Formulas (I) provided herein, or a pharmaceutically acceptable salt, N-oxide, isomer or solvate thereof, or a pharmaceutical composition containing at least one compound of Formula (I) provided herein, concurrently with one or more additional therapeutic agents, for the treatment of one or more of the Hedgehog-related diseases and/or disorders described herein.

In certain embodiments, the combination treatments provided herein include administration of a compound of Formulas (I) provided herein, or a pharmaceutically acceptable salt, N-oxide, isomer or solvate thereof, or a pharmaceutical composition containing at least one compound of Formula (I) provided herein, formulated with one or more additional therapeutic agents, for the treatment of one or more of the Hedgehog-related diseases and/or disorders described herein.

In certain embodiments, compounds of Formula (I) provided herein are administered in therapeutically effective amounts in combination with other therapies, such as radiation therapy, bone marrow transplantation or hormone therapy.

In certain embodiments of the combination therapies described herein, the compounds of Formula (I) provided herein, or a pharmaceutically acceptable salts, N-oxides, isomers or solvates thereof, and the additional therapeutics agent(s) act additively. In other embodiments of the combination therapies described herein, the compounds of Formula (I) provided herein, or a pharmaceutically acceptable salts, N-oxides, isomers or solvates thereof, and the additional therapeutics agent(s) act synergistically.

The additional therapeutic agents used in combination with at least one compound of Formula (I) described herein, or a pharmaceutically acceptable salt, N-oxide, isomer or solvate thereof, include, but are not limited to immunomodulatory, anti-inflammatory substances, other anti-tumor therapeutic agents, chemotherapeutic agents, ablation or other therapeutic hormones, antineoplastic agents and/or monoclonal antibodies useful against lymphomas or myelomas. Some of the well known anti-cancer drugs are described in the art, e.g., *Cancer Therapeutics: Experimental and Clinical Agents*, Teicher (Ed.), Humana Press (1$^{st}$ ed., 1997); and *Goodman and Gilman's The Pharmacological Basis of Therapeutics*, Hardman et al. (Eds.), McGraw-Hill Professional (10$^{th}$ ed., 2001). Examples of suitable anti-cancer drugs include 5-fluorouracil, vinblastine sulfate, estramustine phosphate, suramin and strontium-89. Examples of suitable chemotherapeutic agents include Asparaginase, Bleomycin Sulfate, Cisplatin, Cytarabine, Fludarabine Phosphate, Mitomycin and Streptozocin.

In other embodiments, a compound of Formula (I) described herein, or a pharmaceutically acceptable salt, N-oxide, isomer or solvate thereof, or a pharmaceutical composition containing such compounds of Formula (I), is administered to a patient who has not previously undergone or is not currently undergoing treatment with another therapeutic agent.

Where the compounds of Formula (I) are administered in conjunction with other therapies, dosages of the co-administered compounds will of course vary depending on the type of co-drug employed, on the specific drug employed, on the condition being treated and so forth.

Kits

Also provided herein are pharmaceutical packs or kits that include one or more containers containing a compound of Formula (I) useful for the treatment or prevention of a Hedgehog-related disease or disorder. In other embodiments, such pharmaceutical packs or kits include one or more containers containing a compound of Formula (I) useful for the treatment or prevention of a Hedgehog-related disease or disorder and one or more containers containing an additional therapeutic agent. In certain embodiments, such pharmaceutical packs or kits optionally include instructions for its administration of a compound of Formula (I). In certain embodiments of such kits, the compound of Formula (I) is in free form or in pharmaceutically acceptable salt or N-oxide form.

One of skill in the art will appreciate that the above transformations are only representative of methods for preparation of the compounds of the present invention, and that other well known methods can similarly be used.

EXAMPLES

The compounds provided herein are further exemplified, but not limited, by the following example that illustrates the preparation of compounds of Formula (I).

Example 1

Preparation of (S)-5-(4-Chloro-3-(5-phenyl-1H-imidazol-2-yl)phenylamino)-2-(2,3-dihydroxypropyl)-3, 4-dihydroisoquinolin-1(2H)-one The preparation of (S)-5-(4-Chloro-3-(5-phenyl-1H-imidazol-2-yl)phenylamino)-2-(2,3-dihydroxypropyl)-3,4-dihydroisoquinolin-1(2H)-one is illustrated in scheme 1.

Scheme 1:

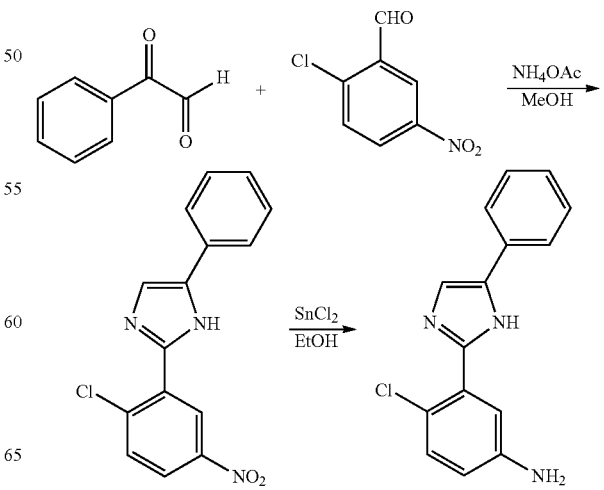

-continued

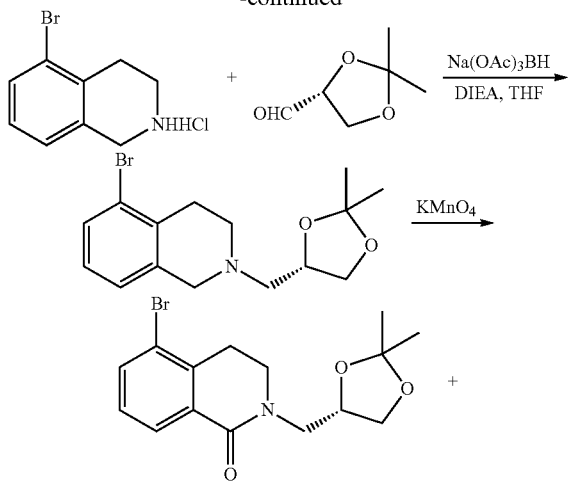

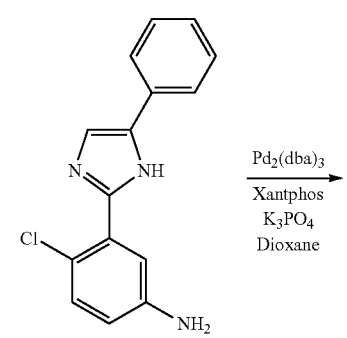

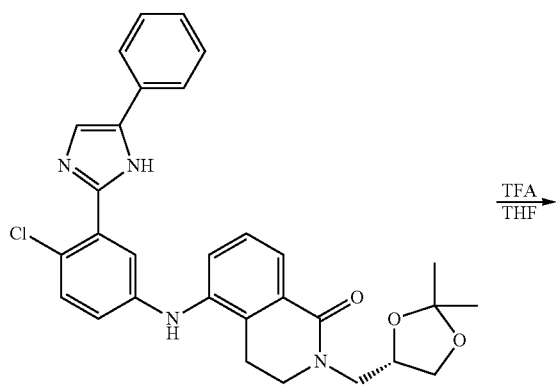

Example 1a 2-(2-Chloro-5-nitrophenyl)-5-phenyl-1H-imidazole

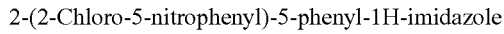

To a solution of phenylglyoxal hydrate (23.55 g, 150 mmol) and 2-chloro-5-nitrobenzaladehylde (57.45 g, 300 mmol) in MeOH (500 ml) is added ammonium acetate (117 g, 500 mmol) in small portions at room temperature. The reaction mixture is stirred at room temperature overnight, and the solvent is then removed by rotary evaporation. The residue is partitioned between dichloromethane (DCM) and water. The organic layer is separated and washed with brine, dried over anhydrous $MgSO_4$ and concentrated to yield 2-(2-Chloro-5-nitrophenyl)-5-phenyl-1H-imidazole (LC-MS m/z: 300.1 (M+1)) which is used without further purification in the next step.

Example 1b

4-Chloro-3-(5-phenyl-1H-imidazol-2-yl) aniline

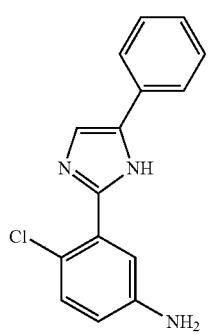 [SMILES: Nc1ccc(Cl)c(-c2ncc(-c3ccccc3)[nH]2)c1]

To a solution of 2-(2-chloro-5-nitrophenyl)-5-phenyl-1H-imidazole (27 g, 90.3 mmol) in EtOH (200 ml) is added $SnCl_2 \cdot 2H_2O$ (71 g, 316 mmol). The mixture is refluxed for 2 hours, cooled to room temperature and then concentrated. Ethyl acetate (200 ml) and NaOH (25 g in 100 ml water) are added to the residue and the mixture is stirred for 10 minutes at room temperature. The solid is removed by filtering through celite pad. The filtrate is separated and the organic layer is further washed with brine, dried over anhydrous $MgSO_4$ and concentrated. The crude product is purified by silica gel flash chromatography, eluted with 40% ethyl acetate in dichloromethane to afford 4-Chloro-3-(5-phenyl-1H-imidazol-2-yl) aniline as a brown solid. LC-MS m/z: 270.1 (M+1).

Example 1c (S)-5-Bromo-2-((2,2-dimethyl-1,3-dioxolan-4-yl)methyl)-1,2,3,4-tetrahydroisoquinoline

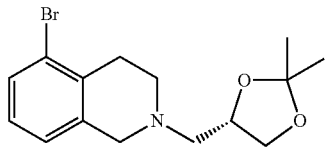 [SMILES: CC1(C)OC[C@H](CN2CCc3c(Br)cccc3C2)O1]

A mixture containing 5-bromo-1,2,3,4-tetrahydroisoquinoline hydrochloride (249 mg, 1 mmol), (R)-(+)-2,2-dimethyl-1,3-dioxolane-4-carboxyaldehyde (260 mg, 2 mmol), DIEA (0.2 ml, 1 mmol) and Na(OAc)$_3$BH (440 mg, 2 mmol) in THF (1 ml) is heated at 45° C. for 18 hours. After cooling to room temperature, the reaction mixture is diluted with ethyl acetate. The organic layer is washed with saturated aqueous NaHCO$_3$ solution, water, brine, dried over MgSO$_4$ and concentrated to dryness by rotary evaporation. The crude product is purified by silica gel flash chromatography, eluted with 30% ethyl acetate in dichloromethane to yield (S)-5-Bromo-2-((2,2-dimethyl-1,3-dioxolan-4-yl)methyl)-1,2,3,4-tetrahydroisoquinoline as a brown oil. LC-MS m/z: 326.1 (M+1).

Example 1d (S)-5-Bromo-2-((2,2-dimethyl-1,3-dioxolan-4-yl)methyl)-3,4-dihydroisoquinolin-1(2H)-one

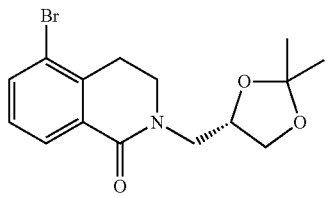 [SMILES: CC1(C)OC[C@H](CN2CCc3c(Br)cccc3C2=O)O1]

A mixture containing (S)-5-bromo-2-((2,2-dimethyl-1,3-dioxolan-4-yl)methyl)-1,2,3,4-tetrahydroisoquinoline (303 mg, 0.93 mmol), KMnO$_4$ (176 mg, 1.12 mmol), 18-crown-6 (245 mg, 0.93 mmol) in dichloromethane (4 ml) is stirred at room temperature for 18 hours. The reaction mixture is filtered through a celite pad and the filtrate is concentrated to dryness by rotary evaporation to give (S)-5-Bromo-2-((2,2-dimethyl-1,3-dioxolan-4-yl)methyl)-3,4-dihydroisoquinolin-1(2H)-one (LC-MS m/z: 341.2 (M+1)), which is used without further purification in the next step.

Example 1e (S)-5-(4-Chloro-3-(5-phenyl-1H-imidazol-2-yl)phenylamino)-2-(2,2-dimethyl-1,3-dioxolan-4-yl)methyl)-3,4-dihydroisoquinolin-1(2H)-one

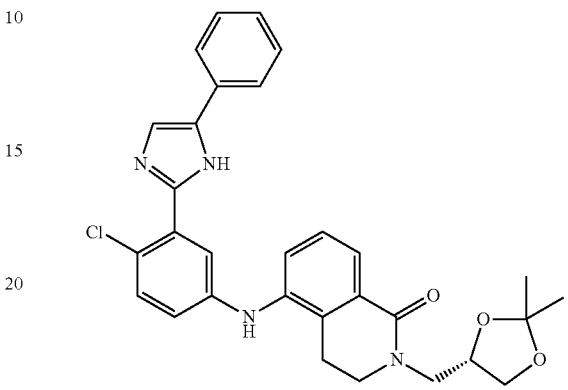

To a round-bottom flask under argon containing (S)-5-bromo-2-((2,2-dimethyl-1,3-dioxolan-4-yl)methyl)-3,4-dihydroisoquinolin-1(2H)-one (227 mg, 0.79 mmol), 4-chloro-3-(5-phenyl-1H-imidazol-2-yl) aniline (213 mg, 0.79 mmol), Pd$_2$(dba)$_3$ (143 mg, 0.158 mmol), xantphos (260 mg, 0.316 mmol), potassium phosphate (505 mg, 2.37 mmol) is added anhydrous dioxane (1.6 ml). The mixture is stirred at 96° C. for 18 hours, cooled to room temperature, filtered through a celite pad and washed with THF. The crude product is purified by flash column chromatography using 1% methanol in dichloromethane as eluent to give S)-5-(4-Chloro-3-(5-phenyl-1H-imidazol-2-yl)phenylamino)-2-(2,2-dimethyl-1,3-dioxolan-4-yl)methyl)-3,4-dihydroisoquinolin-1(2H)-one as a dark brown solid. LC-MS m/z: 530.1 (M+1).

Example 1f (S)-5-(4-Chloro-3-(5-phenyl-1H-imidazol-2-yl)phenylamino)-2-(2,3-dihydroxypropyl)-3,4-dihydroisoquinolin-1(2H)-one

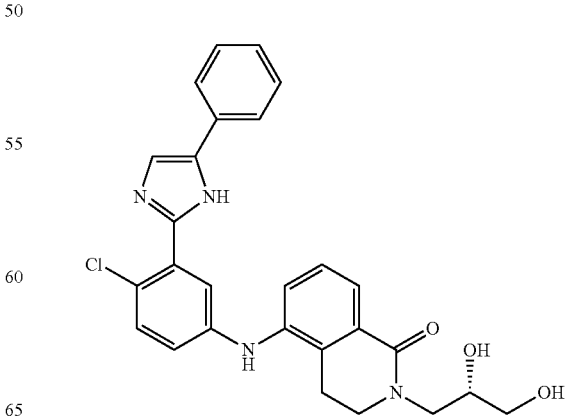

To a solution of (S)-5-(4-chloro-3-(5-phenyl-1H-imidazol-2-yl)phenylamino)-2-((2,2-dimethyl-1,3-dioxolan-4-yl)methyl)-3,4-dihydroisoquinolin-1(2H)-one (210 mg, 0.40 mmol) in THF (1.6 ml) and water (0.4 ml) is added TFA (0.1 ml) at room temperature, and the reaction mixture is stirred for 18 hours. The reaction mixture is concentrated to dryness by rotary evaporation and the crude product is purified by preparative HPLC to afford (S)-5-(4-Chloro-3-(5-phenyl-1H-imidazol-2-yl)phenylamino)-2-(2,3-dihydroxypropyl)-3,4-dihydroisoquinolin-1(2H)-one as an off-white solid. LC-MS m/z: 489.1 (M+1); $^1$H NMR 400 MHz (CDCl$_3$) δ 7.76 (d, 1H, J=7.6 Hz), 7.67-7.63 (m, 3H), 7.40-7.32 (m, 4H), 7.27-7.20 (m, 3H), 6.71-6.68 (m, 1H), 3.89-3.87 (m, 1H), 3.66-3.53 (m, 6H), 2.82 (t, 2H, J=6.8 Hz).

Example 2

2-(2,2-difluoropropyl)-N-(4-methyl-3-(5-methylpyridin-2-yl)phenyl)-1,2,3,4-tetrahydroisoquinolin-5-amine The preparation of 2-(2,2-Difluoropropyl)-N-(4-methyl-3-(5-methylpyridin-2-yl)phenyl)-1,2,3,4-tetrahydroisoquinolin-5-amine is illustrated in scheme 2.

Scheme 2:

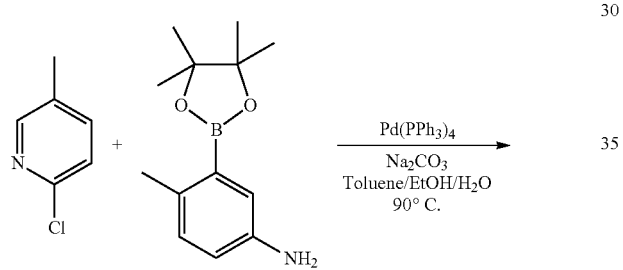

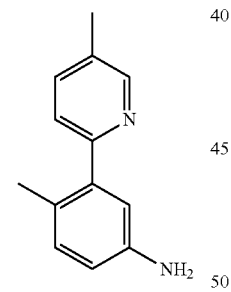

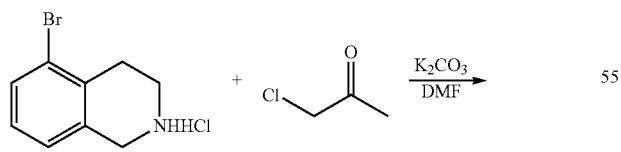

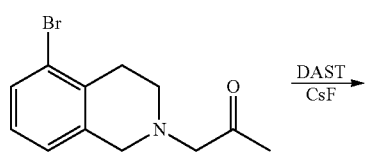

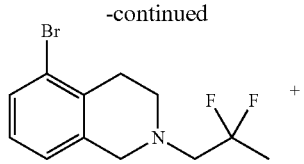

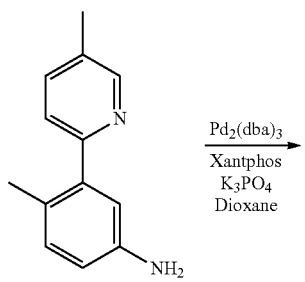

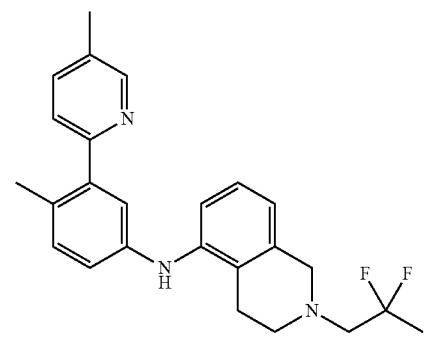

Example 2a

4-Methyl-3-(5-methylpyridin-2-yl)aniline

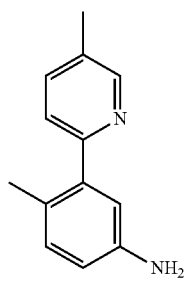

To a round-bottom flask containing 5-amino-2-methylphenylboronic acid pinacol ester (348 mg, 1.5 mmol), 2-chloro-5-methylpyridine (381 mg, 3 mmol), Pd(PPh$_3$)$_4$ (192 mg, 0.15 mmol) is added toluene (12 ml), EtOH (3 ml) and 2M aqueous Na$_2$CO$_3$ solution (3 ml). The flask is purged with argon and sealed. The mixture is stirred at 90° C. for 18 hours, cooled to room temperature and then water (20 ml) and ethyl acetate (20 ml) are added. The organic layer is separated, washed with brine, dried over MgSO$_4$ and concentrated. The residue is purified by silica gel flash chromatography, eluted with 2% methanol in dichloromethane to afford 4-Methyl-3-(5-methylpyridin-2-yl)aniline as a brown oil. LC-MS m/z: 199.1 (M+1).

Example 2b 1-(5-Bromo-3,4-dihydroisoquinolin-2(1H)-yl)propan-2-one

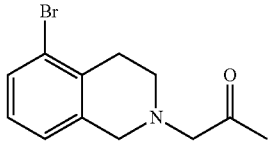

A mixture containing 5-bromo-1,2,3,4-tetrahydroisoquinoline hydrochloride (1 g, 4 mmol), chloroacetone (407 mg, 4.4 mmol) and potassium carbonate (1.38 g, 10 mmol) in dimethyl formamide (DMF) (8 ml) is stirred at room temperature for 18 hours. To this mixture is added water (50 ml) and ethyl acetate (50 ml). The organic layer is separated, washed with brine, dried over MgSO$_4$, and concentrated. The crude product is purified by flash column chromatography using 30% ethyl acetate in dichloromethane as eluent to give 1-(5-Bromo-3,4-dihydroisoquinolin-2(1H)-yl)propan-2-one as an orange oil. LC-MS m/z: 269.1 (M+1).

Example 2c

5-Bromo-2-(2,2-difluoropropyl)-1,2,3,4-tetrahydroisoquinoline

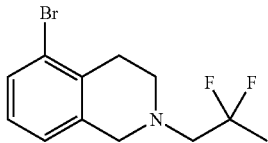 [SMILES: CC(F)(F)CN1CCc2c(Br)cccc2C1]

To a solution of 1-(5-bromo-3,4-dihydroisoquinolin-2 (1H)-yl)propan-2-one (962 mg, 3.59 mmol), diethylamino sulfur trifluoride (1.74 g, 10.8 ml) in DCM (12 ml) is added cesium fluoride (151 mg, 1 mmol) in small portions, then a few drops of TFA at room temperature. The mixture is stirred for 18 hours at room temperature. To this solution is added saturated aqueous NaHCO$_3$ to quench the reaction. The aqueous layer is extracted with DCM (50 ml×3). The combined organic layers are washed with water, brine, dried over MgSO$_4$ and concentrated. The residue is purified by silica gel flash chromatography, eluted with 20% ethyl acetate in hexanes to yield 5-Bromo-2-(2,2-difluoropropyl)-1,2,3,4-tetrahydroisoquinoline as a brown oil. LC-MS m/z: 291.1 (M+1).

Example 2d 2-(2,2-difluoropropyl)-N-(4-methyl-3-(5-methylpyridin-2-yl)phenyl)-1,2,3,4-tetrahydroisoquinolin-5-amine

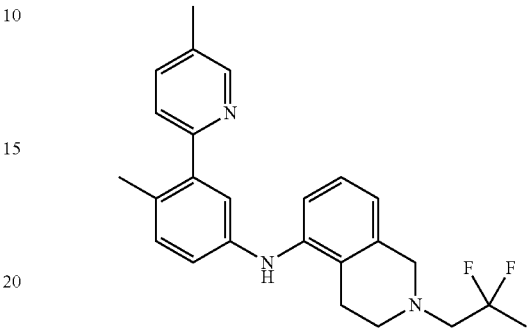

To a reaction tube under argon containing 5-bromo-2-(2, 2-difluoropropyl)-1,2,3,4-tetrahydroisoquinoline (29 mg, 0.1 mmol), 4-methyl-3-(5-methylpyridin-2-yl)aniline (20 mg, 0.1 mmol), Pd$_2$(dba)$_3$ (10 mg, 0.01 mmol), xantphos (17 mg, 0.02 mmol), potassium phosphate (60 mg, 0.3 mmol) is added anhydrous dioxane (0.5 ml). The mixture is stirred at 96° C. under argon for 18 hours, cooled to room temperature and filtered through a celite pad. The filtrate is concentrated and preparative HPLC is used to isolate 2-(2,2-Difluoropropyl)-N-(4-methyl-3-(5-methylpyridin-2-yl)phenyl)-1,2,3,4-tetrahydroisoquinolin-5-amine as a white solid. LC-MS m/z: 408.2 (M+1); $^1$H NMR 400 MHz (CDCl$_3$) δ 8.48 (s, 1H), 7.52 (dd, 2H, J=1.6, 8 Hz), 7.28 (d, 1H, J=8.0 Hz), 7.14 (d, 1H, J=8.0 Hz), 7.07-7.00 (m, 2H), 6.95 (dd, 1H, J=2.4, 8.0 Hz), 6.62 (d, 1H, J=6.8 Hz), 5.30 (s, 1H), 3.77 (s, 2H), 2.92 (t, 2H, J=6.0 Hz), 2.83 (t, 2H, J=13.6 Hz), 2.66 (t, 2H, J=6.0 Hz), 2.36 (s, 3H), 2.27 (s, 3H), 1.66 (t, 3H, J=18.8 Hz).

Example 3

N-(3-(isoquinolin-3-yl)-4-methylphenyl)-2-(1,1-dioxo-thietan-3-yl)-1,2,3,4-tetrahydroisoquinolin-5-amine The preparation of N-(3-(isoquinolin-3-yl)-4-methylphenyl)-2-(1,1-dioxo-thietan-3-yl)-1,2,3,4-tetrahydroisoquinolin-5-amine is illustrated in scheme 3.

Scheme 3:

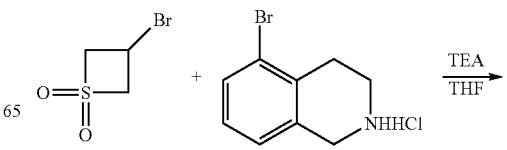

-continued

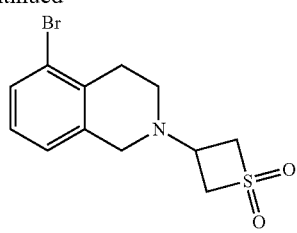

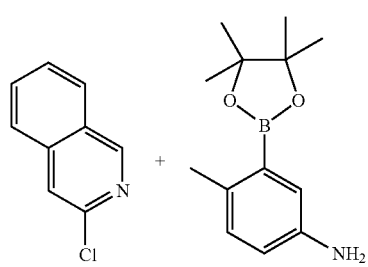

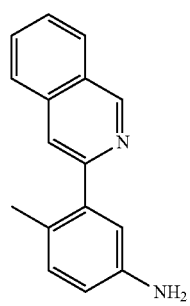

+

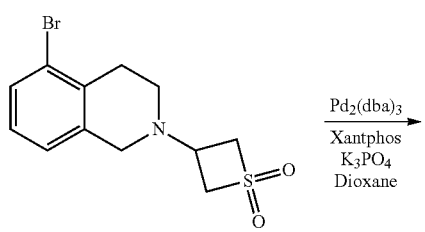

-continued

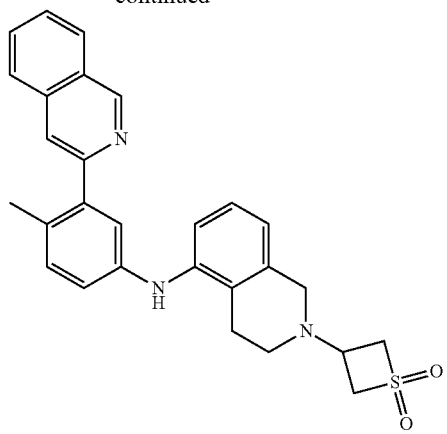

Example 3a

5-Bromo-2-(1,1-dioxo-thietan-3-yl)-1,2,3,4-tetrahydroisoquinoline

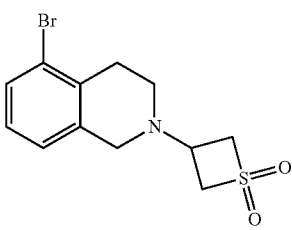 [SMILES: O=S1(=O)CC(N2CCc3c(Br)cccc3C2)C1]

To a suspension of 5-bromo-1,2,3,4-tetrahydroisoquinoline hydrochloride (249 mg, 1 mol) and 3-bromothietane, 1,1-dioxide[1] (185 mg, 1 mmol) in THF (2 ml) is added triethylamine (303 mg, 3 mmol) slowly at room temperature. The reaction mixture is stirred at room temperature for 16 hours. The mixture is diluted with ethyl acetate and washed with saturated aqueous NaHCO$_3$, water and brine. The organic layer obtained is dried over anhydrous MgSO$_4$ and concentrated. The crude residue is purified by silica gel flash chromatography, eluted with ethyl acetate in hexanes from 30% to 40% to afford 5-Bromo-2-(1,1-dioxo-thietan-3-yl)-1,2,3,4-tetrahydroisoquinoline as white solid. LC-MS m/z: 316.1 (M+1)

Example 3b 3-(isoquinolin-3-yl)-4-methylaniline

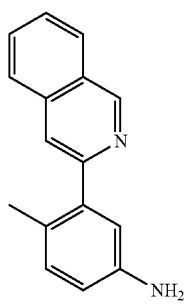 [SMILES: Cc1ccc(N)cc1-c1cc2ccccc2cn1]

To a round-bottom flask containing 5-amino-2-methyl-phenylboronic acid pinacol ester (233 mg, 1 mmol), 3-chloro-isoquinoline (245 mg, 1.5 mmol), Pd(PPh$_3$)$_4$ (128 mg, 0.1 mmol) is added toluene (4 ml), EtOH (1 ml) and aqueous 2M Na$_2$CO$_3$ solution (2 ml). The flask is purged with argon and sealed. The mixture is stirred at 90° C. for 18 hours, cooled to room temperature and extracted using water and ethyl acetate. The organic layer is separated, washed with brine, dried over MgSO$_4$ and concentrated. The residue is subjected to silica gel flash chromatography, eluted with ethyl acetate in hexanes from 30% to 50% to afford 3-(isoquinolin-3-yl)-4-methylaniline as a brown oil. LC-MS m/z: 235.1 (M+1).

Example 3c

N-(3-(isoquinolin-3-yl)-4-methylphenyl)-2-(1,1-dioxo-thietan-3-yl)-1,2,3,4-tetrahydroisoquinolin-5-amine

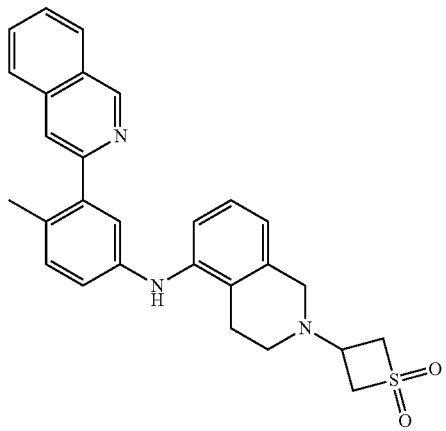 [SMILES: Cc1ccc(Nc2cccc3c2CCN(C2CS(=O)(=O)C2)C3)cc1-c1cc2ccccc2cn1]

To a reaction tube under argon containing 5-bromo-2-(1,1-dioxo-thietan-3-yl)-1,2,3,4-tetrahydroisoquinoline (70 mg, 0.22 mmol), 3-(isoquinolin-3-yl)-4-methylaniline (51 mg, 0.22 mmol), Pd$_2$(dba)$_3$ (22 mg, 0.022 mmol), xantphos (37 mg, 0.044 mmol), potassium phosphate (133 mg, 0.66 mmol) is added anhydrous dioxane (1 ml). The mixture is stirred at 96° C. for 18 hours, cooled to room temperature, filtered through a celite pad to remove solid. The filtrate is concentrated and purified by preparative HPLC to afford N-(3-(Isoquinolin-3-yl)-4-methylphenyl)-2-(1,1-dioxo-thietan-3-yl)-1,2,3,4-tetrahydroisoquinolin-5-amine as a white solid (36.2 mg, 37%). LC-MS m/z: 470.2 (M+1); $^1$H NMR 400 MHz (CDCl$_3$) δ9.31 (s, 1H), 8.00 (d, 2H, J=8.4), 7.83 (d, 1H, J=8.4 Hz), 7.72-7.70 (m, 2H), 7.61 (t, 1H, J=6.8 Hz), 7.20 (d, 1H, J=8.4 Hz), 7.13-7.09 (m, 3H), 6.94 (dd, 1H, J=2.4, 8.0 Hz), 6.70 (d, 1H, J=8.4 Hz), 5.34 (s, 1H), 4.44 (s, 2H), 3.59 (t, 2H, J=6.0 Hz), 2.97 (s, 3H), 2.82-2.78 (m, 6H), 2.34 (s, 3H).

Example 4

N-(3-(isoquinolin-3-yl)-4-methylphenyl)-7-(methylsulfonyl)-5,6,7,8-tetrahydropyrido[3,4-d]pyrimidin-4-amine The preparation of N-(3-(Isoquinolin-3-yl)-4-methylphenyl)-7-(methylsulfonyl)-5,6,7,8-tetrahydropyrido[3,4-d]pyrimidin-4-amine is illustrated in scheme 4.

Scheme 4:

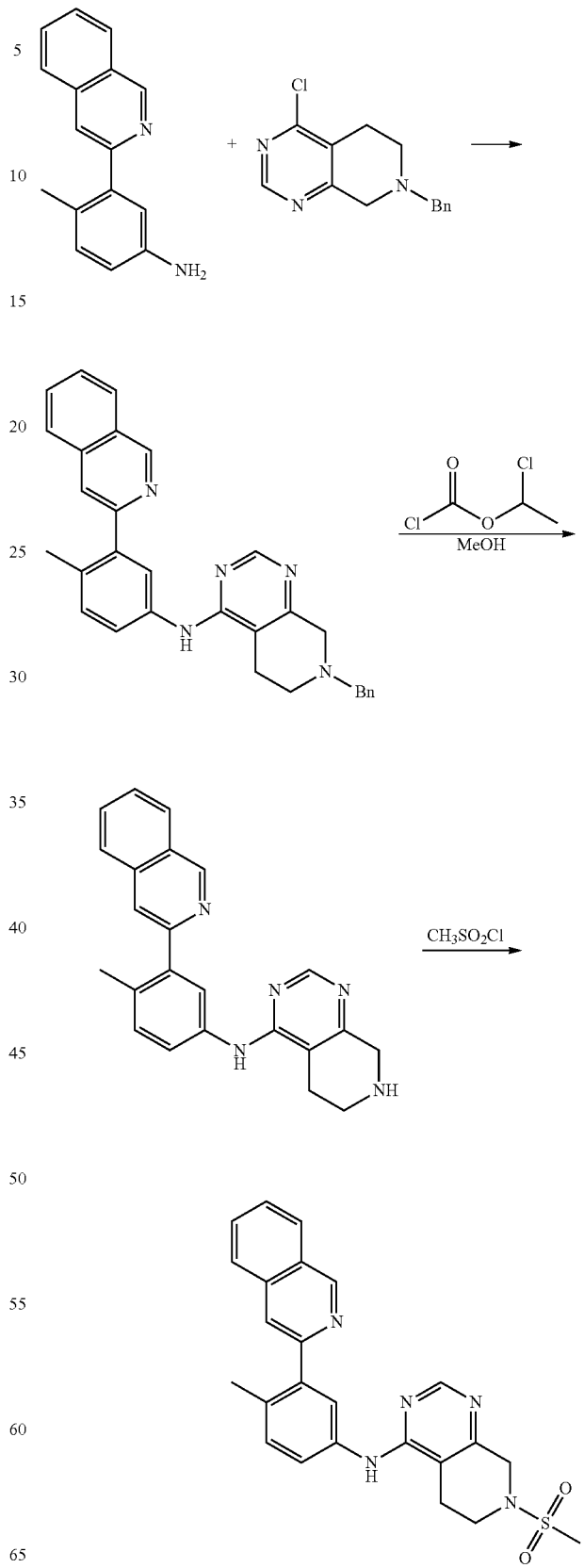

Example 4a

7-Benzyl-N-(3-(isoquinolin-3-yl)-4-methylphenyl)-5,6,7,8-tetrahydropyrido[3,4-d]pyrimidin-4-amine

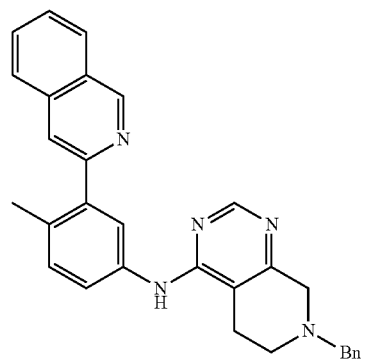 [SMILES: Cc1ccc(Nc2ncnc3c2CCN(Cc2ccccc2)C3)cc1-c1cc2ccccc2cn1]

To a reaction vessel containing 7-benzyl-4-chloro-5,6,7,8-tetrahydropyrido[3,4-d]pyrimidine (518 mg, 2 mmol), 3-(isoquinolin-3-yl)-4-methylaniline (470 mg, 2 mmol), pTSA (144 mg, 0.6 mmol) is added isopropanol (7 ml). The vessel is purged with nitrogen, sealed. The reaction vessel is placed in a microwave reactor and irradiated for 30 minutes at 130° C. The reaction mixture is cooled to room temperature and diluted with ethyl acetate. It is washed with saturated aqueous NaHCO$_3$, water and brine, dried over anhydrous MgSO$_4$ and concentrated. The residue is subjected to silica gel flash chromatography (2% methanol in dichloromethane) to afford 7-Benzyl-N-(3-(isoquinolin-3-yl)-4-methylphenyl)-5,6,7,8-tetrahydropyrido[3,4-d]pyrimidin-4-amine as a brown solid. LC-MS m/z: 458.2 (M+1).

Example 4b

N-(3-(isoquinolin-3-yl)-4-methylphenyl)-5,6,7,8-tetrahydropyrido[3,4-d]pyrimidin-4-amine

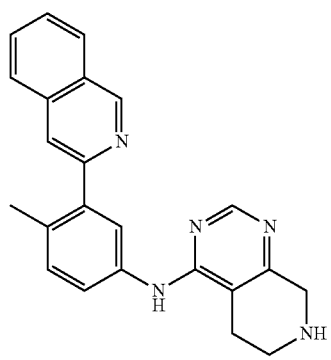 [SMILES: Cc1ccc(Nc2ncnc3c2CCNC3)cc1-c1cc2ccccc2cn1]

To a solution of 7-benzyl-N-(3-(isoquinolin-3-yl)-4-methylphenyl)-5,6,7,8-tetrahydropyrido[3,4-d]pyrimidin-4-amine (500 mg, 1.09 mmol) in dichloroethane (14 ml) is added DIEA (284 mg, 2.2 mmol) and 1-chloroethyl carbonochloridate (313 mg, 2.2 mmol). The reaction mixture is stirred at 90° C. for 12 hours, and cooled. The solvent is removed by rotary evaporation. The residue is redissolved in methanol (20 ml) and stirred at room temperature for 15 hours. After concentration, the crude product is purified by silica gel flash chromatography (eluted with 5% methanol in ethyl acetate) to afford N-(3-(isoquinolin-3-yl)-4-methylphenyl)-5,6,7,8-tetrahydropyrido[3,4-d]pyrimidin-4-amine as a dark yellow solid. LC-MS m/z: 368.2 (M+1).

Example 4c

N-(3-(isoquinolin-3-yl)-4-methylphenyl)-7-(methylsulfonyl)-5,6,7,8-tetrahydropyrido[3,4-d]pyrimidin-4-amine

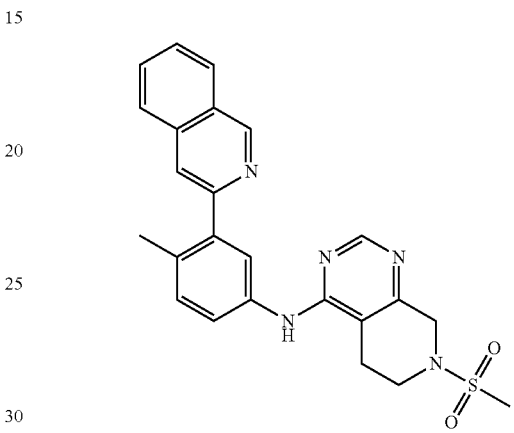

To a solution of N-(3-(isoquinolin-3-yl)-4-methylphenyl)-5,6,7,8-tetrahydropyrido[3,4-d]pyrimidin-4-amine (20 mg, 0.055 mmol) in DCM (0.4 ml) is added DIEA (21 mg, 0.121 mmol) and methylsulfonyl chloride (6.2 mg, 0.055 mmol) subsequently. The reaction mixture is stirred overnight. After concentrated by rotary evaporation, the residue is subject to HPLC to afford N-(3-(isoquinolin-3-yl)-4-methylphenyl)-7-(methylsulfonyl)-5,6,7,8-tetrahydropyrido[3,4-d]pyrimidin-4-amine as a white solid. LC-MS m/z: 446.2 (M+1); $^1$H NMR 400 MHz (CDCl$_3$) δ9.32 (s, 1H), 8.53 (s, 1H), 8.01 (d, 1H, J=8.0 Hz), 7.85 (d, 1H, J=8.0 Hz), 7.77 (s, 1H), 7.72 (t, 2H, J=6.6 Hz), 7.64-7.60 (m, 2H), 7.31 (d, 1H, J=8.4 Hz), 6.47 (s, 1H), 4.35 (s, 2H), 3.64 (t, 2H, J=6.0 Hz), 2.89 (s, 3H), 2.68 (t, 2H, J=5.6 Hz), 2.39 (s, 3H).

Example 5

N-(3-methyl-2,2'-bipyridin-6-yl)-2-(2-(methylsulfonyl)ethyl)-1,2,3,4-tetrahydroisoquinolin-5-amine The preparation of N-(3-methyl-2,2'-bipyridin-6-yl)-2-(2-(methylsulfonyl)ethyl)-1,2,3,4-tetrahydroisoquinolin-5-amine is illustrated in scheme 5.

Scheme 5

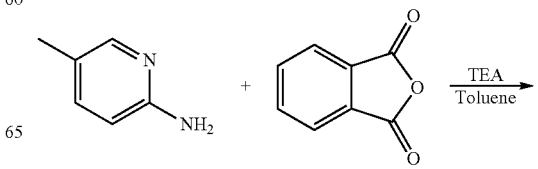

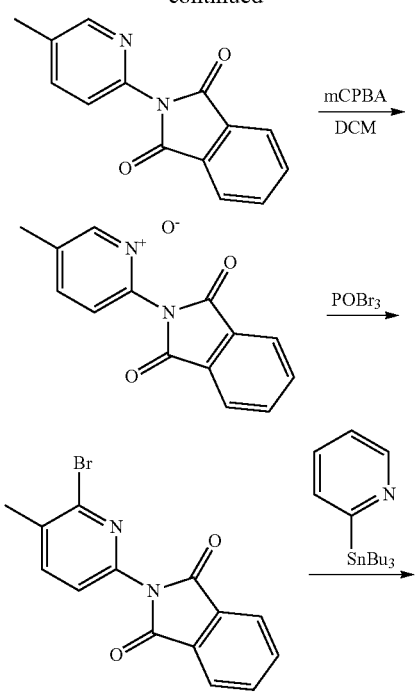
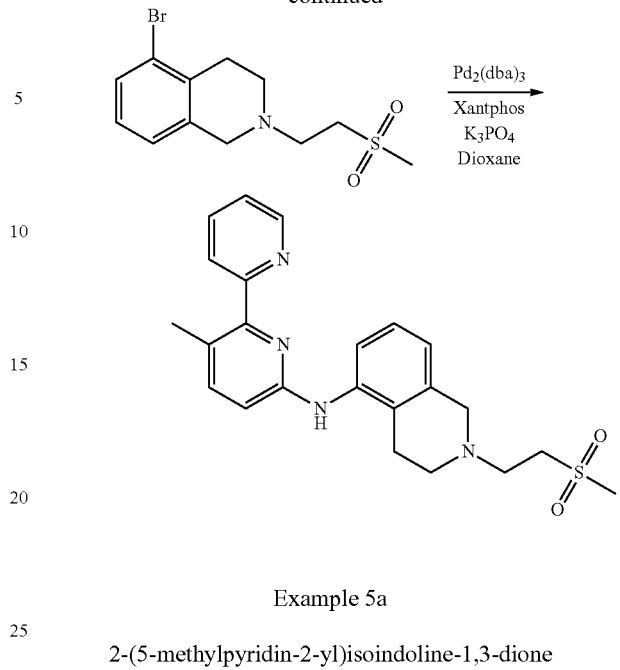
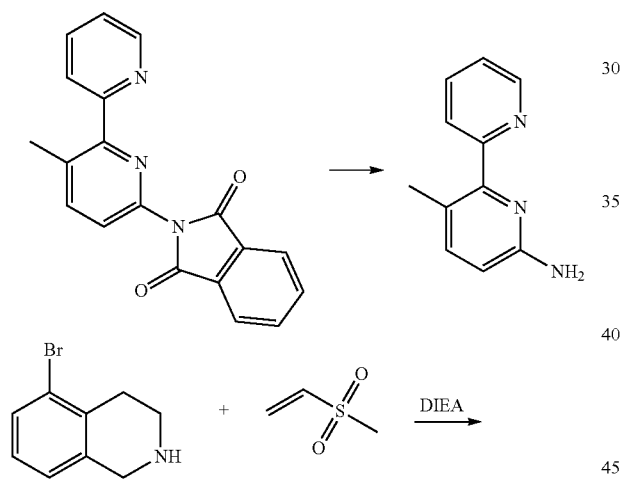
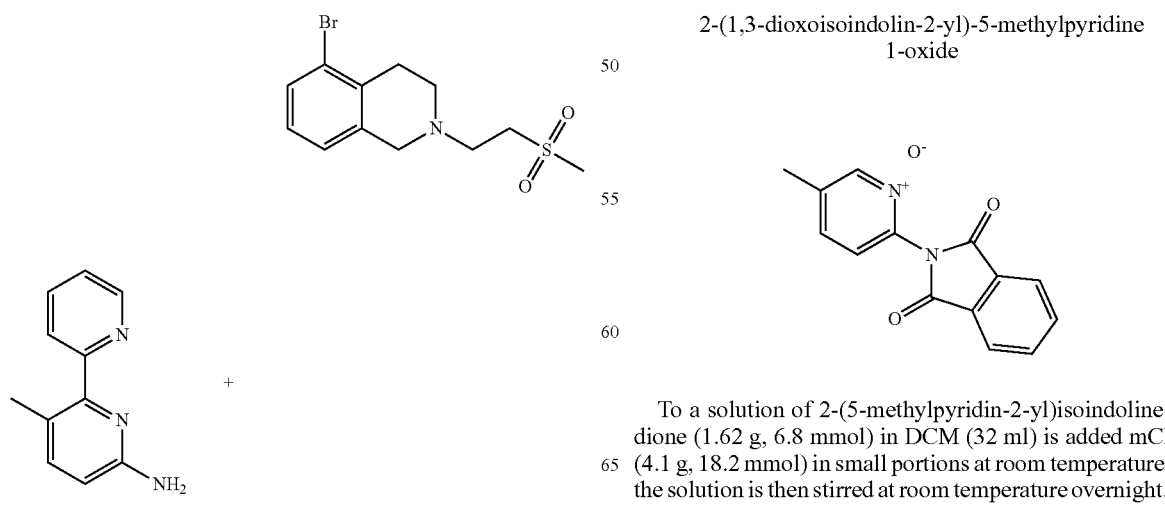

Example 5a 2-(5-methylpyridin-2-yl)isoindoline-1,3-dione

A mixture containing 5-methylpyridin-2-amine (5.4 g, 50 mmol), phthalic anhydride (8.88 g, 60 mmol) and DIEA (19 ml, 110 mmol) in toluene (30 ml) is refluxed for 18 hours, and cooled. The solvent is removed by rotary evaporation. The crude product is purified by silica gel flash chromatography to afford 2-(5-methylpyridin-2-yl)isoindoline-1,3-dione as a dark brown oil. LC-MS m/z: 239.1 (M+1).

Example 5b 2-(1,3-dioxoisoindolin-2-yl)-5-methylpyridine 1-oxide

To a solution of 2-(5-methylpyridin-2-yl)isoindoline-1,3-dione (1.62 g, 6.8 mmol) in DCM (32 ml) is added mCPBA (4.1 g, 18.2 mmol) in small portions at room temperature, and the solution is then stirred at room temperature overnight. The solution is diluted with dichloromethane, washed with aqueous Na₂CO₃ solution, dried over Na₂SO₄ and concentrated to afford 2-(1,3-dioxoisoindolin-2-yl)-5-methylpyridine 1-oxide as a brown solid. It is used without further purification in the next step. LC-MS m/z: 254.1 (M+1).

Example 5c 2-(6-bromo-5-methylpyridin-2-yl)isoindoline-1,3-dione

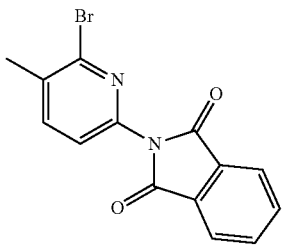 [SMILES: Cc1ccc(N2C(=O)c3ccccc3C2=O)nc1Br]

To a solution of 2-(1,3-dioxoisoindolin-2-yl)-5-methylpyridine 1-oxide (501 mg, 1.97 mmol) in 1,1-dichloroethane (5 ml) is added POBr₃ (679 mg, 2.36 mmol) in small portions at 0° C., and the solution is then heated at 40° C. for 2 hours. The solution is cooled to room temperature, poured into crushed ice, neutralized with Na₂CO₃ and extracted with dichloromethane. The separated organic layer is further washed with water, brine and dried over Na₂SO₄. After concentration, the crude product is purified by silica gel flash chromatography, eluted with 3% ethyl acetate in dichloromethane to afford 2-(6-bromo-5-methylpyridin-2-yl)isoindoline-1,3-dione as an off-white solid. LC-MS m/z: 317.2 (M+1).

Example 5d 2-(3-methyl-2,2'-bipyridin-6-yl)isoindoline-1,3-dione

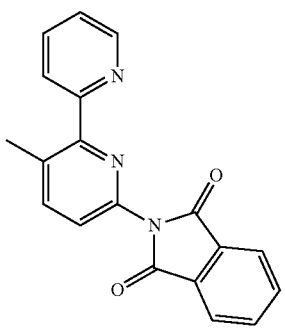 [SMILES: Cc1ccc(N2C(=O)c3ccccc3C2=O)nc1-c1ccccn1]

To a reaction vessel under argon containing 2-(6-bromo-5-methylpyridin-2-yl)isoindoline-1,3-dione (85 mg, 0.27 mmol), 2-(tributylstannyl)pyridine (123 mg, 0.32 mmol), Pd(PPh₃)₄ (31 mg, 0.027 mmol) is added anhydrous toluene (0.7 ml). The mixture is heated to 116° C. with an oil bath for 18 hours, cooled to room temperature, diluted with ethyl acetate and filtered through a celite pad to remove any solids. The filtrate is concentrated to afford 2-(3-methyl-2,2'-bipyridin-6-yl)isoindoline-1,3-dione as a brown solid (LC-MS m/z: 316.1 (M+1)) which is used without further purification in the next step.

Example 5e 3-methyl-2,2'-bipyridin-6-amine

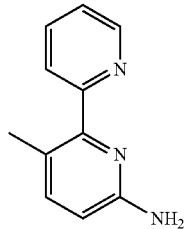

To a solution of 2-(3-methyl-2,2'-bipyridin-6-yl)isoindoline-1,3-dione (129 mg, 0.41 mmol) in ethanol (2 ml) is added a couple of drops of ethylenediamine at room temperature. The solution is stirred at room temperature for 30 minutes. The solvents are removed by rotary evaporation and the crude product is purified by silica gel flash chromatography, eluted with 3% methanol in dichloromethane to afford 3-methyl-2,2'-bipyridin-6-amine as an off-white solid. LC-MS m/z: 186.1 (M+1).

Example 5f 5-bromo-2-(2-(methylsulfonyl)ethyl)-1,2,3,4-tetrahydroisoquinoline

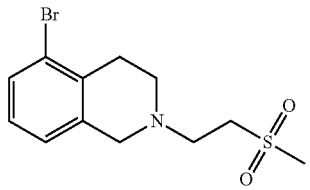 [SMILES: CS(=O)(=O)CCN1CCc2c(Br)cccc2C1]

A mixture containing 5-bromo-1,2,3,4-tetrahydroisoquinoline (212 mg, 1 mmol) and methylsulfonylethene (106 mg, 1 mmol) in dichloromethane is stirred at 35° C. for 14 hours. The solution is concentrated to afford 5-bromo-2-(2-(methylsulfonyl)ethyl)-1,2,3,4-tetrahydroisoquinoline as a brown oil (LC-MS m/z: 318.1 (M+1)) which is used without further purification in the next step.

Example 5g

N-(3-methyl-2,2'-bipyridin-6-yl)-2-(2-(methylsulfonyl)ethyl)-1,2,3,4-tetrahydroisoquinolin-5-amine

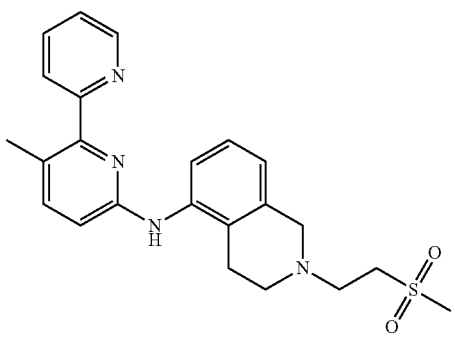

To a reaction tube under argon containing 3-methyl-2,2'-bipyridin-6-amine (20 mg, 0.11 mmol), 5-bromo-2-(2-(methylsulfonyl)ethyl)-1,2,3,4-tetrahydroisoquinoline (35 mg, 0.11 mmol), Pd$_2$(dba)$_3$ (11 mg, 0.011 mmol), xantphos (20 mg, 0.022 mmol), potassium phosphate (66 mg, 0.33 mmol) is added anhydrous dioxane (0.6 ml). The mixture is stirred at 96° C. for 18 hours, cooled to room temperature and filtered through a celite pad to remove any solids. The filtrate is concentrated and purified by preparative HPLC to afford N-(3-methyl-2,2'-bipyridin-6-yl)-2-(2-(methylsulfonyl)ethyl)-1,2,3,4-tetrahydroisoquinolin-5-amine as a white solid. LC-MS m/z: 423.2 (M+1); $^1$H NMR 400 MHz (CDCl$_3$) δ 8.69 (d, 1H, J=5.2 Hz), 7.78 (td, 1H, J=1.6, 7.6 Hz), 7.68 (d, 1H, J=8.0 Hz), 7.39 (d, 1H, J=8.4 Hz), 7.32-7.24 (m, 3H), 7.13 (t, 1H, J=7.6 Hz), 6.79 (d, 1H, J=7.6 Hz), 6.72 (d, 1H, J=8.4 Hz), 6.19 (s, 1H), 3.69 (s, 2H), 3.22-3.20 (m, 2H), 3.03 (t, 2H, J=6.4 Hz), 2.99 (s, 3H), 2.80-2.74 (m, 4H), 2.32 (s, 3H).

Example 6

2-methyl-5-(2-(methylsulfonyl)-1,2,3,4-tetrahydroisoquinolin-5-ylamino)-N-phenylnicotinamide The preparation of 2-methyl-5-(2-(methylsulfonyl)-1,2,3,4-tetrahydroisoquinolin-5-ylamino)-N-phenylnicotinamide is illustrated in scheme 6.

Scheme 6

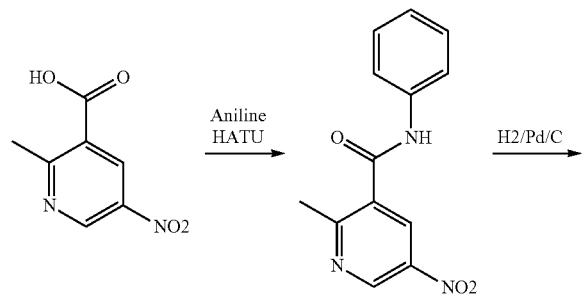

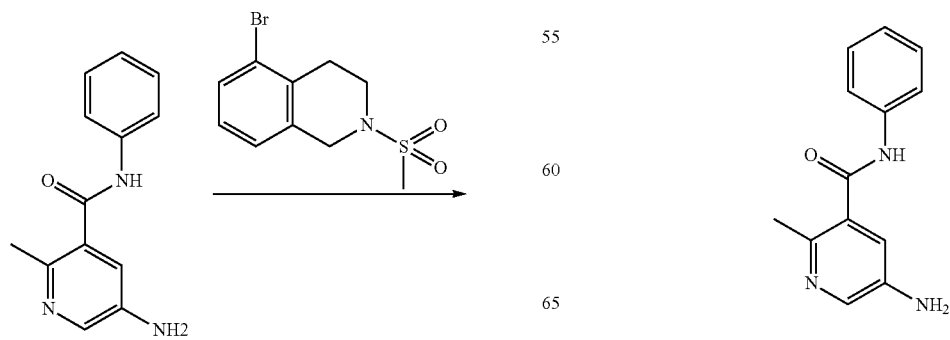

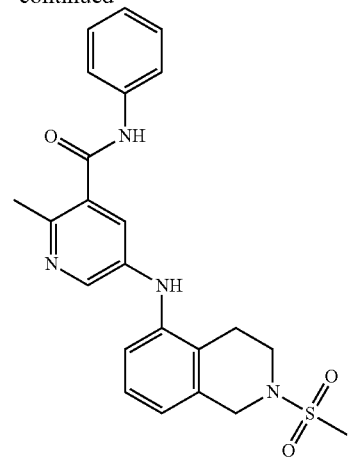

Example 6a 2-methyl-5-nitro-N-phenylnicotinamide

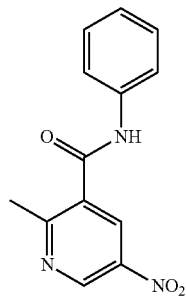 [SMILES: Cc1ncc(N)cc1C(=O)Nc1ccccc1]

To a solution of 2-methyl-5-nitronicotinic acid (364 mg, 2 mmol), aniline (186 mg, 2 mmol) and DIEA (774 mg, 6 mmol) in DMF (6 mL) is added HATU (798 mg, 2.1 mmol). The reaction mixture is stirred at room temperature for 2 hours. The solvent is removed by rotary evaporation and the crude product is purified by silica gel flash chromatography, eluted with 40% ethyl acetate in hexane to afford -methyl-5-nitro-N-phenylnicotinamide as a light green solid. MS m/z 258.1 (M+1).

Example 6b 5-amino-2-methyl-N-phenylnicotinamide

To a solution of 2-methyl-5-nitro-N-phenylnicotinamide (460 mg, 1.79 mmol) in 20 mL of ethanol is added Pd/C (40 mg). The reaction mixture is stirred under H₂ atmosphere for 15 hours. The Pd/C is removed by filtering through a celite pad. The filtrate is dried to afford 5-amino-2-methyl-N-phenylnicotinamide as an off-white solid. MS m/z 228.1 (M+1).

Example 6c 2-methyl-5-(2-(methylsulfonyl)-1,2,3,4-tetrahydroisoquinolin-5-ylamino)-N-phenylnicotinamide

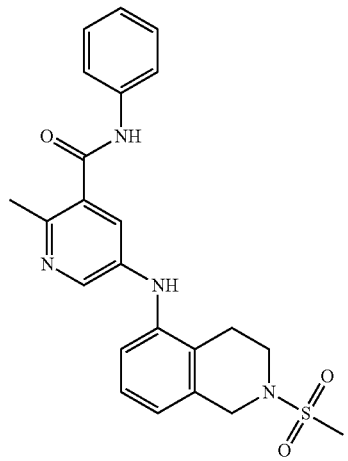

A mixture containing 5-amino-2-methyl-N-phenylnicotinamide (46 mg, 0.2 mmol), 5-bromo-2-(methylsulfonyl)-1,2,3,4-tetrahydroisoquinoline (58 mg, 0.2 mmol), Pd₂(dba)₃ (18 mg, 0.02 mmol), BINAP (25 mg, 0.04 mmol), K₃PO₄ (169 mg, 0.8 mmol) in dioxane (1 mL) is stirred at 110° C. for 15 hours. The reaction mixture is filtered through a celite pad to remove any solids. The filtrate is evaporated and the crude product is purified by HPLC to give 2-methyl-5-(2-(methylsulfonyl)-1,2,3,4-tetrahydroisoquinolin-5-ylamino)-N-phenylnicotinamide as a white solid. MS m/z 437.2 (M+1); ¹H NMR 400 MHz (DMSO-d₆) δ10.58 (s, 1H), 8.20 (m, 2H), 7.71 (d, 2H, J=7.6 Hz), 7.63 (d, 1H), J=2.4 Hz), 7.38 (t, 2H, J=8.4 Hz), 7.23 (m, 2H), 7.15 (t, 1H, J=7.6 Hz), 7.00 (m, 1H), 4.39 (s, 2H), 3.47 (t, 2H, J=6.4 Hz), 2.97 (s, 3H), 2.82 (t, 2H, J=6.4 Hz), 2.54 (s, 3H).

Example 7

[2-(1,1-dioxo-tetrahydro-thiophen-3-yl)-1,2,3,4-tetrahydro-isoquinolin-5-yl]-[3-(6-methoxy-pyridazin-3-yl)-4-methyl-phenyl]-amine The preparation of [2-(1,1-dioxo-tetrahydro-thiophen-3-yl)-1,2,3,4-tetrahydro-isoquinolin-5-yl]-[3-(6-methoxy-pyridazin-3-yl)-4-methyl-phenyl]-amine is illustrated in scheme 7.

Scheme 7

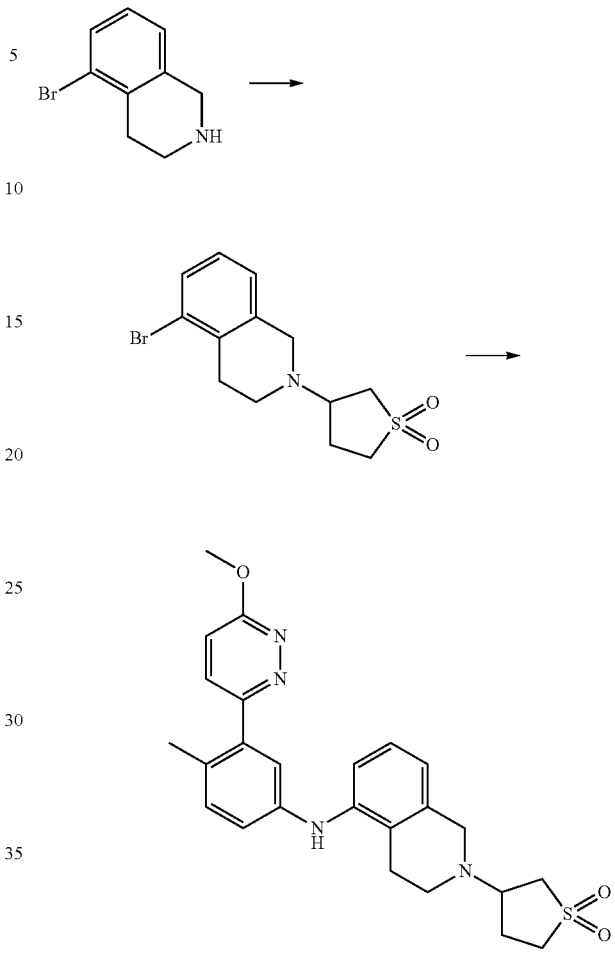

Example 7a 5-bromo-2-(1,1-dioxo-tetrahydro-thiophen-3-yl)-1,2,3,4-tetrahydro-isoquinoline

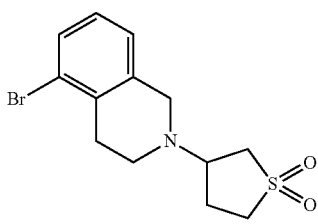 [SMILES: O=S1(=O)CCC(N2CCc3c(Br)cccc3C2)C1]

To a solution containing 5-bromo-1,2,3,4-tetrahydroisoquinoline hydrochloride (1.5 g, 6 mmol) and butadiene sulfone (1.2 g, 10.2 mmol) in water (20 mL) is added 1N KOH (10 mL). The reaction mixture is stirred at 70° C. for 24 hours. After cooling to ambient temperature, the reaction mixture is diluted with saturated NaHCO₃ solution and extracted with dichloromethane three times. The organic phase is washed with brine and dried over Na₂SO₄ before drying by rotary evaporation. The crude product is purified by silica gel flash chromatography to afford 5-bromo-2-(1,1-dioxo-tetrahydro-thiophen-3-yl)-1,2,3,4-tetrahydro-isoquinoline as a wax-like solid. MS m/z 330.1 (M+1).

Example 7b

[2-(1,1-dioxo-tetrahydro-thiophen-3-yl)-1,2,3,4-tetrahydro-isoquinolin-5-yl]-[3-(6-methoxy-pyridazin-3-yl)-4-methyl-phenyl]-amine To the reaction vessel containing 5-Bromo-2-(1,1-dioxo-tetrahydro-thiophen-3-yl)-1,2,3,4-tetrahydro-isoquinoline (460 mg, 1.4 mmol), 3-(6-methoxypyridazin-3-yl)-4-methylaniline (300 mg, 1.4 mmol), Pd$_2$(dba)$_3$ (128 mg, 0.14 mmol), Xantphos (162 mg, 0.28 mmol) and K$_3$PO$_4$ (740 mg, 3.5 mmol) is added anhydrous dioxane. The vessel is flushed with nitrogen, sealed and heated to 100° C. for 15 hours. The reaction is then cooled to ambient temperature, filtered through a celite pad to remove any solids. The filtrate is concentrated and purified by silica gel flash chromatography to afford [2-(1,1-dioxo-tetrahydro-thiophen-3-yl)-1,2,3,4-tetrahydro-isoquinolin-5-yl]-[3-(6-methoxy-pyridazin-3-yl)-4-methyl-phenyl]-amine as an off-white solid. MS m/z 465.2 (M+1); $^1$H NMR 400 MHz (DMSO-d$_6$) δ7.73 (d, 1H, J=6.0 Hz), 7.32 (s, 1H), 7.27 (d, 1H, J=6.0 Hz), 7.16 (d, 1H, J=5.6 Hz), 7.04 (m, 2H), 6.95 (m, 2H), 6.69 (dd, 1H, J1=4.4 Hz, J2=2.8 Hz), 4.07 (s, 3H), 3.72 (d, 1H, J=15.0 Hz), 3.65 (d, 1H, J=15.0 Hz), 3.41 (m, 2H), 3.29 (m, 1H), 3.13 9 m, 2H), 2.77 (m, 2H), 2.66 (t, 2H, J=6.0 Hz), 2.43 (m, 1H), 2.18 (s, 3H), 2.11 (m, 1H).

Example 8

[3-(3,5-difluoro-pyridin-2-yl)-4-methyl-phenyl]-[2-(1,1-dioxo-tetrahydro-thiophen-3-yl)-1,2,3,4-tetrahydro-isoquinolin-5-yl]-amine The preparation of [3-(3,5-difluoro-pyridin-2-yl)-4-methyl-phenyl]-[2-(1,1-dioxo-tetrahydro-thiophen-3-yl)-1,2,3,4-tetrahydro-isoquinolin-5-yl]-amine is illustrated in scheme 8.

Scheme 8

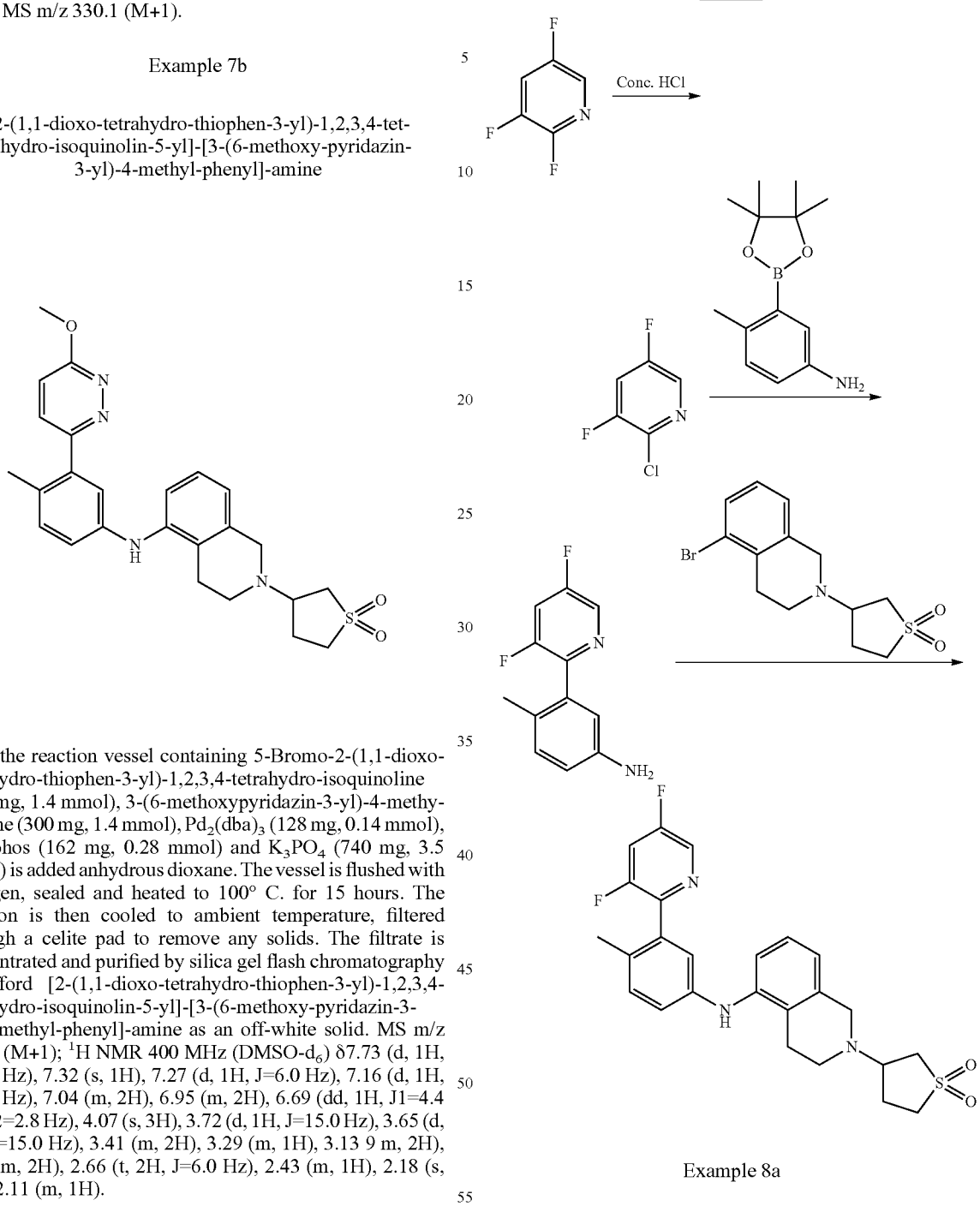

Example 8a 2-chloro-3,5-difluoropyridine

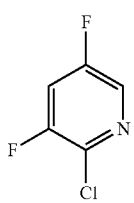

To a microwave tube is added 2,3,5-trifluoropyridine (2.0 g, 15 mmol), concentrated HCl (12.5 mL, 150 mmol). The mixture is irradiated with microwave for 30 min at 130° C. The reaction mixture is cooled to ambient temperature, diluted with 100 mL of water, extracted with dichloromethane three times. The organic phase is further washed with brine, dried over $Na_2SO_4$ and dried to give 2-chloro-3,5-difluoropyridine as a greenish solid. The compound is used without further purification.

Example 8b 3-(3,5-difluoropyridin-2-yl)-4-methylaniline

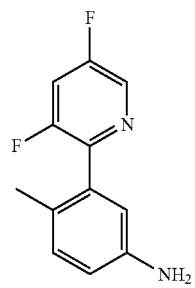 [SMILES: Cc1ccc(N)cc1-c1ncc(F)cc1F]

To a round bottom flask is added 2-chloro-3,5-difluoropyridine (1.5 g, 10 mmol), 4-methyl-3-(4,4,5,5-tetramethyl-1,3,2-dioxaborolan-2-yl)aniline (2.2 g, 10 mmol), $Pd(PPh_3)_4$ (300 mg, 0.26 mmol), toluene (60 mL), ethanol (20 mL) and 2M $Na_2CO_3$ (20 mL, 40 mmol). The reaction is stirred under reflux condition for 15 hours. After cooling, the reaction mixture is diluted with ethyl acetate, washed with brine and dried over $Na_2SO_4$. The organic phase is then dried by rotary evaporation. The crude product is purified by silica gel flash chromatography to afford 3-(3,5-difluoropyridin-2-yl)-4-methylaniline as a light brown solid. MS m/z 221.1 (M+1).

Example 8c

[3-(3,5-difluoro-pyridin-2-yl)-4-methyl-phenyl]-[2-(1,1-dioxo-tetrahydro-thiophen-3-yl)-1,2,3,4-tetrahydro-isoquinolin-5-yl]-amine

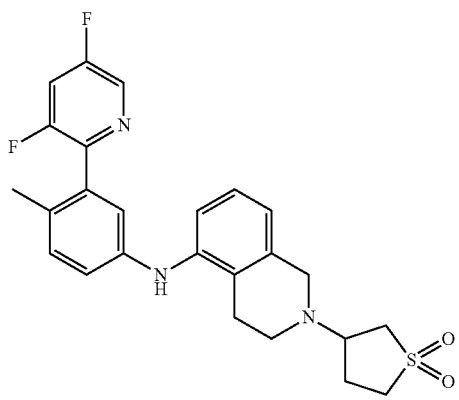 [SMILES: Cc1ccc(Nc2cccc3c2CCN(C2CCS(=O)(=O)C2)C3)cc1-c1ncc(F)cc1F]

To the reaction vessel containing 5-bromo-2-(1,1-dioxo-tetrahydro-thiophen-3-yl)-1,2,3,4-tetrahydro-isoquinoline (50 mg, 0.15 mmol), 3-(3,5-difluoropyridin-2-yl)-4-methylaniline (33 mg, 0.15 mmol), $Pd_2(dba)_3$ (13 mg, 0.014 mmol), Xantphos (16 mg, 0.028 mmol) and $K_3PO_4$ (74 mg, 0.35 mmol) is added anhydrous dioxane (1 mL). The vessel is flushed with nitrogen, sealed and heated to 100° C. for 15 hours. The reaction is then cooled to ambient temperature, filtered through a celite pad to remove salt. The filtrate is concentrated and purified by silica gel flash chromatography to afford [3-(3,5-difluoro-pyridin-2-yl)-4-methyl-phenyl]-[2-(1,1-dioxo-tetrahydro-thiophen-3-yl)-1,2,3,4-tetrahydro-isoquinolin-5-yl]-amine as an off-white solid (45 mg, 65%). MS m/z 470.2 (M+1); $^1$H NMR 400 MHz (DMSO-$d_6$) δ8.67 (d, 1H, J=2.4 Hz), 7.39 (s, 1H), 7.22 (d, 1H, J=8.4 Hz), 7.12 (m, 2H), 7.00 (dd, 1H, J1=8.0 Hz, J2=2.4 Hz), 6.91 (d, 1H, J=2.4 Hz), 6.75 (d, 1H, J=7.2 Hz), 3.79 (d, 1H, J=19.2 Hz), 3.71 (d, 1H, J=19.2 Hz), 3.47 (m, 2H), 3.34 (m, 1H), 3.18 (m, 2H), 2.82 (m, 2H), 2.72 (m, 2H), 2.47 (m, 1H), 2.17 (m, 1H), 2.11 (s, 3H).

Example 9

N-(3-(isoquinolin-3-yl)-4-methylphenyl)-6-(methylsulfonyl)-5,6,7,8-tetrahydro-2,6-naphthyridin-1-amine The preparation of N-(3-(isoquinolin-3-yl)-4-methylphenyl)-6-(methylsulfonyl)-5,6,7,8-tetrahydro-2,6-naphthyridin-1-amine is illustrated in scheme 9.

Scheme 9

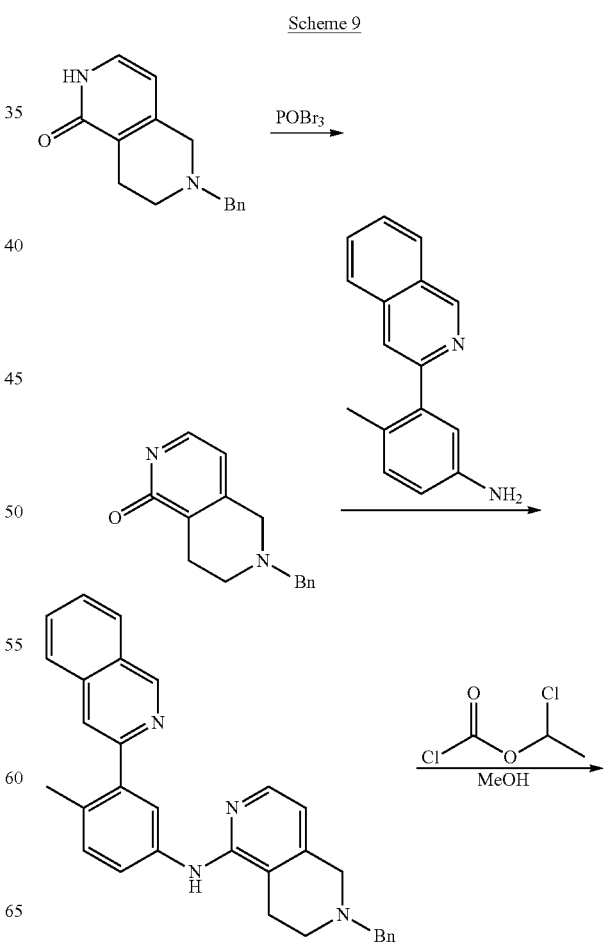

-continued

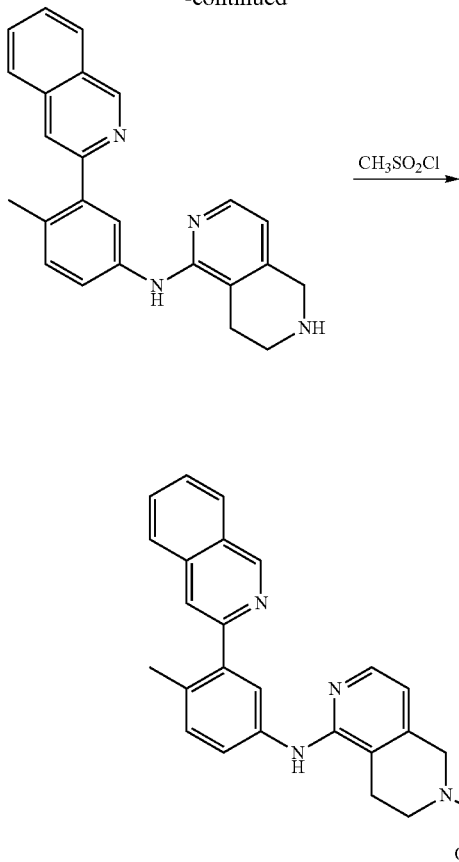

Example 9a 2-benzyl-5-bromo-1,2,3,4-tetrahydro-2,6-naphthyridine

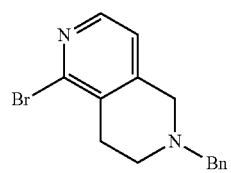 [SMILES: Brc1nccc2c1CCN(Cc1ccccc1)C2]

Phosphorous oxybromide (7.5 g, 26 mmol) is added portion wise to a suspension of 6-benzyl-5,6,7,8-tetrahydro-2,6-naphthyridin-1(2H)-one (1.6 g, 6.7 mmol) in anisole (20 mL) and acetonitrile (10 mL). The reaction mixture is stirred under reflux for 4 hours. The cooled mixture is poured onto ice and diluted with dichloromethane. The mixture is slowly neutralized using saturated sodium bicarbonate solution. The aqueous phase is extracted with dichloromethane three times. The organic phase are combined and washed with brine, dried over Na$_2$SO$_4$ and taken to dryness by rotary evaporation. The crude product as purified by column chromatography on silica gel to afford 2-benzyl-5-bromo-1,2,3,4-tetrahydro-2,6-naphthyridine as a white solid. MS m/z 303.1 (M+1).

Example 9b 6-benzyl-N-(3-(isoquinolin-3-yl)-4-methylphenyl)-5,6,7,8-tetrahydro-2,6-naphthyridin-1-amine

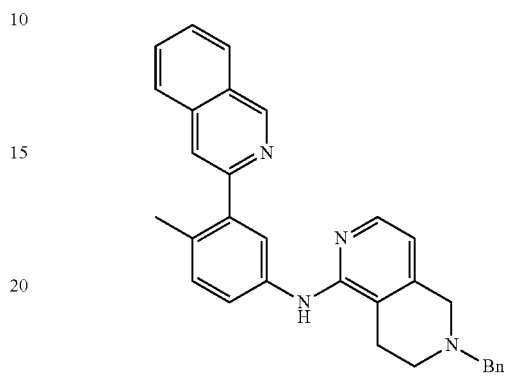

To the reaction vessel containing 2-benzyl-5-bromo-1,2,3,4-tetrahydro-2,6-naphthyridine (272 mg, 0.9 mmol), 3-(isoquinolin-3-yl)-4-methylaniline (210 mg, 0.9 mmol), Pd$_2$(dba)$_3$ (41 mg, 0.045 mmol), Xantphos (52 mg, 0.09 mmol) and K$_3$PO$_4$ (477 mg, 2.25 mmol) is added anhydrous dioxane (5 mL). The vessel is flushed with nitrogen, sealed and heated to 100° C. for 18 hours. The reaction is then cooled to ambient temperature, filtered through a celite pad to remove any salts. The filtrate is concentrated and purified by silica gel flash chromatography to afford 6-benzyl-N-(3-(isoquinolin-3-yl)-4-methylphenyl)-5,6,7,8-tetrahydro-2,6-naphthyridin-1-amine as an off-white solid. MS m/z 457.2 (M+1).

Example 9c

N-(3-(isoquinolin-3-yl)-4-methylphenyl)-5,6,7,8-tetrahydro-2,6-naphthyridin-1-amine

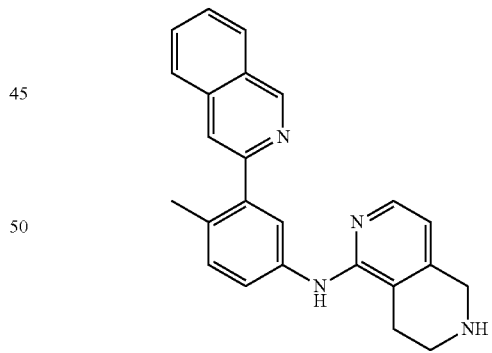

To a solution of 6-benzyl-N-(3-(isoquinolin-3-yl)-4-methylphenyl)-5,6,7,8-tetrahydro-2,6-naphthyridin-1-amine (320 mg, 0.7 mmol) in dichloroethane is added DIEA (225 mg, 1.75 mmol) and 1-chloroethyl carbonochloridate (200 mg, 1.4 mmol). The reaction mixture is stirred at 90° C. for 12 hours. After cooling, the solvent is removed by rotary evaporation. The residue is redissolved in 20 ml of methanol and stirred at room temperature for 15 hours. After removing solvent, the crude product is purified by silica gel flash chromatography, eluted with 5% methanol in ethyl acetate to afford N-(3-(isoquinolin-3-yl)-4-methylphenyl)-5,6,7,8-tetrahydro-2,6-naphthyridin-1-amine as a light yellow solid. MS m/z 367.2 (M+1).

Example 9d

N-(3-(isoquinolin-3-yl)-4-methylphenyl)-6-(methylsulfonyl)-5,6,7,8-tetrahydro-2,6-naphthyridin-1-amine

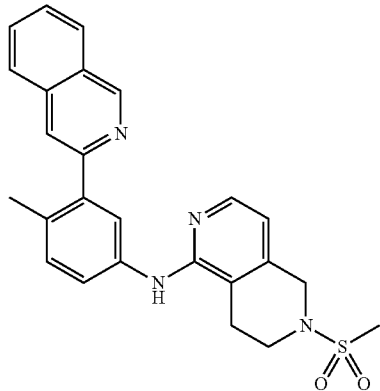

To a solution of N-(3-(isoquinolin-3-yl)-4-methylphenyl)-5,6,7,8-tetrahydro-2,6-naphthyridin-1-amine (37 mg, 0.1 mmol) in THF (2 mL) is added DIEA (26 mg, 0.2 mmol) and methylsulfonyl chloride (14 mg, 0.12 mmol) subsequently. The reaction mixture is stirred overnight. After removing solvent by rotary evaporation, the residue is purified by HPLC to afford N-(3-(isoquinolin-3-yl)-4-methylphenyl)-6-(methylsulfonyl)-5,6,7,8-tetrahydro-2,6-naphthyridin-1-amine as a white solid. MS m/z 445.2 (M+1); $^1$H NMR 400 MHz (DMSO-$d_6$) δ 9.34 (s, 1H), 8.11 (d, 1H, J=8.0 Hz), 7.97 (d, 1H, J=7.6 Hz), 7.88-7.85 (m, 3H), 7.76-7.71 (m, 2H), 7.66-7.63 (m, 2H), 7.16 (d, 1H, J=8.4 Hz), 6.57 (d, 1H, J=5.2 Hz), 4.24 (s, 2H), 3.45 (t, 2H, J=6.0 Hz), 2.91 (s, 3H), 2.75 (t, 2H, J=6.0 Hz), 2.26 (s, 3H).

By repeating the procedures described in the above examples, using appropriate starting materials, the following compounds of Formula I, as identified in Table 1, are obtained.

TABLE 1

| Compound Number | Structure | Physical Data MS (m/z) | IC$_{50}$ Ranges |
|---|---|---|---|
| 1 | 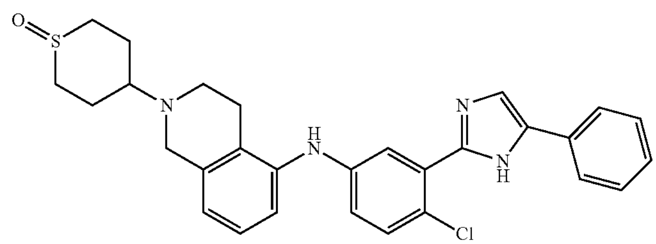 [SMILES: O=S1CCC(N2CCc3c(cccc3Nc3ccc(Cl)c(-c4ncc(-c5ccccc5)[nH]4)c3)C2)CC1] | 517.2 | * |
| 2 | 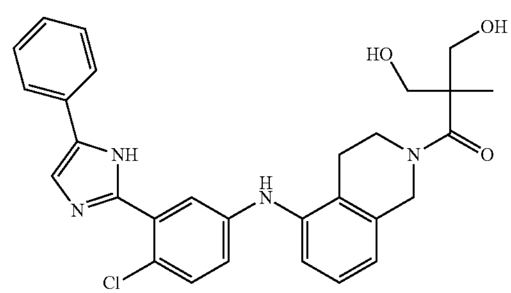 [SMILES: CC(CO)(CO)C(=O)N1CCc2c(cccc2Nc2ccc(Cl)c(-c3ncc(-c4ccccc4)[nH]3)c2)C1] | 517.2 | * |
| 3 | 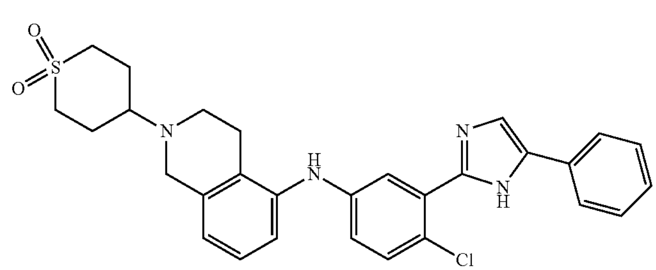 [SMILES: O=S1(=O)CCC(N2CCc3c(cccc3Nc3ccc(Cl)c(-c4ncc(-c5ccccc5)[nH]4)c3)C2)CC1] | 533.2 | * |

TABLE 1-continued

| Compound Number | Structure | Physical Data MS (m/z) | IC$_{50}$ Ranges |
|---|---|---|---|
| 4 | 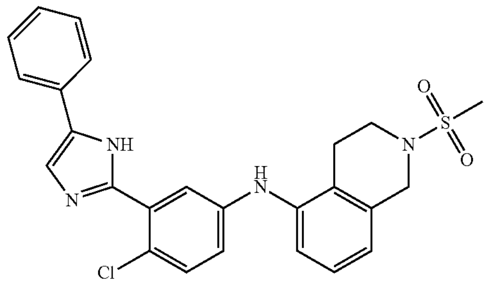 [SMILES: CS(=O)(=O)N1CCc2c(cccc2Nc2ccc(Cl)c(-c3ncc(-c4ccccc4)[nH]3)c2)C1] | 479.1 | * |
| 5 | 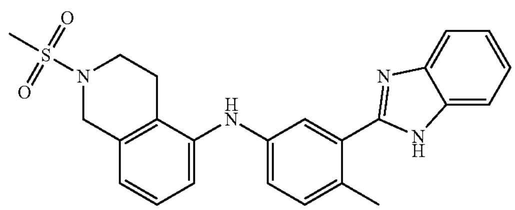 | 433.2 | * |
| 6 | 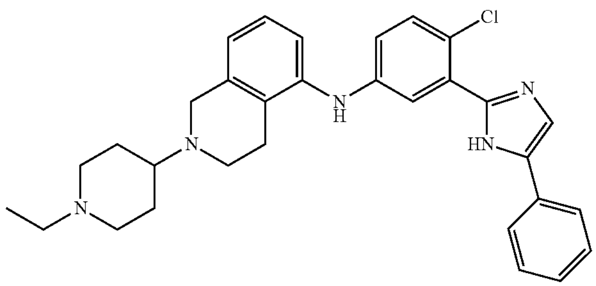 [SMILES: CCN1CCC(N2CCc3c(cccc3Nc3ccc(Cl)c(-c4ncc(-c5ccccc5)[nH]4)c3)C2)CC1] | 512.3 | * |
| 7 | 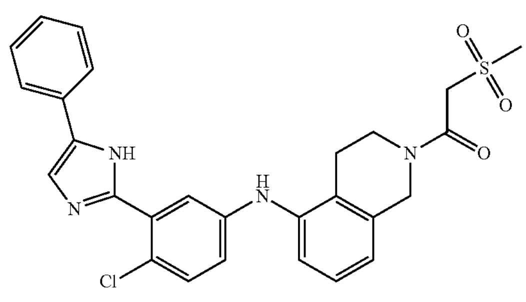 [SMILES: CS(=O)(=O)CC(=O)N1CCc2c(cccc2Nc2ccc(Cl)c(-c3ncc(-c4ccccc4)[nH]3)c2)C1] | 521.1 | * |
| 8 | 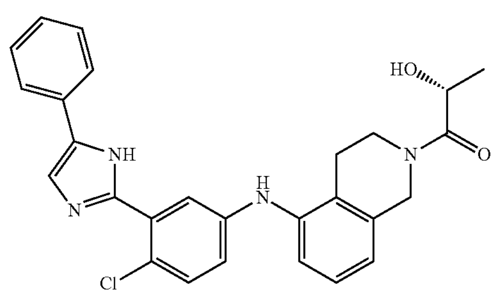 [SMILES: C[C@@H](O)C(=O)N1CCc2c(cccc2Nc2ccc(Cl)c(-c3ncc(-c4ccccc4)[nH]3)c2)C1] | 473.2 | * |

TABLE 1-continued

| Compound Number | Structure | Physical Data MS (m/z) | IC$_{50}$ Ranges |
|---|---|---|---|
| 9 | 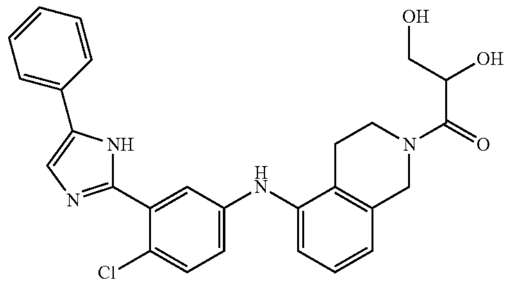 [SMILES: O=C(C(O)CO)N1CCc2c(cccc2Nc2ccc(Cl)c(-c3ncc(-c4ccccc4)[nH]3)c2)C1] | 489.2 | * |
| 10 | 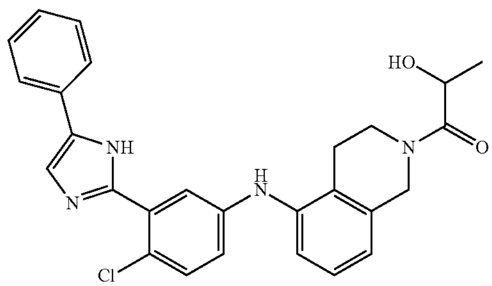 [SMILES: CC(O)C(=O)N1CCc2c(cccc2Nc2ccc(Cl)c(-c3ncc(-c4ccccc4)[nH]3)c2)C1] | 473.2 | * |
| 11 | 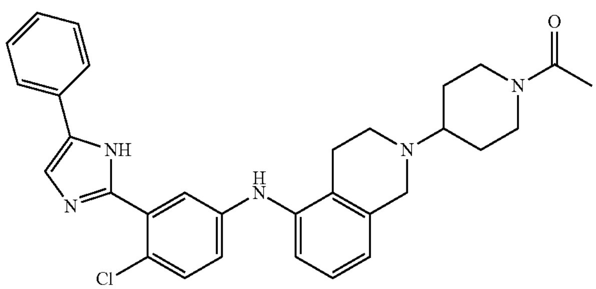 | 526.2 | * |
| 12 | 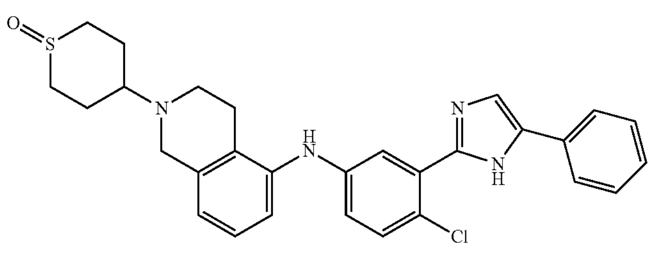 [SMILES: O=S1CCC(N2CCc3c(cccc3Nc3ccc(Cl)c(-c4ncc(-c5ccccc5)[nH]4)c3)C2)CC1] | 517.2 | * |
| 13 | 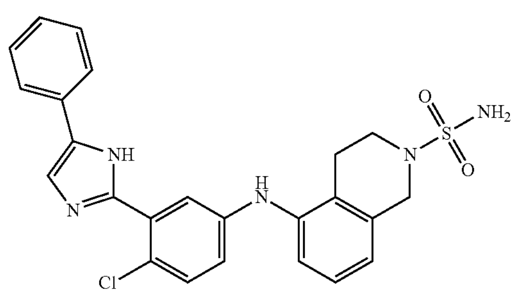 [SMILES: NS(=O)(=O)N1CCc2c(cccc2Nc2ccc(Cl)c(-c3ncc(-c4ccccc4)[nH]3)c2)C1] | 480.1 | ** |

TABLE 1-continued

| Compound Number | Structure | Physical Data MS (m/z) | IC$_{50}$ Ranges |
|---|---|---|---|
| 14 | 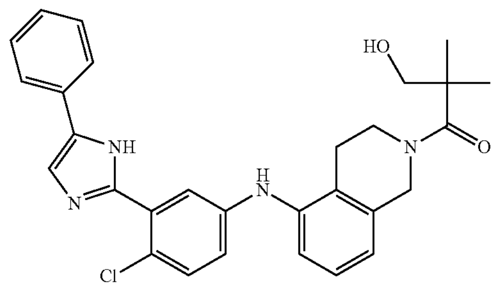 [SMILES: CC(C)(CO)C(=O)N1CCc2c(cccc2Nc2ccc(Cl)c(-c3ncc(-c4ccccc4)[nH]3)c2)C1] | 501.2 | * |
| 15 | 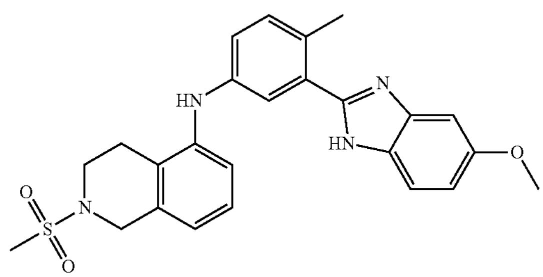 | 463.2 | * |
| 16 | 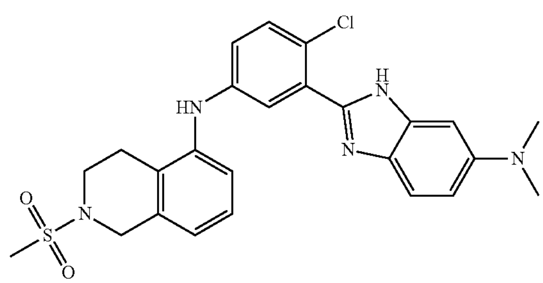 | 496.1 | ** |
| 17 | 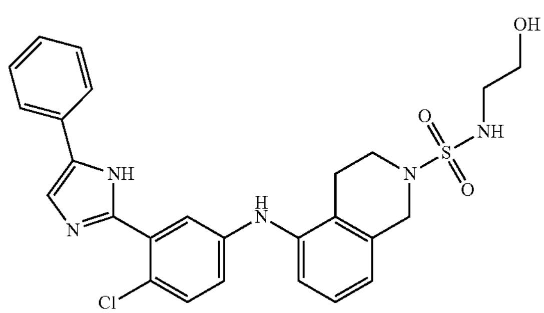 [SMILES: O=S(=O)(NCCO)N1CCc2c(cccc2Nc2ccc(Cl)c(-c3ncc(-c4ccccc4)[nH]3)c2)C1] | 524.1 | * |
| 18 | 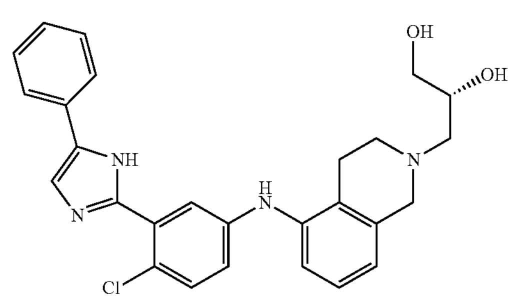 [SMILES: OC[C@H](O)CN1CCc2c(cccc2Nc2ccc(Cl)c(-c3ncc(-c4ccccc4)[nH]3)c2)C1] | 475.2 | * |

TABLE 1-continued

| Compound Number | Structure | Physical Data MS (m/z) | IC$_{50}$ Ranges |
|---|---|---|---|
| 19 | 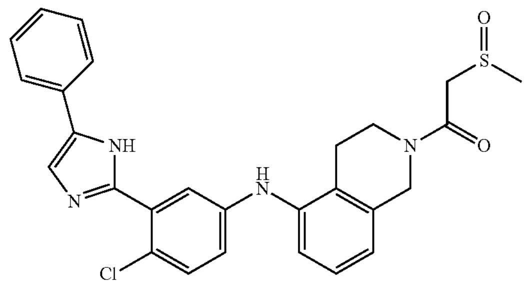 [SMILES: CS(=O)CC(=O)N1CCc2c(cccc2Nc2ccc(Cl)c(-c3ncc(-c4ccccc4)[nH]3)c2)C1] | 505.1 | * |
| 20 | 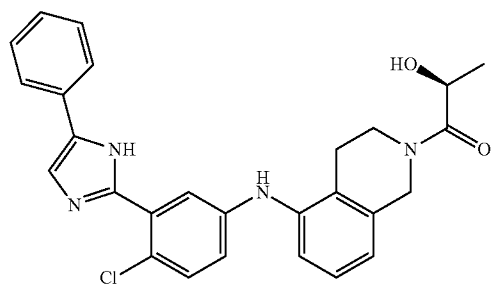 [SMILES: C[C@H](O)C(=O)N1CCc2c(cccc2Nc2ccc(Cl)c(-c3ncc(-c4ccccc4)[nH]3)c2)C1] | 473.2 | ** |
| 21 | 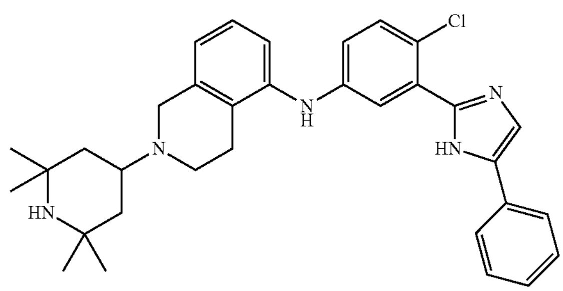 [SMILES: CC1(C)CC(N2CCc3c(cccc3Nc3ccc(Cl)c(-c4ncc(-c5ccccc5)[nH]4)c3)C2)CC(C)(C)N1] | 540.3 | * |
| 22 | 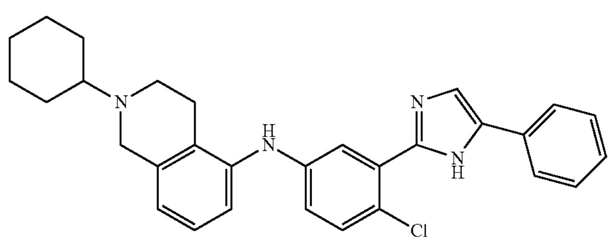 [SMILES: Clc1ccc(Nc2cccc3c2CCN(C2CCCCC2)C3)cc1-c1ncc(-c2ccccc2)[nH]1] | 483.2 | ** |
| 23 | 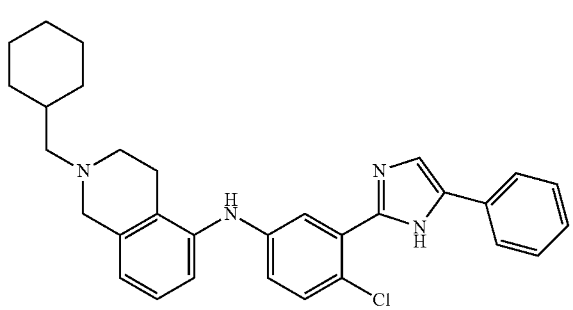 [SMILES: Clc1ccc(Nc2cccc3c2CCN(CC2CCCCC2)C3)cc1-c1ncc(-c2ccccc2)[nH]1] | 497.2 | ** |

TABLE 1-continued

| Compound Number | Structure | Physical Data MS (m/z) | IC$_{50}$ Ranges |
|---|---|---|---|
| 24 | 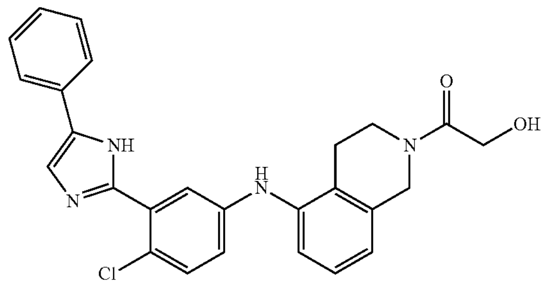 [SMILES: O=C(CO)N1CCc2c(cccc2Nc2ccc(Cl)c(-c3ncc(-c4ccccc4)[nH]3)c2)C1] | 459.2 | * |
| 25 | 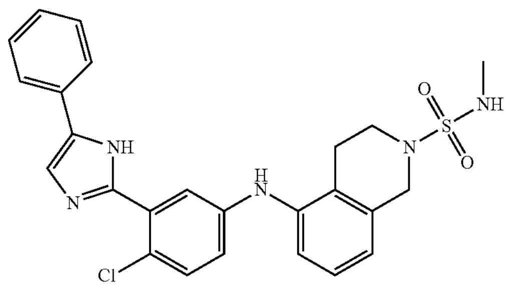 [SMILES: CNS(=O)(=O)N1CCc2c(cccc2Nc2ccc(Cl)c(-c3ncc(-c4ccccc4)[nH]3)c2)C1] | 494.1 | ** |
| 26 | 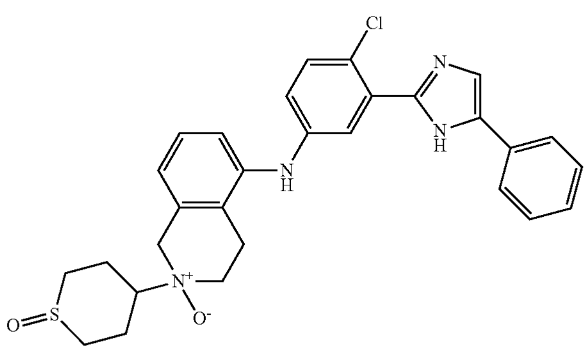 [SMILES: O=S1CCC([N+]2([O-])CCc3c(cccc3Nc3ccc(Cl)c(-c4ncc(-c5ccccc5)[nH]4)c3)C2)CC1] | 533.2 | ** |
| 27 | 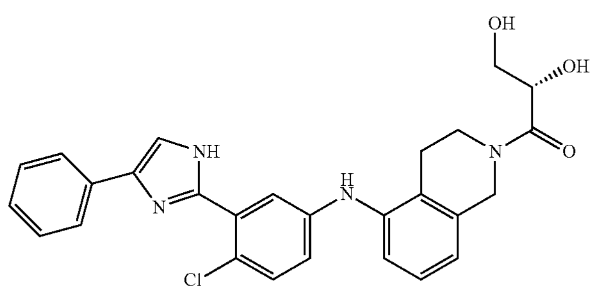 [SMILES: O=C([C@@H](O)CO)N1CCc2c(cccc2Nc2ccc(Cl)c(-c3nc(-c4ccccc4)c[nH]3)c2)C1] | 489.2 | * |
| 28 | 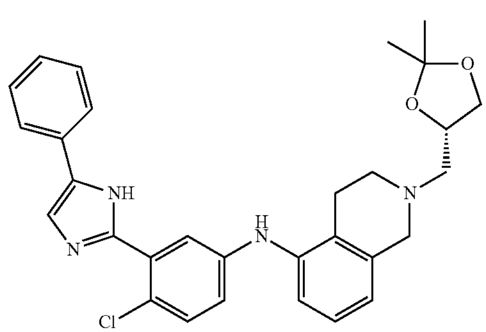 [SMILES: CC1(C)OC[C@H](CN2CCc3c(cccc3Nc3ccc(Cl)c(-c4ncc(-c5ccccc5)[nH]4)c3)C2)O1] | 515.2 | ** |

TABLE 1-continued

| Compound Number | Structure | Physical Data MS (m/z) | IC₅₀ Ranges |
|---|---|---|---|
| 29 | 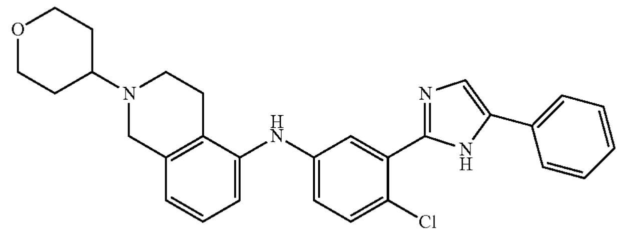 [SMILES: Clc1ccc(Nc2cccc3c2CCN(C2CCOCC2)C3)cc1-c1ncc(-c2ccccc2)[nH]1] | 485.2 | * |
| 30 | 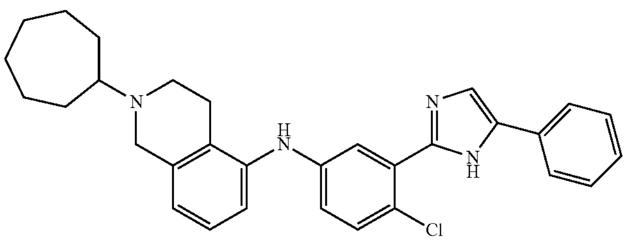 [SMILES: Clc1ccc(Nc2cccc3c2CCN(C2CCCCCC2)C3)cc1-c1ncc(-c2ccccc2)[nH]1] | 497.2 | ** |
| 31 | 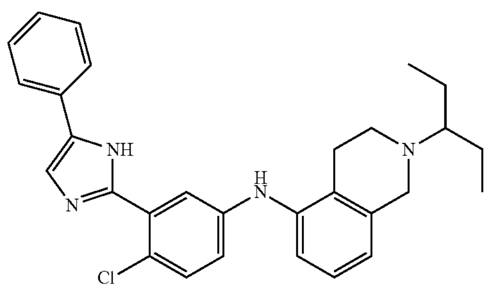 [SMILES: CCC(CC)N1CCc2c(cccc2Nc2ccc(Cl)c(-c3ncc(-c4ccccc4)[nH]3)c2)C1] | 471.2 | * |
| 32 | 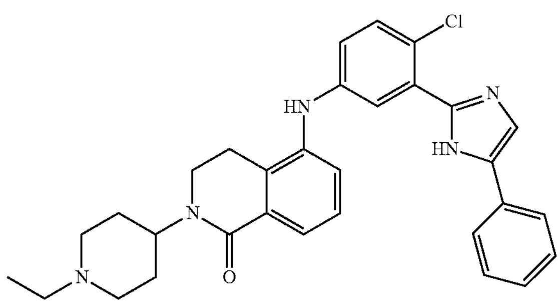 [SMILES: CCN1CCC(N2CCc3c(Nc4ccc(Cl)c(-c5ncc(-c6ccccc6)[nH]5)c4)cccc3C2=O)CC1] | 526.2 | ** |
| 33 | 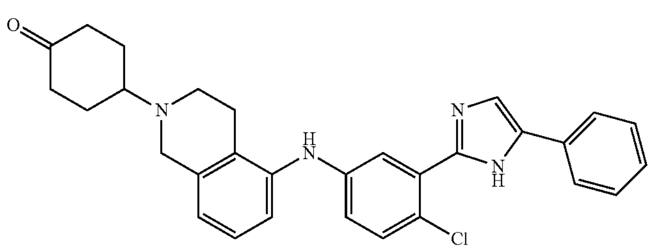 [SMILES: O=C1CCC(N2CCc3c(cccc3Nc3ccc(Cl)c(-c4ncc(-c5ccccc5)[nH]4)c3)C2)CC1] | 497.2 | * |

TABLE 1-continued

| Compound Number | Structure | Physical Data MS (m/z) | IC$_{50}$ Ranges |
|---|---|---|---|
| 34 | 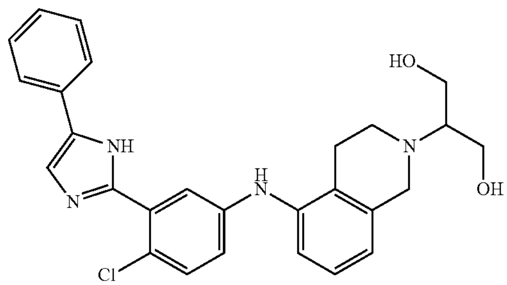 [SMILES: OCC(CO)N1CCc2c(cccc2Nc2ccc(Cl)c(-c3ncc(-c4ccccc4)[nH]3)c2)C1] | 475.2 | ** |
| 35 | 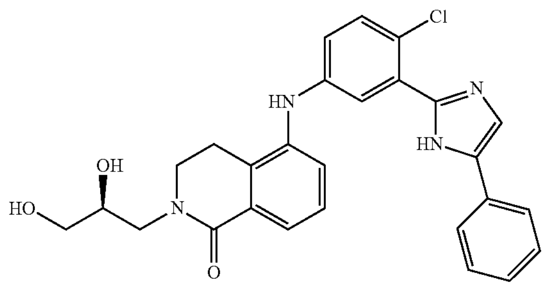 [SMILES: O=C1c2cccc(Nc3ccc(Cl)c(-c4ncc(-c5ccccc5)[nH]4)c3)c2CCN1C[C@H](O)CO] | 489.2 | ** |
| 36 | 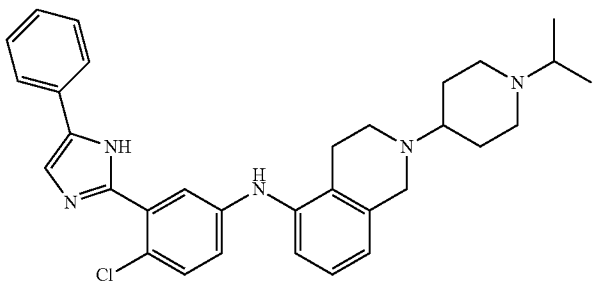 [SMILES: CC(C)N1CCC(N2CCc3c(cccc3Nc3ccc(Cl)c(-c4ncc(-c5ccccc5)[nH]4)c3)C2)CC1] | 526.3 | * |
| 37 | 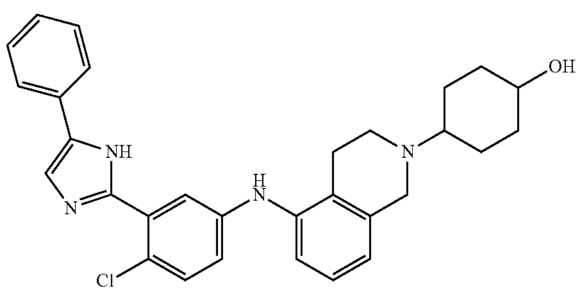 [SMILES: OC1CCC(N2CCc3c(cccc3Nc3ccc(Cl)c(-c4ncc(-c5ccccc5)[nH]4)c3)C2)CC1] | 499.2 | * |
| 38 | 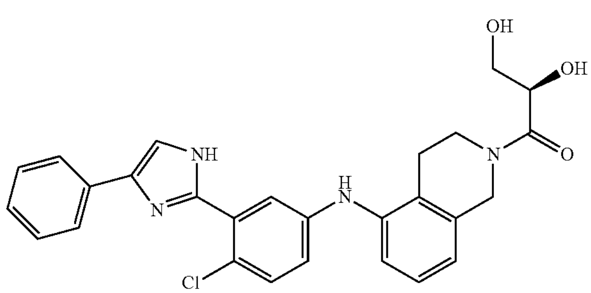 [SMILES: O=C([C@H](O)CO)N1CCc2c(cccc2Nc2ccc(Cl)c(-c3nc(-c4ccccc4)c[nH]3)c2)C1] | 489.2 | * |

TABLE 1-continued
| Compound Number | Structure | Physical Data MS (m/z) | IC$_{50}$ Ranges |
|---|---|---|---|
| 39 | 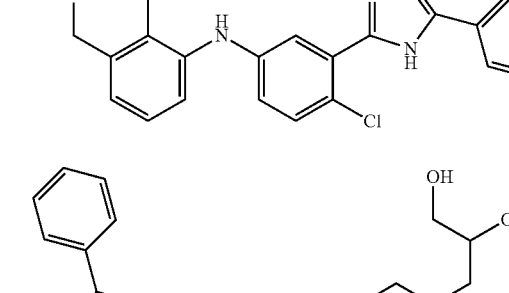 | 499.2 | * |
| 40 | 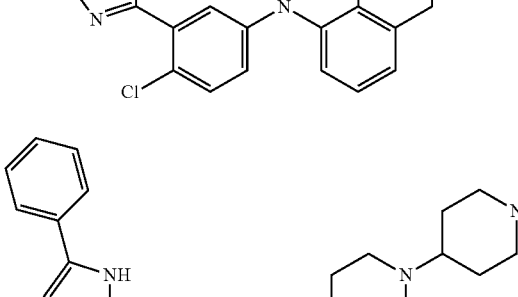 | 475.2 | * |
| 41 | 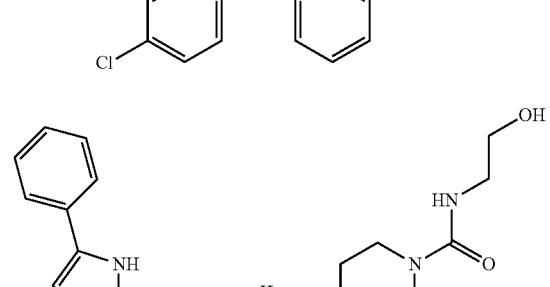 | 498.2 | ** |
| 42 | 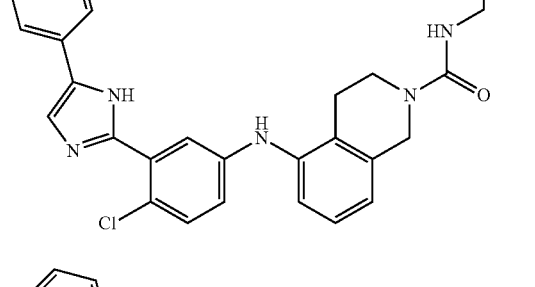 | 488.2 | * |
| 43 | 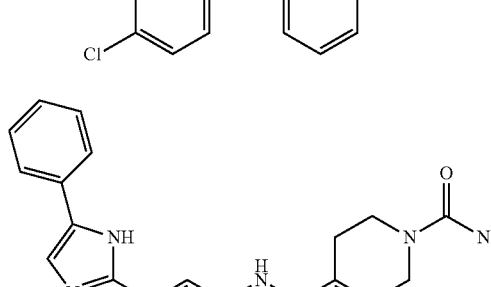 | 444.2 | ** |

TABLE 1-continued

| Compound Number | Structure | Physical Data MS (m/z) | IC$_{50}$ Ranges |
|---|---|---|---|
| 44 | 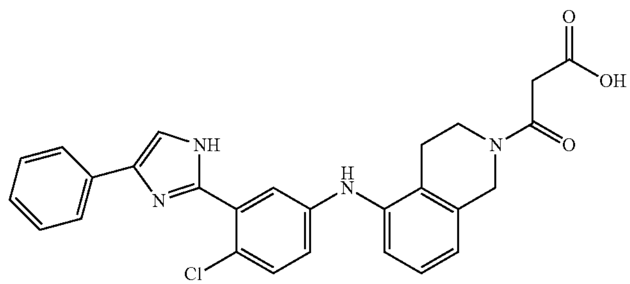 [SMILES: O=C(O)CC(=O)N1CCc2c(cccc2Nc2ccc(Cl)c(-c3nc(-c4ccccc4)c[nH]3)c2)C1] | 487.1 | ** |
| 45 | 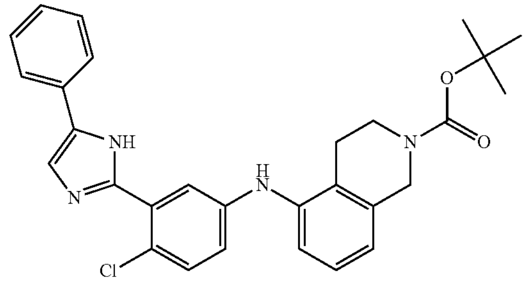 [SMILES: CC(C)(C)OC(=O)N1CCc2c(cccc2Nc2ccc(Cl)c(-c3ncc(-c4ccccc4)[nH]3)c2)C1] | 501.2 | ** |
| 46 | 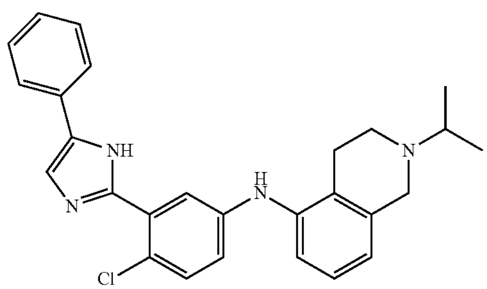 [SMILES: CC(C)N1CCc2c(cccc2Nc2ccc(Cl)c(-c3ncc(-c4ccccc4)[nH]3)c2)C1] | 443.2 | ** |
| 47 | 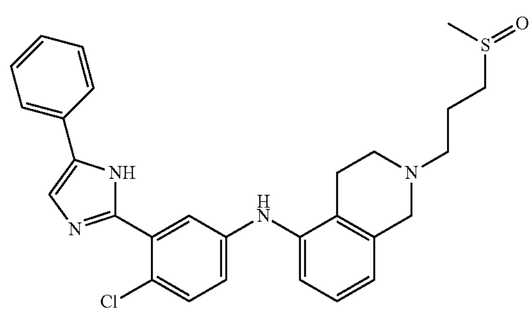 [SMILES: CS(=O)CCCN1CCc2c(cccc2Nc2ccc(Cl)c(-c3ncc(-c4ccccc4)[nH]3)c2)C1] | 505.2 | ** |
| 48 | 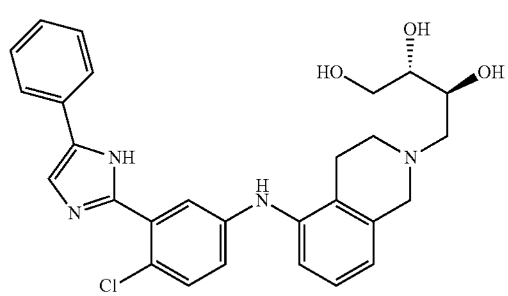 [SMILES: OC[C@H](O)[C@@H](O)CN1CCc2c(cccc2Nc2ccc(Cl)c(-c3ncc(-c4ccccc4)[nH]3)c2)C1] | 505.2 | ** |

TABLE 1-continued

| Compound Number | Structure | Physical Data MS (m/z) | IC$_{50}$ Ranges |
|---|---|---|---|
| 49 | 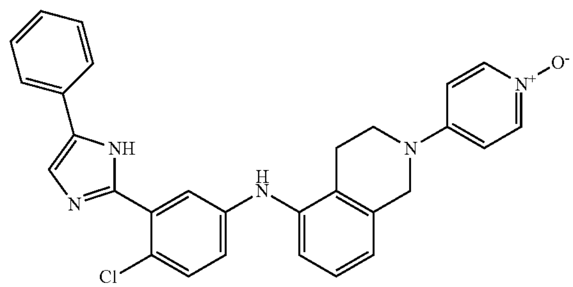 [SMILES: [O-][n+]1ccc(N2CCc3c(cccc3Nc3ccc(Cl)c(-c4ncc(-c5ccccc5)[nH]4)c3)C2)cc1] | 494.2 | ** |
| 50 | 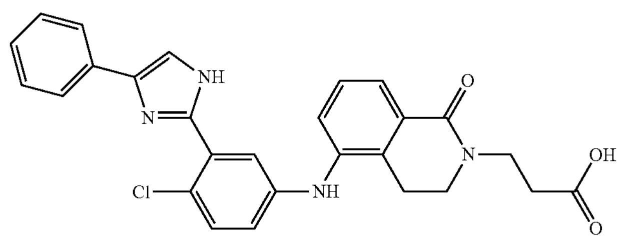 [SMILES: O=C(O)CCN1CCc2c(Nc3ccc(Cl)c(-c4nc(-c5ccccc5)c[nH]4)c3)cccc2C1=O] | 487.1 | *** |
| 51 | 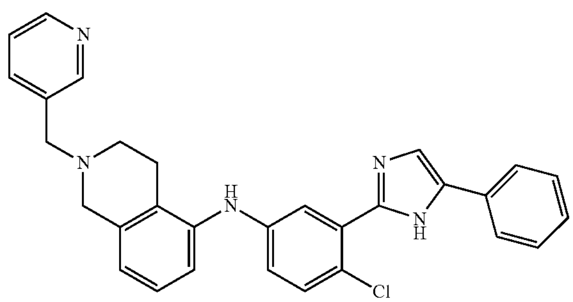 [SMILES: Clc1ccc(Nc2cccc3c2CCN(Cc2cccnc2)C3)cc1-c1ncc(-c2ccccc2)[nH]1] | 492.2 | *** |
| 52 | 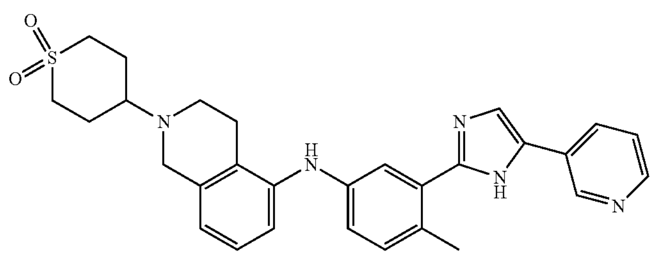 [SMILES: Cc1ccc(Nc2cccc3c2CCN(C2CCS(=O)(=O)CC2)C3)cc1-c1ncc(-c2cccnc2)[nH]1] | 514.2 | *** |
| 53 | 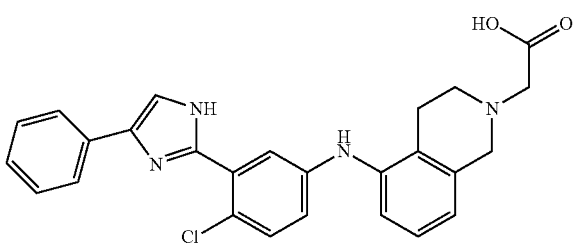 [SMILES: O=C(O)CN1CCc2c(cccc2Nc2ccc(Cl)c(-c3nc(-c4ccccc4)c[nH]3)c2)C1] | 459.2 | *** |

TABLE 1-continued

| Compound Number | Structure | Physical Data MS (m/z) | IC$_{50}$ Ranges |
|---|---|---|---|
| 54 | 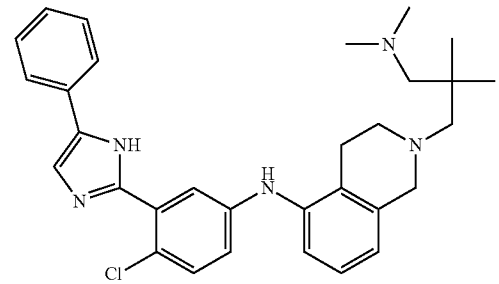 [SMILES: CN(C)CC(C)(C)CN1CCc2c(cccc2Nc2ccc(Cl)c(-c3ncc(-c4ccccc4)[nH]3)c2)C1] | 514.3 | * |
| 55 | 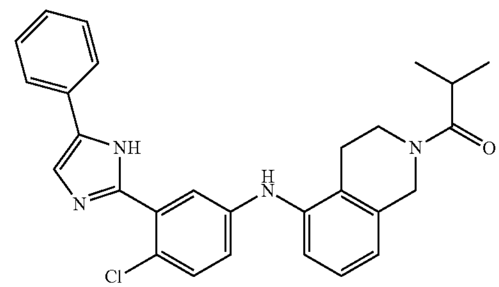 [SMILES: CC(C)C(=O)N1CCc2c(cccc2Nc2ccc(Cl)c(-c3ncc(-c4ccccc4)[nH]3)c2)C1] | 471.2 | ** |
| 56 | 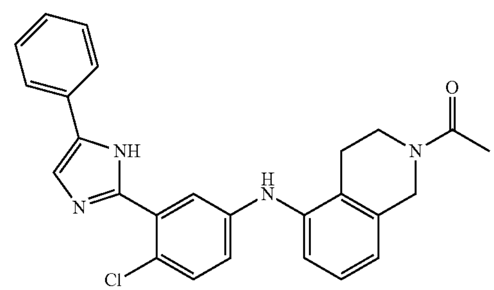 [SMILES: CC(=O)N1CCc2c(cccc2Nc2ccc(Cl)c(-c3ncc(-c4ccccc4)[nH]3)c2)C1] | 443.2 | * |
| 57 | 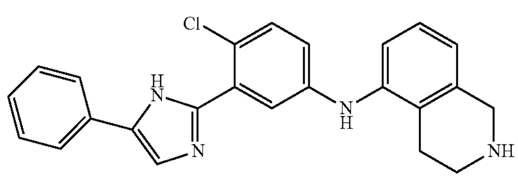 [SMILES: Clc1ccc(Nc2cccc3c2CCNC3)cc1-c1ncc(-c2ccccc2)[nH]1] | 401.1 | *** |
| 58 | 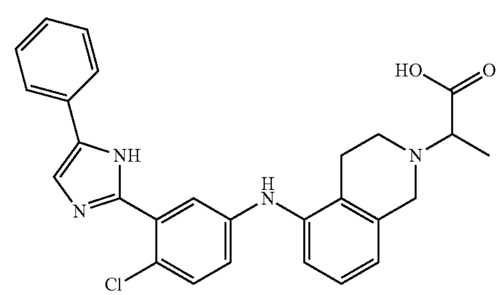 [SMILES: CC(C(=O)O)N1CCc2c(cccc2Nc2ccc(Cl)c(-c3ncc(-c4ccccc4)[nH]3)c2)C1] | 473.2 | ** |
| 59 | 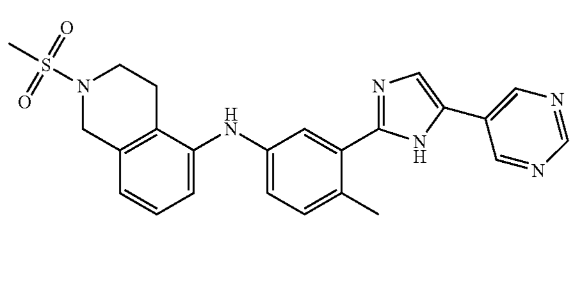 [SMILES: Cc1ccc(Nc2cccc3c2CCN(S(C)(=O)=O)C3)cc1-c1ncc(-c2cncnc2)[nH]1] | 461.2 | ** |

TABLE 1-continued

| Compound Number | Structure | Physical Data MS (m/z) | IC$_{50}$ Ranges |
|---|---|---|---|
| 60 | 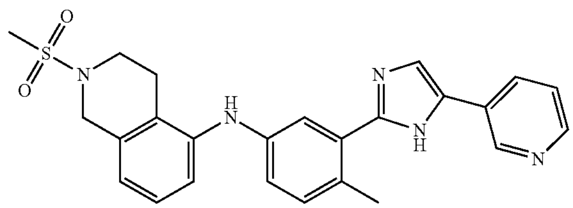 [SMILES: Cc1ccc(Nc2cccc3c2CCN(S(C)(=O)=O)C3)cc1-c1ncc(-c2cccnc2)[nH]1] | 460.2 | * |
| 61 | 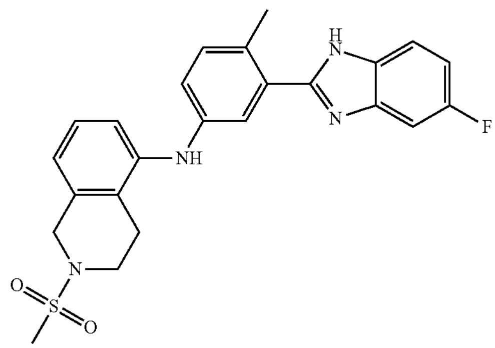 [SMILES: Cc1ccc(Nc2cccc3c2CCN(S(C)(=O)=O)C3)cc1-c1nc2cc(F)ccc2[nH]1] | 451.2 | * |
| 62 | 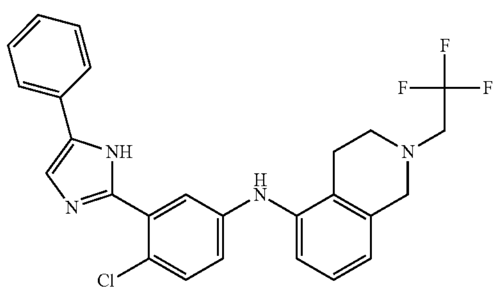 [SMILES: FC(F)(F)CN1CCc2c(cccc2Nc2ccc(Cl)c(-c3ncc(-c4ccccc4)[nH]3)c2)C1] | 483.1 | * |
| 63 | 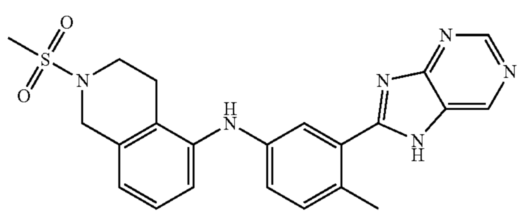 [SMILES: Cc1ccc(Nc2cccc3c2CCN(S(C)(=O)=O)C3)cc1-c1nc2ncncc2[nH]1] | 435.2 | *** |
| 64 | 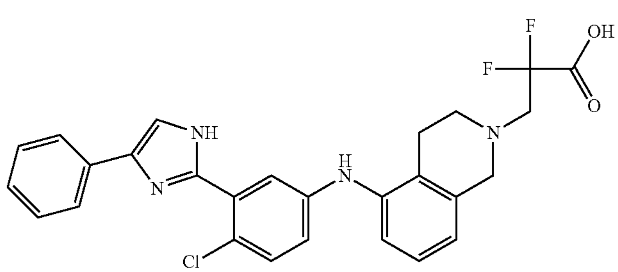 [SMILES: O=C(O)C(F)(F)CN1CCc2c(cccc2Nc2ccc(Cl)c(-c3nc(-c4ccccc4)c[nH]3)c2)C1] | 509.1 | ** |

TABLE 1-continued

| Compound Number | Structure | Physical Data MS (m/z) | IC$_{50}$ Ranges |
|---|---|---|---|
| 65 | 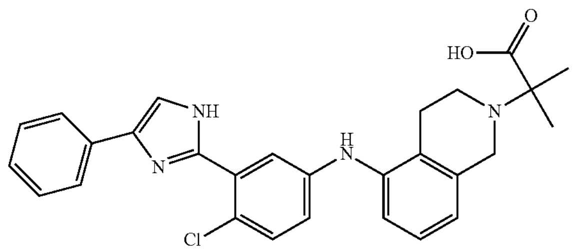 [SMILES: CC(C)(C(=O)O)N1CCc2c(cccc2Nc2ccc(Cl)c(-c3nc(-c4ccccc4)c[nH]3)c2)C1] | 487.2 | ** |
| 66 | 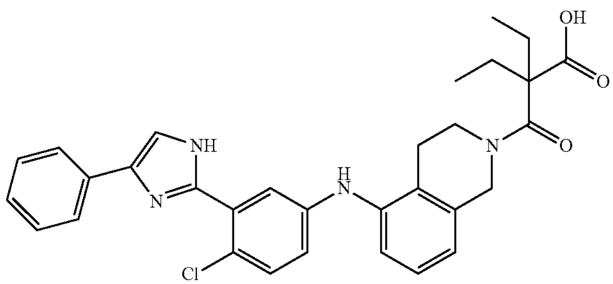 [SMILES: CCC(CC)(C(=O)O)C(=O)N1CCc2c(cccc2Nc2ccc(Cl)c(-c3nc(-c4ccccc4)c[nH]3)c2)C1] | 543.2 | ** |
| 67 | 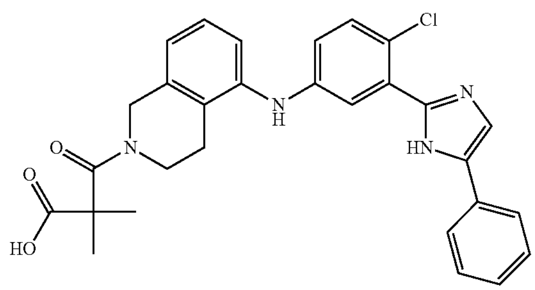 [SMILES: CC(C)(C(=O)O)C(=O)N1CCc2c(cccc2Nc2ccc(Cl)c(-c3ncc(-c4ccccc4)[nH]3)c2)C1] | 515.2 | ** |
| 68 | 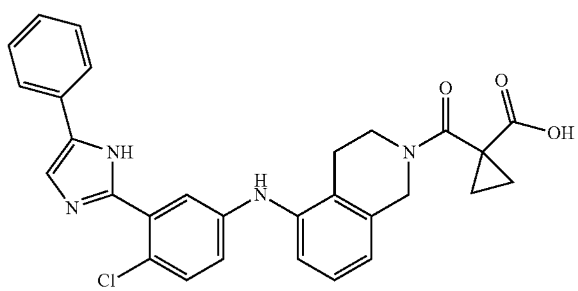 [SMILES: O=C(O)C1(C(=O)N2CCc3c(cccc3Nc3ccc(Cl)c(-c4ncc(-c5ccccc5)[nH]4)c3)C2)CC1] | 513.2 | * |
| 69 | 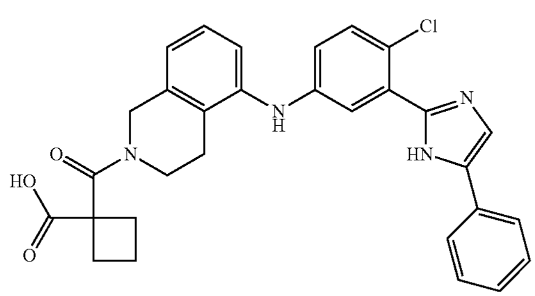 [SMILES: O=C(O)C1(C(=O)N2CCc3c(cccc3Nc3ccc(Cl)c(-c4ncc(-c5ccccc5)[nH]4)c3)C2)CCC1] | 527.2 | ** |

TABLE 1-continued

| Compound Number | Structure | Physical Data MS (m/z) | IC$_{50}$ Ranges |
|---|---|---|---|
| 70 | 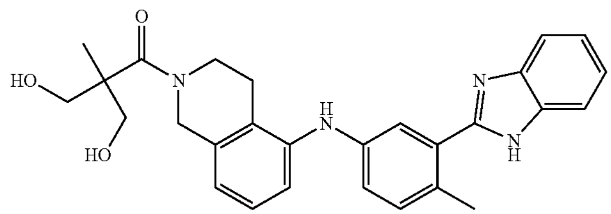 [SMILES: Cc1ccc(Nc2cccc3c2CCN(C(=O)C(C)(CO)CO)C3)cc1-c1nc2ccccc2[nH]1] | 471.2 | * |
| 71 | 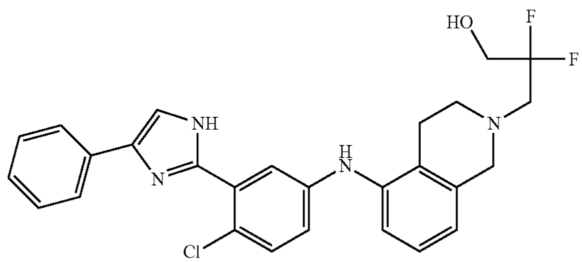 [SMILES: OCC(F)(F)CN1CCc2c(cccc2Nc2ccc(Cl)c(-c3nc(-c4ccccc4)c[nH]3)c2)C1] | 495.2 | * |
| 72 | 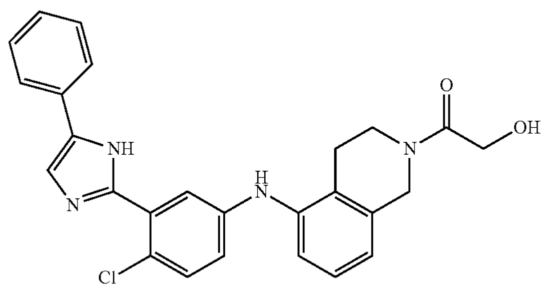 [SMILES: O=C(CO)N1CCc2c(cccc2Nc2ccc(Cl)c(-c3ncc(-c4ccccc4)[nH]3)c2)C1] | 459.2 | * |
| 73 | 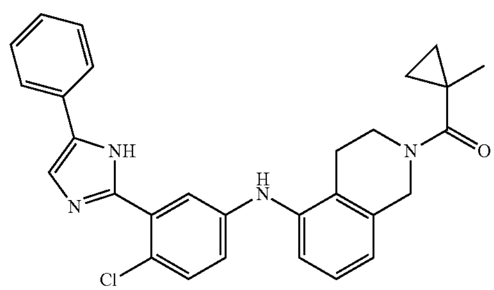 [SMILES: CC1(C(=O)N2CCc3c(cccc3Nc3ccc(Cl)c(-c4ncc(-c5ccccc5)[nH]4)c3)C2)CC1] | 483.2 | * |
| 74 | 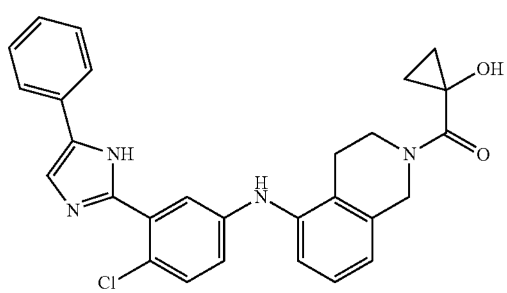 [SMILES: O=C(N1CCc2c(cccc2Nc2ccc(Cl)c(-c3ncc(-c4ccccc4)[nH]3)c2)C1)C1(O)CC1] | 485.2 | * |

TABLE 1-continued

| Compound Number | Structure | Physical Data MS (m/z) | IC$_{50}$ Ranges |
|---|---|---|---|
| 75 | 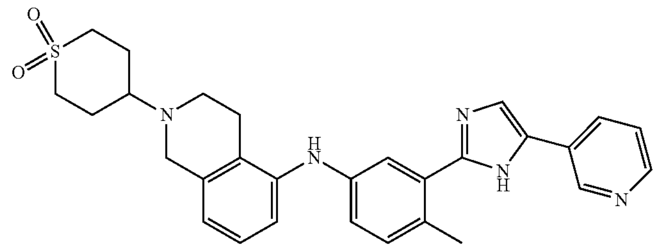 [SMILES: Cc1ccc(Nc2cccc3c2CCN(C2CCS(=O)(=O)CC2)C3)cc1-c1ncc(-c2cccnc2)[nH]1] | 514.2 | ** |
| 76 | 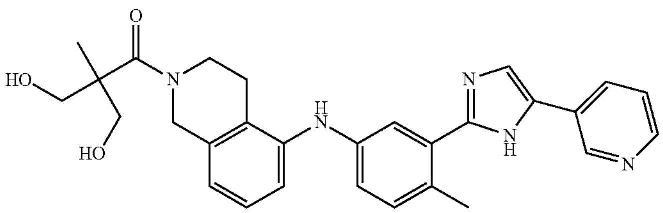 [SMILES: Cc1ccc(Nc2cccc3c2CCN(C(=O)C(C)(CO)CO)C3)cc1-c1ncc(-c2cccnc2)[nH]1] | 498.2 | ** |
| 77 | 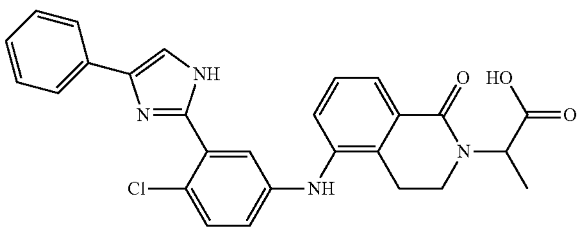 [SMILES: CC(C(=O)O)N1CCc2c(Nc3ccc(Cl)c(-c4nc(-c5ccccc5)c[nH]4)c3)cccc2C1=O] | 487.1 | **** |
| 78 | 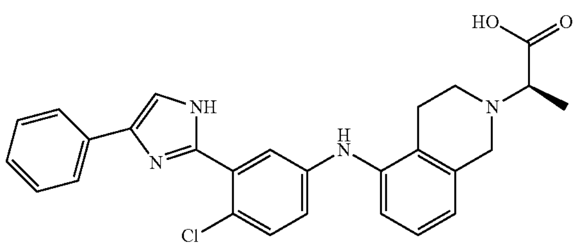 [SMILES: C[C@H](C(=O)O)N1CCc2c(cccc2Nc2ccc(Cl)c(-c3nc(-c4ccccc4)c[nH]3)c2)C1] | 473.2 | ** |
| 79 | 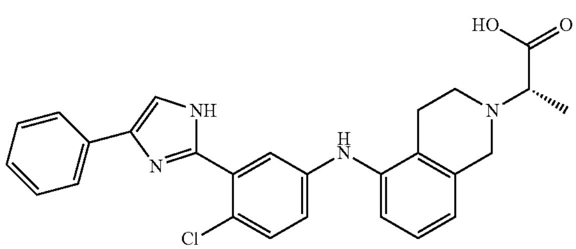 [SMILES: C[C@@H](C(=O)O)N1CCc2c(cccc2Nc2ccc(Cl)c(-c3nc(-c4ccccc4)c[nH]3)c2)C1] | 473.2 | ** |
| 80 | 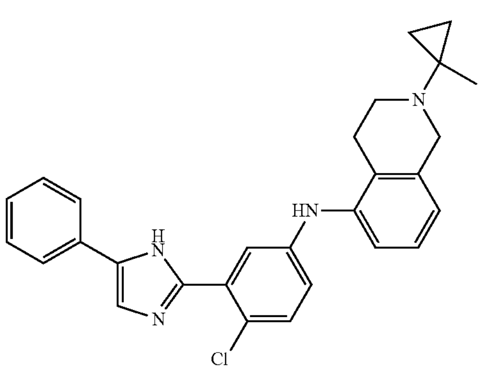 [SMILES: CC1(N2CCc3c(cccc3Nc3ccc(Cl)c(-c4ncc(-c5ccccc5)[nH]4)c3)C2)CC1] | 455.2 | ** |

TABLE 1-continued

| Compound Number | Structure | Physical Data MS (m/z) | IC$_{50}$ Ranges |
|---|---|---|---|
| 81 | 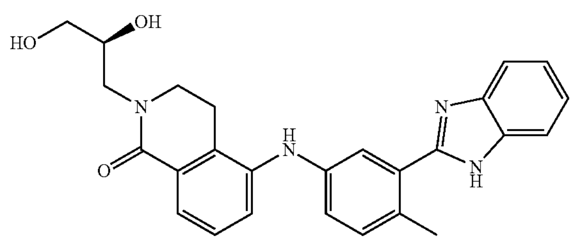 [SMILES: Cc1ccc(Nc2cccc3c2CCN(C[C@H](O)CO)C3=O)cc1-c1nc2ccccc2[nH]1] | 443.2 | *** |
| 82 | 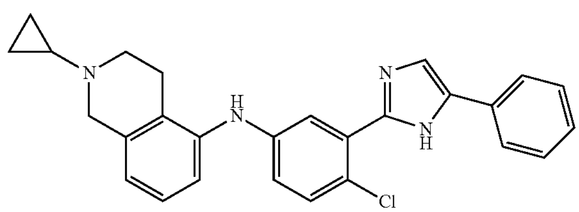 [SMILES: Clc1ccc(Nc2cccc3c2CCN(C2CC2)C3)cc1-c1ncc(-c2ccccc2)[nH]1] | 441.2 | * |
| 83 | 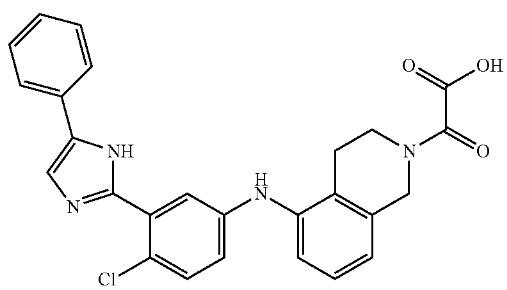 [SMILES: O=C(O)C(=O)N1CCc2c(cccc2Nc2ccc(Cl)c(-c3ncc(-c4ccccc4)[nH]3)c2)C1] | 473.1 | *** |
| 84 | 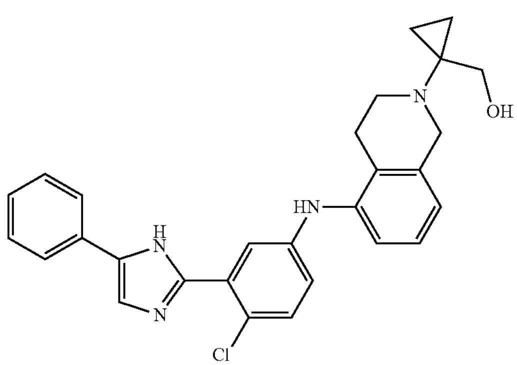 [SMILES: OCC1(N2CCc3c(cccc3Nc3ccc(Cl)c(-c4ncc(-c5ccccc5)[nH]4)c3)C2)CC1] | 471.2 | * |
| 85 | 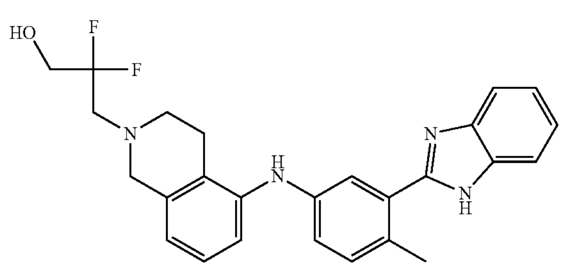 [SMILES: Cc1ccc(Nc2cccc3c2CCN(CC(F)(F)CO)C3)cc1-c1nc2ccccc2[nH]1] | 449.2 | * |

TABLE 1-continued
| Compound Number | Structure | Physical Data MS (m/z) | IC$_{50}$ Ranges |
|---|---|---|---|
| 86 | 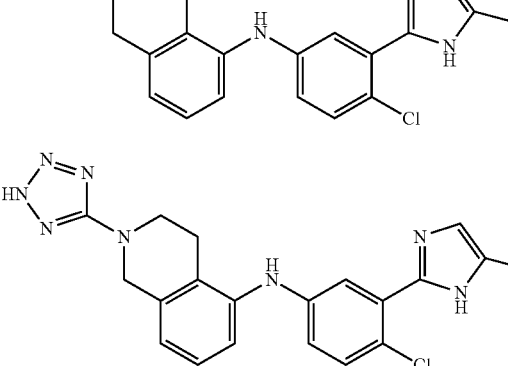 | 483.2 | ** |
| 87 | 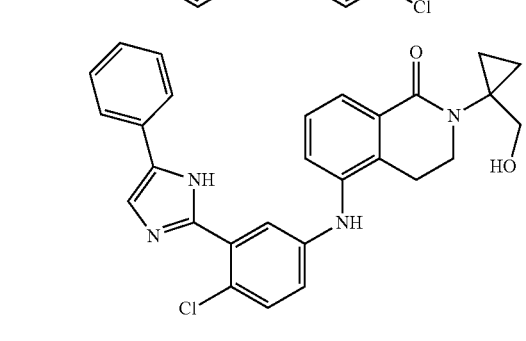 | 469.2 | ** |
| 88 | 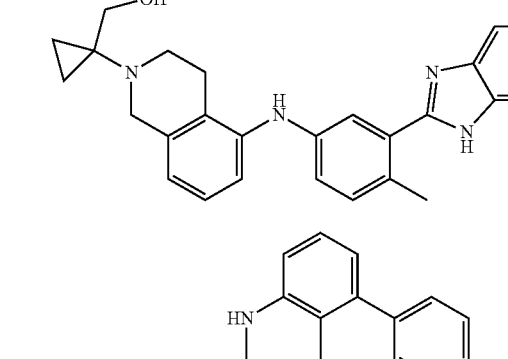 | 485.2 | * |
| 89 | 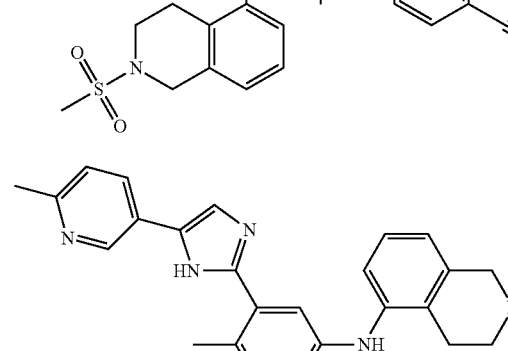 | 425.2 | ** |
| 90 | 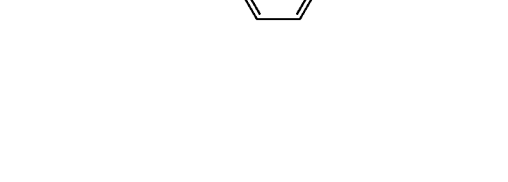 | 418.2 | **** |
| 91 | 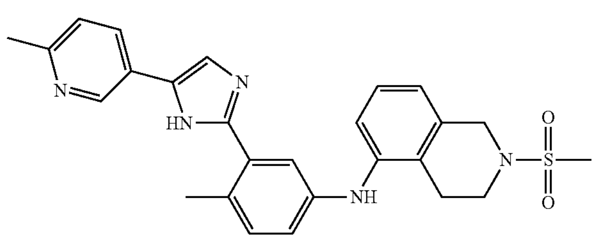 | 474.2 | ** |

TABLE 1-continued

| Compound Number | Structure | Physical Data MS (m/z) | IC$_{50}$ Ranges |
|---|---|---|---|
| 92 | 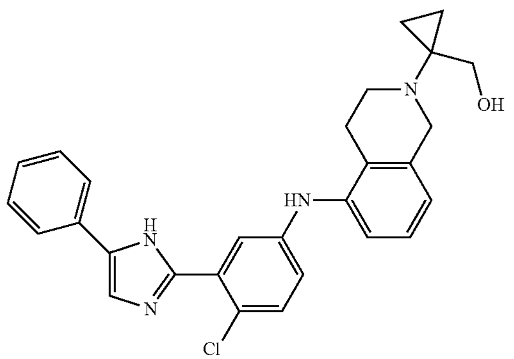 [SMILES: OCC1(N2CCc3c(cccc3Nc3ccc(Cl)c(-c4ncc(-c5ccccc5)[nH]4)c3)C2)CC1] | 471.2 | * |
| 93 | 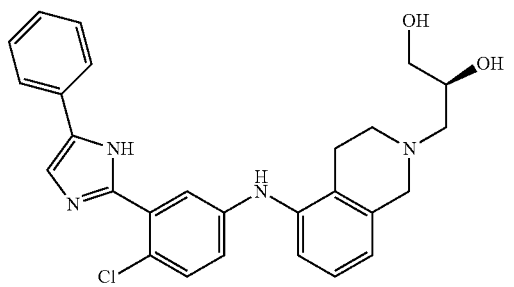 [SMILES: OC[C@@H](O)CN1CCc2c(cccc2Nc2ccc(Cl)c(-c3ncc(-c4ccccc4)[nH]3)c2)C1] | 475.2 | ** |
| 94 | 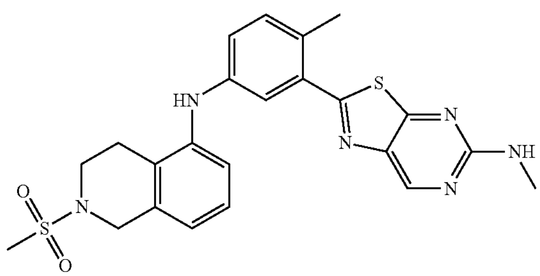 | 481.1 | *** |
| 95 | 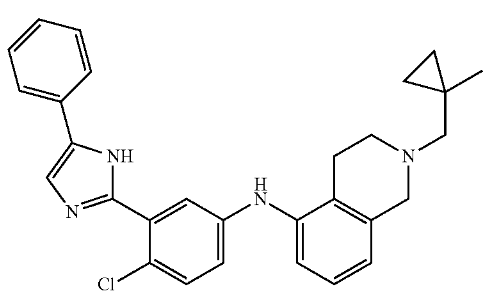 [SMILES: CC1(CN2CCc3c(cccc3Nc3ccc(Cl)c(-c4ncc(-c5ccccc5)[nH]4)c3)C2)CC1] | 469.2 | * |
| 96 | 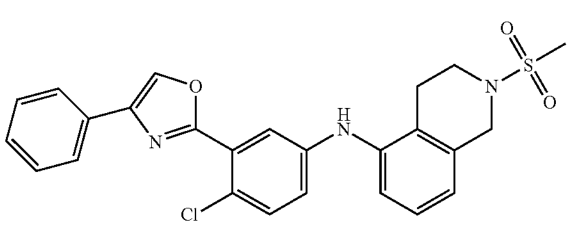 [SMILES: CS(=O)(=O)N1CCc2c(cccc2Nc2ccc(Cl)c(-c3nc(-c4ccccc4)co3)c2)C1] | 480.1 | **** |

TABLE 1-continued

| Compound Number | Structure | Physical Data MS (m/z) | IC$_{50}$ Ranges |
|---|---|---|---|
| 97 | 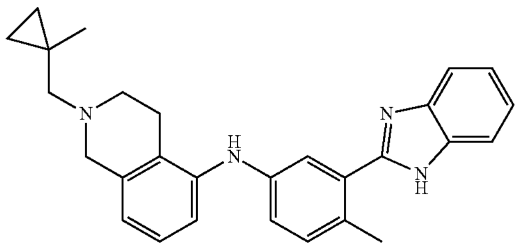 [SMILES: Cc1ccc(Nc2cccc3c2CCN(CC2(C)CC2)C3)cc1-c1nc2ccccc2[nH]1] | 423.2 | ** |
| 98 | 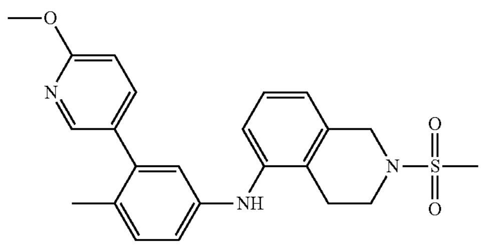 | 424.2 | *** |
| 99 | 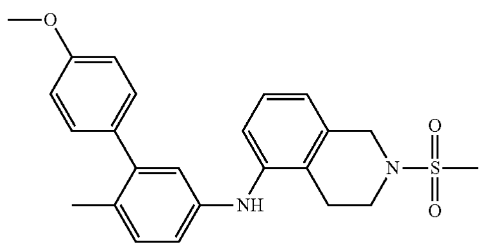 | 423.2 | *** |
| 100 | 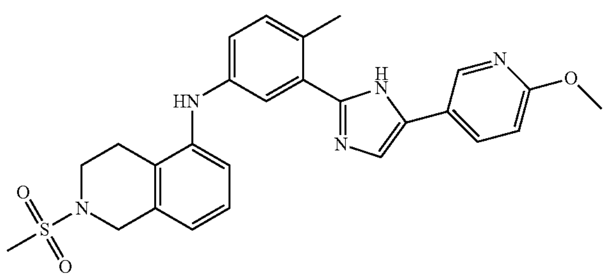 | 490.2 | * |
| 101 | 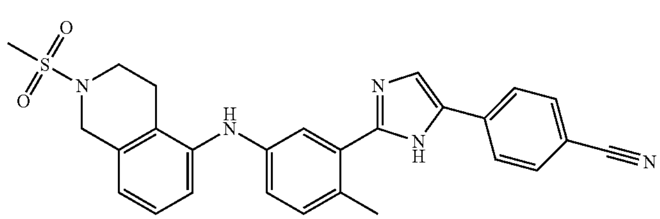 [SMILES: Cc1ccc(Nc2cccc3c2CCN(S(C)(=O)=O)C3)cc1-c1ncc(-c2ccc(C#N)cc2)[nH]1] | 484.2 | * |

TABLE 1-continued

| Compound Number | Structure | Physical Data MS (m/z) | IC$_{50}$ Ranges |
|---|---|---|---|
| 102 | 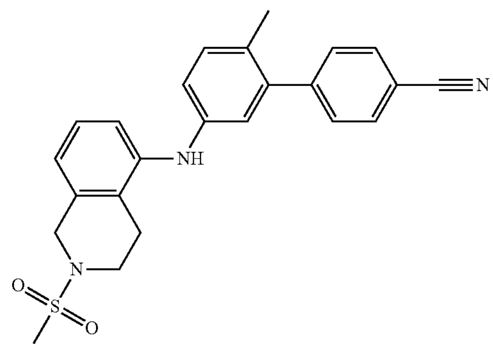 | 418.2 | ** |
| 103 | 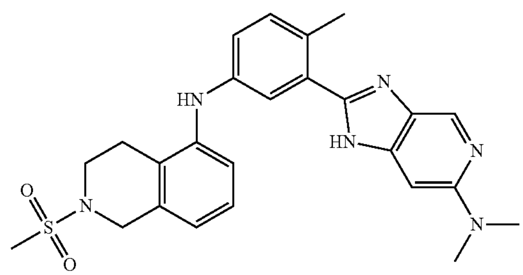 | 477.2 | *** |
| 104 | 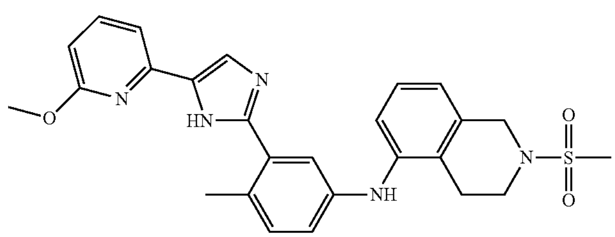 | 490.2 | * |
| 105 | 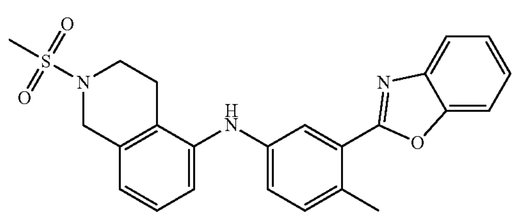 [SMILES: Cc1ccc(Nc2cccc3c2CCN(S(C)(=O)=O)C3)cc1-c1nc2ccccc2o1] | 434.1 | ** |
| 106 | 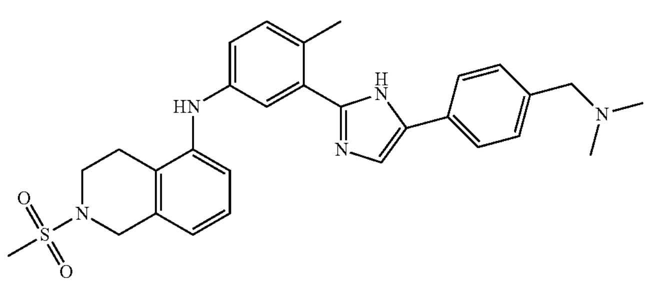 | 516.2 | ** |

TABLE 1-continued

| Compound Number | Structure | Physical Data MS (m/z) | IC$_{50}$ Ranges |
|---|---|---|---|
| 107 | 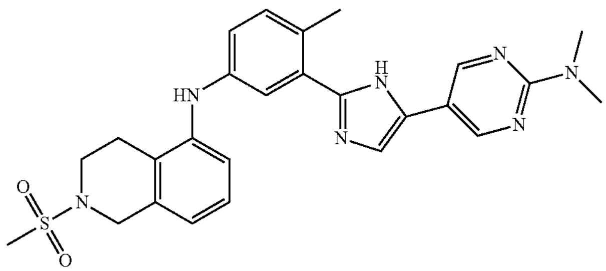 | 504.2 | ** |
| 108 | 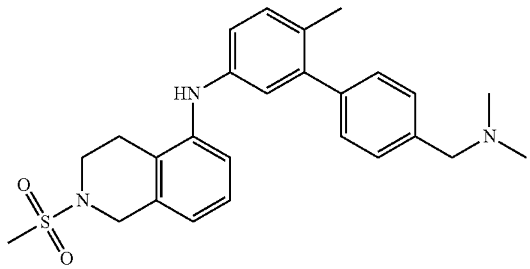 | 450.2 | **** |
| 109 | 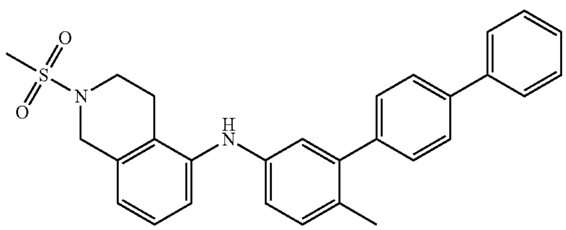 [SMILES: Cc1ccc(Nc2cccc3c2CCN(S(C)(=O)=O)C3)cc1-c1ccc(-c2ccccc2)cc1] | 469.2 | **** |
| 110 | 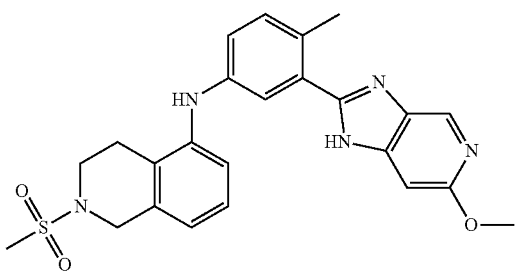 | 464.2 | *** |
| 111 | 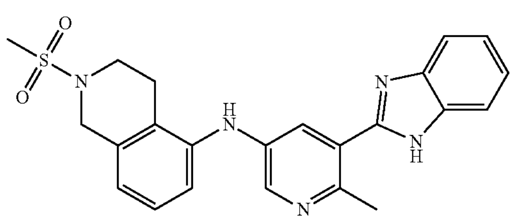 [SMILES: Cc1ncc(Nc2cccc3c2CCN(S(C)(=O)=O)C3)cc1-c1nc2ccccc2[nH]1] | 434.2 | ** |
| 112 | 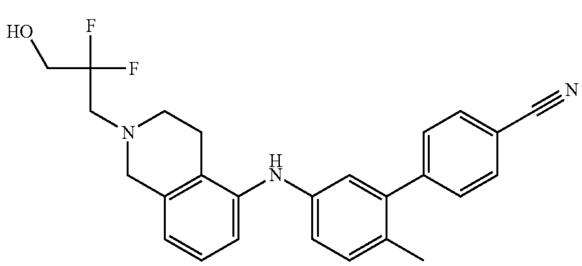 | 434.2 | *** |

TABLE 1-continued

| Compound Number | Structure | Physical Data MS (m/z) | IC$_{50}$ Ranges |
|---|---|---|---|
| 113 | 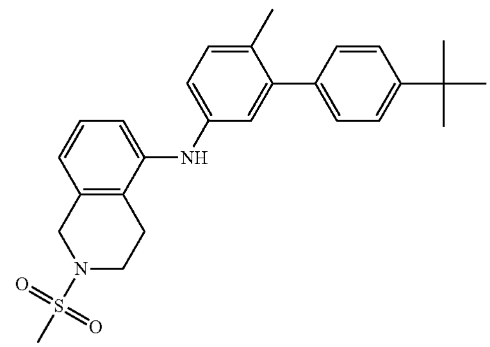 [SMILES: Cc1ccc(Nc2cccc3c2CCN(S(C)(=O)=O)C3)cc1-c1ccc(C(C)(C)C)cc1] | 449.2 | ***** |
| 114 | 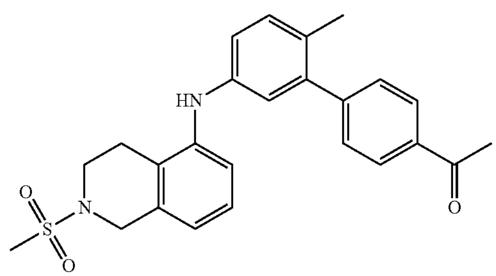 [SMILES: CC(=O)c1ccc(-c2cc(Nc3cccc4c3CCN(S(C)(=O)=O)C4)ccc2C)cc1] | 435.2 | **** |
| 115 | 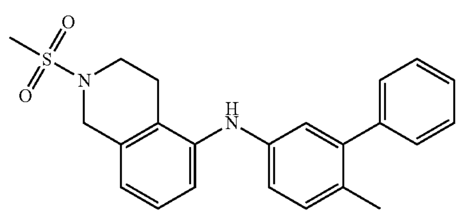 [SMILES: Cc1ccc(Nc2cccc3c2CCN(S(C)(=O)=O)C3)cc1-c1ccccc1] | 393.2 | **** |
| 116 | 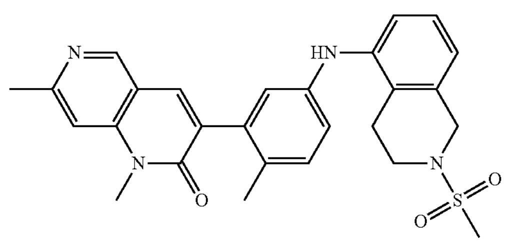 [SMILES: Cc1cc2c(cn1)cc(-c1cc(Nc3cccc4c3CCN(S(C)(=O)=O)C4)ccc1C)c(=O)n2C] | 489.2 | **** |
| 117 | 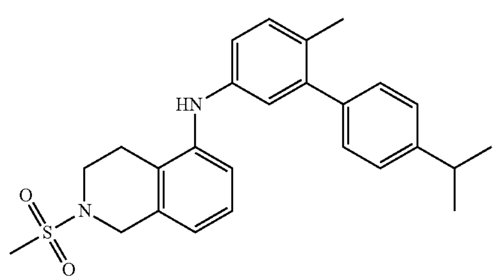 [SMILES: Cc1ccc(Nc2cccc3c2CCN(S(C)(=O)=O)C3)cc1-c1ccc(C(C)C)cc1] | 435.2 | **** |
| 118 | 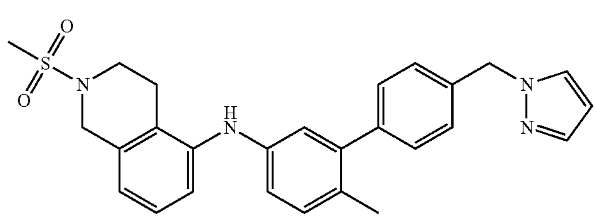 [SMILES: Cc1ccc(Nc2cccc3c2CCN(S(C)(=O)=O)C3)cc1-c1ccc(Cn2cccn2)cc1] | 473.2 | **** |

TABLE 1-continued

| Compound Number | Structure | Physical Data MS (m/z) | IC$_{50}$ Ranges |
|---|---|---|---|
| 119 | 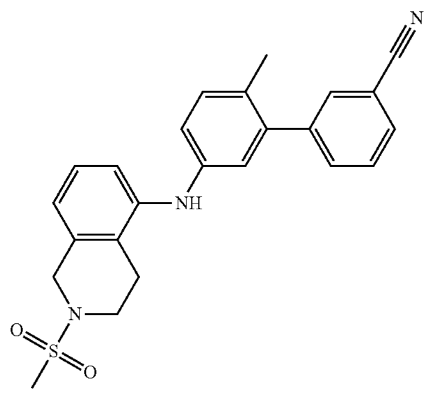 [SMILES: Cc1ccc(Nc2cccc3c2CCN(S(C)(=O)=O)C3)cc1-c1cccc(C#N)c1] | 418.2 | *** |
| 120 | 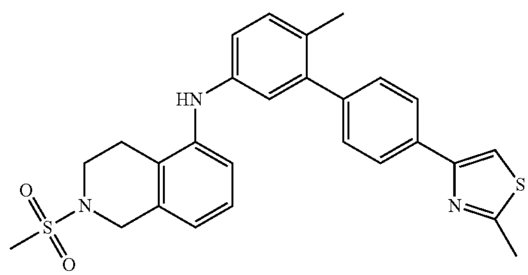 [SMILES: Cc1nc(-c2ccc(-c3cc(Nc4cccc5c4CCN(S(C)(=O)=O)C5)ccc3C)cc2)cs1] | 490.2 | *** |
| 121 | 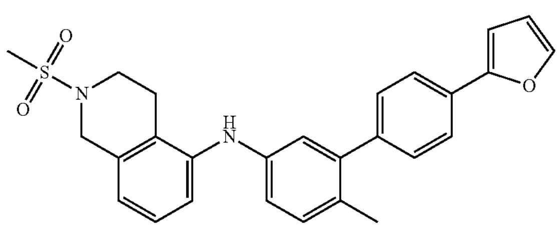 [SMILES: Cc1ccc(Nc2cccc3c2CCN(S(C)(=O)=O)C3)cc1-c1ccc(-c2ccco2)cc1] | 459.2 | **** |
| 122 | 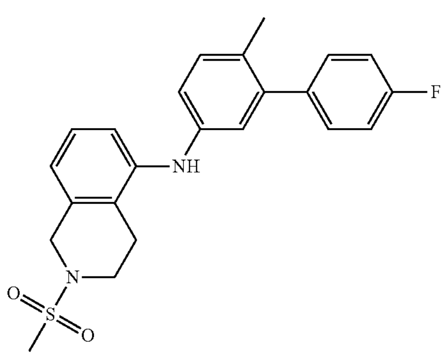 [SMILES: Cc1ccc(Nc2cccc3c2CCN(S(C)(=O)=O)C3)cc1-c1ccc(F)cc1] | 411.1 | **** |

TABLE 1-continued

| Compound Number | Structure | Physical Data MS (m/z) | IC$_{50}$ Ranges |
| --- | --- | --- | --- |
| 123 | 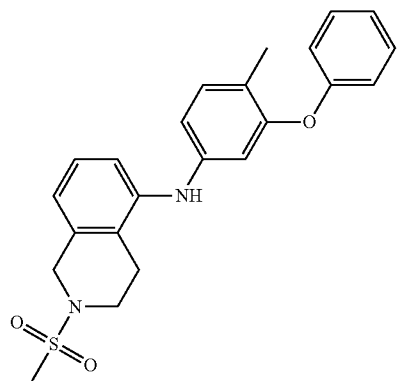 [SMILES: Cc1ccc(Nc2cccc3c2CCN(S(C)(=O)=O)C3)cc1Oc1ccccc1] | 409.2 | **** |
| 124 | 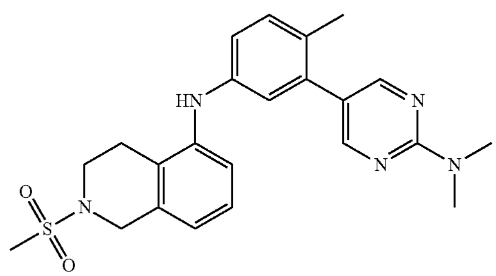 | 438.2 | **** |
| 125 | 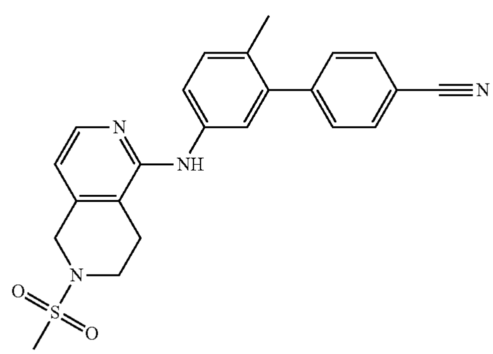 [SMILES: Cc1ccc(Nc2nccc3c2CCN(S(C)(=O)=O)C3)cc1-c1ccc(C#N)cc1] | 419.1 | *** |
| 126 | 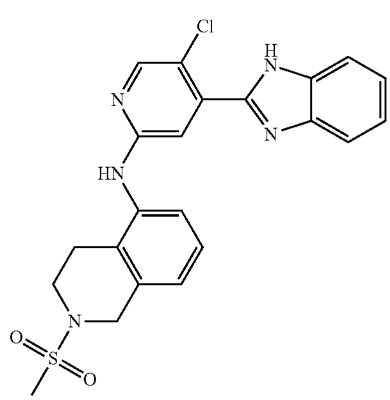 [SMILES: CS(=O)(=O)N1CCc2c(cccc2Nc2cc(-c3nc4ccccc4[nH]3)c(Cl)cn2)C1] | 454.1 | *** |

TABLE 1-continued

| Compound Number | Structure | Physical Data MS (m/z) | IC$_{50}$ Ranges |
|---|---|---|---|
| 127 | 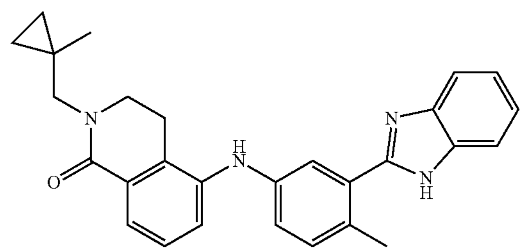 [SMILES: Cc1ccc(Nc2cccc3c2CCN(CC2(C)CC2)C3=O)cc1-c1nc2ccccc2[nH]1] | 437.2 | *** |
| 128 | 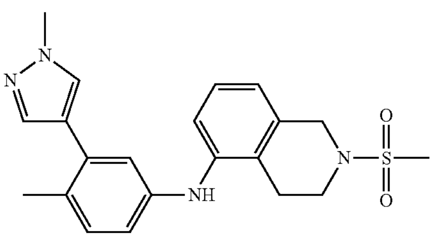 [SMILES: Cc1ccc(Nc2cccc3c2CCN(S(C)(=O)=O)C3)cc1-c1cnn(C)c1] | 397.2 | **** |
| 129 | 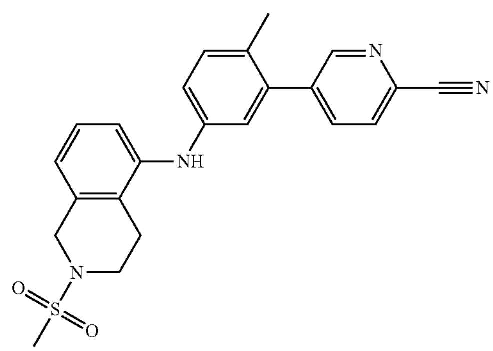 | 419.1 | *** |
| 130 | 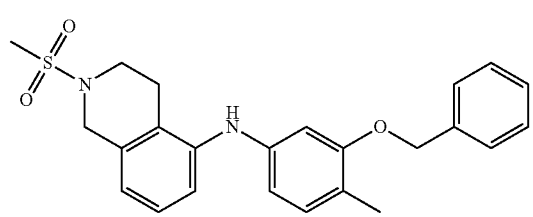 [SMILES: Cc1ccc(Nc2cccc3c2CCN(S(C)(=O)=O)C3)cc1OCc1ccccc1] | 423.2 | ** |
| 131 | 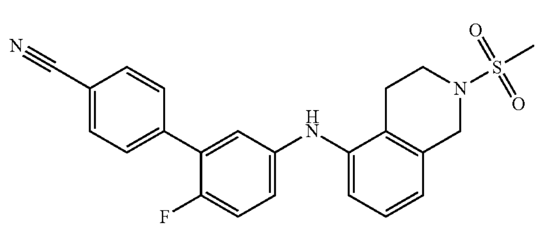 | 422.1 | *** |

TABLE 1-continued

| Compound Number | Structure | Physical Data MS (m/z) | IC$_{50}$ Ranges |
|---|---|---|---|
| 132 | 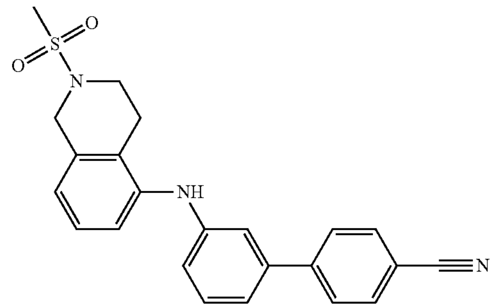 [SMILES: CS(=O)(=O)N1CCc2c(cccc2Nc2cccc(-c3ccc(C#N)cc3)c2)C1] | 404.1 | *** |
| 133 | 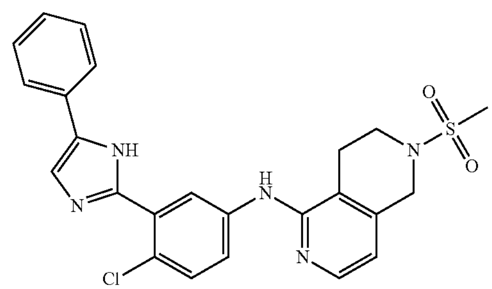 [SMILES: CS(=O)(=O)N1CCc2c(ccnc2Nc2ccc(Cl)c(-c3ncc(-c4ccccc4)[nH]3)c2)C1] | 480.1 | * |
| 134 | 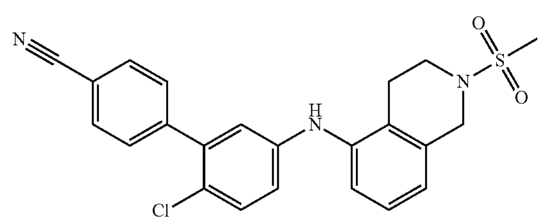 [SMILES: CS(=O)(=O)N1CCc2c(cccc2Nc2ccc(Cl)c(-c3ccc(C#N)cc3)c2)C1] | 438.1 | *** |
| 135 | 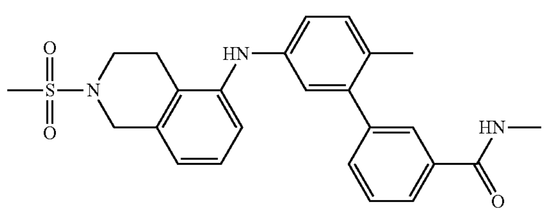 | 450.2 | ***** |
| 136 | 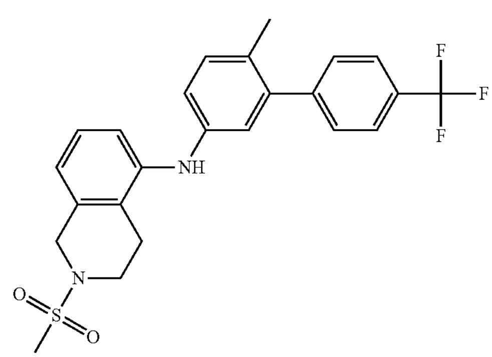 [SMILES: Cc1ccc(Nc2cccc3c2CCN(S(C)(=O)=O)C3)cc1-c1ccc(C(F)(F)F)cc1] | 461.1 | *** |

TABLE 1-continued

| Compound Number | Structure | Physical Data MS (m/z) | IC$_{50}$ Ranges |
|---|---|---|---|
| 137 | 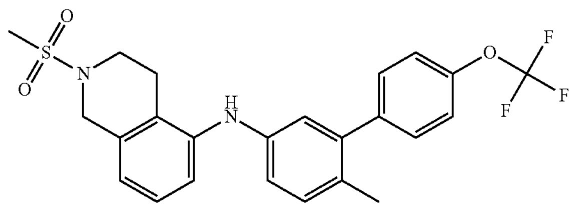 [SMILES: Cc1ccc(Nc2cccc3c2CCN(S(C)(=O)=O)C3)cc1-c1ccc(OC(F)(F)F)cc1] | 477.1 | *** |
| 138 | 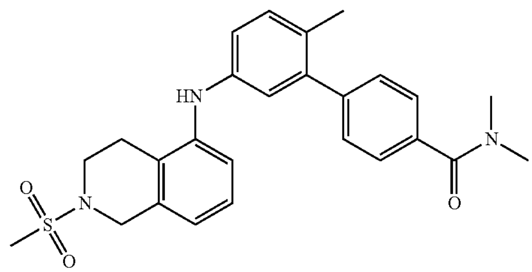 | 464.2 | **** |
| 139 | 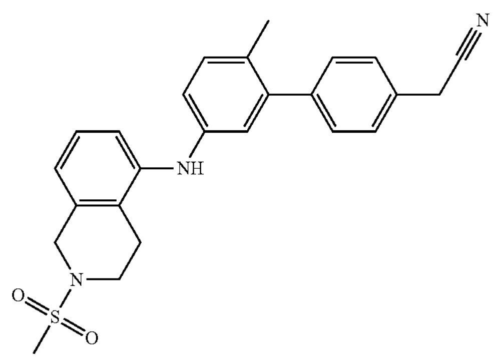 [SMILES: Cc1ccc(Nc2cccc3c2CCN(S(C)(=O)=O)C3)cc1-c1ccc(CC#N)cc1] | 432.2 | **** |
| 140 | 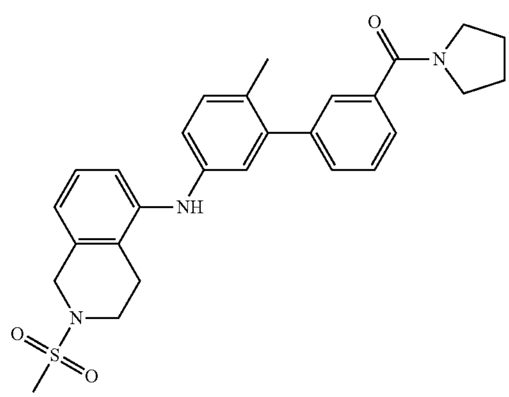 [SMILES: Cc1ccc(Nc2cccc3c2CCN(S(C)(=O)=O)C3)cc1-c1cccc(C(=O)N2CCCC2)c1] | 490.2 | ***** |
| 141 | 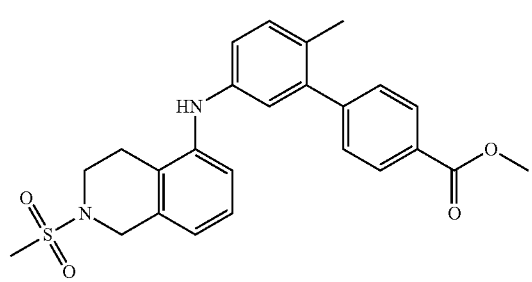 | 451.2 | **** |

TABLE 1-continued

| Compound Number | Structure | Physical Data MS (m/z) | IC$_{50}$ Ranges |
|---|---|---|---|
| 142 | 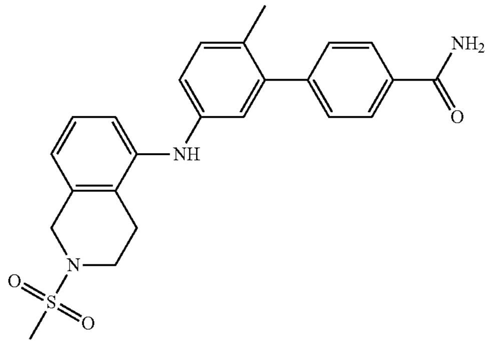 [SMILES: Cc1ccc(Nc2cccc3c2CCN(S(C)(=O)=O)C3)cc1-c1ccc(C(N)=O)cc1] | 436.2 | **** |
| 143 | 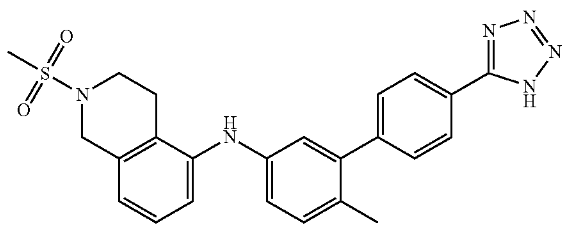 [SMILES: Cc1ccc(Nc2cccc3c2CCN(S(C)(=O)=O)C3)cc1-c1ccc(-c2nnn[nH]2)cc1] | 461.2 | ****** |
| 144 | 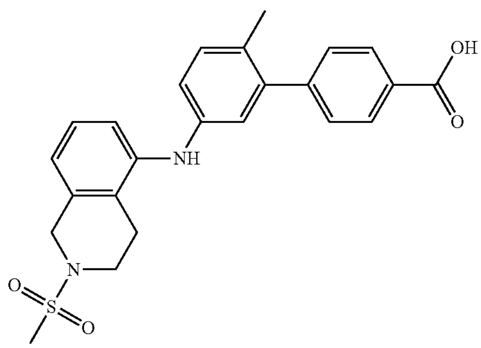 [SMILES: Cc1ccc(Nc2cccc3c2CCN(S(C)(=O)=O)C3)cc1-c1ccc(C(=O)O)cc1] | 437.1 | ***** |
| 145 | 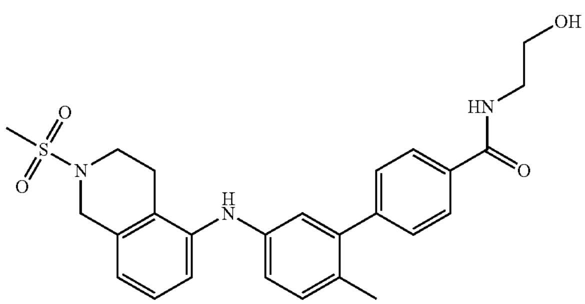 [SMILES: Cc1ccc(Nc2cccc3c2CCN(S(C)(=O)=O)C3)cc1-c1ccc(C(=O)NCCO)cc1] | 480.2 | **** |
| 146 | 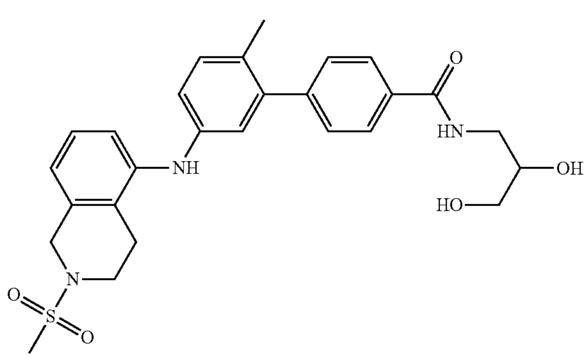 [SMILES: Cc1ccc(Nc2cccc3c2CCN(S(C)(=O)=O)C3)cc1-c1ccc(C(=O)NCC(O)CO)cc1] | 510.2 | ***** |

TABLE 1-continued

| Compound Number | Structure | Physical Data MS (m/z) | IC$_{50}$ Ranges |
|---|---|---|---|
| 147 | 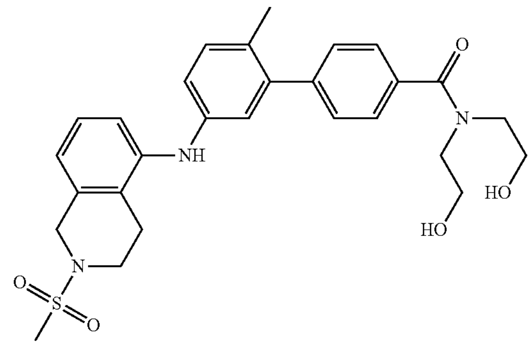 [SMILES: Cc1ccc(Nc2cccc3c2CCN(S(C)(=O)=O)C3)cc1-c1ccc(C(=O)N(CCO)CCO)cc1] | 524.2 | ***** |
| 148 | 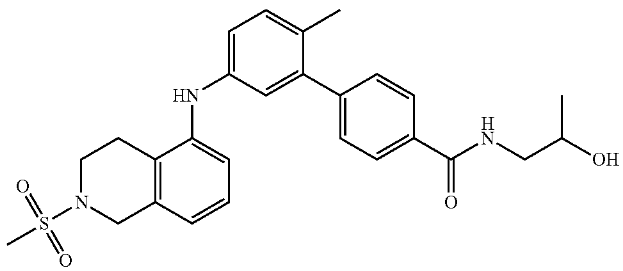 [SMILES: Cc1ccc(Nc2cccc3c2CCN(S(C)(=O)=O)C3)cc1-c1ccc(C(=O)NCC(C)O)cc1] | 494.2 | **** |
| 149 | 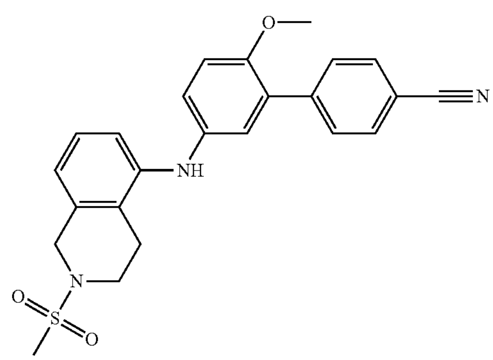 [SMILES: COc1ccc(Nc2cccc3c2CCN(S(C)(=O)=O)C3)cc1-c1ccc(C#N)cc1] | 434.1 | **** |
| 150 | 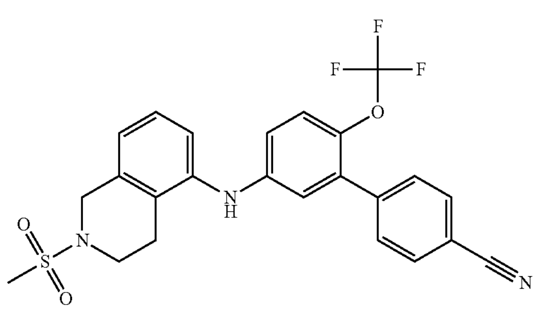 [SMILES: CS(=O)(=O)N1CCc2c(cccc2Nc2ccc(OC(F)(F)F)c(-c3ccc(C#N)cc3)c2)C1] | 488.1 | ***** |
| 151 | 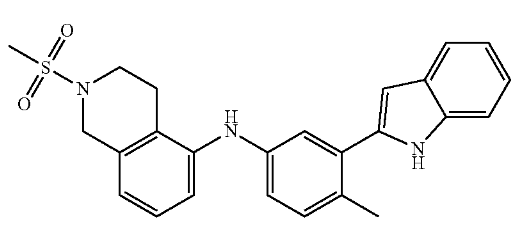 [SMILES: Cc1ccc(Nc2cccc3c2CCN(S(C)(=O)=O)C3)cc1-c1cc2ccccc2[nH]1] | 432.2 | *** |

TABLE 1-continued

| Compound Number | Structure | Physical Data MS (m/z) | IC$_{50}$ Ranges |
|---|---|---|---|
| 152 | 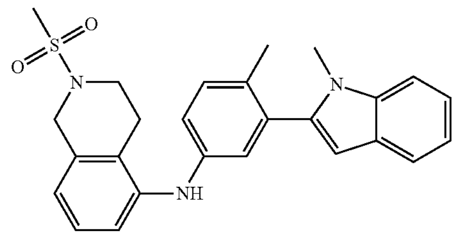 [SMILES: Cc1ccc(Nc2cccc3c2CCN(S(C)(=O)=O)C3)cc1-c1cc2ccccc2n1C] | 446.2 | *** |
| 153 | 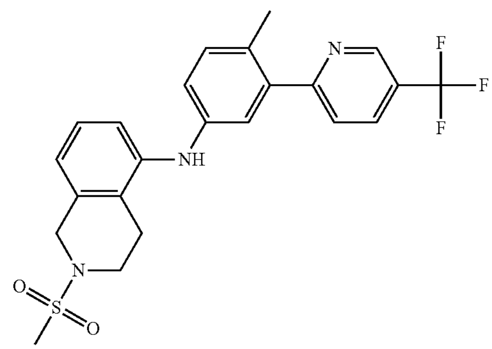 [SMILES: Cc1ccc(Nc2cccc3c2CCN(S(C)(=O)=O)C3)cc1-c1ccc(C(F)(F)F)cn1] | 462.1 | * |
| 154 | 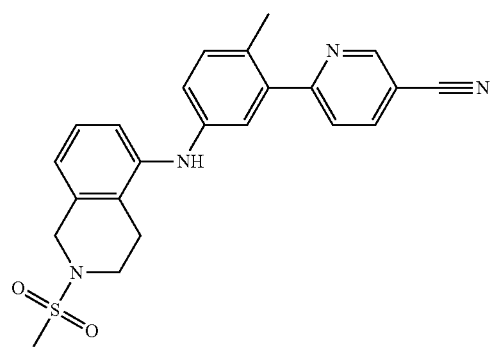 [SMILES: Cc1ccc(Nc2cccc3c2CCN(S(C)(=O)=O)C3)cc1-c1ccc(C#N)cn1] | 419.1 | ** |
| 155 | 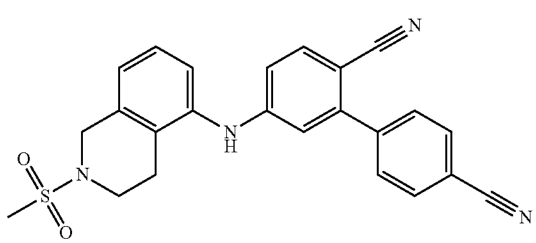 [SMILES: CS(=O)(=O)N1CCc2c(cccc2Nc2ccc(C#N)c(-c3ccc(C#N)cc3)c2)C1] | 429.1 | **** |
| 156 | 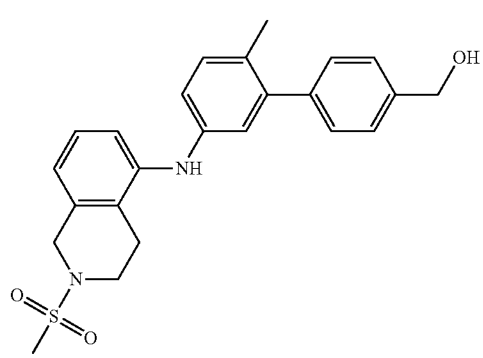 [SMILES: Cc1ccc(Nc2cccc3c2CCN(S(C)(=O)=O)C3)cc1-c1ccc(CO)cc1] | 423.2 | **** |

TABLE 1-continued

| Compound Number | Structure | Physical Data MS (m/z) | IC$_{50}$ Ranges |
|---|---|---|---|
| 157 | 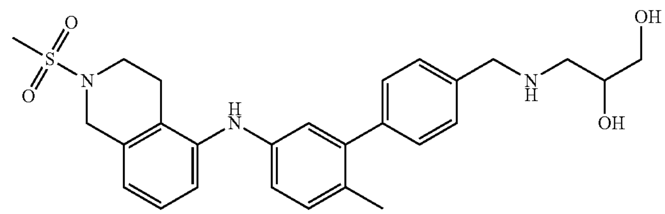 [SMILES: Cc1ccc(Nc2cccc3c2CCN(S(C)(=O)=O)C3)cc1-c1ccc(CNCC(O)CO)cc1] | 496.2 | ***** |
| 158 | 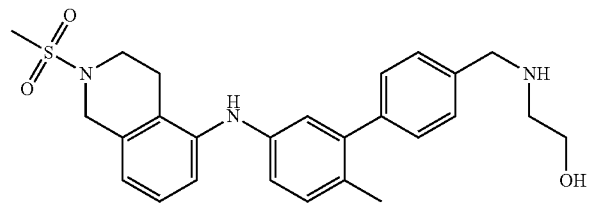 [SMILES: Cc1ccc(Nc2cccc3c2CCN(S(C)(=O)=O)C3)cc1-c1ccc(CNCCO)cc1] | 466.2 | **** |
| 159 | 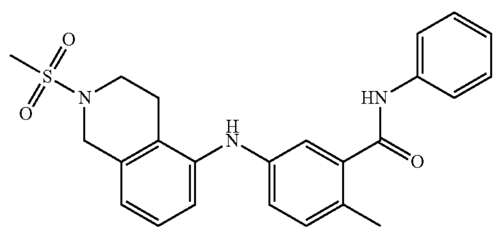 | 436.2 | * |
| 160 | 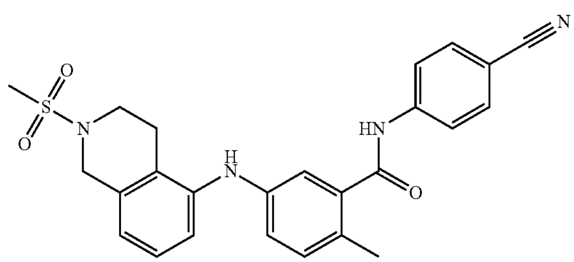 [SMILES: Cc1ccc(Nc2cccc3c2CCN(S(C)(=O)=O)C3)cc1C(=O)Nc1ccc(C#N)cc1] | 461.2 | * |
| 161 | 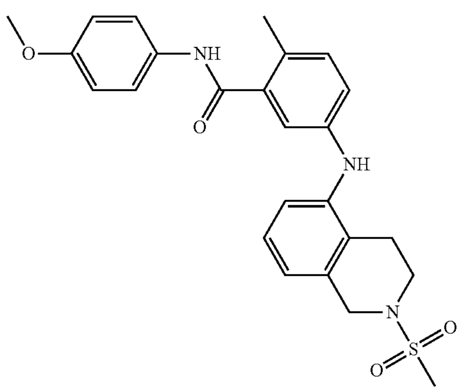 [SMILES: COc1ccc(NC(=O)c2cc(Nc3cccc4c3CCN(S(C)(=O)=O)C4)ccc2C)cc1] | 466.2 | * |
| 162 | 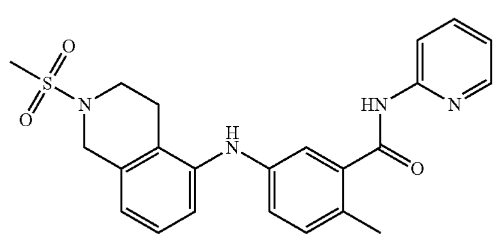 [SMILES: Cc1ccc(Nc2cccc3c2CCN(S(C)(=O)=O)C3)cc1C(=O)Nc1ccccn1] | 437.2 | ** |

TABLE 1-continued

| Compound Number | Structure | Physical Data MS (m/z) | IC$_{50}$ Ranges |
|---|---|---|---|
| 163 | 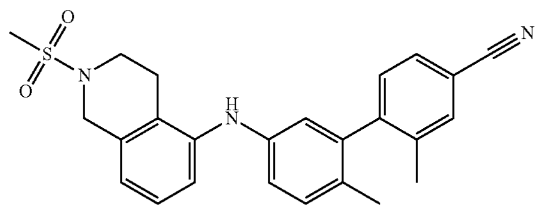 [SMILES: Cc1cc(C#N)ccc1-c1cc(Nc2cccc3c2CCN(S(C)(=O)=O)C3)ccc1C] | 432.2 | *** |
| 164 | 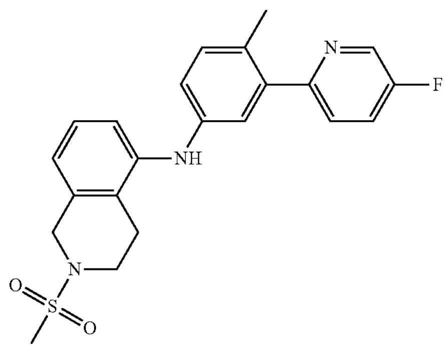 | 412.1 | * |
| 165 | 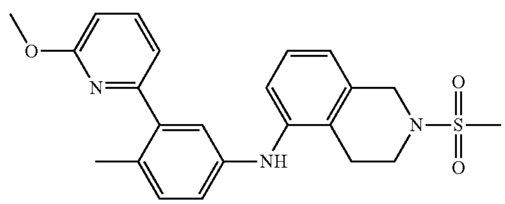 | 424.2 | **** |
| 166 | 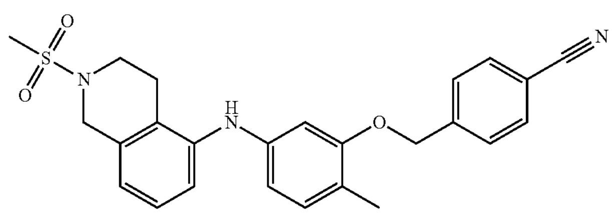 [SMILES: Cc1ccc(Nc2cccc3c2CCN(S(C)(=O)=O)C3)cc1OCc1ccc(C#N)cc1] | 448.2 | *** |
| 167 | 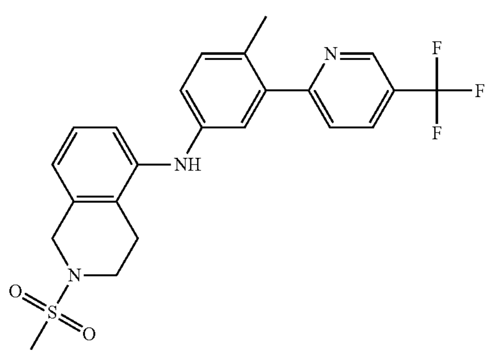 [SMILES: Cc1ccc(Nc2cccc3c2CCN(S(C)(=O)=O)C3)cc1-c1ccc(C(F)(F)F)cn1] | 462.1 | ** |
| 168 | 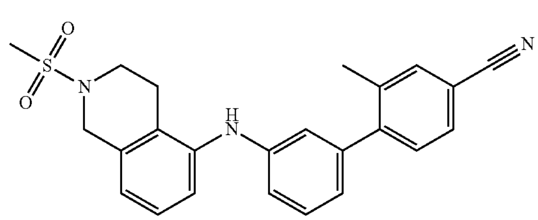 [SMILES: Cc1cc(C#N)ccc1-c1cccc(Nc2cccc3c2CCN(S(C)(=O)=O)C3)c1] | 418.2 | **** |

TABLE 1-continued

| Compound Number | Structure | Physical Data MS (m/z) | IC$_{50}$ Ranges |
|---|---|---|---|
| 169 | 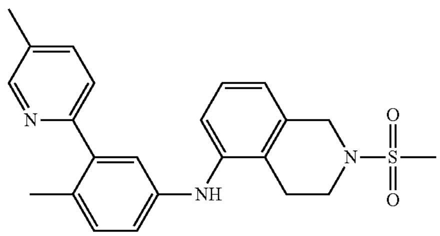 [SMILES: Cc1ccc(-c2cc(Nc3cccc4c3CCN(S(C)(=O)=O)C4)ccc2C)nc1] | 408.2 | * |
| 170 | 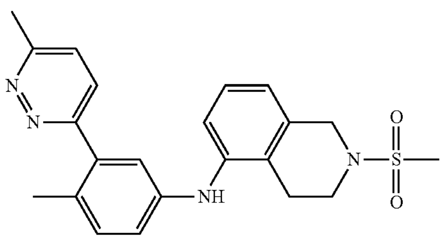 [SMILES: Cc1ccc(-c2cc(Nc3cccc4c3CCN(S(C)(=O)=O)C4)ccc2C)nn1] | 409.2 | ** |
| 171 | 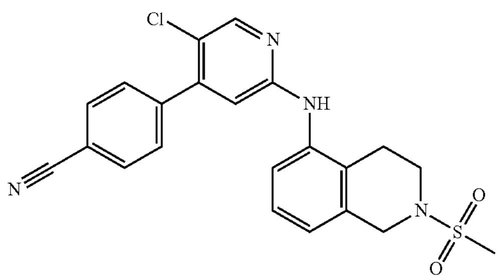 [SMILES: CS(=O)(=O)N1CCc2c(cccc2Nc2cc(-c3ccc(C#N)cc3)c(Cl)cn2)C1] | 439.1 | **** |
| 172 | 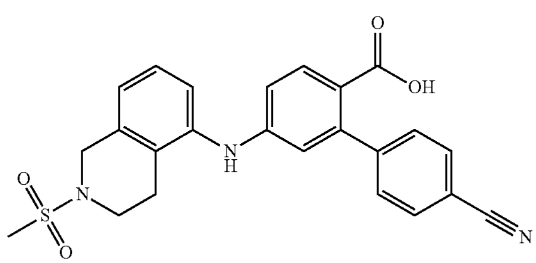 [SMILES: CS(=O)(=O)N1CCc2c(cccc2Nc2ccc(C(=O)O)c(-c3ccc(C#N)cc3)c2)C1] | 448.1 | ****** |
| 173 | 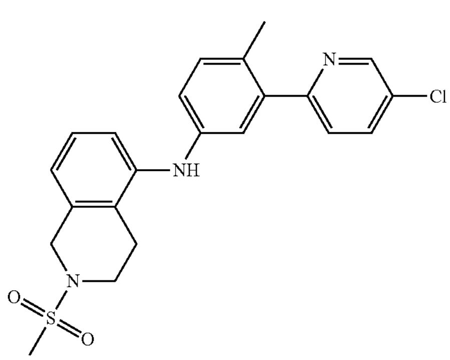 [SMILES: Cc1ccc(Nc2cccc3c2CCN(S(C)(=O)=O)C3)cc1-c1ccc(Cl)cn1] | 428.1 | * |

TABLE 1-continued

| Compound Number | Structure | Physical Data MS (m/z) | IC$_{50}$ Ranges |
|---|---|---|---|
| 174 | 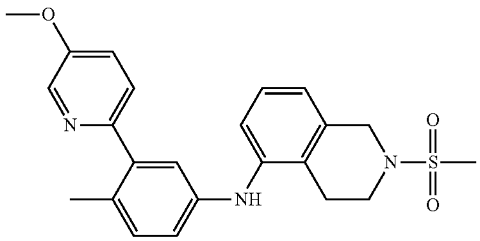 | 424.2 | * |
| 175 | 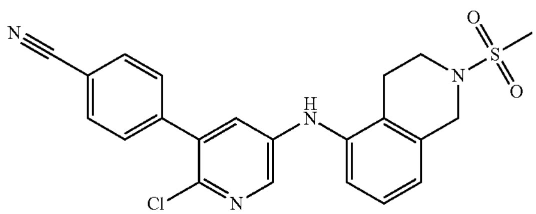 [SMILES: CS(=O)(=O)N1CCc2c(cccc2Nc2cnc(Cl)c(-c3ccc(C#N)cc3)c2)C1] | 439.1 | *** |
| 176 | 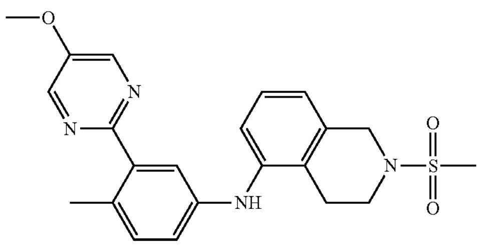 | 425.2 | *** |
| 177 | 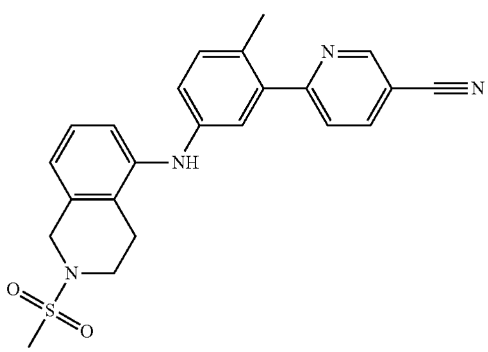 [SMILES: Cc1ccc(Nc2cccc3c2CCN(S(C)(=O)=O)C3)cc1-c1ccc(C#N)cn1] | 419.1 | ** |
| 178 | 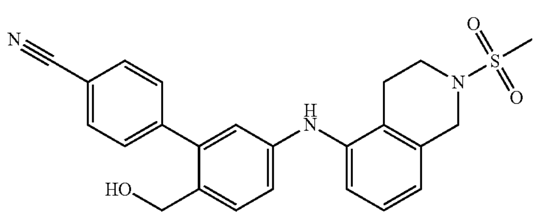 [SMILES: CS(=O)(=O)N1CCc2c(cccc2Nc2ccc(CO)c(-c3ccc(C#N)cc3)c2)C1] | 434.1 | **** |

TABLE 1-continued
| Compound Number | Structure | Physical Data MS (m/z) | IC$_{50}$ Ranges |
|---|---|---|---|
| 179 | 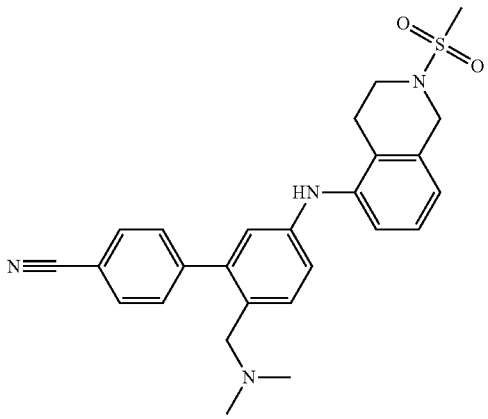 [SMILES: CN(C)Cc1ccc(Nc2cccc3c2CCN(S(C)(=O)=O)C3)cc1-c1ccc(C#N)cc1] | 461.2 | **** |
| 180 | 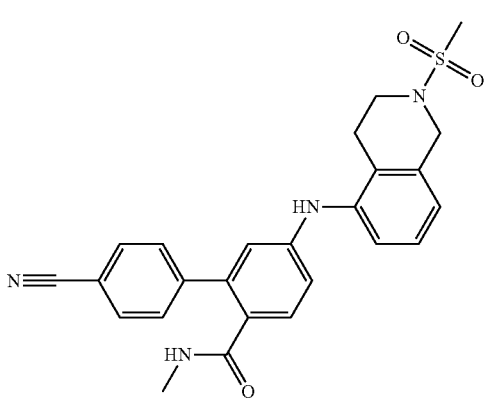 [SMILES: CNC(=O)c1ccc(Nc2cccc3c2CCN(S(C)(=O)=O)C3)cc1-c1ccc(C#N)cc1] | 461.2 | **** |
| 181 | 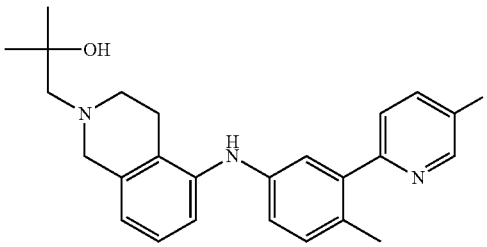 | 406.2 | ** |
| 182 | 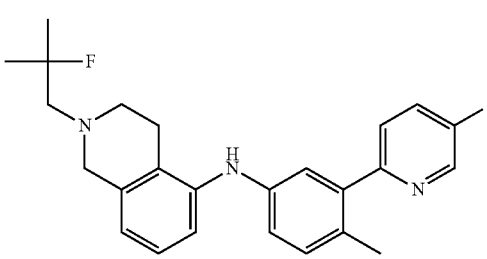 | 408.2 | ** |
| 183 | 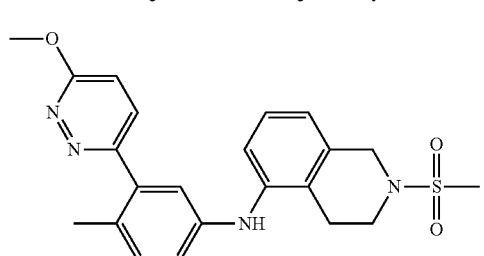 | 425.2 | ** |

TABLE 1-continued

| Compound Number | Structure | Physical Data MS (m/z) | IC$_{50}$ Ranges |
|---|---|---|---|
| 184 | 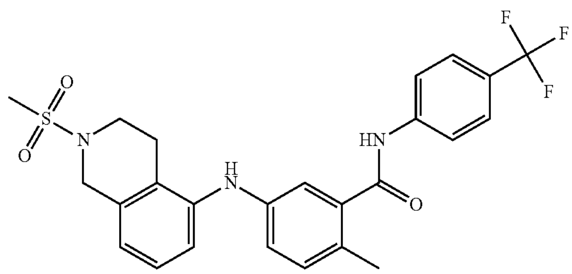 [SMILES: Cc1ccc(Nc2cccc3c2CCN(S(C)(=O)=O)C3)cc1C(=O)Nc1ccc(C(F)(F)F)cc1] | 504.1 | * |
| 185 | 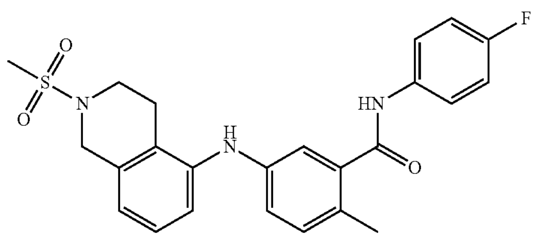 [SMILES: Cc1ccc(Nc2cccc3c2CCN(S(C)(=O)=O)C3)cc1C(=O)Nc1ccc(F)cc1] | 454.2 | * |
| 186 | 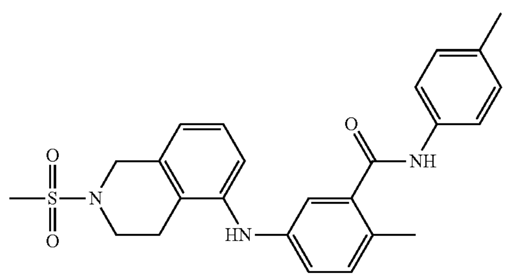 | 450.2 | * |
| 187 | 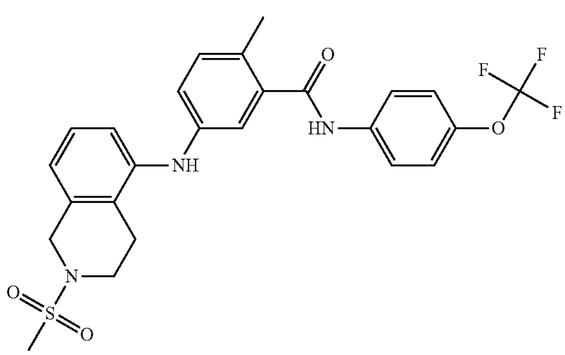 [SMILES: Cc1ccc(Nc2cccc3c2CCN(S(C)(=O)=O)C3)cc1C(=O)Nc1ccc(OC(F)(F)F)cc1] | 520.1 | ** |
| 188 | 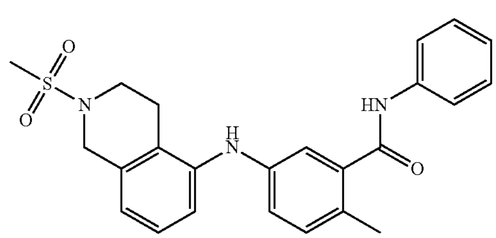 | 436.2 | * |

TABLE 1-continued

| Compound Number | Structure | Physical Data MS (m/z) | IC$_{50}$ Ranges |
|---|---|---|---|
| 189 | 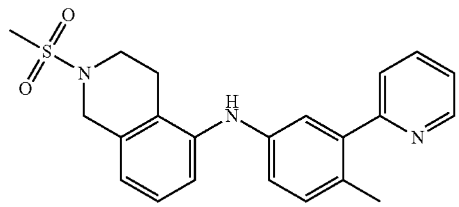 | 394.2 | * |
| 190 | 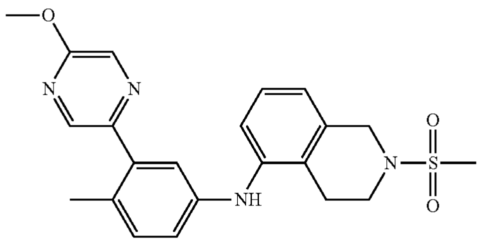 | 425.2 | ** |
| 191 | 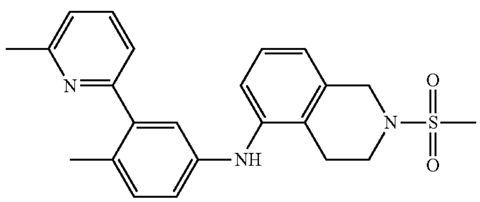 | 408.2 | ** |
| 192 | 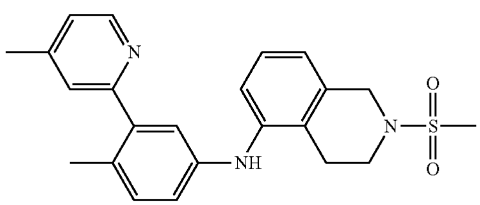 | 408.2 | * |
| 193 | 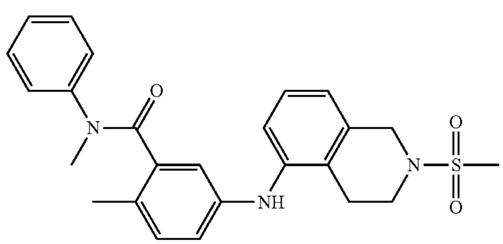 [SMILES: Cc1ccc(Nc2cccc3c2CCN(S(C)(=O)=O)C3)cc1C(=O)N(C)c1ccccc1] | 450.2 | **** |
| 194 | 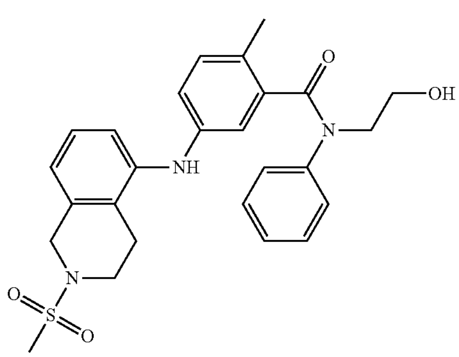 [SMILES: Cc1ccc(Nc2cccc3c2CCN(S(C)(=O)=O)C3)cc1C(=O)N(CCO)c1ccccc1] | 480.2 | **** |

TABLE 1-continued

| Compound Number | Structure | Physical Data MS (m/z) | IC$_{50}$ Ranges |
|---|---|---|---|
| 195 | 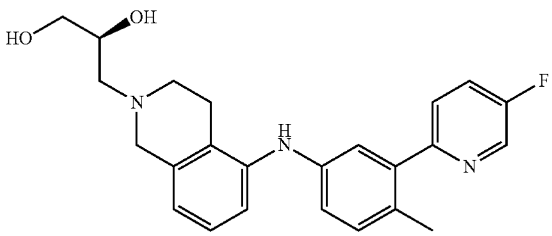 [SMILES: Cc1ccc(Nc2cccc3c2CCN(C[C@H](O)CO)C3)cc1-c1ccc(F)cn1] | 408.2 | ** |
| 196 | 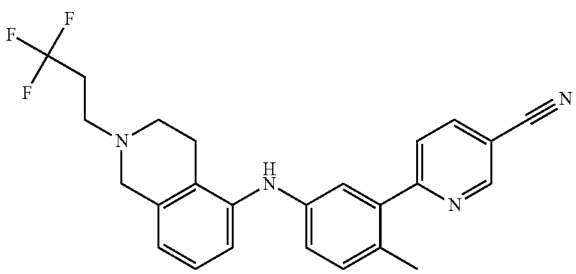 [SMILES: Cc1ccc(Nc2cccc3c2CCN(CCC(F)(F)F)C3)cc1-c1ccc(C#N)cn1] | 437.2 | ** |
| 197 | 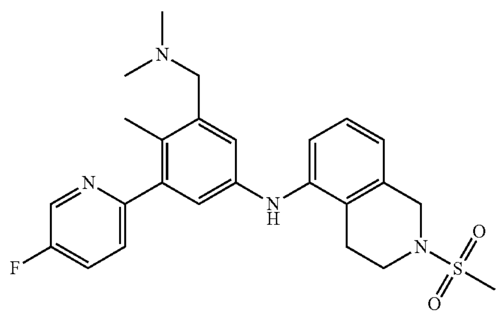 [SMILES: Cc1c(CN(C)C)cc(Nc2cccc3c2CCN(S(C)(=O)=O)C3)cc1-c1ccc(F)cn1] | 469.2 | ***** |
| 198 | 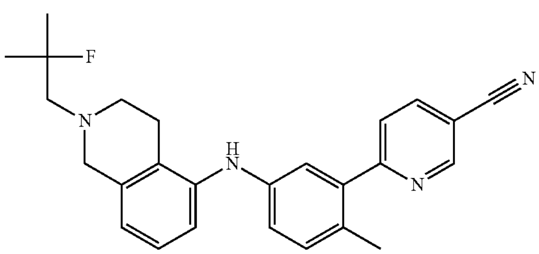 [SMILES: Cc1ccc(Nc2cccc3c2CCN(CC(C)(C)F)C3)cc1-c1ccc(C#N)cn1] | 415.2 | * |
| 199 | 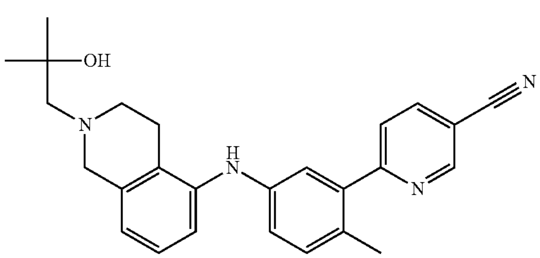 [SMILES: Cc1ccc(Nc2cccc3c2CCN(CC(C)(C)O)C3)cc1-c1ccc(C#N)cn1] | 413.2 | ** |

TABLE 1-continued

| Compound Number | Structure | Physical Data MS (m/z) | IC$_{50}$ Ranges |
|---|---|---|---|
| 200 | 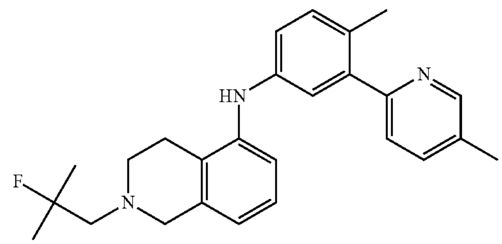 [SMILES: Cc1ccc(-c2cc(Nc3cccc4c3CCN(CC(C)(C)F)C4)ccc2C)nc1] | 404.2 | * |
| 201 | 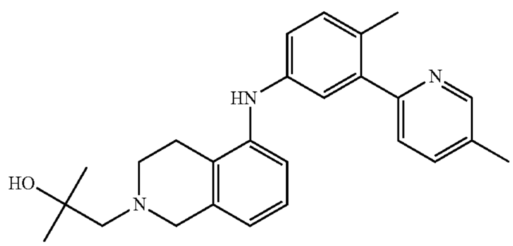 [SMILES: Cc1ccc(-c2cc(Nc3cccc4c3CCN(CC(C)(C)O)C4)ccc2C)nc1] | 402.2 | * |
| 202 | 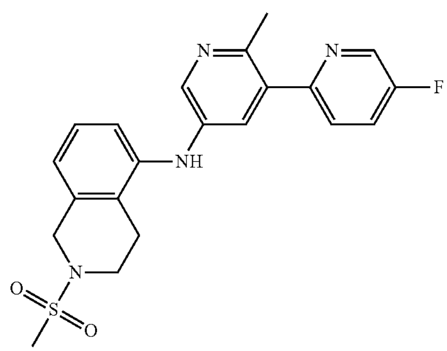 [SMILES: Cc1ncc(Nc2cccc3c2CCN(S(C)(=O)=O)C3)cc1-c1ccc(F)cn1] | 413.1 | *** |
| 203 | 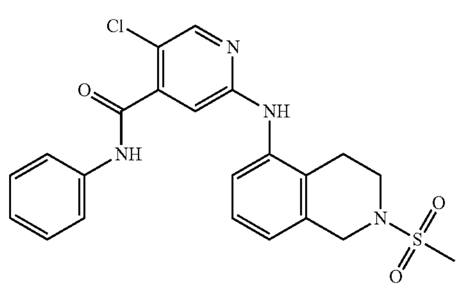 [SMILES: CS(=O)(=O)N1CCc2c(cccc2Nc2cc(C(=O)Nc3ccccc3)c(Cl)cn2)C1] | 457.1 | ** |
| 204 | 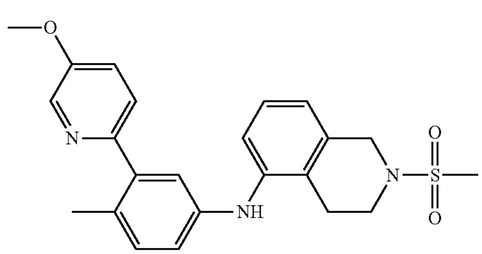 | 424.2 | * |

TABLE 1-continued

| Compound Number | Structure | Physical Data MS (m/z) | IC$_{50}$ Ranges |
|---|---|---|---|
| 205 | 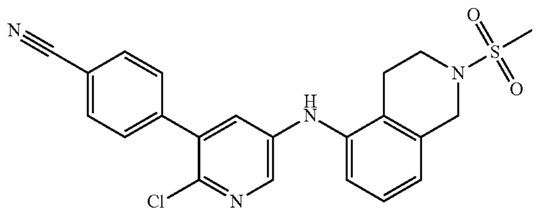 [SMILES: CS(=O)(=O)N1CCc2c(cccc2Nc2cnc(Cl)c(-c3ccc(C#N)cc3)c2)C1] | 439.1 | *** |
| 206 | 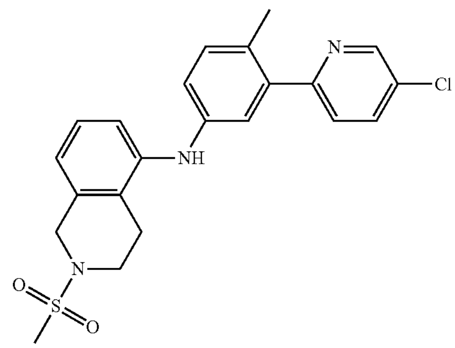 [SMILES: Cc1ccc(Nc2cccc3c2CCN(S(C)(=O)=O)C3)cc1-c1ccc(Cl)cn1] | 428.1 | * |
| 207 | 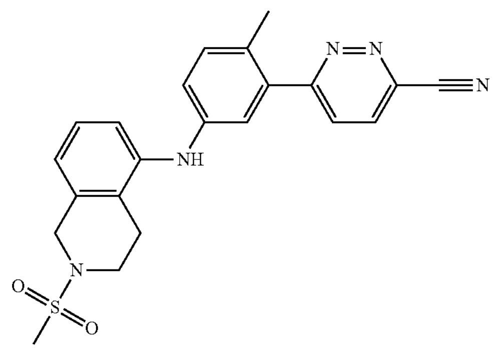 [SMILES: Cc1ccc(Nc2cccc3c2CCN(S(C)(=O)=O)C3)cc1-c1ccc(C#N)nn1] | 420.1 | *** |
| 208 | 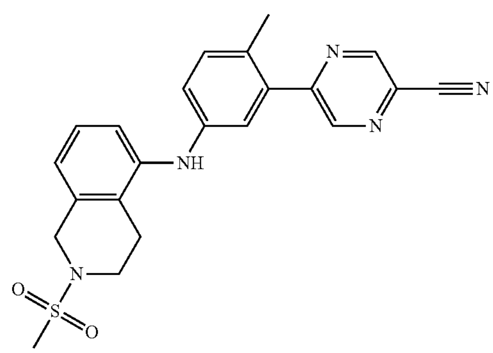 [SMILES: Cc1ccc(Nc2cccc3c2CCN(S(C)(=O)=O)C3)cc1-c1cnc(C#N)cn1] | 420.1 | **** |
| 209 | 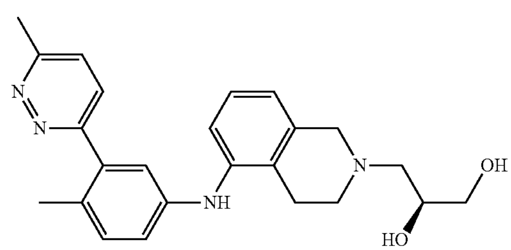 [SMILES: Cc1ccc(-c2cc(Nc3cccc4c3CCN(C[C@H](O)CO)C4)ccc2C)nn1] | 405.2 | **** |

TABLE 1-continued

| Compound Number | Structure | Physical Data MS (m/z) | IC₅₀ Ranges |
|---|---|---|---|
| 210 | 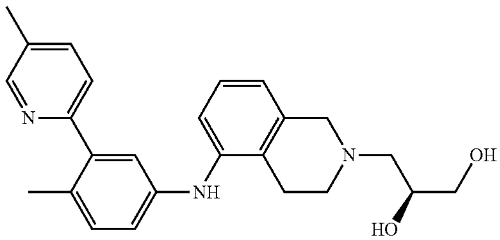 [SMILES: Cc1ccc(-c2cc(Nc3cccc4c3CCN(C[C@H](O)CO)C4)ccc2C)nc1] | 404.2 | ** |
| 211 | 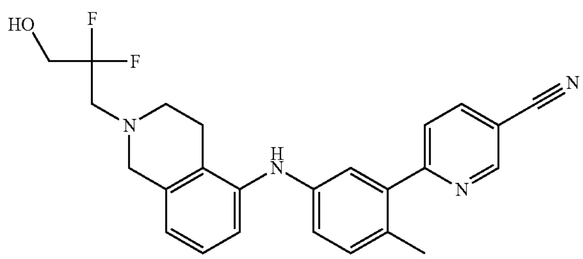 [SMILES: Cc1ccc(Nc2cccc3c2CCN(CC(F)(F)CO)C3)cc1-c1ccc(C#N)cn1] | 435.2 | * |
| 212 | 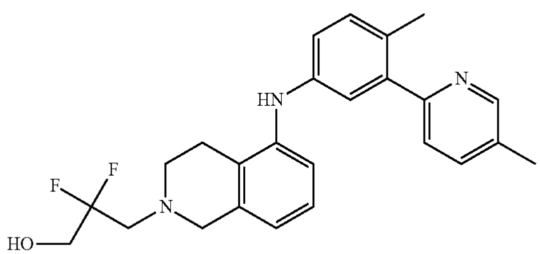 [SMILES: Cc1ccc(-c2cc(Nc3cccc4c3CCN(CC(F)(F)CO)C4)ccc2C)nc1] | 424.2 | * |
| 213 | 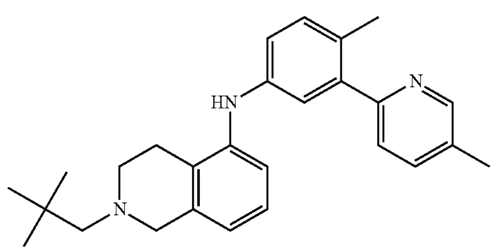 [SMILES: Cc1ccc(-c2cc(Nc3cccc4c3CCN(CC(C)(C)C)C4)ccc2C)nc1] | 400.3 | ** |
| 214 | 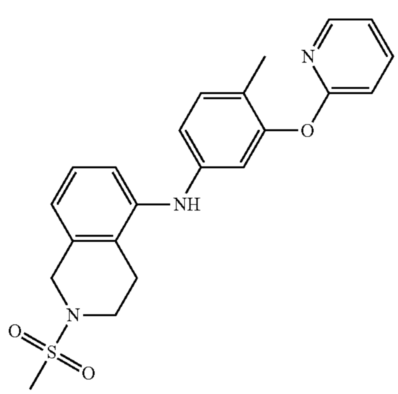 [SMILES: Cc1ccc(Nc2cccc3c2CCN(S(C)(=O)=O)C3)cc1Oc1ccccn1] | 410.1 | **** |

TABLE 1-continued

| Compound Number | Structure | Physical Data MS (m/z) | IC$_{50}$ Ranges |
|---|---|---|---|
| 215 | 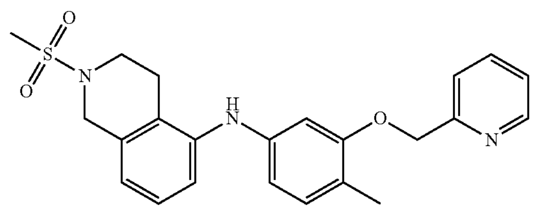 [SMILES: Cc1ccc(Nc2cccc3c2CCN(S(C)(=O)=O)C3)cc1OCc1ccccn1] | 424.2 | *** |
| 216 | 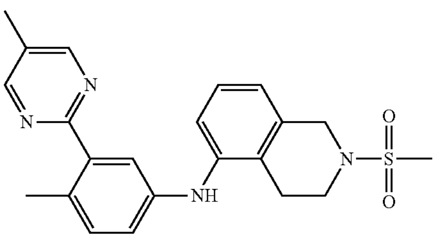 [SMILES: Cc1cnc(-c2cc(Nc3cccc4c3CCN(S(C)(=O)=O)C4)ccc2C)nc1] | 409.2 | *** |
| 217 | 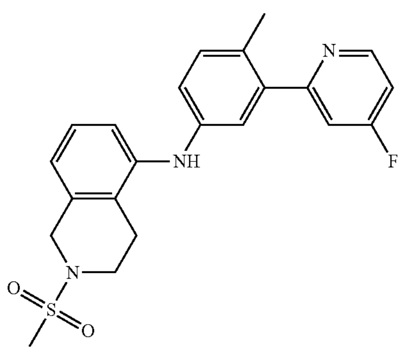 [SMILES: Cc1ccc(Nc2cccc3c2CCN(S(C)(=O)=O)C3)cc1-c1cc(F)ccn1] | 412.1 | ** |
| 218 | 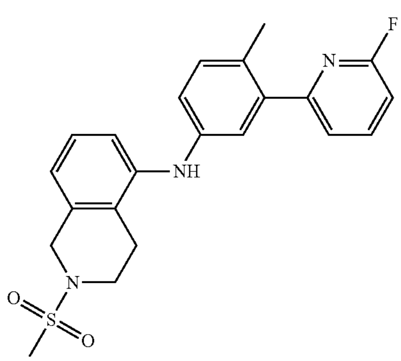 [SMILES: Cc1ccc(Nc2cccc3c2CCN(S(C)(=O)=O)C3)cc1-c1cccc(F)n1] | 412.1 | *** |
| 219 | 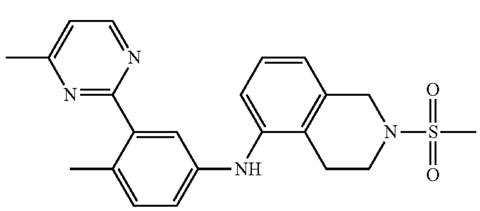 | 409.2 | *** |

TABLE 1-continued

| Compound Number | Structure | Physical Data MS (m/z) | IC$_{50}$ Ranges |
|---|---|---|---|
| 220 | 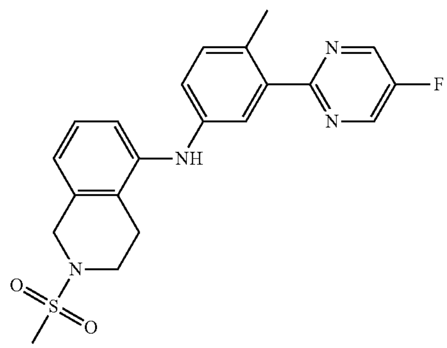 [SMILES: Cc1ccc(Nc2cccc3c2CCN(S(C)(=O)=O)C3)cc1-c1ncc(F)cn1] | 413.1 | ** |
| 221 | 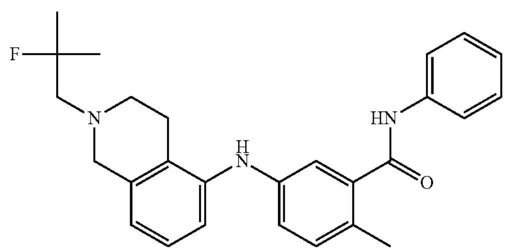 [SMILES: Cc1ccc(Nc2cccc3c2CCN(CC(C)(C)F)C3)cc1C(=O)Nc1ccccc1] | 432.2 | ** |
| 222 | 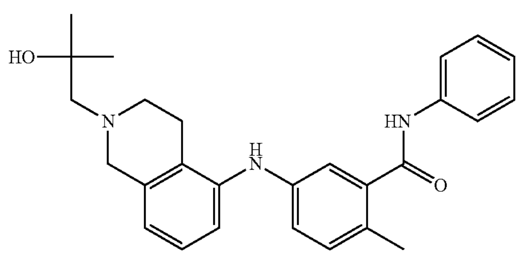 [SMILES: Cc1ccc(Nc2cccc3c2CCN(CC(C)(C)O)C3)cc1C(=O)Nc1ccccc1] | 430.2 | ** |
| 223 | 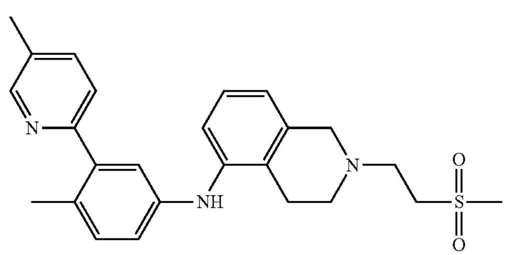 | 436.2 | * |
| 224 | 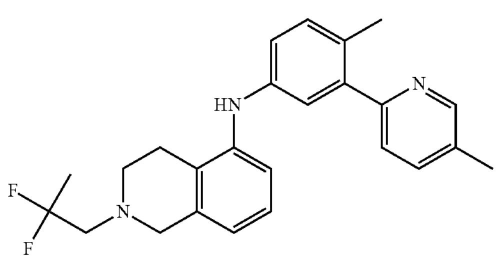 [SMILES: Cc1ccc(-c2cc(Nc3cccc4c3CCN(CC(C)(F)F)C4)ccc2C)nc1] | 408.2 | * |

TABLE 1-continued

| Compound Number | Structure | Physical Data MS (m/z) | IC$_{50}$ Ranges |
|---|---|---|---|
| 225 | 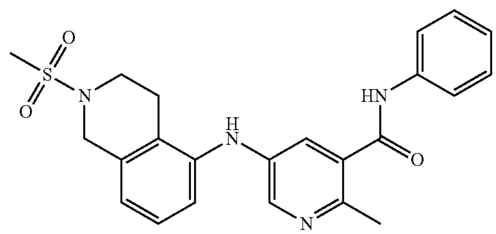 [SMILES: Cc1ncc(Nc2cccc3c2CCN(S(C)(=O)=O)C3)cc1C(=O)Nc1ccccc1] | 437.2 | ** |
| 226 | 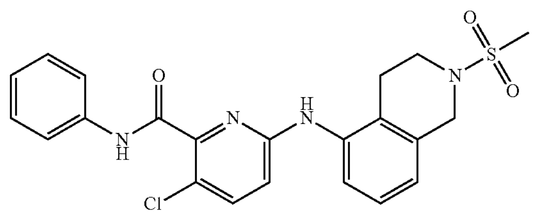 [SMILES: CS(=O)(=O)N1CCc2c(cccc2Nc2ccc(Cl)c(C(=O)Nc3ccccc3)n2)C1] | 457.1 | * |
| 227 | 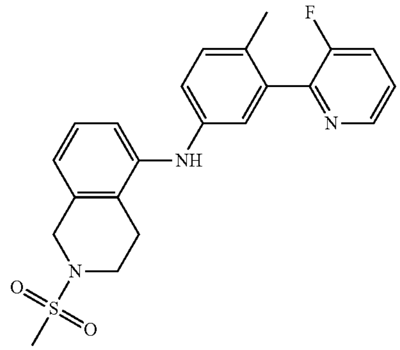 [SMILES: Cc1ccc(Nc2cccc3c2CCN(S(C)(=O)=O)C3)cc1-c1ncccc1F] | 412.1 | * |
| 228 | 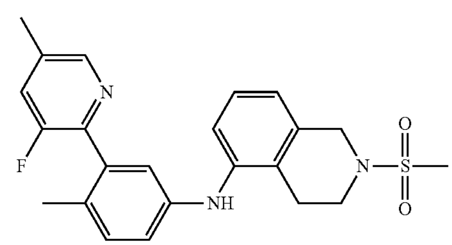 [SMILES: Cc1cnc(-c2cc(Nc3cccc4c3CCN(S(C)(=O)=O)C4)ccc2C)c(F)c1] | 426.2 | * |
| 229 | 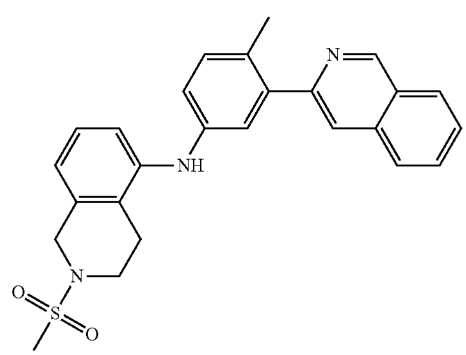 [SMILES: Cc1ccc(Nc2cccc3c2CCN(S(C)(=O)=O)C3)cc1-c1cc2ccccc2cn1] | 444.2 | * |

TABLE 1-continued

| Compound Number | Structure | Physical Data MS (m/z) | IC$_{50}$ Ranges |
|---|---|---|---|
| 230 | 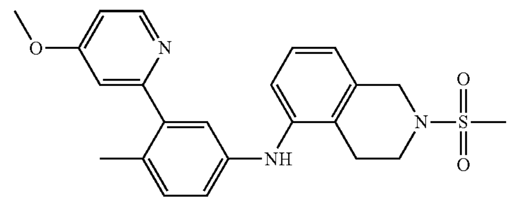 | 424.2 | * |
| 231 | 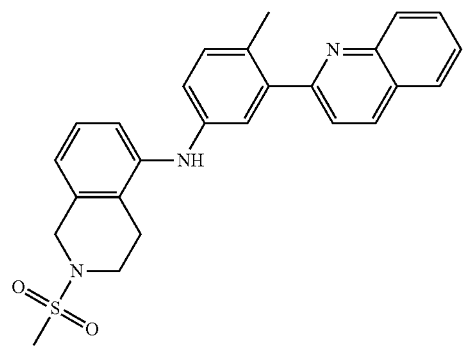 [SMILES: Cc1ccc(Nc2cccc3c2CCN(S(C)(=O)=O)C3)cc1-c1ccc2ccccc2n1] | 444.2 | * |
| 232 | 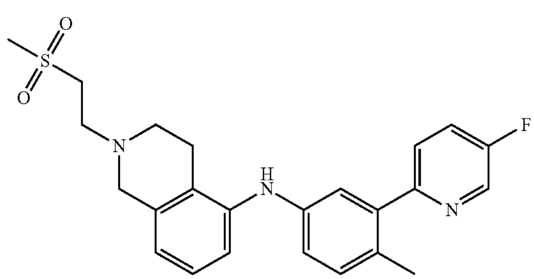 [SMILES: Cc1ccc(Nc2cccc3c2CCN(CCS(C)(=O)=O)C3)cc1-c1ccc(F)cn1] | 440.2 | ** |
| 233 | 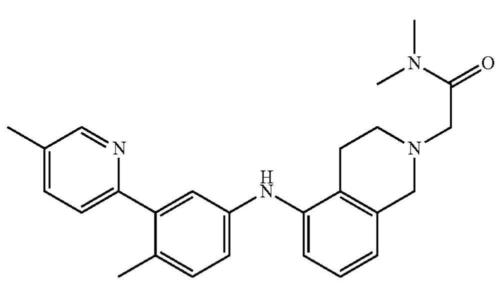 [SMILES: Cc1ccc(-c2cc(Nc3cccc4c3CCN(CC(=O)N(C)C)C4)ccc2C)nc1] | 415.2 | ** |
| 234 | 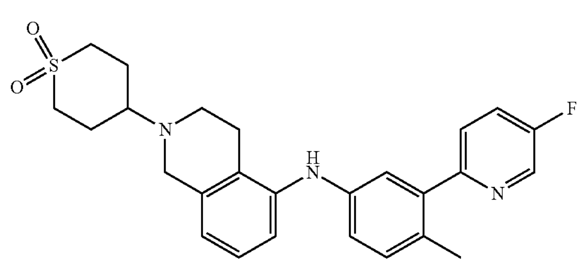 [SMILES: Cc1ccc(Nc2cccc3c2CCN(C2CCS(=O)(=O)CC2)C3)cc1-c1ccc(F)cn1] | 466.2 | * |

TABLE 1-continued
| Compound Number | Structure | Physical Data MS (m/z) | IC$_{50}$ Ranges |
|---|---|---|---|
| 235 | 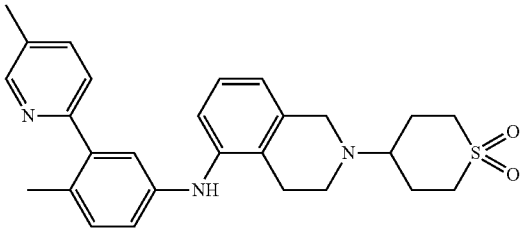 | 462.2 | * |
| 236 | 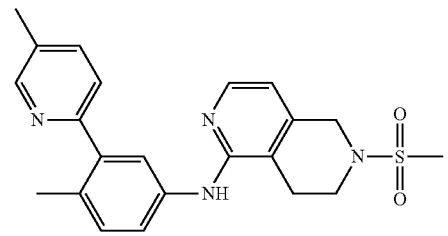 [SMILES: Cc1ccc(-c2cc(Nc3nccc4c3CCN(S(C)(=O)=O)C4)ccc2C)nc1] | 409.2 | *** |
| 237 | 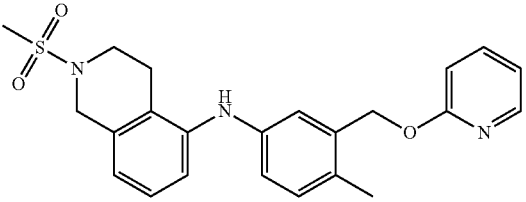 [SMILES: Cc1ccc(Nc2cccc3c2CCN(S(C)(=O)=O)C3)cc1COc1ccccn1] | 424.2 | **** |
| 238 | 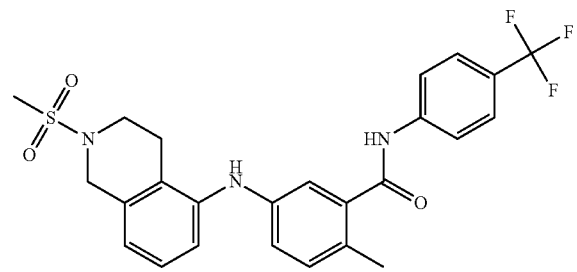 [SMILES: Cc1ccc(Nc2cccc3c2CCN(S(C)(=O)=O)C3)cc1C(=O)Nc1ccc(C(F)(F)F)cc1] | 504.1 | |
| 239 | 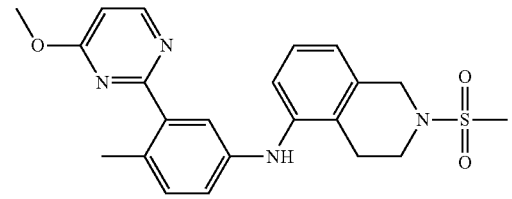 | 425.2 | *** |
| 240 | 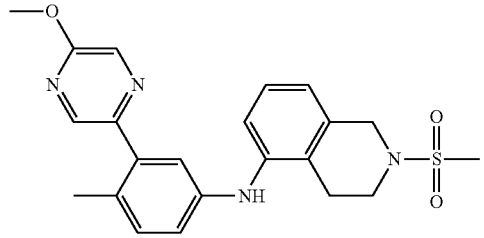 | 425.2 | ** |

TABLE 1-continued

| Compound Number | Structure | Physical Data MS (m/z) | IC$_{50}$ Ranges |
|---|---|---|---|
| 241 | 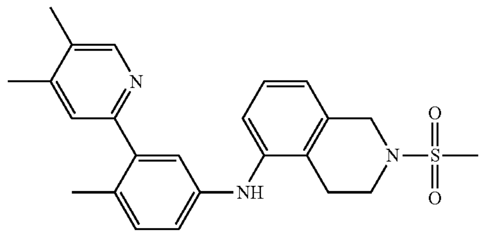 | 422.2 | * |
| 242 | 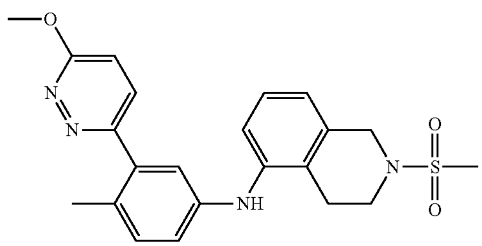 | 425.2 | ** |
| 243 | 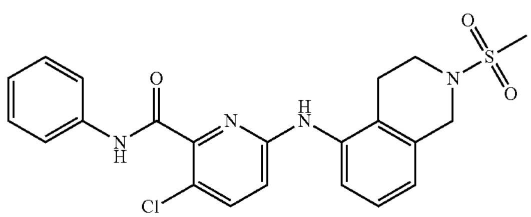 [SMILES: CS(=O)(=O)N1CCc2c(cccc2Nc2ccc(Cl)c(C(=O)Nc3ccccc3)n2)C1] | 457.1 | * |
| 244 | 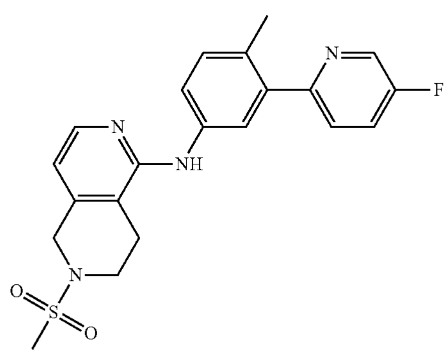 [SMILES: Cc1ccc(Nc2nccc3c2CCN(S(C)(=O)=O)C3)cc1-c1ccc(F)cn1] | 413.1 | **** |
| 245 | 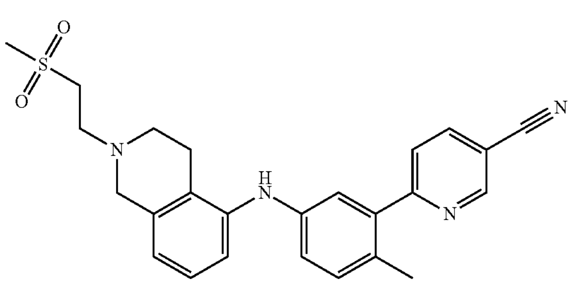 [SMILES: Cc1ccc(Nc2cccc3c2CCN(CCS(C)(=O)=O)C3)cc1-c1ccc(C#N)cn1] | 447.2 | ** |

TABLE 1-continued

| Compound Number | Structure | Physical Data MS (m/z) | IC$_{50}$ Ranges |
|---|---|---|---|
| 246 | 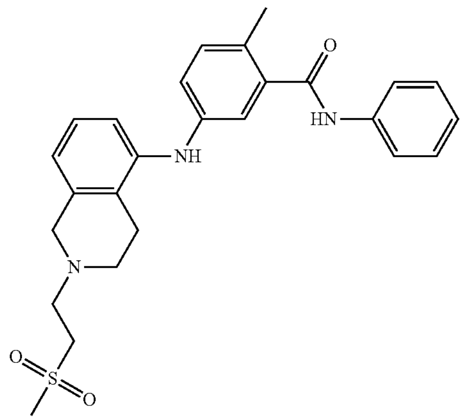 [SMILES: Cc1ccc(Nc2cccc3c2CCN(CCS(C)(=O)=O)C3)cc1C(=O)Nc1ccccc1] | 464.2 | *** |
| 247 | 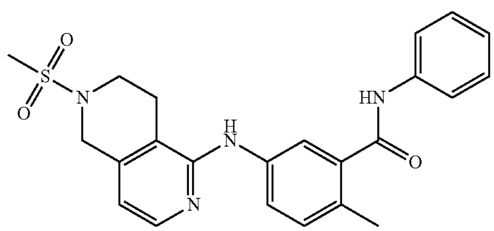 [SMILES: Cc1ccc(Nc2nccc3c2CCN(S(C)(=O)=O)C3)cc1C(=O)Nc1ccccc1] | 437.2 | *** |
| 248 | 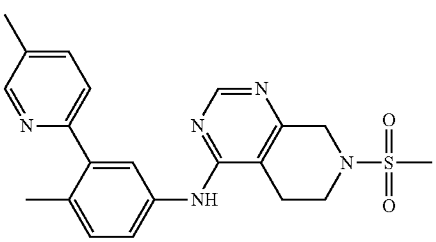 | 410.2 | ** |
| 249 | 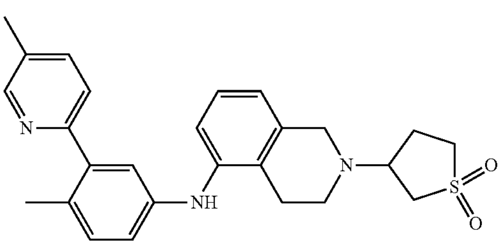 [SMILES: Cc1ccc(-c2cc(Nc3cccc4c3CCN(C3CCS(=O)(=O)C3)C4)ccc2C)nc1] | 448.2 | * |
| 250 | 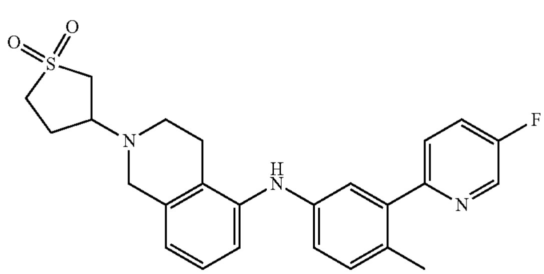 [SMILES: Cc1ccc(Nc2cccc3c2CCN(C2CCS(=O)(=O)C2)C3)cc1-c1ccc(F)cn1] | 452.2 | * |

TABLE 1-continued

| Compound Number | Structure | Physical Data MS (m/z) | IC$_{50}$ Ranges |
|---|---|---|---|
| 251 | 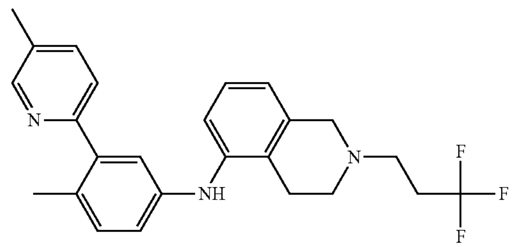 [SMILES: Cc1ccc(-c2cc(Nc3cccc4c3CCN(CCC(F)(F)F)C4)ccc2C)nc1] | 426.2 | * |
| 252 | 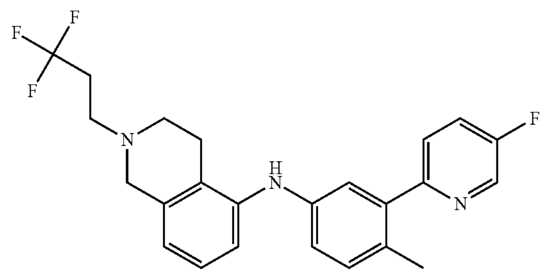 [SMILES: Cc1ccc(Nc2cccc3c2CCN(CCC(F)(F)F)C3)cc1-c1ccc(F)cn1] | 430.2 | * |
| 253 | 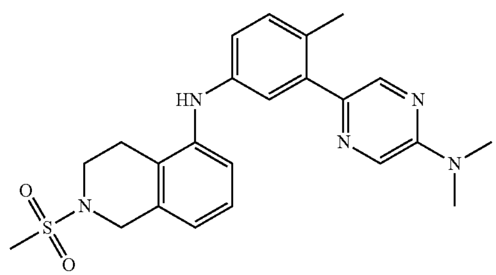 | 438.2 | ** |
| 254 | 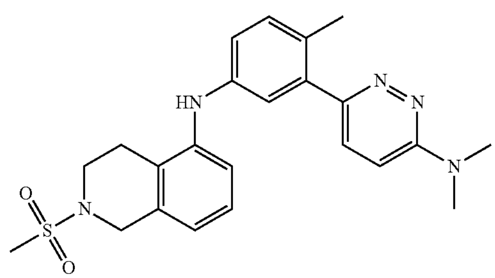 | 438.2 | ** |
| 255 | 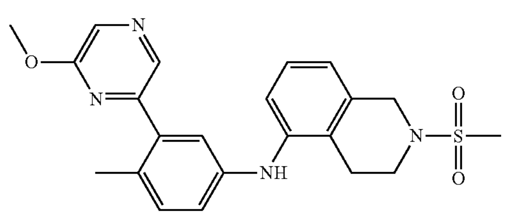 | 425.2 | **** |
| 256 | 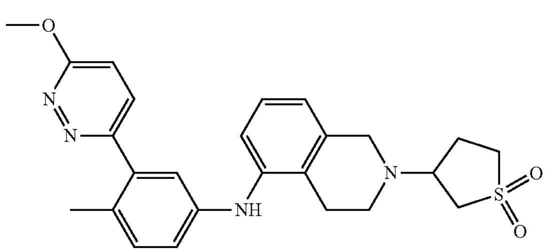 [SMILES: COc1ccc(-c2cc(Nc3cccc4c3CCN(C3CCS(=O)(=O)C3)C4)ccc2C)nn1] | 465.2 | * |

TABLE 1-continued

| Compound Number | Structure | Physical Data MS (m/z) | IC$_{50}$ Ranges |
|---|---|---|---|
| 257 | 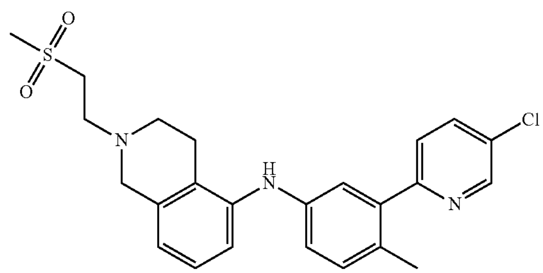 [SMILES: Cc1ccc(Nc2cccc3c2CCN(CCS(C)(=O)=O)C3)cc1-c1ccc(Cl)cn1] | 456.1 | * |
| 258 | 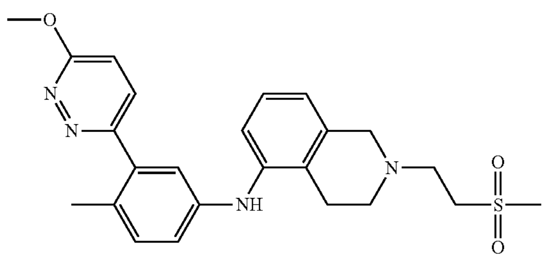 | 453.2 | ** |
| 259 | 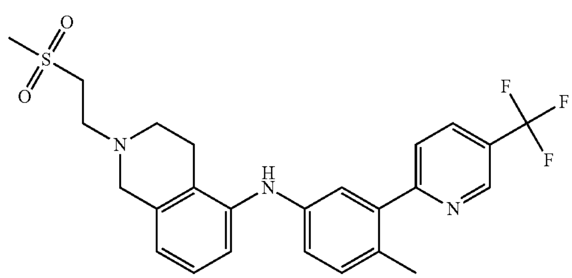 [SMILES: Cc1ccc(Nc2cccc3c2CCN(CCS(C)(=O)=O)C3)cc1-c1ccc(C(F)(F)F)cn1] | 490.2 | ** |
| 260 | 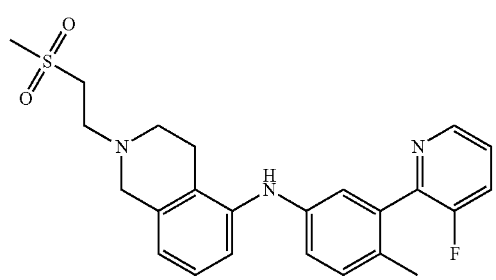 [SMILES: Cc1ccc(Nc2cccc3c2CCN(CCS(C)(=O)=O)C3)cc1-c1ncccc1F] | 440.2 | ** |
| 261 | 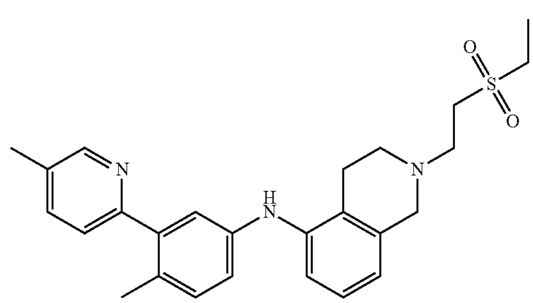 [SMILES: CCS(=O)(=O)CCN1CCc2c(cccc2Nc2ccc(C)c(-c3ccc(C)cn3)c2)C1] | 450.2 | * |

TABLE 1-continued

| Compound Number | Structure | Physical Data MS (m/z) | IC$_{50}$ Ranges |
|---|---|---|---|
| 262 | 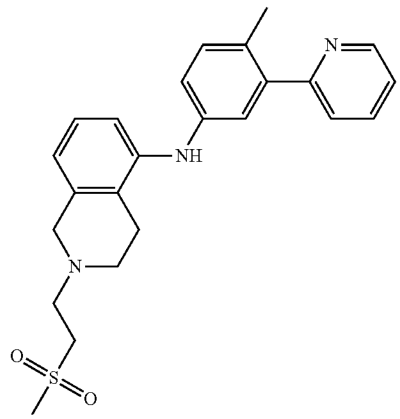 [SMILES: Cc1ccc(Nc2cccc3c2CCN(CCS(C)(=O)=O)C3)cc1-c1ccccn1] | 422.2 | ** |
| 263 | 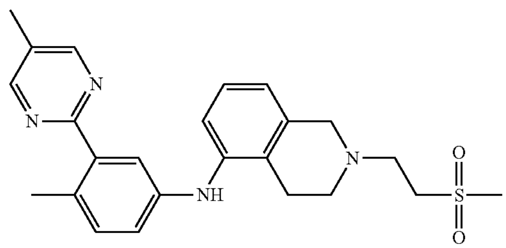 [SMILES: Cc1cnc(-c2cc(Nc3cccc4c3CCN(CCS(C)(=O)=O)C4)ccc2C)nc1] | 437.2 | **** |
| 264 | 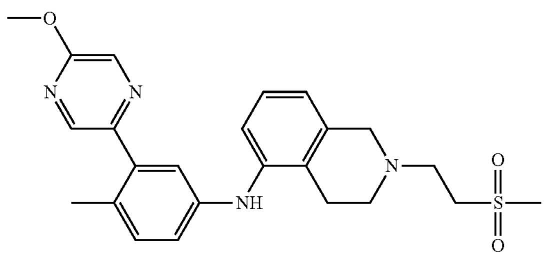 | 453.2 | ** |
| 265 | 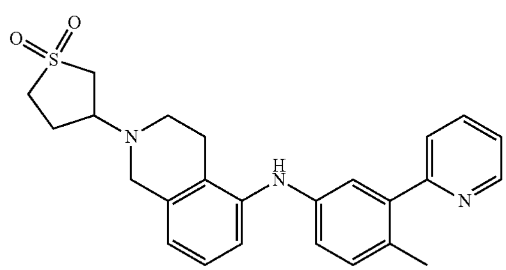 [SMILES: Cc1ccc(Nc2cccc3c2CCN(C2CCS(=O)(=O)C2)C3)cc1-c1ccccn1] | 434.2 | * |
| 266 | 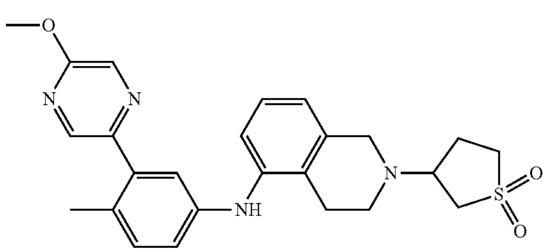 | 465.2 | ** |

TABLE 1-continued

| Compound Number | Structure | Physical Data MS (m/z) | IC$_{50}$ Ranges |
|---|---|---|---|
| 267 | 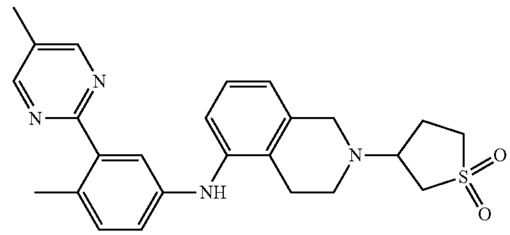 | 449.2 | *** |
| 268 | 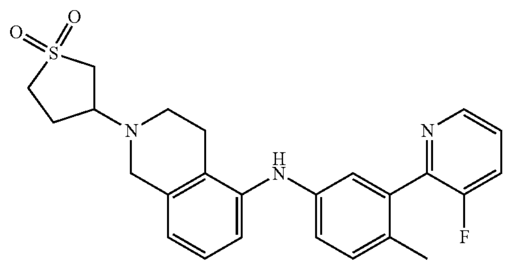 [SMILES: Cc1ccc(Nc2cccc3c2CCN(C2CCS(=O)(=O)C2)C3)cc1-c1ncccc1F] | 452.2 | * |
| 269 | 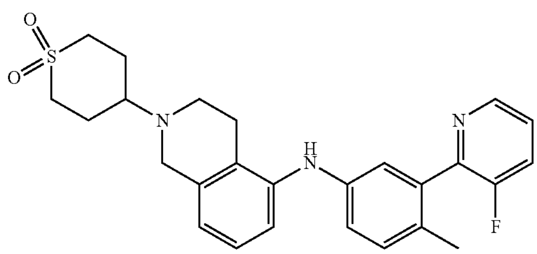 [SMILES: Cc1ccc(Nc2cccc3c2CCN(C2CCS(=O)(=O)CC2)C3)cc1-c1ncccc1F] | 466.2 | * |
| 270 | 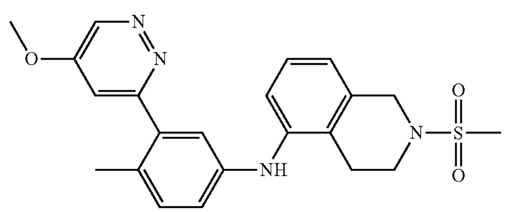 | 425.2 | *** |
| 271 | 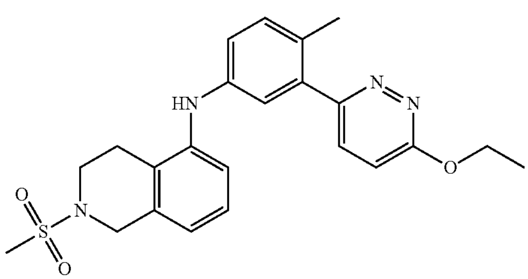 [SMILES: CCOc1ccc(-c2cc(Nc3cccc4c3CCN(S(C)(=O)=O)C4)ccc2C)nn1] | 439.2 | * |
| 272 | 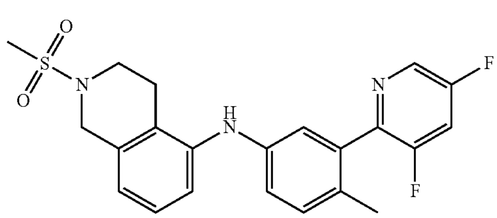 [SMILES: Cc1ccc(Nc2cccc3c2CCN(S(C)(=O)=O)C3)cc1-c1ncc(F)cc1F] | 430.1 | ** |

TABLE 1-continued

| Compound Number | Structure | Physical Data MS (m/z) | IC$_{50}$ Ranges |
|---|---|---|---|
| 273 | 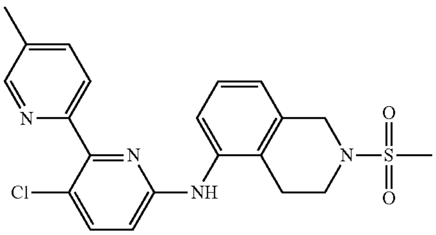 | 429.1 | * |
| 274 | 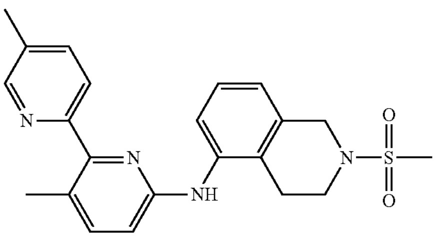 | 409.2 | * |
| 275 | 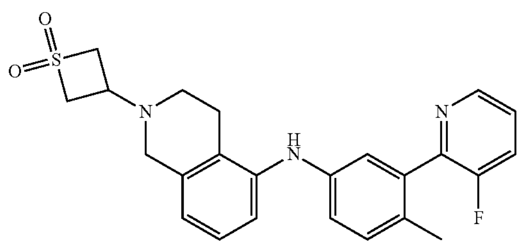 [SMILES: Cc1ccc(Nc2cccc3c2CCN(C2CS(=O)(=O)C2)C3)cc1-c1ncccc1F] | 438.2 | ** |
| 276 | 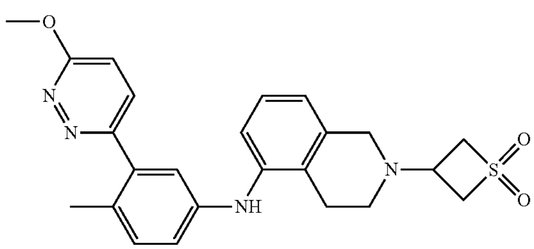 [SMILES: COc1ccc(-c2cc(Nc3cccc4c3CCN(C3CS(=O)(=O)C3)C4)ccc2C)nn1] | 451.2 | ** |
| 277 | 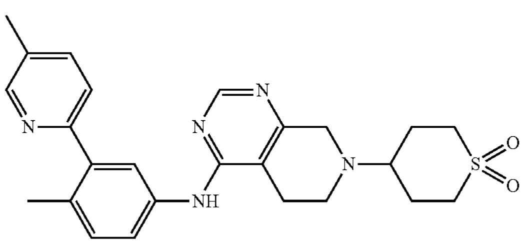 | 464.2 | *** |
| 278 | 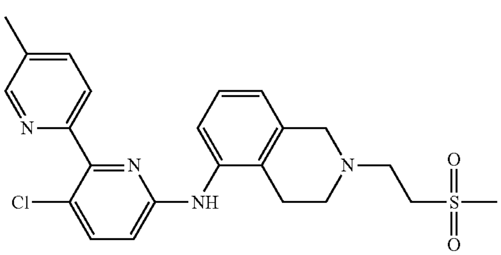 [SMILES: Cc1ccc(-c2nc(Nc3cccc4c3CCN(CCS(C)(=O)=O)C4)ccc2Cl)nc1] | 457.1 | ** |

TABLE 1-continued

| Compound Number | Structure | Physical Data MS (m/z) | IC₅₀ Ranges |
|---|---|---|---|
| 279 | 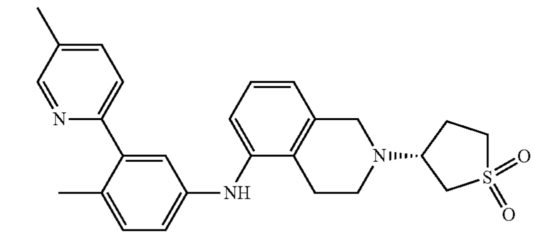 | 448.2 | * |
| 280 | 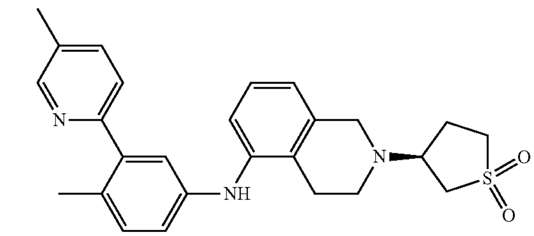 | 448.2 | * |
| 281 | 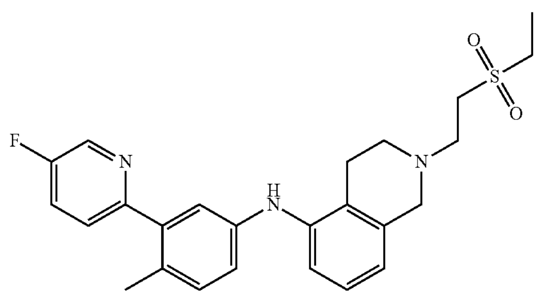 [SMILES: CCS(=O)(=O)CCN1CCc2c(cccc2Nc2ccc(C)c(-c3ccc(F)cn3)c2)C1] | 454.2 | ** |
| 282 | 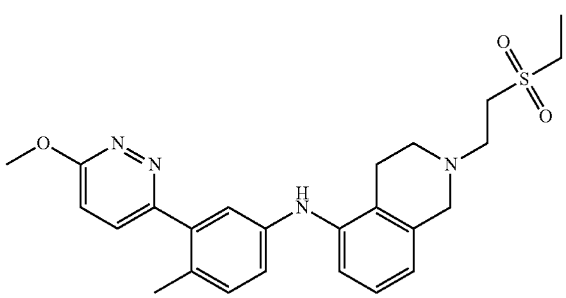 [SMILES: CCS(=O)(=O)CCN1CCc2c(cccc2Nc2ccc(C)c(-c3ccc(OC)nn3)c2)C1] | 467.2 | ** |
| 283 | 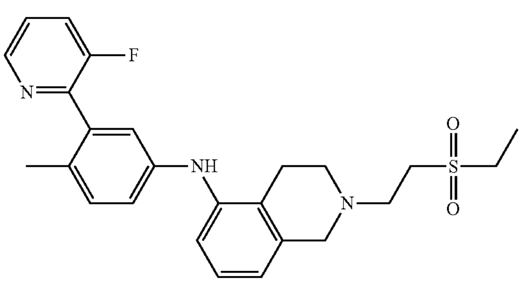 [SMILES: CCS(=O)(=O)CCN1CCc2c(cccc2Nc2ccc(C)c(-c3ncccc3F)c2)C1] | 454.2 | ** |

TABLE 1-continued

| Compound Number | Structure | Physical Data MS (m/z) | IC$_{50}$ Ranges |
|---|---|---|---|
| 284 | 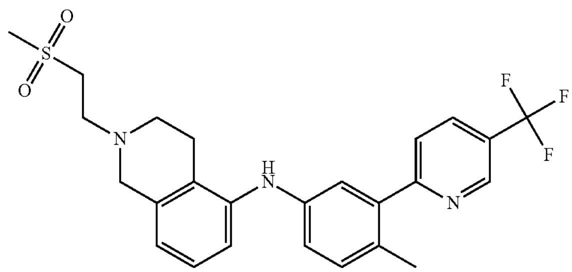 [SMILES: Cc1ccc(Nc2cccc3c2CCN(CCS(C)(=O)=O)C3)cc1-c1ccc(C(F)(F)F)cn1] | 490.2 | ** |
| 285 | 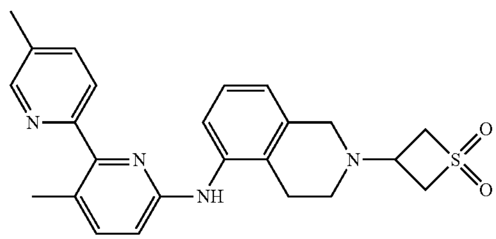 [SMILES: Cc1ccc(-c2nc(Nc3cccc4c3CCN(C3CS(=O)(=O)C3)C4)ccc2C)nc1] | 435.2 | *** |
| 286 | 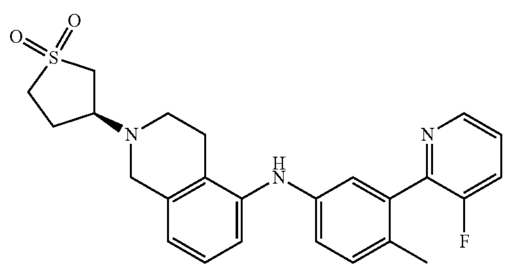 [SMILES: Cc1ccc(Nc2cccc3c2CCN([C@H]2CCS(=O)(=O)C2)C3)cc1-c1ncccc1F] | 452.2 | * |
| 287 | 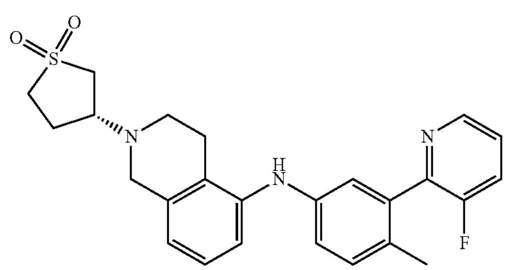 | 452.2 | ** |
| 288 | 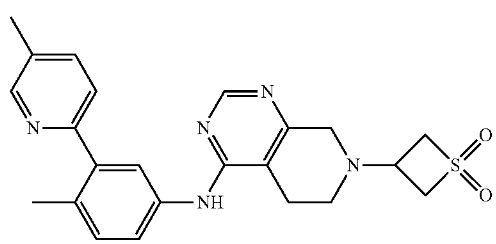 [SMILES: Cc1ccc(-c2cc(Nc3ncnc4c3CCN(C3CS(=O)(=O)C3)C4)ccc2C)nc1] | 436.2 | *** |
| 289 | 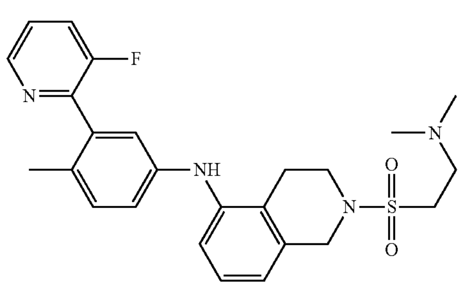 [SMILES: Cc1ccc(Nc2cccc3c2CCN(S(=O)(=O)CCN(C)C)C3)cc1-c1ncccc1F] | 469.2 | * |

TABLE 1-continued

| Compound Number | Structure | Physical Data MS (m/z) | IC$_{50}$ Ranges |
|---|---|---|---|
| 290 | 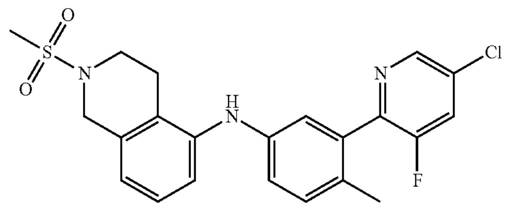 [SMILES: Cc1ccc(Nc2cccc3c2CCN(S(C)(=O)=O)C3)cc1-c1ncc(Cl)cc1F] | 446.1 | * |
| 291 | 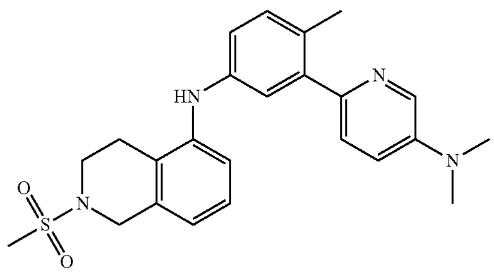 | 437.2 | * |
| 292 | 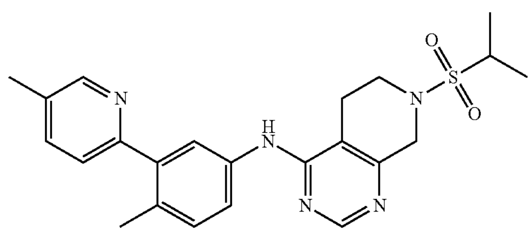 [SMILES: Cc1ccc(-c2cc(Nc3ncnc4c3CCN(S(=O)(=O)C(C)C)C4)ccc2C)nc1] | 438.2 | ** |
| 293 | 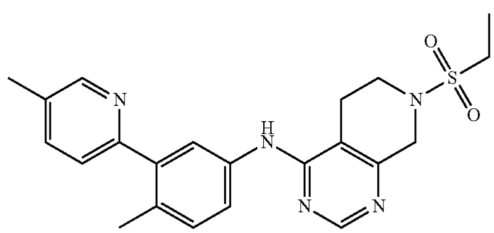 [SMILES: CCS(=O)(=O)N1CCc2c(ncnc2Nc2ccc(C)c(-c3ccc(C)cn3)c2)C1] | 424.2 | * |
| 294 | 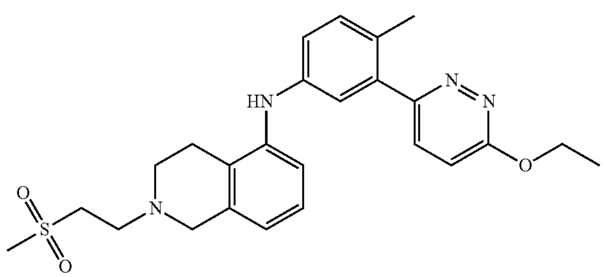 [SMILES: CCOc1ccc(-c2cc(Nc3cccc4c3CCN(CCS(C)(=O)=O)C4)ccc2C)nn1] | 467.2 | ** |
| 295 | 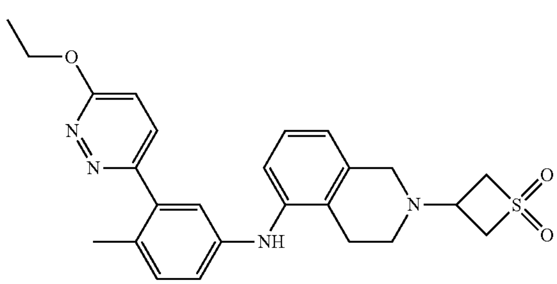 | 465.2 | ** |

TABLE 1-continued

| Compound Number | Structure | Physical Data MS (m/z) | IC$_{50}$ Ranges |
|---|---|---|---|
| 296 | 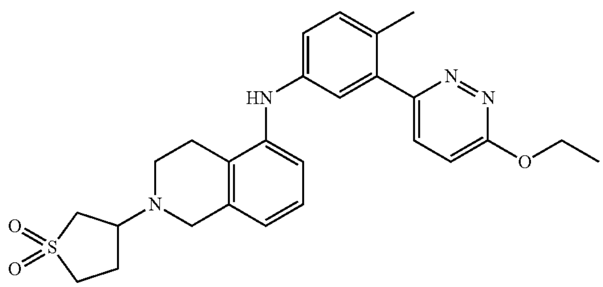 [SMILES: CCOc1ccc(-c2cc(Nc3cccc4c3CCN(C3CCS(=O)(=O)C3)C4)ccc2C)nn1] | 479.2 | ** |
| 297 | 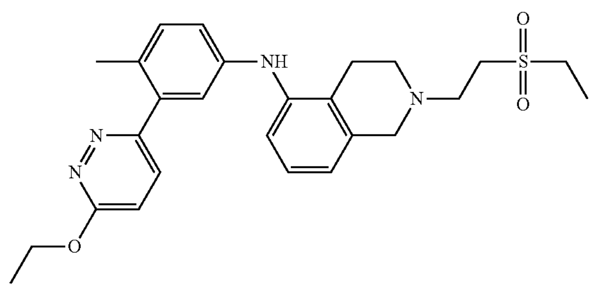 [SMILES: CCOc1ccc(-c2cc(Nc3cccc4c3CCN(CCS(=O)(=O)CC)C4)ccc2C)nn1] | 481.2 | ** |
| 298 | 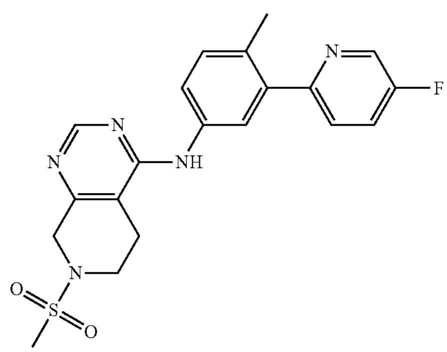 [SMILES: Cc1ccc(Nc2ncnc3c2CCN(S(C)(=O)=O)C3)cc1-c1ccc(F)cn1] | 414.1 | *** |
| 299 | 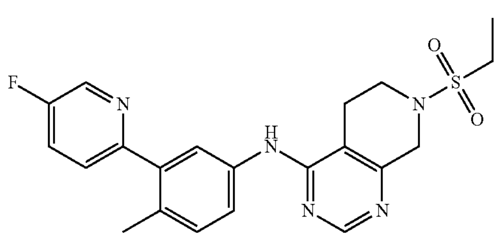 [SMILES: CCS(=O)(=O)N1CCc2c(ncnc2Nc2ccc(C)c(-c3ccc(F)cn3)c2)C1] | 428.1 | * |
| 300 | 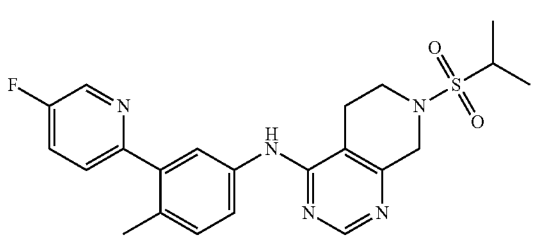 [SMILES: Cc1ccc(Nc2ncnc3c2CCN(S(=O)(=O)C(C)C)C3)cc1-c1ccc(F)cn1] | 442.2 | * |

TABLE 1-continued

| Compound Number | Structure | Physical Data MS (m/z) | IC$_{50}$ Ranges |
|---|---|---|---|
| 301 | 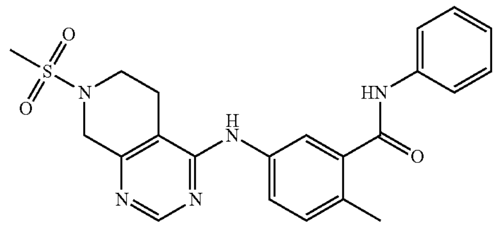 [SMILES: Cc1ccc(Nc2ncnc3c2CCN(S(C)(=O)=O)C3)cc1C(=O)Nc1ccccc1] | 438.2 | **** |
| 302 | 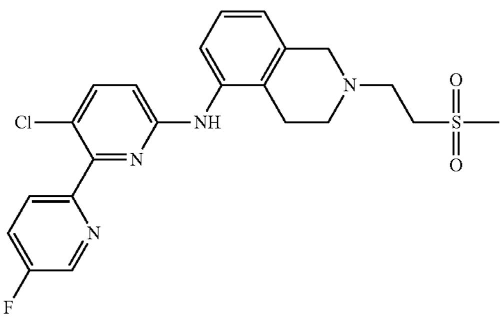 [SMILES: CS(=O)(=O)CCN1CCc2c(cccc2Nc2ccc(Cl)c(-c3ccc(F)cn3)n2)C1] | 461.1 | *** |
| 303 | 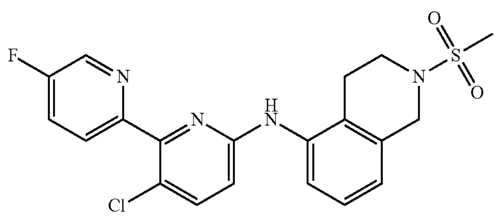 [SMILES: CS(=O)(=O)N1CCc2c(cccc2Nc2ccc(Cl)c(-c3ccc(F)cn3)n2)C1] | 433.1 | ** |
| 304 | 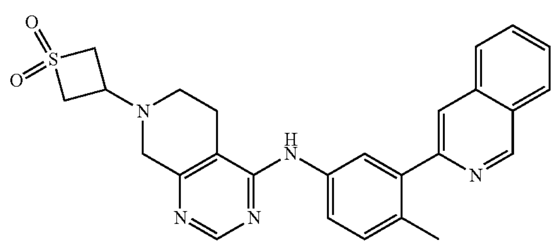 [SMILES: Cc1ccc(Nc2ncnc3c2CCN(C2CS(=O)(=O)C2)C3)cc1-c1cc2ccccc2cn1] | 472.2 | *** |
| 305 | 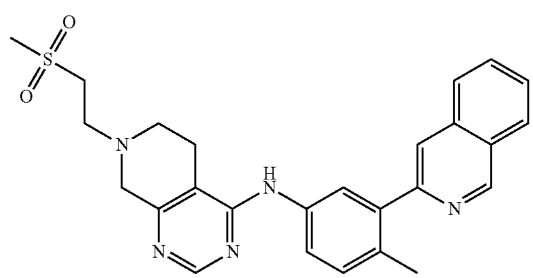 [SMILES: Cc1ccc(Nc2ncnc3c2CCN(CCS(C)(=O)=O)C3)cc1-c1cc2ccccc2cn1] | 474.2 | *** |
| 306 | 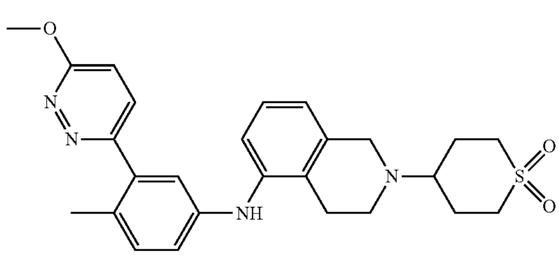 [SMILES: COc1ccc(-c2cc(Nc3cccc4c3CCN(C3CCS(=O)(=O)CC3)C4)ccc2C)nn1] | 479.2 | ** |

TABLE 1-continued

| Compound Number | Structure | Physical Data MS (m/z) | IC$_{50}$ Ranges |
|---|---|---|---|
| 307 | 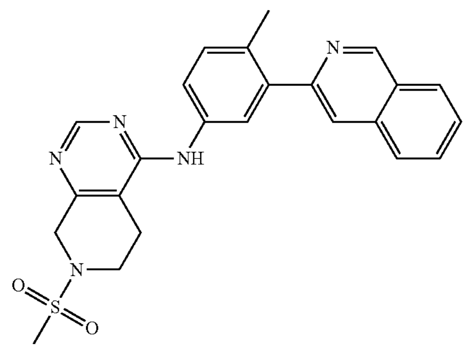 [SMILES: Cc1ccc(Nc2ncnc3c2CCN(S(C)(=O)=O)C3)cc1-c1cc2ccccc2cn1] | 446.2 | * |
| 308 | 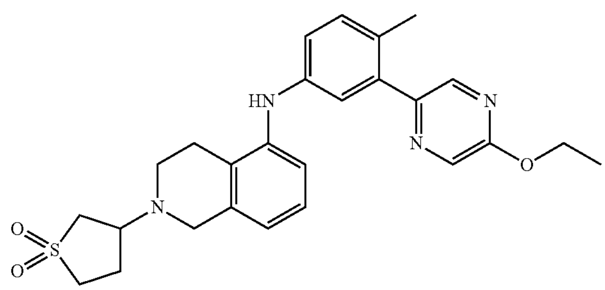 [SMILES: CCOc1cnc(-c2cc(Nc3cccc4c3CCN(C3CCS(=O)(=O)C3)C4)ccc2C)cn1] | 479.2 | ** |
| 309 | 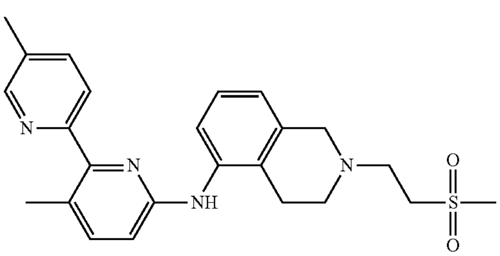 [SMILES: Cc1ccc(-c2nc(Nc3cccc4c3CCN(CCS(C)(=O)=O)C4)ccc2C)nc1] | 437.2 | *** |
| 310 | 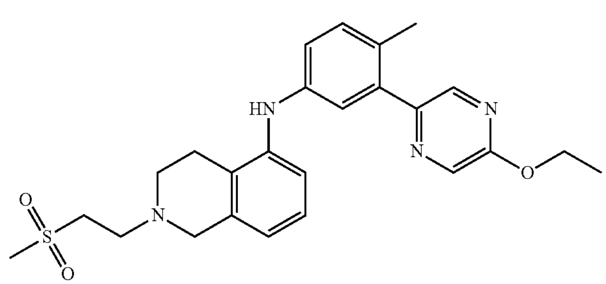 [SMILES: CCOc1cnc(-c2cc(Nc3cccc4c3CCN(CCS(C)(=O)=O)C4)ccc2C)cn1] | 467.2 | ** |

TABLE 1-continued

| Compound Number | Structure | Physical Data MS (m/z) | IC$_{50}$ Ranges |
|---|---|---|---|
| 311 | 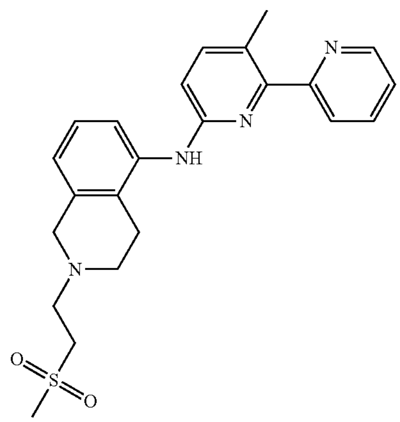 [SMILES: Cc1ccc(Nc2cccc3c2CCN(CCS(C)(=O)=O)C3)nc1-c1ccccn1] | 423.2 | *** |
| 312 | 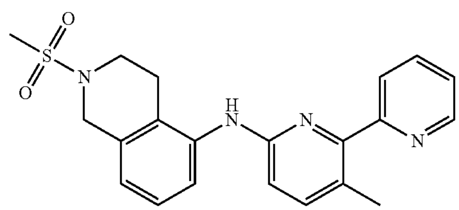 [SMILES: Cc1ccc(Nc2cccc3c2CCN(S(C)(=O)=O)C3)nc1-c1ccccn1] | 395.1 | ** |
| 313 | 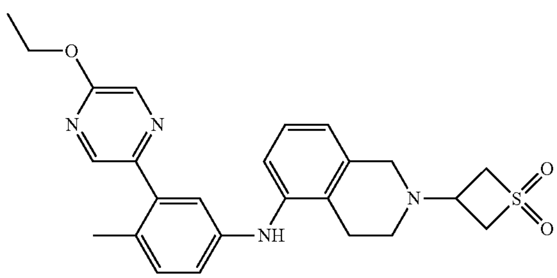 [SMILES: CCOc1cnc(-c2cc(Nc3cccc4c3CCN(C3CS(=O)(=O)C3)C4)ccc2C)cn1] | 465.2 | ** |
| 314 | 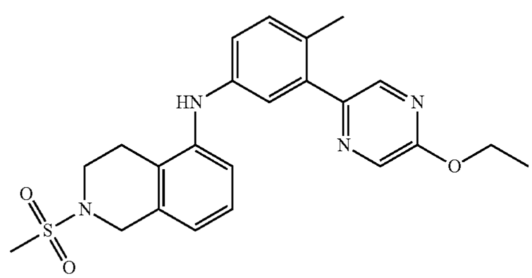 [SMILES: CCOc1cnc(-c2cc(Nc3cccc4c3CCN(S(C)(=O)=O)C4)ccc2C)cn1] | 439.2 | * |
| 315 | 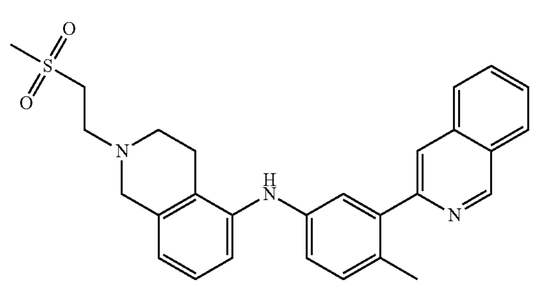 [SMILES: Cc1ccc(Nc2cccc3c2CCN(CCS(C)(=O)=O)C3)cc1-c1cc2ccccc2cn1] | 472.2 | * |

TABLE 1-continued
| Compound Number | Structure | Physical Data MS (m/z) | IC$_{50}$ Ranges |
|---|---|---|---|
| 316 | 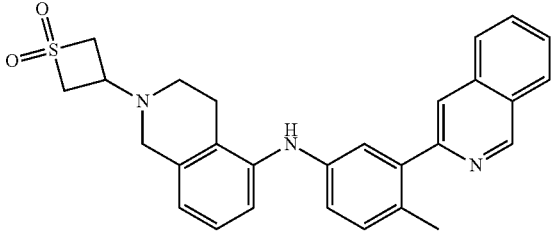 [SMILES: Cc1ccc(Nc2cccc3c2CCN(C2CS(=O)(=O)C2)C3)cc1-c1cc2ccccc2cn1] | 470.2 | * |
| 317 | 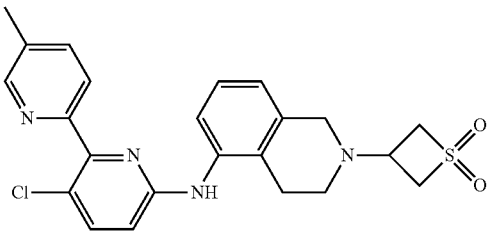 | 455.1 | * |
| 318 | 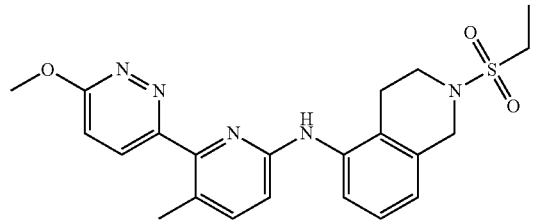 [SMILES: CCS(=O)(=O)N1CCc2c(cccc2Nc2ccc(C)c(-c3ccc(OC)nn3)n2)C1] | 440.2 | ** |
| 319 | 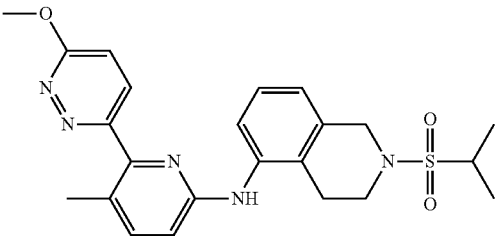 [SMILES: COc1ccc(-c2nc(Nc3cccc4c3CCN(S(=O)(=O)C(C)C)C4)ccc2C)nn1] | 454.2 | ** |
| 320 | 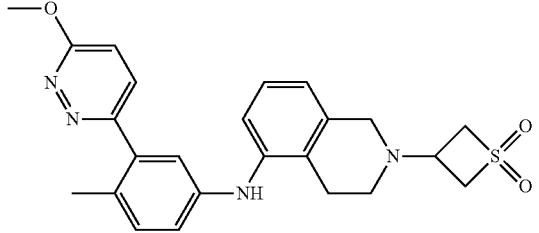 [SMILES: COc1ccc(-c2cc(Nc3cccc4c3CCN(C3CS(=O)(=O)C3)C4)ccc2C)nn1] | 451.2 | ** |
| 321 | 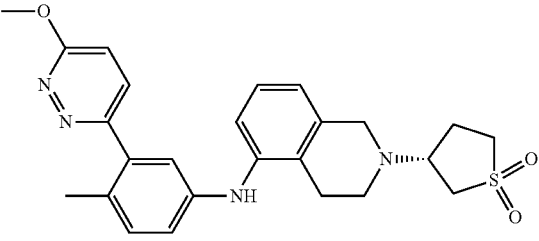 | 465.2 | ** |

TABLE 1-continued

| Compound Number | Structure | Physical Data MS (m/z) | IC$_{50}$ Ranges |
|---|---|---|---|
| 322 | 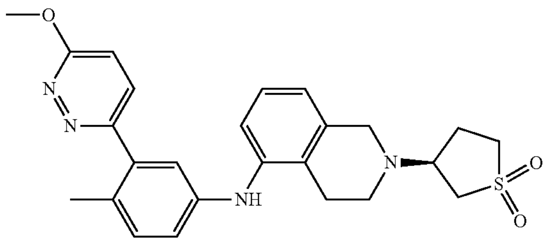 [SMILES: COc1ccc(-c2cc(Nc3cccc4c3CCN([C@H]3CCS(=O)(=O)C3)C4)ccc2C)nn1] | 465.2 | ** |
| 323 | 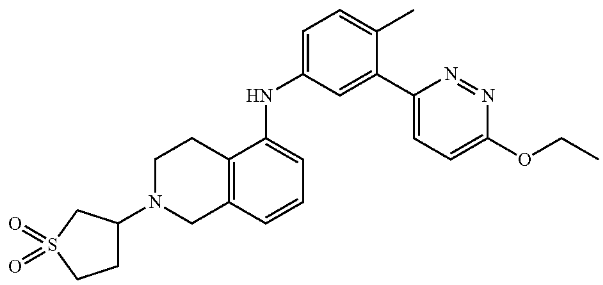 [SMILES: CCOc1ccc(-c2cc(Nc3cccc4c3CCN(C3CCS(=O)(=O)C3)C4)ccc2C)nn1] | 479.2 | ** |
| 324 | 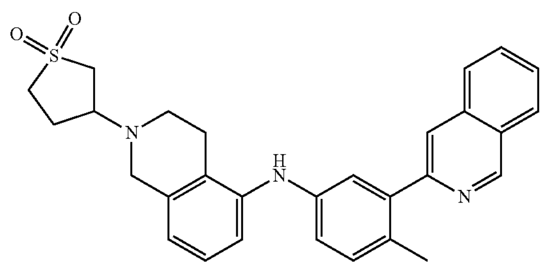 [SMILES: Cc1ccc(Nc2cccc3c2CCN(C2CCS(=O)(=O)C2)C3)cc1-c1cc2ccccc2cn1] | 484.2 | * |
| 325 | 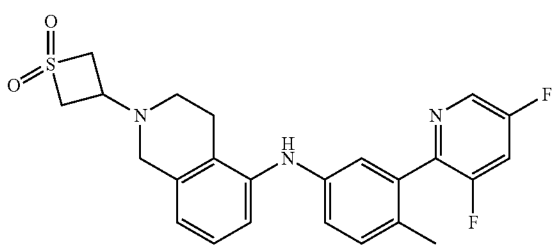 [SMILES: Cc1ccc(Nc2cccc3c2CCN(C2CS(=O)(=O)C2)C3)cc1-c1ncc(F)cc1F] | 456.1 | * |
| 326 | 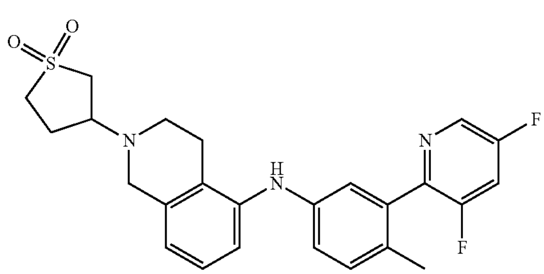 [SMILES: Cc1ccc(Nc2cccc3c2CCN(C2CCS(=O)(=O)C2)C3)cc1-c1ncc(F)cc1F] | 470.2 | * |

TABLE 1-continued

| Compound Number | Structure | Physical Data MS (m/z) | IC$_{50}$ Ranges |
|---|---|---|---|
| 327 | 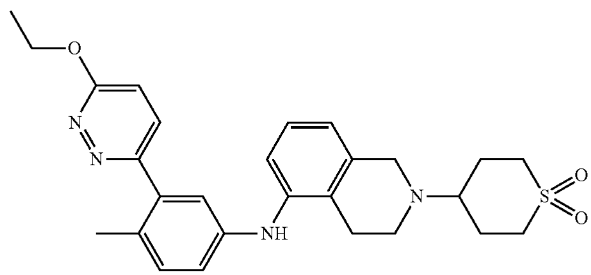 [SMILES: CCOc1ccc(-c2cc(Nc3cccc4c3CCN(C3CCS(=O)(=O)CC3)C4)ccc2C)nn1] | 493.2 | ** |
| 328 | 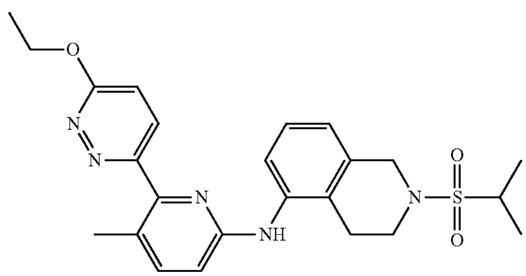 [SMILES: CCOc1ccc(-c2nc(Nc3cccc4c3CCN(S(=O)(=O)C(C)C)C4)ccc2C)nn1] | 468.2 | ** |
| 329 | 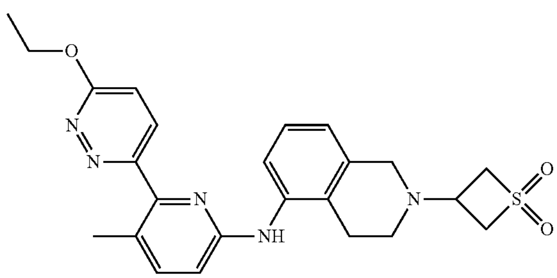 [SMILES: CCOc1ccc(-c2nc(Nc3cccc4c3CCN(C3CS(=O)(=O)C3)C4)ccc2C)nn1] | 466.2 | *** |
| 330 | 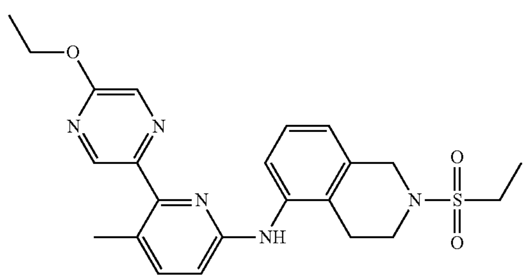 [SMILES: CCOc1cnc(-c2nc(Nc3cccc4c3CCN(S(=O)(=O)CC)C4)ccc2C)cn1] | 454.2 | ** |
| 331 | 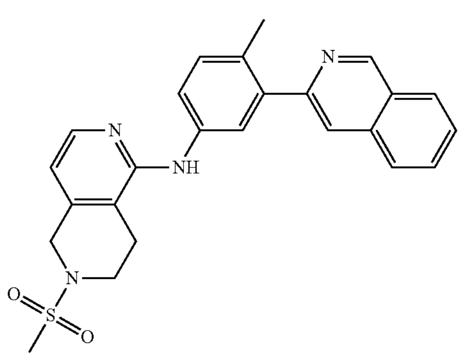 [SMILES: Cc1ccc(Nc2nccc3c2CCN(S(C)(=O)=O)C3)cc1-c1cc2ccccc2cn1] | 445.2 | *** |

TABLE 1-continued

| Compound Number | Structure | Physical Data MS (m/z) | IC$_{50}$ Ranges |
|---|---|---|---|
| 332 | 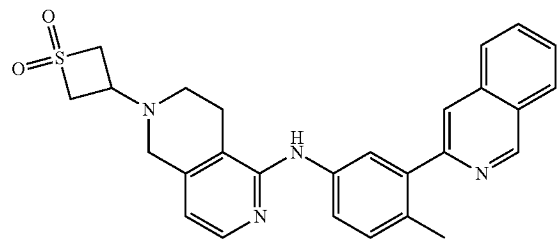 [SMILES: Cc1ccc(Nc2nccc3c2CCN(C2CS(=O)(=O)C2)C3)cc1-c1cc2ccccc2cn1] | 471.2 | *** |
| 333 | 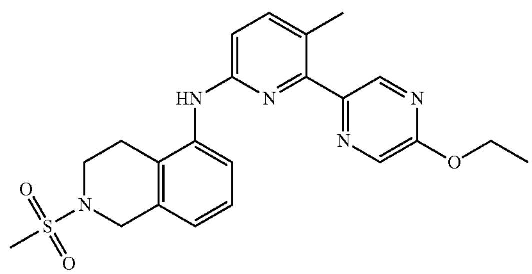 [SMILES: CCOc1cnc(-c2nc(Nc3cccc4c3CCN(S(C)(=O)=O)C4)ccc2C)cn1] | 440.2 | *** |
| 334 | 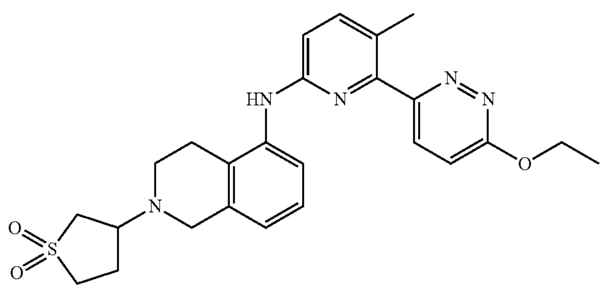 [SMILES: CCOc1ccc(-c2nc(Nc3cccc4c3CCN(C3CCS(=O)(=O)C3)C4)ccc2C)nn1] | 480.2 | *** |
| 335 | 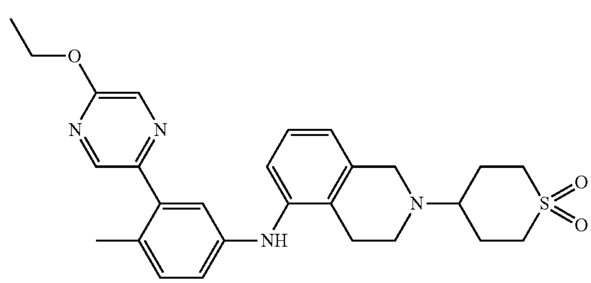 [SMILES: CCOc1cnc(-c2cc(Nc3cccc4c3CCN(C3CCS(=O)(=O)CC3)C4)ccc2C)cn1] | 493.2 | ** |
| 336 | 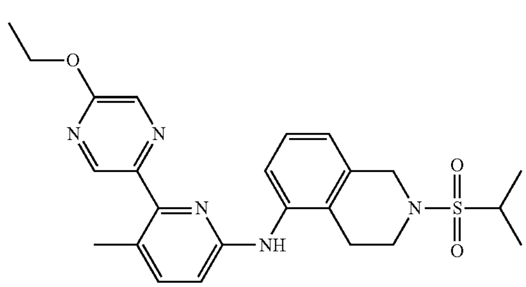 [SMILES: CCOc1cnc(-c2nc(Nc3cccc4c3CCN(S(=O)(=O)C(C)C)C4)ccc2C)cn1] | 468.2 | *** |

TABLE 1-continued

| Compound Number | Structure | Physical Data MS (m/z) | IC₅₀ Ranges |
|---|---|---|---|
| 337 | 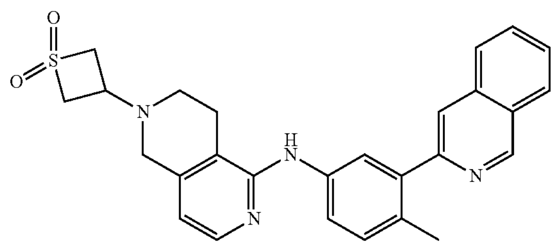 [SMILES: Cc1ccc(Nc2nccc3c2CCN(C2CS(=O)(=O)C2)C3)cc1-c1cc2ccccc2cn1] | 471.2 | *** |
| 338 | 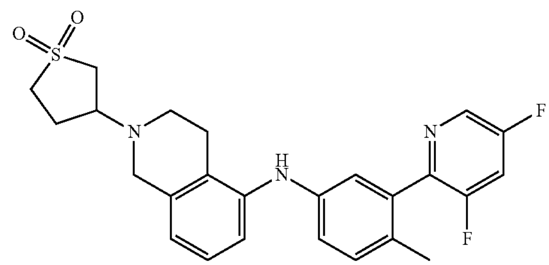 [SMILES: Cc1ccc(Nc2cccc3c2CCN(C2CCS(=O)(=O)C2)C3)cc1-c1ncc(F)cc1F] | 470.2 | * |
| 339 | 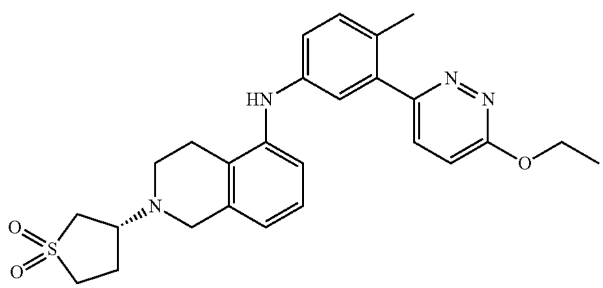 [SMILES: CCOc1ccc(-c2cc(Nc3cccc4c3CCN([C@@H]3CCS(=O)(=O)C3)C4)ccc2C)nn1] | 479.2 | ** |
| 340 | 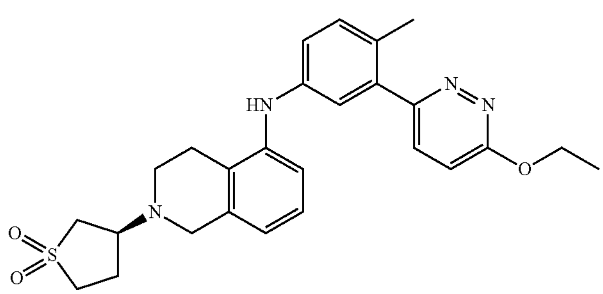 [SMILES: CCOc1ccc(-c2cc(Nc3cccc4c3CCN([C@H]3CCS(=O)(=O)C3)C4)ccc2C)nn1] | 479.2 | ** |
| 341 | 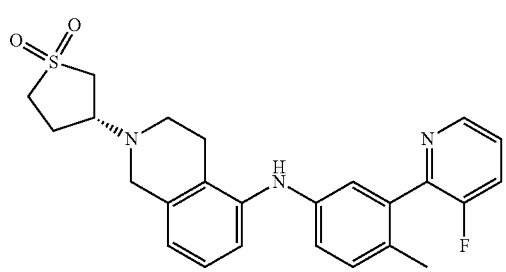 [SMILES: Cc1ccc(Nc2cccc3c2CCN([C@@H]2CCS(=O)(=O)C2)C3)cc1-c1ncccc1F] | 452.2 | * |

TABLE 1-continued

| Compound Number | Structure | Physical Data MS (m/z) | IC$_{50}$ Ranges |
|---|---|---|---|
| 342 | 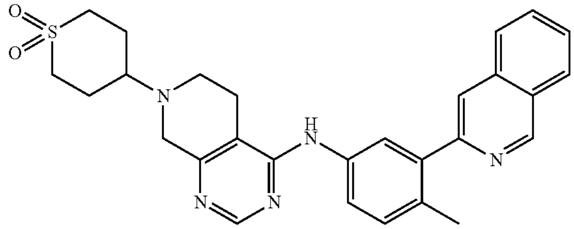 [SMILES: Cc1ccc(Nc2ncnc3c2CCN(C2CCS(=O)(=O)CC2)C3)cc1-c1cc2ccccc2cn1] | 500.2 | ** |
| 343 | 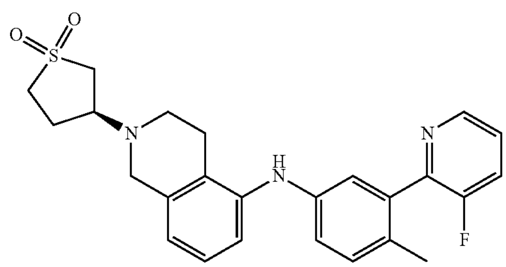 [SMILES: Cc1ccc(Nc2cccc3c2CCN([C@H]2CCS(=O)(=O)C2)C3)cc1-c1ncccc1F] | 452.2 | * |
| 344 | 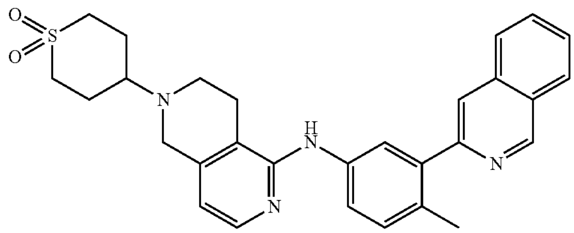 [SMILES: Cc1ccc(Nc2nccc3c2CCN(C2CCS(=O)(=O)CC2)C3)cc1-c1cc2ccccc2cn1] | 499.2 | * |
| 345 | 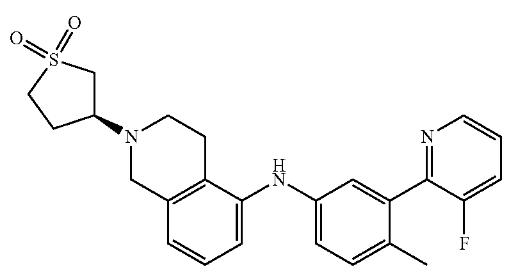 [SMILES: Cc1ccc(Nc2cccc3c2CCN([C@H]2CCS(=O)(=O)C2)C3)cc1-c1ncccc1F] | 452.2 | * |
| 346 | 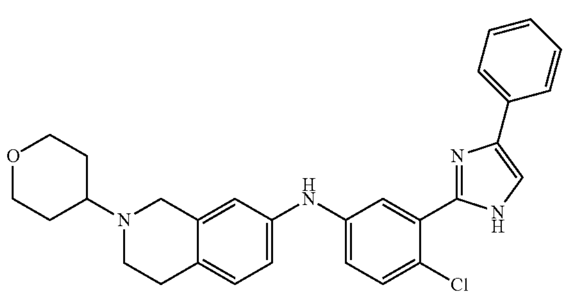 [SMILES: Clc1ccc(Nc2ccc3c(c2)CN(C2CCOCC2)CC3)cc1-c1nc(-c2ccccc2)c[nH]1] | 485.2 | *** |
| 347 | 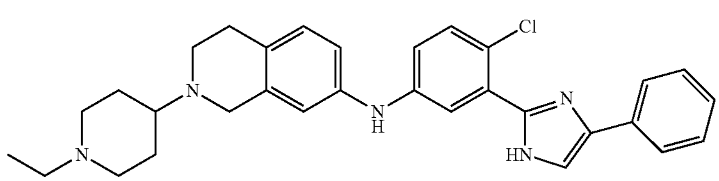 [SMILES: CCN1CCC(N2CCc3ccc(Nc4ccc(Cl)c(-c5nc(-c6ccccc6)c[nH]5)c4)cc3C2)CC1] | 512.3 | *** |

TABLE 1-continued

| Compound Number | Structure | Physical Data MS (m/z) | IC$_{50}$ Ranges |
|---|---|---|---|
| 348 | 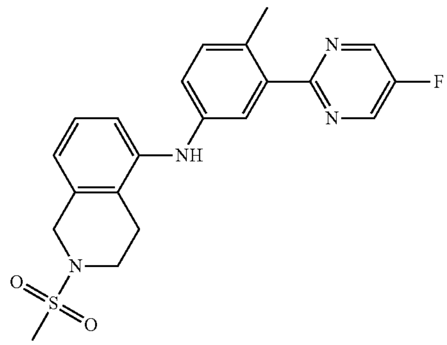 | 413.1 | ** |
| 349 | 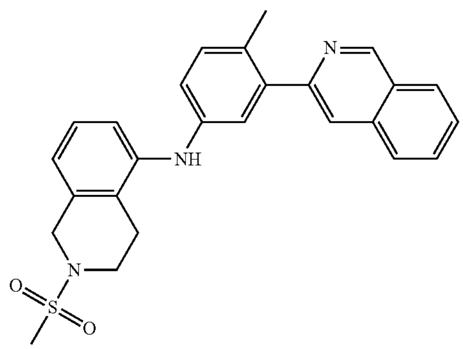 [SMILES: Cc1ccc(Nc2cccc3c2CCN(S(C)(=O)=O)C3)cc1-c1cc2ccccc2cn1] | 444.2 | * |

Assays

General materials and methods for the analysis of compounds of the invention are described in PCT application number PCT/US2007/038171 "Compounds and Compositions for Treating Lymphoma and Myeloma"; Dierks and Warmuth. The full disclosure of this application is incorporated herein by reference in its entirety and for all purposes.

Compounds of the present invention are assayed to evaluate their capacity to inhibit the hedgehog signaling pathway.

Gli-Luc Reporter Assay for Hh Pathway Inhibition

Mouse TM3 cells (obtained from American Type Culture Collection, ATCC, Manassas, Va.) are cultured in DMEM/F12 medium (Gibco/Invitrogen, Carlsbad, Calif.) supplemented with 5% heat inactivated horse serum and 2.5% FBS (Gibco/Invitrogen, Carlsbad, Calif.), 50 unit/mL penicillin and 50 μg/mL of streptomycin (Gibco/Invitrogen, Carlsbad, Calif.) at 37° C. with 5% $CO_2$ in air atmosphere. TM3 cells were transfected with pTA-8×Gli-Luc reporter plasmid. A stably transfected clone termed TMHh-12 was selected. TMHh-12 clone showed good response to Shh-N stimulation. To evaluate the IC$_{50}$s of the antagonists, 8000 TMHh-12 cells were plated into each wells in 384-well plates with 50% DMEM/F12 medium supplemented with 2% FBS. After 12 hours, Hh pathway is activated by adding recombinant mouse Shh protein (expressed in E. coli, 8 μg/mL) or by adding Smo agonists. The testing compounds are added into plates with different concentrations. After 48 hours, the firefly luciferase luciferase activities are assayed with the Bright-Glo™ Luciferase Assay System (Promega, Madison, Wis.). The IC$_{50}$ is measured when the effect of the compound reduces the luminescence signal by 50%. Toxicity of these compounds are evaluated in TM3 cells using CellTiter Glo assays or by TM3-Luc cell line (a TM3 cell stably transfected with a constitutive luciferase expression vector).

Various compounds of Formula (I) in the examples and Table 1, in free form or in pharmaceutically acceptable salt form, exhibit pharmacological properties, for example, as indicated by the tests described herein. In some certain embodiments, compounds of Formula (I) have IC$_{50}$ values in the range from 1 pM to 10 μM. In some certain embodiments, compounds of Formula (I) have IC$_{50}$ values in the range from 1 pM to 1 nM. In other embodiments, compounds of Formula (I) have IC$_{50}$ values in the range from 1 pM to 10 nM. In other embodiments, compounds of Formula (I) have IC$_{50}$ values in the range from 1 pM to 100 nM. In other embodiments, compounds of Formula (I) have IC$_{50}$ values in the range from 1 pM to 1 μM. In other embodiments, compounds of Formula (I) have IC$_{50}$ values in the range from 1 pM to 10 μM. In other embodiments, compounds of Formula (I) have IC$_{50}$ values greater than 10 μM. In other examples, compounds of Formula (I) have IC$_{50}$ values from 1 pM to 1 nM. In other examples, compounds of Formula (I) have IC$_{50}$ values from 1 nM to 10 nM. In other examples, compounds of Formula (I) have IC$_{50}$ values from 10 nM to 100 nM. In other examples, compounds of Formula (I) have IC$_{50}$ values from 100 nM to 1 μM. In other examples, compounds of Formula (I) have IC$_{50}$ values from 1 μM to 10 μM.

Psoriasis Assay

Compounds of the invention are tested form their ability to treat psoriatic skin lesions according to the assay described in Tas & Avci, Pharmacology and Treatment, Dermatology 2004; 209:126-131.

Certain Assay Results

By way of example only, the IC$_{50}$ for Hedgehog inhibition by certain other compounds of Formula (I) are listed in Table 2 below. The compound No. corresponds to the compounds listed in Table 1.

TABLE 2

| Compound No. | Hedgehog Inhibition IC$_{50}$ (nM) (Ag1.5 1 nM) |
|---|---|
| 2 | 0.45 |
| 3 | 0.06 |
| 5 | 0.1 |
| 7 | 0.25 |
| 13 | 1.6 |
| 16 | 3.8 |
| 21 | 0.86 |
| 23 | 2 |
| 30 | 1.2 |
| 33 | 0.7 |
| 34 | 1.8 |
| 35 | 2.6 |
| 37 | 0.73 |
| 42 | 0.0017 |
| 43 | 4.5 |
| 45 | 3 |
| 51 | 11 |
| 57 | 22.7 |
| 66 | 5.3 |
| 69 | 1.4 |
| 73 | 0.5 |
| 90 | 490 |
| 96 | 263 |
| 103 | 59 |
| 113 | 1030 |
| 115 | 362 |
| 116 | 694 |
| 123 | 738 |
| 124 | 135 |
| 129 | 52 |
| 135 | 4175 |
| 136 | 90 |
| 139 | 101 |
| 140 | 2939 |
| 143 | >10000 |
| 156 | 564 |
| 159 | 0.1 |
| 160 | 1 |
| 162 | 2.1 |
| 163 | 47 |
| 184 | 0.7 |
| 185 | 0.4 |
| 187 | 1.1 |
| 216 | 15 |
| 229 | 0.3 |
| 276 | 9.8 |

In addition, Table 1 list IC$_{50}$ ranges for each compound from enzymatic and cellular assays for the inhibition of hedgehog signaling pathways: * indicates a range from 1 pM to 1 nM;  indicates a range from 1 nM to 10 nM; * indicates a range from 10 nM to 100 nM; ** indicates a range from 0.1 μM to 1 μM, * 1 μM to 10 μM, and **** indicates values greater than 10 μM.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A compound having the structure of Formula I:

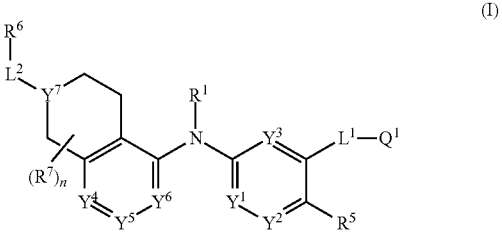

wherein:

Q$^1$ is selected from an aryl, heteroaryl, cycloalkyl, and heterocycloalkyl, wherein the aryl, heteroaryl, cycloalkyl and heterocycloalkyl of Q$^1$ are optionally substituted with 1 to 3 substituents independently selected from R$^9$, R$^{10}$, R$^{11}$, R$^{12}$ and R$^{13}$;

Y$^1$ is N or CR$^3$;

Y$^2$ is N or CR$^4$;

Y$^3$ is N or CR$^2$;

Y$^4$ and Y$^6$ are independently selected from CR$^8$;

Y$^5$ is CR$^8$;

Y$^7$ is N or N$^+$O$^-$;

L$^1$ is selected from a bond, —O—, —O(CR$^{14}$R$^{14}$)$_m$—, —(CR$^{14}$R$^{14}$)$_m$O—, and —C(O)NR$^{16}$—;

L$^2$ is selected from a bond, —(CR$^{14}$R$^{14}$)$_m$—, —(CR$^{14}$R$^{15}$)$_m$—, —C(O)—, —C(O)(CR$^{14}$R$^{14}$)$_m$— and —C(O)(CR$^{14}$R$^{15}$)$_m$;

each L$^3$ is independently selected from a bond, —(CR$^{14}$R$^{14}$)$_m$—, —C(O)—, —C(O)O—, and —O(CR$^{14}$R$^{15}$)$_m$—;

R$^1$ is H or C$_1$-C$_6$alkyl;

R$^2$, R$^3$ and R$^4$ are each independently selected from H, C$_1$-C$_6$alkyl and L$^3$NR$^{16}$R$^{17}$;

each R$^5$ is independently selected from H, CN, halogen, C$_1$-C$_6$alkyl, C$_1$-C$_6$alkoxy, halosubstituted-C$_1$-C$_6$alkoxy, L$^3$OR$^{13}$, C(O)OR$^{13}$ and L$^3$NR$^{16}$R$^{17}$;

each R$^6$ is independently selected from H, S(O)R$^{13}$, SO$_2$R$^{13}$, SO$_2$NR$^{16}$R$^{17}$, L$^3$NR$^{16}$R$^{17}$, C(O)OR$^{13}$, OR$^{13}$, NR$^{16}$R$^{17}$, C(O)NR$^{16}$R$^{17}$, C$_1$-C$_6$alkyl, C$_1$-C$_6$haloalkyl, C$_3$-C$_8$cycloalkyl, heteroaryl, heterocycloalkyl,

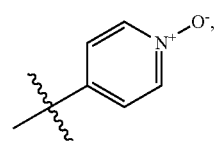

a cyclic sulfinyl selected from

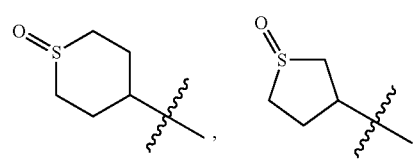

and

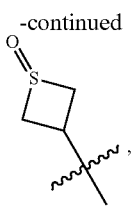

a cyclic sulfonyl selected from

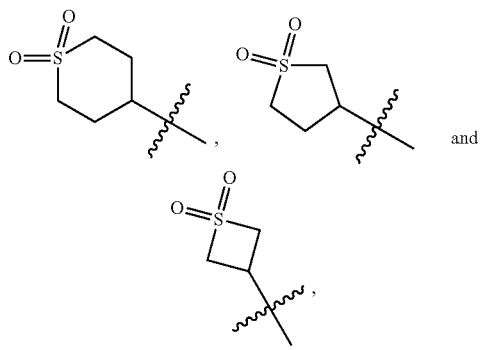

an aryl and a $C_1$-$C_6$alkyl substituted with 1-4 OH groups, wherein the heteroaryl, $C_3$-$C_8$cycloalkyl, cyclic sulfinyl, cyclic sulfonyl and aryl of $R^6$ are optionally substituted with 1-4 substituents selected from halo, CN, $C_1$-$C_6$alkyl, halosubstituted-$C_1$-$C_6$alkyl, $C_1$-$C_6$alkoxy, halosubstituted-$C_1$-$C_6$alkoxy and $C_1$-$C_6$alkyl substituted with 1-4 —OH groups;

each $R^7$ is independently selected from H and $C_1$-$C_6$alkyl, or n is 1 and $R^7$ is oxo;

each $R^8$ is independently selected from H and $C_1$-$C_6$alkyl;

each $R^9$, $R^{10}$, $R^{11}$ and $R^{12}$ are independently selected from H, CN, halo, $C_1$-$C_6$alkyl, halosubstituted-$C_1$-$C_6$alkyl, $C_1$-$C_6$alkoxy, halosubstituted-$C_1$-$C_6$alkoxy, $L^3OR^{13}$, $L^3NR^{16}R^{17}$, $L^3R^{13}$, $L^3R^{14}$, phenyl optionally substituted with 1 to 3 substituents selected from $C_1$-$C_6$alkyl, halo, CN, $L^3NR^{16}R^{17}$ and $OR^{13}$, and heteroaryl optionally substituted with 1 to 3 substituents selected from $C_1$-$C_6$alkyl, halo, CN, $L^3NR^{16}R^{17}$ and $L^3OR^{13}$;

alternatively $R^{10}$ and $R^{11}$ together with the carbon atoms to which they are attached form a phenyl optionally substituted with 1 to 3 substituents selected from $C_1$-$C_6$alkyl, halo, CN, $L^3NR^{16}R^{17}$ and $L^3OR^{13}$, or $R^{10}$ and $R^{11}$ together with the carbons atom to which they are attached form a 5-6 membered heteroaryl optionally substituted with 1 to 3 substituents selected from $C_1$-$C_6$alkyl, halo, CN, $L^3NR^{16}R^{17}$ and $L^3OR^{13}$;

each $R^{13}$ is independently selected from H, $C_1$-$C_6$alkyl, $C_1$-$C_6$haloalkyl, $C_3$-$C_8$cycloalkyl, $C_3$-$C_8$heterocycloalkyl, heteroaryl, aryl and a $C_1$-$C_6$alkyl substituted with 1-4 —OH groups, where the heteroaryl and aryl of $R^{13}$ are optionally substituted with 1 to 3 substituents selected from $C_1$-$C_6$alkyl, $C_1$-$C_6$haloalkyl, $C_3$-$C_8$cycloalkyl, $C_3$-$C_8$heterocycloalkyl, and $C_1$-$C_6$alkyl substituted with 1-4 —OH groups;

each $R^{14}$ and $R^{15}$ are independently selected from H, halo, OH, CN, $C_1$-$C_6$alkyl, $C_1$-$C_6$alkyl substituted with 1-4 —OH groups, halosubstituted-$C_1$-$C_6$alkyl, $C_1$-$C_6$alkoxy and halosubstituted-$C_1$-$C_6$alkoxy;

or $R^{14}$ and $R^{15}$ together with the carbon to which they are attached form a $C_3$-$C_8$cycloalkyl;

each $R^{16}$ and $R^{17}$ are independently selected from H, $C_1$-$C_6$alkyl, and $C_1$-$C_6$alkyl substituted with 1-4 —OH groups;

each m is independently 1, 2, 3, 4, 5 or 6;

each n is independently 1, 2, 3, 4, 5 or 6, and the pharmaceutically acceptable salts, N-oxides, stereoisomers and diastereoisomers thereof.

2. The compound of claim 1, wherein $R^1$ is H.

3. The compound of claim 2, wherein $Q^1$ is selected from phenyl, pyrazolyl, pyrrolyl, imidazolyl, benzimidazolyl, benzoxazolyl, purinyl, thiazolyl, oxazolyl, pyridinyl, indolyl, thiazolo[5,4-d]pyrimidinyl, 1H-imidazo[4,5-c]pyridinyl, pyrimidinyl pyridazinyl, pyrazinyl, quinolinyl and isoquinolinyl, each of which is optionally substituted with 1 to 3 substituents independently selected from $R^9$ and $R^{13}$.

4. The compound of claim 3, wherein $L^1$ is a bond, and $Q^1$ is selected from phenyl, imidazolyl, benzimidazolyl, benzoxazolyl, purinyl, thiazolo[5,4-d]pyrimidinyl, oxazolyl, pyrazolyl, pyridinyl, 1H-imidazo[4,5-c]pyridinyl, indolyl, pyrimidinyl, pyridazinyl, pyrazinyl, quinolinyl and isoquinolinyl, each of which is optionally substituted with 1 to 3 substituents independently selected from $R^9$ and $R^{13}$;

or $L^1$ is —O—, —O$(CR^{14}R^{14})_m$—, —$(CR^{14}R^{14})_mO$— or —C(O)$NR^{16}$—, and $Q^1$ is selected from phenyl and pyridinyl, each of which is optionally substituted with 1 to 3 substituents independently selected from $R^9$ and $R^{13}$.

5. The compound of claim 4, wherein $L^2$ is a bond, and each $R^6$ is independently selected from H, $S(O)R^{13}$, $SO_2R^{13}$, $SO_2NR^{16}R^{17}$, $C_1$-$C_6$alkyl, $C_1$-$C_6$haloalkyl, $C_3$-$C_8$cycloalkyl, heteroaryl, heterocycloalkyl,

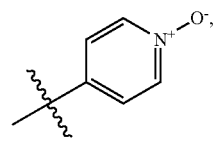

a cyclic sulfinyl selected from

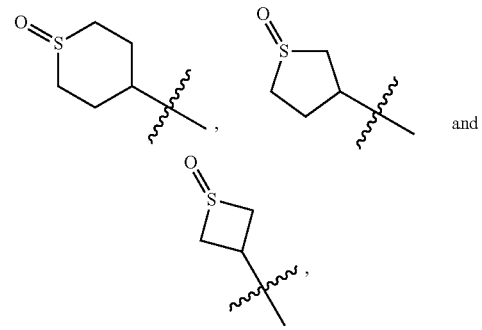

a cyclic sulfonyl selected from

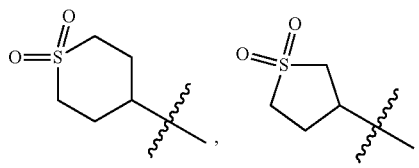

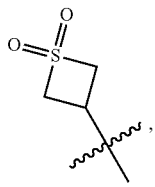

and a $C_1$-$C_6$alkyl substituted with 1-4 OH groups,
wherein the heteroaryl, heterocycloalkyl, $C_3$-$C_8$cycloalkyl, cyclic sulfinyl, and cyclic sulfonyl of $R^6$ are optionally substituted with 1-4 substituents selected from $C_1$-$C_6$alkyl and $C_1$-$C_6$alkyl substituted with 1-4 —OH groups;

or
$L^2$ is —$(CR^{14}R^{14})_m$—, —$(CR^{14}R^{15})_m$—, —C(O)$(CR^{14}R^{14})_m$—, or —C(O)$(CR^{14}R^{15})_m$—, and each $R^6$ is independently selected from S(O)$R^{13}$, SO$_2$$R^{13}$, NR$^{16}$R$^{17}$, OR$^{13}$, —C(O)OR$^{13}$, C(O)NR$^{16}$R$^{17}$, $C_1$-$C_6$haloalkyl, heteroaryl, heterocycloalkyl, $C_3$-$C_8$cycloalkyl and $C_1$-$C_6$alkyl substituted with 1-4 OH groups,
wherein the heteroaryl, heterocycloalkyl and $C_3$-$C_8$cycloalkyl of $R^6$ are optionally substituted with 1-4 substituents selected from $C_1$-$C_6$alkyl and $C_1$-$C_6$alkyl substituted with 1-4 —OH groups, or
$L^2$ is —C(O)—, and
each $R^6$ is independently selected from —NR$^{16}$R$^{17}$, —OR$^{13}$, C(O)OR$^{13}$, $C_1$-$C_6$alkyl, $C_3$-$C_8$cycloalkyl, and $C_1$-$C_6$alkyl substituted with 1-4 OH groups,
wherein the $C_3$-$C_8$cycloalkyl of $R^6$ is optionally substituted with 1-4 substituents selected from $C_1$-$C_6$alkyl and $C_1$-$C_6$alkyl substituted with 1-4 —OH groups.

6. The compound of claim 5, wherein
$L^2$ is a bond, and
each $R^6$ is independently selected from H, S(O)$R^{13}$, SO$_2$$R^{13}$, SO$_2$NR$^{16}$R$^{17}$, $C_1$-$C_6$alkyl, $C_1$-$C_6$haloalkyl, cyclopropyl, cyclohexyl, cycloheptyl,

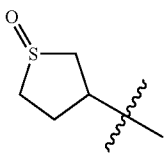

tetrazolyl, piperidinyl, dioxolanyl, tetrahyrdopyanyl, a cyclic sulfinyl selected from

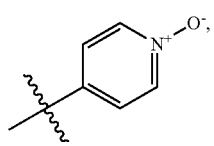

a cyclic sulfonyl selected from

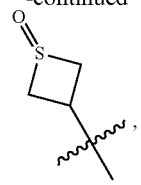

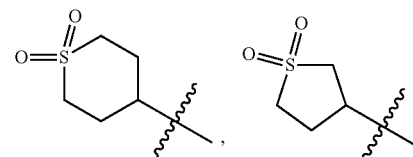

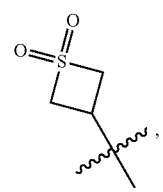

and a $C_1$-$C_6$alkyl substituted with 1-4 OH groups,
wherein the cyclopropyl, cyclohexyl, cycloheptyl, tetrazolyl, piperidinyl, dioxolanyl, tetrahyrdopyanyl, cyclic sulfinyl, and cyclic sulfonyl of $R^6$ are optionally substituted with 1-4 substituents selected from $C_1$-$C_6$alkyl and $C_1$-$C_6$alkyl substituted with 1-4 —OH groups;

or
$L^2$ is —$(CR^{14}R^{14})_m$—, —$(CR^{14}R^{15})_m$—, —C(O)$(CR^{14}R^{14})_m$—, or —C(O)$(CR^{14}R^{15})_m$—, and each $R^6$ is independently selected from S(O)$R^{13}$, SO$_2$$R^{13}$, NN$^{16}$R$^{17}$, OR$^{13}$, —C(O)OR$^{13}$, C(O)NR$^{16}$R$^{17}$, $C_1$-$C_6$haloalkyl, $C_1$-$C_6$alkyl substituted with 1-4 OH groups, cyclopropyl, cyclohexyl, cycloheptyl,

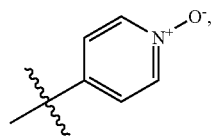

tetrazolyl, piperidinyl, dioxolanyl, tetrahyrdopyanyl, and a $C_1$-$C_6$alkyl substituted with 1-4 oH groups,
wherein the cyclopropyl, cyclohexyl, cycloheptyl,

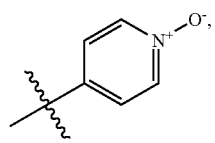

tetrazolyl, piperidinyl, dioxolanyl, tetrahyrdopyanyl, of $R^6$ are optionally substituted with 1-4 substituents selected from $C_1$-$C_6$alkyl and $C_1$-$C_6$alkyl substituted with 1-4 —OH groups, or L² is —C(O)—, and each R⁶ is independently selected from —NR¹⁶R¹⁷, —OR¹³, C(O)OR¹³, C₁-C₆alkyl, cyclopropyl, cyclohexyl, cycloheptyl, and a C₁-C₆alkyl substituted with 1-4 OH groups, wherein the cyclopropyl, cyclohexyl, cycloheptyl of R⁶ is optionally substituted with 1-4 substituents selected from C₁-C₆alkyl and C₁-C₆alkyl substituted with 1-4 —OH groups.

7. The compound of claim 6, wherein each R⁹ is independently selected from H, CN, F, Cl, methyl, ethyl, isopropyl, tert-butyl, —CF₃, —OCH₃, —OCH₂CH₃, —OCF₃, L³OR¹³, L³NR¹⁶R¹⁷, L³R¹³, L³R¹⁴, pyridinyl, pyrimidinyl, thiazolyl, furanyl, tetrazolyl and phenyl optionally substituted with 1 to 2 substituents selected from CN, L³NR¹⁶R¹⁷ and OR¹³, wherein the pyridinyl, pyrimidinyl, thiazolyl, furanyl and tetrazolyl are optionally substituted with 1 to 2 substituents selected from C₁-C₆alkyl, L³NR¹⁶R¹⁷ and L³OR¹³.

8. The compound of claim 7, wherein each R¹³ is independently selected from H, C₁-C₆alkyl and heteroaryl, where the heteroaryl of R¹³ are optionally substituted with 1 to 3 substituents selected from C₁-C₆alkyl and C₁-C₆alkyl substituted with 1-4 —OH groups.

9. The compound of claim 8, wherein each R¹³ is independently selected from H, methyl, ethyl, isopropyl, tert-butyl and pyrazolyl.

10. The compound of claim 9, wherein each R¹⁴ and R¹⁵ are independently selected from H, F methyl ethyl, OH and CN.

11. The compound of claim 10, wherein each R¹⁶ and R¹⁷ are independently selected from H, methyl, ethyl and C₁-C₆alkyl substituted with 1-4 —OH groups.

12. The compound of claim 11, wherein R² and R³ are each H, and R⁴ is H or —C(O)N(CH₃)₂.

13. The compound of claim 12, wherein each R⁵ is independently selected from H, Cl, F, CN, methyl, methoxy, —OCF₃, —CH₂OH, —C(O)OH, —CH₂N(CH₃)₂ and —C(O)NHCH₃.

14. The compound of claim 13, wherein each R is —Cl or methyl.

15. The compound of claim 14, wherein Y¹ is CH; Y² is CH; Y³ is CH; Y⁴ is CH; Y⁵ is CH; Y⁶ is CH and Y⁷ is N.

16. The compound of claim 1, selected from 4-(5-{[4-chloro-3-(5-phenyl-1H-imidazol-2-yl)phenyl]amino}-1,2,3,4-tetrahydroisoquinolin-2-yl)-1-1{4}-thian-1-one;

1-(5-{[4-chloro-3-(5-phenyl-1H-imidazol-2-yl)phenyl]amino}-1,2,3,4-tetrahydroisoquinolin-2-yl)-3-hydroxy-2-(hydroxymethyl)-2-methylpropan-1-one;

4-(5-{[4-chloro-3-(5-phenyl-1H-imidazol-2-yl)phenyl]amino}-1,2,3,4-tetrahydroisoquinolin-2-yl)-thiane-1,1-dione;

N-[4-chloro-3-(5-phenyl-1H-imidazol-2-yl)phenyl]-2-methanesulfonyl-1,2,3,4-tetrahydroisoquinolin-5-amine;

N-[3-(1H-1,3-benzodiazol-2-yl)-4-methylphenyl]-2-methanesulfonyl-1,2,3,4-tetrahydroisoquinolin-5-amine;

N-[4-chloro-3-(5-phenyl-1H-imidazol-2-yl)phenyl]-2-(1-ethylpiperidin-4-yl)-1,2,3,4-tetrahydroisoquinolin-5-amine;

1-(5-{[4-chloro-3-(5-phenyl-1H-imidazol-2-yl)phenyl]amino}-1,2,3,4-tetrahydroisoquinolin-2-yl)-2-methanesulfonylethan-1-one;

(2R)-1-(5-{[4-chloro-3-(5-phenyl-1H-imidazol-2-yl)phenyl]amino}-1,2,3,4-tetrahydroisoquinolin-2-yl)-2-hydroxypropan-1-one;

1-(5-{[4-chloro-3-(5-phenyl-1H-imidazol-2-yl)phenyl]amino}-1,2,3,4-tetrahydroisoquinolin-2-yl)-2,3-dihydroxypropan-1-one;

1-(5-{[4-chloro-3-(5-phenyl-1H-imidazol-2-yl)phenyl]amino}-1,2,3,4-tetrahydroisoquinolin-2-yl)-2-hydroxypropan-1-one;

1-[4-(5-{[4-chloro-3-(5-phenyl-1H-imidazol-2-yl)phenyl]amino}-1,2,3,4-tetrahydroisoquinolin-2-yl)piperidin-1-yl]ethan-1-one;

4-(5-{[4-chloro-3-(5-phenyl-1H-imidazol-2-yl)phenyl]amino}-1,2,3,4-tetrahydroisoquinolin-2-yl)-thian-1-one;

5-{[4-chloro-3-(5-phenyl-1H-imidazol-2-yl)phenyl]amino}-1,2,3,4-tetrahydroisoquinoline-2-sulfonamide;

1-(5-{[4-chloro-3-(5-phenyl-1H-imidazol-2-yl)phenyl]amino}-1,2,3,4-tetrahydroisoquinolin-2-yl)-3-hydroxy-2,2-dimethylpropan-1-one;

2-methanesulfonyl-N-[3-(5-methoxy-1H-1,3-benzodiazol-2-yl)-4-methylphenyl]-1,2,3,4-tetrahydroisoquinolin-5-amine;

N-{4-chloro-3-[6-(dimethylamino)-1H-1,3-benzodiazol-2-yl]phenyl}-2-methanesulfonyl-1,2,3,4-tetrahydroisoquinolin-5-amine;

2-[(5-{[4-chloro-3-(5-phenyl-1H-imidazol-2-yl)phenyl]amino}-1,2,3,4-tetrahydroisoquinoline-2-sulfonyl)amino]ethan-1-ol;

(2R)-3-(5-{[4-chloro-3-(5-phenyl-1H-imidazol-2-yl)phenyl]amino}-1,2,3,4-tetrahydroisoquinolin-2-yl)propane-1,2-diol;

1-(5-{[4-chloro-3-(5-phenyl-1H-imidazol-2-yl)phenyl]amino}-1,2,3,4-tetrahydroisoquinolin-2-yl)-2-methanesulfinylethan-1-one;

(2S)-1-(5-{[4-chloro-3-(5-phenyl-1H-imidazol-2-yl)phenyl]amino}-1,2,3,4-tetrahydroisoquinolin-2-yl)-2-hydroxypropan-1-one;

N-[4-chloro-3-(5-phenyl-1H-imidazol-2-yl)phenyl]-2-(2,2,6,6-tetramethylpiperidin-4-yl)-1,2,3,4-tetrahydroisoquinolin-5-amine;

N-[4-chloro-3-(5-phenyl-1H-imidazol-2-yl)phenyl]-2-cyclohexyl-1,2,3,4-tetrahydroisoquinolin-5-amine;

N-[4-chloro-3-(5-phenyl-1H-imidazol-2-yl)phenyl]-2-(cyclohexylmethyl)-1,2,3,4-tetrahydroisoquinolin-5-amine;

1-(5-{[4-chloro-3-(5-phenyl-1H-imidazol-2-yl)phenyl]amino}-1,2,3,4-tetrahydroisoquinolin-2-yl)-2-hydroxyethan-1-one;

5-{[4-chloro-3-(5-phenyl-1H-imidazol-2-yl)phenyl]amino}-N-methyl-1,2,3,4-tetrahydroisoquinoline-2-sulfonamide;

5-{[4-chloro-3-(5-phenyl-1H-imidazol-2-yl)phenyl]amino}-2-oxido-2-(1-oxo-thian-4-yl)-1,2,3,4-tetrahydroisoquinolin-2-ium;

(2S)-1-(5-{[4-chloro-3-(4-phenyl-1H-imidazol-2-yl)phenyl]amino}-1,2,3,4-tetrahydroisoquinolin-2-yl)-2,3-dihydroxypropan-1-one;

N-[4-chloro-3-(5-phenyl-1H-imidazol-2-yl)phenyl]-2-{[(4S)-2,2-dimethyl-1,3-dioxolan-4-yl]methyl}-1,2,3,4-tetrahydroisoquinolin-5-amine;

N-[4-chloro-3-(5-phenyl-1H-imidazol-2-yl)phenyl]-2-(oxan-4-yl)-1,2,3,4-tetrahydroisoquinolin-5-amine;

N-[4-chloro-3-(5-phenyl-1H-imidazol-2-yl)phenyl]-2-cycloheptyl-1,2,3,4-tetrahydroisoquinolin-5-amine;

N-[4-chloro-3-(5-phenyl-1H-imidazol-2-yl)phenyl]-2-(pentan-3-yl)-1,2,3,4-tetrahydroisoquinolin-5-amine;

5-{[4-chloro-3-(5-phenyl-1H-imidazol-2-yl)phenyl]amino}-2-(1-ethylpiperidin-4-yl)-1,2,3,4-tetrahydroisoquinolin-1-one;

2-(5-{[4-chloro-3-(5-phenyl-1H-imidazol-2-yl)phenyl]amino}-1,2,3,4-tetrahydroisoquinolin-2-yl)propane-1,3-diol;

5-{[4-chloro-3-(5-phenyl-1H-imidazol-2-yl)phenyl]amino}-2-[(2S)-2,3-dihydroxypropyl]-1,2,3,4-tetrahydroisoquinolin-1-one;

N-[4-chloro-3-(5-phenyl-1H-imidazol-2-yl)phenyl]-2-[1-(propan-2-yl)piperidin-4-yl]-1,2,3,4-tetrahydroisoquinolin-5-amine;

(2R)-1-(5-{[4-chloro-3-(4-phenyl-1H-imidazol-2-yl)phenyl]amino}-1,2,3,4-tetrahydroisoquinolin-2-yl)-2,3-dihydroxypropan-1-one;

N-[4-chloro-3-(5-phenyl-1H-imidazol-2-yl)phenyl]-2-(oxan-4-ylmethyl)-1,2,3,4-tetrahydroisoquinolin-5-amine;

3-(5-{[4-chloro-3-(5-phenyl-1H-imidazol-2-yl)phenyl]amino}-1,2,3,4-tetrahydroisoquinolin-2-yl)propane-1,2-diol;

N-[4-chloro-3-(5-phenyl-1H-imidazol-2-yl)phenyl]-2-(1-methylpiperidin-4-yl)-1,2,3,4-tetrahydroisoquinolin-5-amine;

5-{[4-chloro-3-(5-phenyl-1H-imidazol-2-yl)phenyl]amino}-N-(2-hydroxyethyl)-1,2,3,4-tetrahydroisoquinoline-2-carboxamide;

5-{[4-chloro-3-(5-phenyl-1H-imidazol-2-yl)phenyl]amino}-1,2,3,4-tetrahydroisoquinoline-2-carboxamide;

3-(5-{[4-chloro-3-(4-phenyl-1H-imidazol-2-yl)phenyl]amino}-1,2,3,4-tetrahydroisoquinolin-2-yl)-3-oxopropanoic acid;

tert-butyl 5-{[4-chloro-3-(5-phenyl-1H-imidazol-2-yl)phenyl]amino}-1,2,3,4-tetrahydroisoquinoline-2-carboxylate;

N-[4-chloro-3-(5-phenyl-1H-imidazol-2-yl)phenyl]-2-(propan-2-yl)-1,2,3,4-tetrahydroisoquinolin-5-amine;

N-[4-chloro-3-(5-phenyl-1H-imidazol-2-yl)phenyl]-2-(3-methanesulfinylpropyl)-1,2,3,4-tetrahydroisoquinolin-5-amine;

(2S,3S)-4-(5-{[4-chloro-3-(5-phenyl-1H-imidazol-2-yl)phenyl]amino}-1,2,3,4-tetrahydroisoquinolin-2-yl)butane-1,2,3-triol;

4-(5-{[4-chloro-3-(5-phenyl-1H-imidazol-2-yl)phenyl]amino}-1,2,3,4-tetrahydroisoquinolin-2-yl)-1-oxidopyridin-1-ium;

3-(5-{[4-chloro-3-(4-phenyl-1H-imidazol-2-yl)phenyl]amino}-1-oxo-1,2,3,4-tetrahydroisoquinolin-2-yl)propanoic acid;

N-[4-chloro-3-(5-phenyl-1H-imidazol-2-yl)phenyl]-2-(pyridin-3-ylmethyl)-1,2,3,4-tetrahydroisoquinolin-5-amine;

4-[5-({4-methyl-3-[5-(pyridin-3-yl)-1H-imidazol-2-yl]phenyl}amino)-1,2,3,4-tetrahydroisoquinolin-2-yl]-thiane-1,1-dione;

2-(5-{[4-chloro-3-(4-phenyl-1H-imidazol-2-yl)phenyl]amino}-1,2,3,4-tetrahydroisoquinolin-2-yl)acetic acid;

N-[4-chloro-3-(5-phenyl-1H-imidazol-2-yl)phenyl]-2-{2-[(dimethylamino)methyl]-2-methylpropyl}-1,2,3,4-tetrahydroisoquinolin-5-amine;

1-(5-{[4-chloro-3-(5-phenyl-1H-imidazol-2-yl)phenyl]amino}-1,2,3,4-tetrahydroisoquinolin-2-yl)-2-methylpropan-1-one;

1-(5-{[4-chloro-3-(5-phenyl-1H-imidazol-2-yl)phenyl]amino}-1,2,3,4-tetrahydroisoquinolin-2-yl)ethan-1-one;

N-[4-chloro-3-(5-phenyl-1H-imidazol-2-yl)phenyl]-1,2,3,4-tetrahydroisoquinolin-5-amine;

2-(5-{[4-chloro-3-(5-phenyl-1H-imidazol-2-yl)phenyl]amino}-1,2,3,4-tetrahydroisoquinolin-2-yl)propanoic acid;

2-methanesulfonyl-N-[4-methyl-3-{5-(pyrimidin-5-yl)-1H-imidazol-2-yl]phenyl}-1,2,3,4-tetrahydroisoquinolin-5-amine;

2-methanesulfonyl-N-[4-methyl-3-{5-(pyridin-3-yl)-1H-imidazol-2-yl]phenyl}-1,2,3,4-tetrahydroisoquinolin-5-amine;

N-[3-(5-fluoro-1H-1,3-benzodiazol-2-yl)-4-methylphenyl]-2-methanesulfonyl-1,2,3,4-tetrahydroisoquinolin-5-amine;

N-[4-chloro-3-(5-phenyl-1H-imidazol-2-yl)phenyl]-2-(2,2,2-trifluoroethyl)-1,2,3,4-tetrahydroisoquinolin-5-amine;

2-methanesulfonyl-N-[4-methyl-3-(7H-purin-8-yl)phenyl]-1,2,3,4-tetrahydroisoquinolin-5-amine;

3-(5-{[4-chloro-3-(4-phenyl-1H-imidazol-2-yl)phenyl]amino}-1,2,3,4-tetrahydroisoquinolin-2-yl)-2,2-difluoropropanoic acid;

2-(5-{[4-chloro-3-(4-phenyl-1H-imidazol-2-yl)phenyl]amino}-1,2,3,4-tetrahydroisoquinolin-2-yl)-2-methylpropanoic acid;

2-[(5-{[4-chloro-3-(5-phenyl-1H-imidazol-2-yl)phenyl]amino}-1,2,3,4-tetrahydroisoquinolin-2-yl)carbonyl]-2-ethylbutanoic acid;

3-(5-{[4-chloro-3-(5-phenyl-1H-imidazol-2-yl)phenyl]amino}-1,2,3,4-tetrahydroisoquinolin-2-yl)-2,2-dimethyl-3-oxopropanoic acid;

1-[(5-{[4-chloro-3-(5-phenyl-1H-imidazol-2-yl)phenyl]amino}-1,2,3,4-tetrahydroisoquinolin-2-yl)carbonyl]cyclopropane-1-carboxylic acid;

1-[(5-{[4-chloro-3-(5-phenyl-1H-imidazol-2-yl)phenyl]amino}-1,2,3,4-tetrahydroisoquinolin-2-yl)carbonyl]cyclobutane-1-carboxylic acid;

1-(5-{[3-(1H-1,3-benzodiazol-2-yl)-4-methylphenyl]amino}-1,2,3,4-tetrahydroisoquinolin-2-yl)-3-hydroxy-2-(hydroxymethyl)-2-methylpropan-1-one;

3-(5-{[4-chloro-3-(4-phenyl-1H-imidazol-2-yl)phenyl]amino}-1,2,3,4-tetrahydroisoquinolin-2-yl)-2,2-difluoropropan-1-ol;

1-(5-{[4-chloro-3-(5-phenyl-1H-imidazol-2-yl)phenyl]amino}-1,2,3,4-tetrahydroisoquinolin-2-yl)-2-hydroxyethan-1-one;

N-[4-chloro-3-(5-phenyl-1H-imidazol-2-yl)phenyl]-2-[(1-methylcyclopropyl)carbonyl]-1,2,3,4-tetrahydroisoquinolin-5-amine;

1-[(5-{[4-chloro-3-(5-phenyl-1H-imidazol-2-yl)phenyl]amino}-1,2,3,4-tetrahydroisoquinolin-2-yl)carbonyl]cyclopropan-1-ol;

4-[5-({4-methyl-3-[5-(pyridin-3-yl)-1H-imidazol-2-yl]phenyl}amino)-1,2,3,4-tetrahydroisoquinolin-2-yl]-thiane-1,1-dione;

3-hydroxy-2-(hydroxymethyl)-2-methyl-1-[5-({4-methyl-3-[5-(pyridin-3-yl)-1H-imidazol-2-yl]phenyl}amino)-1,2,3,4-tetrahydroisoquinolin-2-yl]propan-1-one;

2-(5-{[4-chloro-3-(4-phenyl-1H-imidazol-2-yl)phenyl]amino}-1-oxo-1,2,3,4-tetrahydroisoquinolin-2-yl)propanoic acid;

(2R)-2-(5-{[4-chloro-3-(4-phenyl-1H-imidazol-2-yl)phenyl]amino}-1,2,3,4-tetrahydroisoquinolin-2-yl)propanoic acid;

(2S)-2-(5-{[4-chloro-3-(4-phenyl-1H-imidazol-2-yl)phenyl]amino}-1,2,3,4-tetrahydroisoquinolin-2-yl)propanoic acid;
N-[4-chloro-3-(5-phenyl-1H-imidazol-2-yl)phenyl]-2-(1-methylcyclopropyl)-1,2,3,4-tetrahydroisoquinolin-5-amine;
5-{[3-(1H-1,3-benzodiazol-2-yl)-4-methylphenyl]amino}-2-[(2S)-2,3-dihydroxypropyl]-1,2,3,4-tetrahydroisoquinolin-1-one;
N-[4-chloro-3-(5-phenyl-1H-imidazol-2-yl)phenyl]-2-cyclopropyl-1,2,3,4-tetrahydroisoquinolin-5-amine;
2-(5-{[4-chloro-3-(5-phenyl-1H-imidazol-2-yl)phenyl]amino}-1,2,3,4-tetrahydroisoquinolin-2-yl)-2-oxoacetic acid;
[1-(5-{[4-chloro-3-(5-phenyl-1H-imidazol-2-yl)phenyl]amino}-1,2,3,4-tetrahydroisoquinolin-2-yl)cyclopropyl]methanol;
3-(5-{[3-(1H-1,3-benzodiazol-2-yl)-4-methylphenyl]amino}-1,2,3,4-tetrahydroisoquinolin-2-yl)-2,2-difluoropropan-1-ol;
N-[4-chloro-3-(5-phenyl-1H-imidazol-2-yl)phenyl]-2-(2H-1,2,3,4-tetrazol-5-ylmethyl)-1,2,3,4-tetrahydroisoquinolin-5-amine;
N-[4-chloro-3-(5-phenyl-1H-imidazol-2-yl)phenyl]-2-(2H-1,2,3,4-tetrazol-5-yl)-1,2,3,4-tetrahydroisoquinolin-5-amine;
5-{[4-chloro-3-(5-phenyl-1H-imidazol-2-yl)phenyl]amino}-2-[1-(hydroxymethyl)cyclopropyl]-1,2,3,4-tetrahydroisoquinolin-1-one;
[1-(5-{[3-(1H-1,3-benzodiazol-2-yl)-4-methylphenyl]amino}-1,2,3,4-tetrahydroisoquinolin-2-yl)cyclopropyl]methanol;
4-{3-[(2-methanesulfonyl-1,2,3,4-tetrahydroisoquinolin-5-yl)amino]-2-methylphenyl}benzonitrile;
2-methanesulfonyl-N-{4-methyl-3-[5-(6-methylpyridin-3-yl)-1H-imidazol-2-yl]phenyl}-1,2,3,4-tetrahydroisoquinolin-5-amine;
[1-(5-{[4-chloro-3-(5-phenyl-1H-imidazol-2-yl)phenyl]amino}-1,2,3,4-tetrahydroisoquinolin-2-yl)cyclopropyl]methanol;
(2S)-3-(5-{[4-chloro-3-(5-phenyl-1H-imidazol-2-yl)phenyl]amino}-1,2,3,4-tetrahydroisoquinolin-2-yl)propane-1,2-diol;
2-methanesulfonyl-N-{4-methyl-3-[5-(methylamino)pyrimido[5,4-d][1,3]thiazol-2-yl]phenyl}-1,2,3,4-tetrahydroisoquinolin-5-amine;
N-[4-chloro-3-(5-phenyl-1H-imidazol-2-yl)phenyl]-2-[(1-methylcyclopropyl)methyl]-1,2,3,4-tetrahydroisoquinolin-5-amine;
N-[4-chloro-3-(4-phenyl-1,3-oxazol-2-yl)phenyl]-2-methanesulfonyl-1,2,3,4-tetrahydroisoquinolin-5-amine;
N-[3-(1H-1,3-benzodiazol-2-yl)-4-methylphenyl]-2-[(1-methylcyclopropyl)methyl]-1,2,3,4-tetrahydroisoquinolin-5-amine;
2-methanesulfonyl-N-[3-(6-methoxypyridin-3-yl)-4-methylphenyl]-1,2,3,4-tetrahydroisoquinolin-5-amine;
2-methanesulfonyl-N-[3-(4-methoxyphenyl)-4-methylphenyl]-1,2,3,4-tetrahydroisoquinolin-5-amine;
2-methanesulfonyl-N-{3-[5-(6-methoxypyridin-3-yl)-1H-imidazol-2-yl]-4-methylphenyl}-1,2,3,4-tetrahydroisoquinolin-5-amine;
4-(2-{5-[(2-methanesulfonyl-1,2,3,4-tetrahydroisoquinolin-5-yl)amino]-2-methylphenyl}-1H-imidazol-5-yl)benzonitrile;
4-{5-[(2-methanesulfonyl-1,2,3,4-tetrahydroisoquinolin-5-yl)amino]-2-methylphenyl}benzonitrile;
N-{3-[6-(dimethylamino)-1H-imidazo[4,5-c]pyridin-2-yl]-4-methylphenyl}-2-methanesulfonyl-1,2,3,4-tetrahydroisoquinolin-5-amine;
2-methanesulfonyl-N-{3-[5-(6-methoxypyridin-2-yl)-1H-imidazol-2-yl]-4-methylphenyl}-1,2,3,4-tetrahydroisoquinolin-5-amine;
N-[3-(1,3-benzoxazol-2-yl)-4-methylphenyl]-2-methanesulfonyl-1,2,3,4-tetrahydroisoquinolin-5-amine;
N-[3-(5-{4-[(dimethylamino)methyl]phenyl}-1H-imidazol-2-yl)-4-methylphenyl]-2-methanesulfonyl-1,2,3,4-tetrahydroisoquinolin-5-amine;
N-(3-{5-[2-(dimethylamino)pyrimidin-5-yl]-1H-imidazol-2-yl}-4-methylphenyl)-2-methanesulfonyl-1,2,3,4-tetrahydroisoquinolin-5-amine;
N-(3-{4-[(dimethylamino)methyl]phenyl}-4-methylphenyl)-2-methanesulfonyl-1,2,3,4-tetrahydroisoquinolin-5-amine;
2-methanesulfonyl-N-[4-methyl-3-(4-phenylphenyl)phenyl]-1,2,3,4-tetrahydroisoquinolin-5-amine;
2-methanesulfonyl-N-(3-{6-methoxy-1H-imidazo[4,5-c]pyridin-2-yl}-4-methylphenyl)-1,2,3,4-tetrahydroisoquinolin-5-amine;
N-[5-(1H-1,3-benzodiazol-2-yl)-6-methylpyridin-3-yl]-2-methanesulfonyl-1,2,3,4-tetrahydroisoquinolin-5-amine;
4-(5-{[2-(2,2-difluoro-3-hydroxypropyl)-1,2,3,4-tetrahydroisoquinolin-5-yl]amino}-2-methylphenyl)benzonitrile;
N-[3(4-tert-butylphenyl)-4-methylphenyl]-2-methanesulfonyl-1,2,3,4-tetrahydroisoquinolin-5-amine;
1-(4-{5-[(2-methanesulfonyl-1,2,3,4-tetrahydroisoquinolin-5-yl)amino]-2-methylphenyl}phenyl)ethan-1-one;
2-methanesulfonyl-N-(4-methyl-3-phenylphenyl)-1,2,3,4-tetrahydroisoquinolin-5-amine;
2-methanesulfonyl-N-{4-methyl-3-[4-(propan-2-yl)phenyl]phenyl}-1,2,3,4-tetrahydroisoquinolin-5-amine;
2-methanesulfonyl-N-{4-methyl-3-[4(1H-pyrazol-1-ylmethyl)phenyl]phenyl}-1,2,3,4-tetrahydroisoquinolin-5-amine;
3-{5-[(2-methanesulfonyl-1,2,3,4-tetrahydroisoquinolin-5-yl)amino]-2-methylphenyl}benzonitrile;
2-methanesulfonyl-N-{4-methyl-3-[4-(2-methyl-1,3-thiazol-4-yl)phenyl]phenyl}-1,2,3,4-tetrahydroisoquinolin-5-amine;
N-{3-[4-(furan-2-yl)phenyl]-4-methylphenyl}-2-methanesulfonyl-1,2,3,4-tetrahydroisoquinolin-5-amine;
N-[3-(4-fluorophenyl)-4-methylphenyl]-2-methanesulfonyl-1,2,3,4-tetrahydroisoquinolin-5-amine;
2-methanesulfonyl-N-(4-methyl-3-phenoxyphenyl)-1,2,3,4-tetrahydroisoquinolin-5-amine;
N-{3-[2-(dimethylamino)pyrimidin-5-yl]-4-methylphenyl}-2-methanesulfonyl-1,2,3,4-tetrahydroisoquinolin-5-amine;
N-[4-(1H-1,3-benzodiazol-2-yl)-5-chloropyridin-2-yl]-2-methanesulfonyl-1,2,3,4-tetrahydroisoquinolin-5-amine;
5-{[3-(1H-1,3-benzodiazol-2-yl)-4-methylphenyl]amino}-2-[(1-methylcyclopropyl)methyl]-1,2,3,4-tetrahydroisoquinolin-1-one;
2-methanesulfonyl-N-[4-methyl-3-(1-methyl-1H-pyrazol-4-yl)phenyl]-1,2,3,4-tetrahydroisoquinolin-5-amine;
5-{5-[(2-methanesulfonyl-1,2,3,4-tetrahydroisoquinolin-5-yl)amino]-2-methylphenyl}pyridine-2-carbonitrile;
N-[3-(benzyloxy)-4-methylphenyl]-2-methanesulfonyl-1,2,3,4-tetrahydroisoquinolin-5-amine;

4-{2-fluoro-5-[(2-methanesulfonyl-1,2,3,4-tetrahydroisoquinolin-5-yl)amino]phenyl}benzonitrile;
4-{3-[(2-methanesulfonyl-1,2,3,4-tetrahydroisoquinolin-5-yl)amino]phenyl}benzonitrile;
4-{2-chloro-5-[(2-methanesulfonyl-1,2,3,4-tetrahydroisoquinolin-5-yl)amino]phenyl}benzonitrile;
3-{5-[(2-methanesulfonyl-1,2,3,4-tetrahydroisoquinolin-5-yl)amino]-2-methylphenyl}-N-methylbenzamide;
2-methanesulfonyl-N-{4-methyl-3-[4-(trifluoromethyl)phenyl]phenyl}-1,2,3,4-tetrahydroisoquinolin-5-amine;
2-methanesulfonyl-N-{4-methyl-3-[4-(trifluoromethoxy)phenyl]phenyl}-1,2,3,4-tetrahydroisoquinolin-5-amine;
4-{5-[(2-methanesulfonyl-1,2,3,4-tetrahydroisoquinolin-5-yl)amino]-2-methylphenyl}-N,N-dimethylbenzamide;
2-(4-{5-[(2-methanesulfonyl-1,2,3,4-tetrahydroisoquinolin-5-yl)amino]-2-methylphenyl}phenyl)acetonitrile;
2-methanesulfonyl-N-{4-methyl-3-[3-(pyrrolidin-1-ylcarbonyl)phenyl]phenyl}-1,2,3,4-tetrahydroisoquinolin-5-amine;
methyl 4-{5-[(2-methanesulfonyl-1,2,3,4-tetrahydroisoquinolin-5-yl)amino]-2-methylphenyl}benzoate
4-{5-[(2-methanesulfonyl-1,2,3,4-tetrahydroisoquinolin-5-yl)amino]-2-methylphenyl}benzamide;
2-methanesulfonyl-N-{4-methyl-3-[4-(1H-1,2,3,4-tetrazol-5-yl)phenyl]phenyl}-1,2,3,4-tetrahydroisoquinolin-5-amine;
4-{5-[(2-methanesulfonyl-1,2,3,4-tetrahydroisoquinolin-5-yl)amino]-2-methylphenyl}benzoic acid;
N-(2-hydroxyethyl)-4-{5-[(2-methanesulfonyl-1,2,3,4-tetrahydroisoquinolin-5-yl)amino]-2-methylphenyl}benzamide;
N-(2,3-dihydroxypropyl)-4-[5-[(2-methanesulfonyl-1,2,3,4-tetrahydroisoquinolin-5-yl)amino]-2-methylphenyl]benzamide;
N,N-bis(2-hydroxyethyl)-4-[5-[(2-methanesulfonyl-1,2,3,4-tetrahydroisoquinolin-5-yl)amino]-2-methylphenyl]benzamide;
N-(2-hydroxypropyl)-4-{5-[(2-methanesulfonyl-1,2,3,4-tetrahydroisoquinolin-5-yl)amino]-2-methylphenyl}benzamide;
4-{5-[(2-methanesulfonyl-1,2,3,4-tetrahydroisoquinolin-5-yl)amino]-2-methoxyphenyl}benzonitrile;
4-{5-[(2-methanesulfonyl-1,2,3,4-tetrahydroisoquinolin-5-yl)amino]-2-(trifluoromethoxy)phenyl}benzonitrile;
N-[3-(1H-indol-2-yl)-4-methylphenyl]-2-methanesulfonyl-1,2,3,4-tetrahydroisoquinolin-5-amine;
2-methanesulfonyl-N-[4-methyl-3-(1-methyl-1H-indol-2-yl)phenyl]-1,2,3,4-tetrahydroisoquinolin-5-amine;
2-methanesulfonyl-N-{4-methyl-3-[5-(trifluoromethyl)pyridin-2-yl]phenyl}-1,2,3,4-tetrahydroisoquinolin-5-amine;
6-{5-[(2-methanesulfonyl-1,2,3,4-tetrahydroisoquinolin-5-yl)amino]-2-methylphenyl}pyridine-3-carbonitrile;
2-(4-cyanophenyl)-4-[(2-methanesulfonyl-1,2,3,4-tetrahydroisoquinolin-5-yl)amino]benzonitrile;
(4-{5-[(2-methanesulfonyl-1,2,3,4-tetrahydroisoquinolin-5-yl)amino]-2-methylphenyl}phenyl)methanol;
3-{[(4-{5-[(2-methanesulfonyl-1,2,3,4-tetrahydroisoquinolin-5-yl)amino]-2-methylphenyl}-phenyl)methyl]amino}propane-1,2-diol;
2-{[(4-{5-[(2-methanesulfonyl-1,2,3,4-tetrahydroisoquinolin-5-yl)amino]-2-methylphenyl}-phenyl)methyl]amino}ethan-1-ol;
5-[(2-methanesulfonyl-1,2,3,4-tetrahydroisoquinolin-5-yl)amino]-2-methyl-N-phenylbenzamide;
N-(4-cyanophenyl)-5-[(2-methanesulfonyl-1,2,3,4-tetrahydroisoquinolin-5-yl)amino]-2-methylbenzamide;
5-[(2-methanesulfonyl-1,2,3,4-tetrahydroisoquinolin-5-yl)amino]-N-(4-methoxyphenyl)-2-methylbenzamide;
5-[(2-methanesulfonyl-1,2,3,4-tetrahydroisoquinolin-5-yl)amino]-2-methyl-N-(pyridin-2-yl)benzamide;
4-{5-[(2-methanesulfonyl-1,2,3,4-tetrahydroisoquinolin-5-yl)amino]-2-methylphenyl}-3-methylbenzonitrile;
N-[3-(5-fluoropyridin-2-yl)-4-methylphenyl]-2-methanesulfonyl-1,2,3,4-tetrahydroisoquinolin-5-amine;
2-methanesulfonyl-N-[3-(6-methoxypyridin-2-yl)-4-methylphenyl]-1,2,3,4-tetrahydroisoquinolin-5-amine;
4-{5-[(2-methanesulfonyl-1,2,3,4-tetrahydroisoquinolin-5-yl)amino]-2-methylphenoxymethyl}benzonitrile;
2-methanesulfonyl-N-{4-methyl-3-[5-(trifluoromethyl)pyridin-2-yl]phenyl}-1,2,3,4-tetrahydroisoquinolin-5-amine;
4-{3-[(2-methanesulfonyl-1,2,3,4-tetrahydroisoquinolin-5-yl)amino]phenyl}-3-methylbenzonitrile;
2-methanesulfonyl-N-[4-methyl-3-(5-methylpyridin-2-yl)phenyl]-1,2,3,4-tetrahydroisoquinolin-5-amine;
2-methanesulfonyl-N-[4-methyl-3-(6-methylpyridazin-3-yl)phenyl]-1,2,3,4-tetrahydroisoquinolin-5-amine;
4-{5-chloro-2-[(2-methanesulfonyl-1,2,3,4-tetrahydroisoquinolin-5-yl)amino]pyridin-4-yl}benzonitrile;
2-(4-cyanophenyl)-4-[(2-methanesulfonyl-1,2,3,4-tetrahydroisoquinolin-5-yl)amino]benzoic acid;
N-[3-(5-chloropyridin-2-yl)-4-methylphenyl]-2-methanesulfonyl-1,2,3,4-tetrahydroisoquinolin-5-amine;
2-methanesulfonyl-N-[3-(5-methoxypyridin-2-yl)-4-methylphenyl]-1,2,3,4-tetrahydroisoquinolin-5-amine;
4-{2-chloro-5-[(2-methanesulfonyl-1,2,3,4-tetrahydroisoquinolin-5-yl)amino]pyridin-3-yl}benzonitrile;
2-methanesulfonyl-N-[3-(5-methoxypyrimidin-2-yl)-4-methylphenyl]-1,2,3,4-tetrahydroisoquinolin-5-amine;
6-{5-[(2-methanesulfonyl-1,2,3,4-tetrahydroisoquinolin-5-yl)amino]-2-methylphenyl}pyridine-3-carbonitrile;
4-[2-(hydroxymethyl)-5-[(2-methanesulfonyl-1,2,3,4-tetrahydroisoquinolin-5-yl)amino]phenyl]benzonitrile;
4-{2-[(dimethylamino)methyl]-5-[(2-methanesulfonyl-1,2,3,4-tetrahydroisoquinolin-5-yl)amino]phenyl}benzonitrile;
2-(4-cyanophenyl)-4-[(2-methanesulfonyl-1,2,3,4-tetrahydroisoquinolin-5-yl)amino]-N-methylbenzamide;
1-(5-{[3-(5-fluoropyridin-2-yl)-4-methylphenyl]amino}-1,2,3,4-tetrahydroisoquinolin-2-yl)-2-methylpropan-2-ol;
2-(2-fluoro-2-methylpropyl)-N-[3-(5-fluoropyridin-2-yl)-4-methylphenyl]-1,2,3,4-tetrahydroisoquinolin-5-amine;
2-methanesulfonyl-N-[3-(6-methoxypyridazin-3-yl)-4-methylphenyl]-1,2,3,4-tetrahydroisoquinolin-5-amine;
5-[(2-methanesulfonyl-1,2,3,4-tetrahydroisoquinolin-5-yl)amino]-2-methyl-N-[4-(trifluoromethyl)phenyl]benzamide;
N-(4-fluorophenyl)-5-[(2-methanesulfonyl-1,2,3,4-tetrahydroisoquinolin-5-yl)amino]-2-methylbenzamide;
5-[(2-methanesulfonyl-1,2,3,4-tetrahydroisoquinolin-5-yl)amino]-2-methyl-N-(4-methylphenyl)benzamide;
5-[(2-methanesulfonyl-1,2,3,4-tetrahydroisoquinolin-5-yl)amino]-2-methyl-N-[4-(trifluoromethoxy)phenyl]benzamide;
5-[(2-methanesulfonyl-1,2,3,4-tetrahydroisoquinolin-5-yl)amino]-2-methyl-N-phenylbenzamide;

2-methanesulfonyl-N-[4-methyl-3-(pyridin-2-yl)phenyl]-1,2,3,4-tetrahydroisoquinolin-5-amine;
2-methanesulfonyl-N-[3-(5-methoxypyrazin-2-yl)-4-methylphenyl]-1,2,3,4-tetrahydroisoquinolin-5-amine;
2-methanesulfonyl-N-[4-methyl-3-(6-methylpyridin-2-yl)phenyl]-1,2,3,4-tetrahydroisoquinolin-5-amine;
2-methanesulfonyl-N-[4-methyl-3-(4-methylpyridin-2-yl)phenyl]-1,2,3,4-tetrahydroisoquinolin-5-amine;
5-[(2-methanesulfonyl-1,2,3,4-tetrahydroisoquinolin-5-yl)amino]-N,2-dimethyl-N-phenylbenzamide;
N-(2-hydroxyethyl)-5-[(2-methanesulfonyl-1,2,3,4-tetrahydroisoquinolin-5-yl)amino]-2-methyl-N-phenylbenzamide;
(2S)-3-(5-{[3-(5-fluoropyridin-2-yl)-4-methylphenyl]amino}-1,2,3,4-tetrahydroisoquinolin-2-yl)propane-1,2-diol;
6-(2-methyl-5-{[2-(3,3,3-trifluoropropyl)-1,2,3,4-tetrahydroisoquinolin-5-yl]amino}-phenyl)pyridine-3-carbonitrile;
N-{3-[(dimethylamino)methyl]-5-(5-fluoropyridin-2-yl)-4-methylphenyl}-2-methanesulfonyl-1,2,3,4-tetrahydroisoquinolin-5-amine;
6-(5-{[2-(2-fluoro-2-methylpropyl)-1,2,3,4-tetrahydroisoquinolin-5-yl]amino}-2-methylphenyl)pyridine-3-carbonitrile;
6-(5-{[2-(2-hydroxy-2-methylpropyl)-1,2,3,4-tetrahydroisoquinolin-5-yl]amino}-2-methylphenyl)pyridine-3-carbonitrile;
2-(2-fluoro-2-methylpropyl)-N-[4-methyl-3-(5-methylpyridin-2-yl)phenyl]-1,2,3,4-tetrahydroisoquinolin-5-amine;
2-methyl-1-(5-{[4-methyl-3-(5-methylpyridin-2-yl)phenyl]amino}-1,2,3,4-tetrahydroisoquinolin-2-yl)propan-2-ol;
N-[5-(5-fluoropyridin-2-yl)-6-methylpyridin-3-yl]-2-methanesulfonyl-1,2,3,4-tetrahydroisoquinolin-5-amine;
5-chloro-2-[(2-methanesulfonyl-1,2,3,4-tetrahydroisoquinolin-5-yl)amino]-N-phenylpyridine-4-carboxamide;
2-methanesulfonyl-N-[3-(5-methoxypyridin-2-yl)-4-methylphenyl]-1,2,3,4-tetrahydroisoquinolin-5-amine;
4-{2-chloro-5-[(2-methanesulfonyl-1,2,3,4-tetrahydroisoquinolin-5-yl)amino]pyridin-3-yl}benzonitrile;
N-[3-(5-chloropyridin-2-yl)-4-methylphenyl]-2-methanesulfonyl-1,2,3,4-tetrahydroisoquinolin-5-amine;
6-{5-[(2-methanesulfonyl-1,2,3,4-tetrahydroisoquinolin-5-yl)amino]-2-methylphenyl}pyridazine-3-carbonitrile;
5-{5-[(2-methanesulfonyl-1,2,3,4-tetrahydroisoquinolin-5-yl)amino]-2-methylphenyl}pyrazine-2-carbonitrile;
(2S)-3-(5-{[4-methyl-3-(6-methylpyridazin-3-yl)phenyl]amino}-1,2,3,4-tetrahydroisoquinolin-2-yl)propane-1,2-diol;
(2S)-3-(5-{[4-methyl-3-(5-methylpyridin-2-yl)phenyl]amino}-1,2,3,4-tetrahydroisoquinolin-2-yl)propane-1,2-diol;
6-(5-{[2-(2,2-difluoro-3-hydroxypropyl)-1,2,3,4-tetrahydroisoquinolin-5-yl]amino}-2-methylphenyl)pyridine-3-carbonitrile;
2,2-difluoro-3-(5-{[4-methyl-3-(5-methylpyridin-2-yl)phenyl]amino}-1,2,3,4-tetrahydroisoquinolin-2-yl)propan-1-ol;
2-(2,2-dimethylpropyl)-N-[4-methyl-3-(5-methylpyridin-2-yl)phenyl]-1,2,3,4-tetrahydroisoquinolin-5-amine;
2-methanesulfonyl-N-[4-methyl-3-(pyridin-2-yloxy)phenyl]-1,2,3,4-tetrahydroisoquinolin-5-amine;
2-methanesulfonyl-N-[4-methyl-3-(pyridin-2-ylmethoxy)phenyl]-1,2,3,4-tetrahydroisoquinolin-5-amine;
2-methanesulfonyl-N-[4-methyl-3-(5-methylpyrimidin-2-yl)phenyl]-1,2,3,4-tetrahydroisoquinolin-5-amine;
N-[3-(4-fluoropyridin-2-yl)-4-methylphenyl]-2-methanesulfonyl-1,2,3,4-tetrahydroisoquinolin-5-amine;
N-[3-(6-fluoropyridin-2-yl)-4-methylphenyl]-2-methanesulfonyl-1,2,3,4-tetrahydroisoquinolin-5-amine;
2-methanesulfonyl-N-[4-methyl-3-(4-methylpyrimidin-2-yl)phenyl]-1,2,3,4-tetrahydroisoquinolin-5-amine;
N-[3-(5-fluoropyrimidin-2-yl)-4-methylphenyl]-2-methanesulfonyl-1,2,3,4-tetrahydroisoquinolin-5-amine;
5-{[2-(2-fluoro-2-methylpropyl)-1,2,3,4-tetrahydroisoquinolin-5-yl]amino}-2-methyl-N-phenylbenzamide;
5-{[2-(2-hydroxy-2-methylpropyl)-1,2,3,4-tetrahydroisoquinolin-5-yl]amino}-2-methyl-N-phenylbenzamide;
2-(2-methanesulfonylethyl)-N-[4-methyl-3-(5-methylpyridin-2-yl)phenyl]-1,2,3,4-tetrahydroisoquinolin-5-amine;
2-(2,2-difluoropropyl)-N-[4-methyl-3-(5-methylpyridin-2-yl)phenyl]-1,2,3,4-tetrahydroisoquinolin-5-amine;
5-[(2-methanesulfonyl-1,2,3,4-tetrahydroisoquinolin-5-yl)amino]-2-methyl-N-phenylpyridine-3-carboxamide;
3-chloro-6-[(2-methanesulfonyl-1,2,3,4-tetrahydroisoquinolin-5-yl)amino]-N-phenylpyridine-2-carboxamide;
N-[3-(3-fluoropyridin-2-yl)-4-methylphenyl]-2-methanesulfonyl-1,2,3,4-tetrahydroisoquinolin-5-amine;
N-[3-(3-fluoro-5-methylpyridin-2-yl)-4-methylphenyl]-2-methanesulfonyl-1,2,3,4-tetrahydroisoquinolin-5-amine;
N-[3-(isoquinolin-3-yl)-4-methylphenyl]-2-methanesulfonyl-1,2,3,4-tetrahydroisoquinolin-5-amine;
2-methanesulfonyl-N-[3-(4-methoxypyridin-2-yl)-4-methylphenyl]-1,2,3,4-tetrahydroisoquinolin-5-amine;
2-methanesulfonyl-N-[4-methyl-3-(quinolin-2-yl)phenyl]-1,2,3,4-tetrahydroisoquinolin-5-amine;
N-[3-(5-fluoropyridin-2-yl)-4-methylphenyl]-2-(2-methanesulfonylethyl)-1,2,3,4-tetrahydroisoquinolin-5-amine;
N,N-dimethyl-2-(5-{[4-methyl-3-(5-methylpyridin-2-yl)phenyl]amino}-1,2,3,4-tetrahydroisoquinolin-2-yl)acetamide;
4-(5-{[3-(5-fluoropyridin-2-yl)-4-methylphenyl]amino}-1,2,3,4-tetrahydroisoquinolin-2-yl)-thiane-1,1-dione;
4-(5-{[4-methyl-3-(5-methylpyridin-2-yl)phenyl]amino}-1,2,3,4-tetrahydroisoquinolin-2-yl)-thiane-1,1-dione;
2-methanesulfonyl-N-{4-methyl-3-[(pyridin-2-yloxy)methyl]phenyl}-1,2,3,4-tetrahydroisoquinolin-5-amine;
5-[(2-methanesulfonyl-1,2,3,4-tetrahydroisoquinolin-5-yl)amino]-2-methyl-N-[4-(trifluoromethyl)phenyl]benzamide;
2-methanesulfonyl-N-[3-(4-methoxypyrimidin-2-yl)-4-methylphenyl]-1,2,3,4-tetrahydroisoquinolin-5-amine;
2-methanesulfonyl-N-[3-(5-methoxypyrazin-2-yl)-4-methylphenyl]-1,2,3,4-tetrahydroisoquinolin-5-amine;
N-[3-(4,5-dimethylpyridin-2-yl)-4-methylphenyl]-2-methanesulfonyl-1,2,3,4-tetrahydroisoquinolin-5-amine;
2-methanesulfonyl-N-[3-(6-methoxypyridazin-3-yl)-4-methylphenyl]-1,2,3,4-tetrahydroisoquinolin-5-amine;
3-chloro-6-[(2-methanesulfonyl-1,2,3,4-tetrahydroisoquinolin-5-yl)amino]-N-phenylpyridine-2-carboxamide;

6-(5-{[2-(2-methanesulfonylethyl)-1,2,3,4-tetrahydroisoquinolin-5-yl]amino}-2-methylphenyl)pyridine-3-carbonitrile;
5-{[2-(2-methanesulfonylethyl)-1,2,3,4-tetrahydroisoquinolin-5-yl]amino}-2-methyl-N-phenylbenzamide;
3-(5-{[4-methyl-3-(5-methylpyridin-2-yl)phenyl]amino}-1,2,3,4-tetrahydroisoquinolin-2-yl)-thiolane-1,1-dione;
3-(5-{[3-(5-fluoropyridin-2-yl)-4-methylphenyl]amino}-1,2,3,4-tetrahydroisoquinolin-2-yl)-thiolane-1,1-dione;
N-[4-methyl-3-(5-methylpyridin-2-yl)phenyl]-2-(3,3,3-trifluoropropyl)-1,2,3,4-tetrahydroisoquinolin-5-amine;
N-[3-(5-fluoropyridin-2-yl)-4-methylphenyl]-2-(3,3,3-trifluoropropyl)-1,2,3,4-tetrahydroisoquinolin-5-amine;
N-{3-[5-(dimethylamino)pyrazin-2-yl]-4-methylphenyl}-2-methanesulfonyl-1,2,3,4-tetrahydroisoquinolin-5-amine;
N-[3-(5-fluoropyrimidin-2-yl)-4-methylphenyl]-2-methanesulfonyl-1,2,3,4-tetrahydroisoquinolin-5-amine;
N-{3-[6-(dimethylamino)pyridazin-3-yl]-4-methylphenyl}-2-methanesulfonyl-1,2,3,4-tetrahydroisoquinolin-5-amine;
2-methanesulfonyl-N-[3-(6-methoxypyrazin-2-yl)-4-methylphenyl]-1,2,3,4-tetrahydroisoquinolin-5-amine;
3-(5-{[3-(6-methoxypyridazin-3-yl)-4-methylphenyl]amino}-1,2,3,4-tetrahydroisoquinolin-2-yl)-thiolane-1,1-dione;
N-[3-(5-chloropyridin-2-yl)-4-methylphenyl]-2-(2-methanesulfonylethyl)-1,2,3,4-tetrahydroisoquinolin-5-amine;
2-(2-methanesulfonylethyl)-N-[3-(6-methoxypyridazin-3-yl)-4-methylphenyl]-1,2,3,4-tetrahydroisoquinolin-5-amine;
2-(2-methanesulfonylethyl)-N-{4-methyl-3-[5-(trifluoromethyl)pyridin-2-yl]phenyl}-1,2,3,4-tetrahydroisoquinolin-5-amine;
N-[3-(3-fluoropyridin-2-yl)-4-methylphenyl]-2-(2-methanesulfonylethyl)-1,2,3,4-tetrahydroisoquinolin-5-amine;
2-[2-(ethanesulfonyl)ethyl]-N-[4-methyl-3-(5-methylpyridin-2-yl)phenyl]-1,2,3,4-tetrahydroisoquinolin-5-amine;
2-(2-methanesulfonylethyl)-N-[4-methyl-3-(pyridin-2-yl)phenyl]-1,2,3,4-tetrahydroisoquinolin-5-amine;
2-(2-methanesulfonylethyl)-N-[4-methyl-3-(5-methylpyrimidin-2-yl)phenyl]-1,2,3,4-tetrahydroisoquinolin-5-amine;
2-(2-methanesulfonylethyl)-N-[3-(5-methoxypyrazin-2-yl)-4-methylphenyl]-1,2,3,4-tetrahydroisoquinolin-5-amine;
3-(5-{[4-methyl-3-(pyridin-2-yl)phenyl]amino}-1,2,3,4-tetrahydroisoquinolin-2-yl)-thiolane-1,1-dione;
3-(5-{[3-(5-methoxypyrazin-2-yl)-4-methylphenyl]amino}-1,2,3,4-tetrahydroisoquinolin-2-yl)-thiolane-1,1-dione;
3-(5-{[4-methyl-3-(5-methylpyrimidin-2-yl)phenyl]amino}-1,2,3,4-tetrahydroisoquinolin-2-yl)-thiolane-1,1-dione;
3-(5-{[3-(3-fluoropyridin-2-yl)-4-methylphenyl]amino}-1,2,3,4-tetrahydroisoquinolin-2-yl)-thiolane-1,1-dione;
4-(5-{[3-(3-fluoropyridin-2-yl)-4-methylphenyl]amino}-1,2,3,4-tetrahydroisoquinolin-2-yl)-thiane-1,1-dione;
2-methanesulfonyl-N-[3-(5-methoxypyridazin-3-yl)-4-methylphenyl]-1,2,3,4-tetrahydroisoquinolin-5-amine;
N-[3-(6-ethoxypyridazin-3-yl)-4-methylphenyl]-2-methanesulfonyl-1,2,3,4-tetrahydroisoquinolin-5-amine;
N-[3-(3,5-difluoropyridin-2-yl)-4-methylphenyl]-2-methanesulfonyl-1,2,3,4-tetrahydroisoquinolin-5-amine;
N-[5-chloro-6-(5-methylpyridin-2-yl)pyridin-2-yl]-2-methanesulfonyl-1,2,3,4-tetrahydroisoquinolin-5-amine;
2-methanesulfonyl-N-[5-methyl-6-(5-methylpyridin-2-yl)pyridin-2-yl]-1,2,3,4-tetrahydroisoquinolin-5-amine;
3-(5-{[3-(3-fluoropyridin-2-yl)-4-methylphenyl]amino}-1,2,3,4-tetrahydroisoquinolin-2-yl)-thietane-1,1-dione;
3-(5-{[3-(6-methoxypyridazin-3-yl)-4-methylphenyl]amino}-1,2,3,4-tetrahydroisoquinolin-2-yl)-thietane-1,1-dione;
N-[5-chloro-6-(5-methylpyridin-2-yl)pyridin-2-yl]-2-(2-methanesulfonylethyl)-1,2,3,4-tetrahydroisoquinolin-5-amine;
(3R)-3-(5-{[4-methyl-3-(5-methylpyridin-2-yl)phenyl]amino}-1,2,3,4-tetrahydroisoquinolin-2-yl)-thiolane-1,1-dione;
(3S)-3-(5-{[4-methyl-3-(5-methylpyridin-2-yl)phenyl]amino}-1,2,3,4-tetrahydroisoquinolin-2-yl)-thiolane-1,1-dione;
2-[2-(ethanesulfonyl)ethyl]-N-[3-(5-fluoropyridin-2-yl)-4-methylphenyl]-1,2,3,4-tetrahydroisoquinolin-5-amine;
2-[2-(ethanesulfonyl)ethyl]-N-[3-(6-methoxypyridazin-3-yl)-4-methylphenyl]-1,2,3,4-tetrahydroisoquinolin-5-amine;
2-[2-(ethanesulfonyl)ethyl]-N-[3-(3-fluoropyridin-2-yl)-4-methylphenyl]-1,2,3,4-tetrahydroisoquinolin-5-amine;
2-(2-methanesulfonylethyl)-N-{4-methyl-3-[5-(trifluoromethyl)pyridin-2-yl]phenyl}-1,2,3,4-tetrahydroisoquinolin-5-amine;
3-(5-{[5-methyl-6-(5-methylpyridin-2-yl)pyridin-2-yl]amino}-1,2,3,4-tetrahydroisoquinolin-2-yl)-thietane-1,1-dione;
(3S)-3-(5-{[3-(3-fluoropyridin-2-yl)-4-methylphenyl]amino}-1,2,3,4-tetrahydroisoquinolin-2-yl)-thiolane-1,1-dione;
(3R)-3-(5-{[3-(3-fluoropyridin-2-yl)-4-methylphenyl]amino}-1,2,3,4-tetrahydroisoquinolin-2-yl)-thiolane-1,1-dione;
N-[3-(5-chloro-3-fluoropyridin-2-yl)-4-methylphenyl]-2-methanesulfonyl-1,2,3,4-tetrahydroisoquinolin-5-amine;
N-{3-[5-(dimethylamino)pyridin-2-yl]-4-methylphenyl}-2-methanesulfonyl-1,2,3,4-tetrahydroisoquinolin-5-amine;
N-[3-(6-ethoxypyridazin-3-yl)-4-methylphenyl]-2-(2-methanesulfonylethyl)-1,2,3,4-tetrahydroisoquinolin-5-amine;
3-(5-{[3-(6-ethoxypyridazin-3-yl)-4-methylphenyl]amino}-1,2,3,4-tetrahydroisoquinolin-2-yl)-thietane-1,1-dione;
3-(5-{[3-(6-ethoxypyridazin-3-yl)-4-methylphenyl]amino}-1,2,3,4-tetrahydroisoquinolin-2-yl)-thiolane-1,1-dione;
2-[2-(ethanesulfonyl)ethyl]-N-[3-(6-ethoxypyridazin-3-yl)-4-methylphenyl]-1,2,3,4-tetrahydroisoquinolin-5-amine;
N-[5-chloro-6-(5-fluoropyridin-2-yl)pyridin-2-yl]-2-(2-methanesulfonylethyl)-1,2,3,4-tetrahydroisoquinolin-5-amine;

N-[5-chloro-6-(5-fluoropyridin-2-yl)pyridin-2-yl]-2-methanesulfonyl-1,2,3,4-tetrahydroisoquinolin-5-amine;
N-[3-(isoquinolin-3-yl)-4-methylphenyl]-2-methanesulfonyl-1,2,3,4-tetrahydroisoquinolin-5-amine;
4-(5-{[3-(6-methoxypyridazin-3-yl)-4-methylphenyl]amino}-1,2,3,4-tetrahydroisoquinolin-2-yl)-thiane-1,1-dione;
3-(5-{[3-(5-ethoxypyrazin-2-yl)-4-methylphenyl]amino}-1,2,3,4-tetrahydroisoquinolin-2-yl)-thiolane-1,1-dione;
2-(2-methanesulfonylethyl)-N-[5-methyl-6-(5-methylpyridin-2-yl)pyridin-2-yl]-1,2,3,4-tetrahydroisoquinolin-5-amine;
N-[3-(5-ethoxypyrazin-2-yl)-4-methylphenyl]-2-(2-methanesulfonylethyl)-1,2,3,4-tetrahydroisoquinolin-5-amine;
2-(2-methanesulfonylethyl)-N-[5-methyl-6-(pyridin-2-yl)pyridin-2-yl]-1,2,3,4-tetrahydroisoquinolin-5-amine;
2-methanesulfonyl-N-[5-methyl-6-(pyridin-2-yl)pyridin-2-yl]-1,2,3,4-tetrahydroisoquinolin-5-amine;
3-(5-{[3-(5-ethoxypyrazin-2-yl)-4-methylphenyl]amino}-1,2,3,4-tetrahydroisoquinolin-2-yl)-thietane-1,1-dione;
N-[3-(5-ethoxypyrazin-2-yl)-4-methylphenyl]-2-methanesulfonyl-1,2,3,4-tetrahydroisoquinolin-5-amine;
N-[3-(isoquinolin-3-yl)-4-methylphenyl]-2-(2-methanesulfonylethyl)-1,2,3,4-tetrahydroisoquinolin-5-amine;
3-(5-{[3-(isoquinolin-3-yl)-4-methylphenyl]amino}-1,2,3,4-tetrahydroisoquinolin-2-yl)-thietane-1,1-dione;
3-(5-{[5-chloro-6-(5-methylpyridin-2-yl)pyridin-2-yl]amino}-1,2,3,4-tetrahydroisoquinolin-2-yl)-thiolane-1,1-dione;
2-(ethanesulfonyl)-N-[6-(6-methoxypyridazin-3-yl)-5-methylpyridin-2-yl]-1,2,3,4-tetrahydroisoquinolin-5-amine;
N-[6-(6-methoxypyridazin-3-yl)-5-methylpyridin-2-yl]-2-(propane-2-sulfonyl)-1,2,3,4-tetrahydroisoquinolin-5-amine;
3-(5-{[3-(6-methoxypyridazin-3-yl)-4-methylphenyl]amino}-1,2,3,4-tetrahydroisoquinolin-2-yl)-thietane-1,1-dione;
(3R)-3-(5-{[3-(6-methoxypyridazin-3-yl)-4-methylphenyl]amino}-1,2,3,4-tetrahydroisoquinolin-2-yl)-thiolane-1,1-dione;
(3S)-3-(5-{[3-(6-methoxypyridazin-3-yl)-4-methylphenyl]amino}-1,2,3,4-tetrahydroisoquinolin-2-yl)-thiolane-1,1-dione;
3-(5-{[3-(6-ethoxypyridazin-3-yl)-4-methylphenyl]amino}-1,2,3,4-tetrahydroisoquinolin-2-yl)-thiolane-1,1-dione;
3-(5-{[3-(isoquinolin-3-yl)-4-methylphenyl]amino}-1,2,3,4-tetrahydroisoquinolin-2-yl)-thiolane-1,1-dione;
3-(5-{[3-(3,5-difluoropyridin-2-yl)-4-methylphenyl]amino}-1,2,3,4-tetrahydroisoquinolin-2-yl)-thiolane-1,1-dione;
3-(5-{[3-(3,5-difluoropyridin-2-yl)-4-methylphenyl]amino}-1,2,3,4-tetrahydroisoquinolin-2-yl)-thiolane-1,1-dione;
4-(5-{[3-(6-ethoxypyridazin-3-yl)-4-methylphenyl]amino}-1,2,3,4-tetrahydroisoquinolin-2-yl)-thiane-1,1-dione;
N-[6-(6-ethoxypyridazin-3-yl)-5-methylpyridin-2-yl]-2-(propane-2-sulfonyl)-1,2,3,4-tetrahydroisoquinolin-5-amine;
3-(5-{[6-(6-ethoxypyridazin-3-yl)-5-methylpyridin-2-yl]amino}-1,2,3,4-tetrahydroisoquinolin-2-yl)-thietane-1,1-dione;
2-(ethanesulfonyl)-N-[6-(5-ethoxypyrazin-2-yl)-5-methylpyridin-2-yl]-1,2,3,4-tetrahydroisoquinolin-5-amine;
N-[6-(5-ethoxypyrazin-2-yl)-5-methylpyridin-2-yl]-2-methanesulfonyl-1,2,3,4-tetrahydroisoquinolin-5-amine;
3-(5-{[6-(6-ethoxypyridazin-3-yl)-5-methylpyridin-2-yl]amino}-1,2,3,4-tetrahydroisoquinolin-2-yl)-thiolane-1,1-dione;
4-(5-{[3-(5-ethoxypyrazin-2-yl)-4-methylphenyl]amino}-1,2,3,4-tetrahydroisoquinolin-2-yl)-thiane-1,1-dione;
N-[6-(5-ethoxypyrazin-2-yl)-5-methylpyridin-2-yl]-2-(propane-2-sulfonyl)-1,2,3,4-tetrahydroisoquinolin-5-amine;
3-(5-{[3-(3,5-difluoropyridin-2-yl)-4-methylphenyl]amino}-1,2,3,4-tetrahydroisoquinolin-2-yl)-thiolane-1,1-dione;
(3R)-3-(5-{[3-(6-ethoxypyridazin-3-yl)-4-methylphenyl]amino}-1,2,3,4-tetrahydroisoquinolin-2-yl)-thiolane-1,1-dione;
(3S)-3-(5-{[3-(6-ethoxypyridazin-3-yl)-4-methylphenyl]amino}-1,2,3,4-tetrahydroisoquinolin-2-yl)-thiolane-1,1-dione;
(3R)-3-(5-{[3-(3-fluoropyridin-2-yl)-4-methylphenyl]amino}-1,2,3,4-tetrahydroisoquinolin-2-yl)-thiolane-1,1-dione;
(3S)-3-(5-{[3-(3-fluoropyridin-2-yl)-4-methylphenyl]amino}-1,2,3,4-tetrahydroisoquinolin-2-yl)-thiolane-1,1-dione;
N-(4-chloro-3-(4-phenyl-1H-imidazol-2-yl)phenyl)-2-(1-ethylpiperidin-4-yl)-1,2,3,4-tetrahydroisoquinolin-7-amine;
and
N-(3-(isoquinolin-3-yl)-4-methylphenyl)-2-(methylsulfonyl)-1,2,3,4-tetrahydroisoquinolin-5-amine.

17. A compound selected from
N-(3-(isoquinolin-3-yl)-4-methylphenyl)-2-(methylsulfonyl)-1,2,3,4-tetrahydroisoquinolin-5-amine;
4-(5-{[4-chloro-3-(5-phenyl-1H-imidazol-2-yl)phenyl]amino}-1,2,3,4-tetrahydroisoquinolin-2-yl)cyclohexan-1-one;
4-(5-{[4-chloro-3-(5-phenyl-1H-imidazol-2-yl)phenyl]amino}-1,2,3,4-tetrahydroisoquinolin-2-yl)cyclohexan-1-ol;
3-{5-[(2-methanesulfonyl-1,2,3,4-tetrahydroisoquinolin-5-yl)amino]-2-methylphenyl}-1,7-dimethyl-1,2-dihydro-1,6-naphthyridin-2-one;
N-(3-(5-fluoropyrimidin-2-yl)-4-methylphenyl)-2-(methylsulfonyl)-1,2,3,4-tetrahydroisoquinolin-5-amine, and
2-{[2-(dimethylamino)ethane]sulfonyl}-N-[3-(3-fluoropyridin-2-yl)-4-methylphenyl]-1,2,3,4-tetrahydroisoquinolin-5-amine.

18. A pharmaceutical compositions comprising a therapeutically effective amount of a compound of Formula (I) of claim 1 and one or more pharmaceutically acceptable excipients.

* * * * *